United States Patent
Schaeffer et al.

(10) Patent No.: US 11,875,903 B2
(45) Date of Patent: Jan. 16, 2024

(54) METHOD AND PROCESS FOR PREDICTING AND ANALYZING PATIENT COHORT RESPONSE, PROGRESSION, AND SURVIVAL

(71) Applicant: Tempus Labs, Inc., Chicago, IL (US)

(72) Inventors: Jeff Schaeffer, Chicago, IL (US); Hailey Lefkofsky, Chicago, IL (US); Carin Fishel Queen, Chicago, IL (US); Abigail Lammers, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 17/461,986

(22) Filed: Aug. 30, 2021

(65) Prior Publication Data

US 2022/0044826 A1    Feb. 10, 2022

Related U.S. Application Data

(63) Continuation-in-part of application No. 16/732,168, filed on Dec. 31, 2019.

(Continued)

(51) Int. Cl.
*G16H 50/70* (2018.01)
*G16H 10/60* (2018.01)
(Continued)

(52) U.S. Cl.
CPC ............. *G16H 50/70* (2018.01); *G06F 17/18* (2013.01); *G06F 18/214* (2023.01); *G06F 18/22* (2023.01);
(Continued)

(58) Field of Classification Search
CPC ... G16H 50/70; G16H 10/00–20; G16H 10/60
See application file for complete search history.

(56) References Cited

U.S. PATENT DOCUMENTS 10,049,772 B1 * 8/2018 Price, Jr. ............... G16H 50/70
10,395,772 B1    8/2019 Lucas
(Continued)

FOREIGN PATENT DOCUMENTS

WO    2016118771 A1    7/2016
WO    2017186048 A1    11/2017

OTHER PUBLICATIONS

Kopcke et al., Evaluation of data completeness in the electronic health record for the purpose of patient recruitment into clinical trials: a retrospective analysis of element presence, 2013, BMC Medical Informatics and Decision Making 13:37 (Year: 2013).*

(Continued)

*Primary Examiner* — Karen A Hranek
(74) *Attorney, Agent, or Firm* — Quarles & Brady LLP

(57) ABSTRACT

A system and method for analyzing a data store of de-identified patient data to generate one or more dynamic user interfaces usable to predict an expected response of a particular patient population or cohort when provided with a certain treatment. The automated analysis of patterns occurring in patient clinical, molecular, phenotypic, and response data, as facilitated by the various user interfaces, provides an efficient, intuitive way for clinicians to evaluate large data sets to aid in the potential discovery of insights of therapeutic significance.

19 Claims, 58 Drawing Sheets

Related U.S. Application Data

(60) Provisional application No. 62/786,739, filed on Dec. 31, 2018.

(51) Int. Cl.

| | | |
|---|---|---|
| *G06F 18/22* | (2023.01) | |
| *G16H 50/20* | (2018.01) | |
| *G06N 20/00* | (2019.01) | |
| *G06F 17/18* | (2006.01) | |
| *G16H 30/00* | (2018.01) | |
| *G16H 80/00* | (2018.01) | |
| *G06F 21/60* | (2013.01) | |
| *G06F 21/62* | (2013.01) | |
| *G06F 18/24* | (2023.01) | |
| *G06F 18/214* | (2023.01) | |
| *G06N 5/01* | (2023.01) | |

(52) U.S. Cl.
CPC ............ *G06F 18/24* (2023.01); *G06F 21/604* (2013.01); *G06F 21/62* (2013.01); *G06N 5/01* (2023.01); *G06N 20/00* (2019.01); *G16H 10/60* (2018.01); *G16H 30/00* (2018.01); *G16H 50/20* (2018.01); *G16H 80/00* (2018.01)

(56) References Cited

U.S. PATENT DOCUMENTS

| | | | |
|---|---|---|---|
| 2002/0049740 A1 | 4/2002 | Arning et al. | |
| 2003/0061228 A1 | 3/2003 | Kamath et al. | |
| 2005/0074795 A1 | 4/2005 | Hoffman et al. | |
| 2005/0108753 A1 | 5/2005 | Saidi | |
| 2007/0178501 A1 | 8/2007 | Rabinowitz et al. | |
| 2009/0043172 A1 | 2/2009 | Zagorchev | |
| 2009/0061422 A1 | 3/2009 | Linke et al. | |
| 2009/0076845 A1* | 3/2009 | Bellin ................... | G16H 40/20 715/781 |
| 2009/0319244 A1 | 12/2009 | West | |
| 2010/0114900 A1* | 5/2010 | Anderson ........... | G06F 16/2228 707/741 |
| 2012/0021935 A1 | 1/2012 | Cazaux | |
| 2012/0131484 A1* | 5/2012 | Neumann ............ | G06F 16/367 715/810 |
| 2013/0085980 A1 | 4/2013 | Alemi | |
| 2013/0185096 A1 | 7/2013 | Giusti | |
| 2013/0226612 A1 | 8/2013 | Carmeli et al. | |
| 2013/0232103 A1 | 9/2013 | Saeed | |
| 2014/0066328 A1 | 3/2014 | Modlin | |
| 2014/0108379 A1* | 4/2014 | Gotz ..................... | G06F 16/904 707/722 |
| 2014/0162887 A1 | 6/2014 | Martin | |
| 2014/0236618 A1* | 8/2014 | Rawlings ............. | G16H 50/70 705/2 |
| 2014/0244625 A1 | 8/2014 | Seghezzi | |
| 2014/0249761 A1 | 9/2014 | Carroll | |
| 2014/0279775 A1 | 9/2014 | Chu et al. | |
| 2015/0221110 A1* | 8/2015 | Holmen ................ | G16H 40/63 345/440 |
| 2015/0227610 A1* | 8/2015 | Chowdry ............ | G06F 16/9535 707/769 |
| 2015/0331909 A1 | 11/2015 | Sundquist | |
| 2016/0019666 A1 | 1/2016 | Amarasingham | |
| 2016/0063212 A1 | 3/2016 | Monier et al. | |
| 2016/0098541 A1* | 4/2016 | Haskell ................ | G16H 10/20 705/2 |
| 2016/0196398 A1* | 7/2016 | Vivero ................. | G16H 15/00 705/2 |
| 2016/0253469 A1 | 9/2016 | Donovan | |
| 2016/0317077 A1 | 11/2016 | Sillay | |
| 2017/0091394 A1* | 3/2017 | Gurupur ............... | G16H 10/60 |
| 2017/0177597 A1 | 6/2017 | Asimenos | |
| 2017/0177822 A1 | 6/2017 | Fogel | |
| 2017/0199965 A1 | 7/2017 | Dekel | |
| 2017/0237805 A1 | 8/2017 | Worley | |
| 2017/0322217 A1 | 11/2017 | Batagov | |
| 2018/0144003 A1 | 5/2018 | Formoso | |
| 2018/0165604 A1 | 6/2018 | Minkin et al. | |
| 2018/0226153 A1 | 8/2018 | Rubenstein | |
| 2018/0268937 A1 | 9/2018 | Spetzler | |
| 2018/0285526 A1* | 10/2018 | Wickson ............... | G16H 10/20 |
| 2018/0300454 A1* | 10/2018 | Chan ..................... | G16H 50/20 |
| 2018/0300456 A1 | 10/2018 | Eltoukhy et al. | |
| 2018/0300640 A1* | 10/2018 | Birnbaum ............. | G16H 10/60 |
| 2018/0336487 A1 | 11/2018 | Moore et al. | |
| 2019/0034591 A1 | 1/2019 | Mossin et al. | |
| 2019/0108912 A1 | 4/2019 | Spurlock, III | |
| 2019/0206529 A1* | 7/2019 | Kartoun ................ | G16H 50/20 |
| 2019/0250975 A1 | 8/2019 | Bertiger et al. | |
| 2019/0371443 A1 | 12/2019 | Petricoin, III et al. | |
| 2019/0371450 A1 | 12/2019 | Lou et al. | |
| 2020/0058382 A1* | 2/2020 | Birnbaum ............. | G16H 10/20 |
| 2020/0098451 A1 | 3/2020 | Kirshnan et al. | |
| 2020/0105413 A1 | 4/2020 | Vladimirova | |
| 2020/0126675 A1* | 4/2020 | Park ..................... | G16H 70/20 |
| 2020/0211716 A1 | 7/2020 | Lefkofsky et al. | |
| 2020/0219619 A1 | 7/2020 | Feczko | |
| 2020/0258601 A1 | 8/2020 | Lau | |
| 2020/0334228 A1 | 10/2020 | Matyska et al. | |
| 2021/0142910 A1 | 5/2021 | Hafez | |

OTHER PUBLICATIONS

Nasir et al., A New Paradigm to Analyze Data Completeness of Patient Data, 2016, Applied Clinical Informatics (Year: 2016).*

Weber et al., Biases introduced by filtering electronic health records for patients with 'complete data', Aug. 2017, Journal of the American Medical Informatics Association, 24(6) (Year: 2017).*

Austin, PC "An Introduction to Propensity Score Methods for Reducing the Effects of Confounding in Observational Studies." Multivariate Behavioral Research 46.3 (2011): 399.

Austin, The use of propensity score methods with survival or time-to-event outcomes: reporting measures of effect similar to those used in randomized experiments, Statistics in Medicine (2013), 33:1242-1258.

Caris Life Sciences. Code: Comprehensive Oncology Data Explorer. Slideshow May 2017. Accessed on Dec. 16, 2020 at https://www.karmanos.org/Uploads/Public/Documents/Karmanos/CODE%20slides_5.2017.pptx%20.

DNAnexus. Working with UK Biobank: A Research Guide. Accessed online on Dec. 31, 2020. Available at https://web.archive.org/save/https://dna-nexus-prod-s3-assets-51tcpaqcp0pd.s3.amazonaws.com/images/files/DNAnexus_WhitePaper_Working-with-UKB-Data_2.pdf.

International Searching Authority, International Search Report & Written Opinion for application PCT/US2019/069149, dated Apr. 29, 2020.

Rokach L., Maimon O., Decision Trees, 2005, Data Mining and Knowledge Discovery Handbook, pp. 165-192 (Year: 2005).

Rosenbaum & Rubin. The central role of the propensity score in observational studies for causal effects, Biometrika (1983), 70(1):41-55.

Stuart, E. Matching methods for causal inference: a review and a look forward, Statistical Science (2010) 25(1):1-21.

Al-Nachawati et al., Tree-Structured Analysis of Survival Data and Its Application Using SAS Software, Journal of King Saud University (Science), 2010, 22:251-255.

Carrasquinha et al., Consensus Outlier Detection in Survival Analysis Using the Rank Product Test, bioRxiv preprint doi: https://doi.org/10.1101/421917, Sep. 20, 2018, pp. 1-27.

Dean, A Method for Detecting Optimal Splits Over Time in Survival Analysis Using Tree-Structured Models, Submitted to Graduate School of Public Health of the University of Pittsburgh, 2007, 24 pages.

Jeffares, Decision Trees: A Complete Introduction, Published in Towards Data Science, Jul. 25, 2018, 12 pages.

Jin et al., Alternative Tree-Structured Survival Analysis Based on Variance of Survival Time, Medical Decision Making, Nov.-Dec. 2004, pp. 670-680.

(56) References Cited

OTHER PUBLICATIONS

Kourou et al., Machine Learning Applications in Cancer Prognosis and Prediction, Computational and Structural Biotechnology Journal, 2015, 13:8-17.
Lee et al., Third-Generation Sequencing and the Future of Genomics, bioRxiv preprint doi: https://doi.org/10.1101/048603, Apr. 13, 2016, 20 pages.
Mostafa et al., Overviews of "Next-Generation Sequencing", Research and Reports in Forensic Medical Science, 2015, 5:1-5.
Negassa et al., Tree-Structured Subgroup Analysis for Censored Survival Data: Validation of Computationally Inexpensive Model Selection Criteria, Statistics and Computing, 2005, 15:231-239.
Sinsel, Ensemble Learning for Ranking Interesting Attributes, Master Thesis, West Virginia University, 2005, 90 pages.
Ture et al., Using Kaplan-Meier Analysis Together with Decision Tree Methods (C&RT, Chaid, Quest, C4.5 and ID3) in Determining Recurrence-Free Survival of Breast Cancer Patients, Expert Systems with Applications, 2009, 36:2017-2026.
Zhang et al., Recursive Partitioning for Tumor Classification with Gene Expression Microarray Data, PNAS, 2001, 98(12):6730-6735.
European Patent Office, Extended Search Report, Application No. 19907146.5, dated Aug. 5, 2022, 18 pages.

\* cited by examiner

24 →

| TEMPUS | COHORT FUNNEL | SURVIVAL CURVES | SURVIVAL TREE | PATIENT TIMELINE | EXPLORATORY DATA VISUALIZER | ASK GENE |

236

META — 200

PROJECT NAME
[SELECT...] — 204
GENDER
[SELECT...] — 206
RACE
[SELECT...] — 208

CANCER
CANCER SITE NAME
[SELECT...] — 210
CANCER NAME
[SELECT...] — 212
METASTASIS CANCER NAME
[SELECT...] — 214

TUMOR FINDING ← 202
TUMOR FINDING
[SELECT...] — 216
STAGE
[SELECT...] — 218
M STAGE
[SELECT...] — 220

MEDICATION
MEDICATION NAME
[SELECT...] — 222
INGREDIENT NAME
[SELECT...] — 224

SEQUENCING
GENE NAME + VARIANT
[SELECT...] — 226
IMMUNO MSI STATUS
[SELECT...] — 228

PROCEDURE
PROCEDURE NAME
[SELECT...] — 230

DEATH
EVENT
[SELECT...] — 232
CAUSE OF DEATH
[SELECT...] — 234

FIG. 2

| feature | value |
|---|---|
| last stage | 0.14485 |
| cancer: breast_cancer | 0.06266 |
| historical-took_medication: gemcitabine | 0.04721 |
| historical-took_medication: paclitaxel | 0.04686 |
| cancer: lung_cancer | 0.03740 |
| sequencing: pgr:positive | 0.03522 |
| historical-took_medication: carboplatin | 0.03478 |
| historical-took_medication: bevacizumab | 0.03350 |
| cancer: pancreatic_cancer | 0.03221 |
| historical-got_radiotherapy: radiotherapy,_not_otherwise_specified | 0.03046 |

FIG. 27A

| feature | value |
|---|---|
| historical-took_medication: irinotecan | 0.06544 |
| historical-took_medication: bevacizumab | 0.05002 |
| historical-took_medication: oxaliplatin | 0.03810 |
| historical-took_medication: capecitabine | 0.03777 |
| took_medication: oxaliplatin | 0.03711 |
| historical-took_medication: leucovorin | 0.03680 |
| historical-took_medication: fluorouracil | 0.03317 |
| historical-took_medication: cetuximab | 0.03271 |
| took_medication: fluorouracil | 0.02646 |
| sequencing: kras:mutation | 0.02238 |

FIG. 27B

| feature | value |
| --- | --- |
| duplicate_column_1 | 0.06544 |
| historical-took_medication: irinotecan | 0.06544 |
| historical-took_medication: bevacizumab | 0.05002 |
| historical-took_medication: oxaliplatin | 0.03810 |
| duplicate_column_2 | 0.03777 |
| historical-took_medication: capecitabine | 0.03777 |
| took_medication: oxaliplatin | 0.03711 |
| historical-took_medication: leucovorin | 0.03680 |
| historical-took_medication: fluorouracil | 0.03317 |
| historical-took_medication: cetuximab | 0.03271 |

FIG. 27C

WELCOME TO TEMPUS LENS 2,159,671
PATIENTS AVAILABLE

3804 — [ DEFINE A COHORT ]

SAVED FOR LATER

| NAME | PATIENT COUNT | LAST UPDATED |
|---|---|---|
| LUNG | 71,244 | SEPT 15, 2020, 11:40 AM |
| PANCREAS | 16,015 | SEPT 10, 2020, 3:17 PM |
| BLADDER | 3,954 | SEPT 7, 2020, 4:09 PM |

TEMPUS

🔍 SEARCH | HOME | ACCOUNT ▽ | HELP ▽ | 🔔

PATIENT NAME
BORN 01/23/1955
INVASIVE DUCTAL
CARCINOMA, BREAST

RESULTS
SUMMARY
ORDERS
TRACKING

INTERACTIVE TOOLS
CLINICAL TRAILS

SUMMARY

[NEW] REPORT | xT-648 GENE PANEL (ADDENDUM) VIEW REPORT →

2 PENDING REPORTS     VIEW REPORT → xT, IHC: ORDERED ON MAY 2, 2020     ⬇ DOWNLOAD

TEMPUS | ORDER SUMMARY     GENERATED: JAN 21, 2021

SUMMARY    PATIENT    TEST & SPECIMEN

▦ POTENTIAL ACTIONABLE VARIANTS     ⚠ IMMUNE BIOMARKERS & ADDITIONAL INFORMATION

TP53
p.V197L MISSENSE VARIANT-LOF     TUMOR MUTATION BURDEN 1.6 m/MB, 14TH PERCENTILE
MICROSATELLITE INSTABILITY STATUS: STABLE
KRAS
p.V197L MISSENSE VARIANT-LOF     HRD: POSITIVE, GENOME-WIDE LOS OF HETEROZYGOSITY, 42.7%

BIOLOGICALLY RELEVANT: ZNFX43, TP53, AR, COND2, IRF1, KRAS, RAD50

◻ RNA FUSIONS     PD-L1 22C3: NEGATIVE TUMOR PROPORTION SCORE (TPS) 1%,
COMBINED POSITIVE SCORE (CPS) 1
RNA SEQUENCING ANALYSIS COMPLETED
AND NO FUSIONS FOUND     MMR: NORMAL, ALL STAINS PRESENT

---

4808 →

2,350
SIMILAR PATIENTS     4812 → (PRIMARY SITE: BLADDER)

⊙ SEE MORE PATIENTS LIKE YOURS ← 4816

CLINICAL HISTORY
CLINICAL HISTORY IS BASED ON THE CLINICAL
DOCUMENTS WE RECEIVED AND ABSTRACT WHICH
MAY NOT REFLECT THE COMPLETE TREATMENT
HISTORY

| DIAGNOSIS | PROCEDURES |
|---|---|
| DIAGNOSED ON | BREAST, PARTIAL MASTECTOMY |
| 1/30/2015 | 08/2018 |
| RADIATION | THERAPIES |
| RADIOTHERAPY | — |
| UNKNOWN | |

CONTRIBUTE TO PATIENT'S CLINICAL HISTORY
UPLOAD DOCUMENTS SUCH AS PROGRESS NOTES;

[UPLOAD]

| TEMPUS | ○ SEARCH | | HOME | ACCOUNT ▽ | HELP ▽ | 🔔 |

PATIENT NAME
BORN 01/23/1955
INVASIVE DUCTAL
CARCINOMA, BREAST

5100 ⟶

SUM  ENTERING LENS
YOU ARE ABOUT TO LEAVE THE CLINICAL PORTAL
ACCESS OUR RESEARCH TOOL, LENS, EXPLORE OUR
COLLECTION OF REAL WORLD DATA TO IDENTIFY
PATTERNS ABOUT PATIENTS WHO ARE SIMILAR
TO YOURS.

*LENS SHOULD NOT BE USED FOR CLINICAL
DECISION MAKING

[CONTINUE] ⟵ 5108

RESULTS
SUMMARY
ORDERS
TRACKING

INTERACTIVE TOOLS
CLINICAL TRIALS

5104 ⟶

TEMPUS
PRIMARY SITE
744

744
SIMILAR PATIENTS
⊙ SOMATIC VARIANT:TP53  MSI:STABLE ⊙
SEE MORE PATIENTS LIKE YOURS

SUMMARY       PATIENT       TEST & SPECIMEN

▣ POTENTIAL ACTIONABLE VARIANTS       ♨ IMMUNE BIOMARKERS & ADDITIONAL INFORMATION
TP53
p.V197L MISSENSE VARIANT-LOF
KRAS
p.V197L MISSENSE VARIANT-LOF

TUMOR MUTATION BURDEN:1.6 m/MB, 14TH PERCENTILE
MICROSATELLITE INSTABILITY STATUS: STABLE
HRD: POSITIVE, GENOME-WIDE LOS OF HETEROZYGOSITY: 42.7%
BIOLOGICALLY RELEVANT: ZMYM3, TP53, AR, CCND2, RF1, KRAS, RAD50
PD-L1:22C3: NEGATIVE TUMOR PROPORTION SCORE (TPS) 1%,
COMBINED POSITIVE SCORE (CPS) 1
MMR: NORMAL, ALL STAINS PRESENT

◨ RNA FUSIONS
RNA SEQUENCING ANALYSIS COMPLETED
AND NO FUSIONS FOUND

CLINICAL HISTORY
CLINICAL HISTORY IS BASED ON THE CLINICAL
DOCUMENTS WE RECEIVED AND ABSTRACT WHICH
MAY NOT REFLECT THE COMPLETE TREATMENT
HISTORY

DIAGNOSIS                          PROCEDURES
DIAGNOSED ON                  BREAST, PARTIAL MASTECTOMY
1/30/2015                            08/2018
RADIATION                         THERAPIES
RADIOTHERAPY                  —
UNKNOWN

CONTRIBUTE TO PATIENT'S CLINICAL HISTORY
UPLOAD DOCUMENTS SUCH AS PROGRESS NOTES,

[UPLOAD]

FIG. 52

METHOD AND PROCESS FOR PREDICTING AND ANALYZING PATIENT COHORT RESPONSE, PROGRESSION, AND SURVIVAL

CROSS-REFERENCE TO RELATED APPLICATIONS

This application is a continuation-in-part of U.S. application Ser. No. 16/732,168, filed Dec. 31, 2019, and titled "Method and Process for Predicting and Analyzing Patient Cohort Response, Progression, and Survival," which claims the benefit of priority to U.S. provisional application 62/786,739, filed Dec. 31, 2018, the contents of both which are incorporated by reference herein in their entirety.

BACKGROUND

In certain medical fields, for example the areas of cancer research and treatment, voluminous amounts of data may be generated and collected for each patient. This data may include demographic information, such as the patient's age, gender, height, weight, smoking history, geographic location, and other, non-medical information. The data also may include clinical components, such as tumor type, location, size, and stage, as well as treatment data including medications, dosages, treatment therapies, mortality rates, and other outcome/response data. Moreover, more advanced analysis also may include genomic information about the patient and/or tumor, including genetic markers, mutations, as well as other information from fields including proteome, transcriptome, epigenome, metabolome, microbiome, and other multi-omic fields.

Despite this wealth of data, there is a dearth of meaningful ways to compile and analyze the data quickly, efficiently, and comprehensively.

Thus what are needed are a user interface, system, and method that overcome one or more of these challenges.

SUMMARY OF THE INVENTION

In one aspect, a system and user interface are provided to predict an expected response of a particular patient population or cohort when provided with a certain treatment. In order to accomplish those predictions, the system uses a pre-existing dataset to define a sample patient population, or "cohort," and identifies one or more key inflection points in the distribution of patients exhibiting each attribute of interest in the cohort, relative to a general patient population distribution, thereby targeting the prediction of expected survival and/or response for a particular patient population.

The system described herein facilitates the discovery of insights of therapeutic significance, through the automated analysis of patterns occurring in patient clinical, molecular, phenotypic, and response data, and enabling further exploration via a fully integrated, reactive user interface.

In one embodiment the invention provides a method for identifying an outlier group of patients, including: 1) selecting a cohort of patients including a plurality of patients; 2) calculating an average survival rate for the cohort of patients; 3) selecting a plurality of clinical or molecular characteristics associated with the cohort of patients; 4) for each characteristic of the plurality of characteristics: a) identifying a plurality of data values associated with the characteristic, b) for each data value of the plurality of data values associated with the characteristic: i) dividing the cohort of patients into a first subgroup and a second subgroup of the plurality of patients based on whether each patient of the plurality of patients survived during an outlier time period, ii) determining a difference between a number of patients in the first subgroup and the second subgroup, and iii) selecting a data value that results in the difference that is a largest difference between a number of patients in the first subgroup and the second subgroup; 5) creating a new node of a tree structure based on the data value that results in the largest difference between the number of patients in the first subgroup and the second subgroup; 6) creating a first branch from the new node based on the first subgroup; 7) creating a second branch from the new node based on the second subgroup; 8) for each of the first branch and the second branch, repeating steps of 4) b) i-iii) and 5) based on patients in the first subgroup and the second subgroup, respectively, until either: a maximum number of nodes or branches has been created, or a node contains fewer than a minimum number of patients; and 9) identifying at least one node containing an outlier group of patients.

In yet another embodiment the invention provides a method for implementing a prediction model, including: receiving a plurality of data for a plurality of patients for a period of time; identifying, for each of the plurality of patients, a plurality of patient timepoints within the period of time; for each patient of the plurality of patients and for each patient timepoint of the plurality of patient timepoints and based on the plurality of data for the plurality of patients: calculating an outcome target for an outcome event within a horizon time window, identifying a plurality of prior features, and determining a state of each of the plurality of prior features at the patient timepoint; identifying, for each patient timepoint of the plurality of timepoints having a valid outcome target and for each combination of horizon time window and outcome event, a plurality of forward features; and generating a plurality of sets of predictions for the plurality of patients based on the plurality of prior features and the plurality of forward features.

In still another embodiment the invention provides a method, including: receiving patient information for one or more patients; identifying one or more interactions for each of the one or more patients based at least in part on the received patient information; generating, for one or more targets at each of the one or more interactions, one or more timeline metrics identifying whether each of the one or more targets occurs within a time period of an occurrence of the interaction; identifying, for each timeline metric of the one or more timeline metrics, whether a patient may incur one or more status characteristics within the time period; training a target prediction model for each of the one or more targets based at least in part on the one or more status characteristics; and associating predictions for each patient from the target prediction model for each of the one or more targets with a respective one or more timeline metrics of the one or more timeline metrics.

In some embodiments the method may further include: 1) selecting a cohort of patients including a group of patients of the plurality of patients; 2) identifying a common anchor point in time from a set of anchor points associated with each of the group of patients, the common anchor point being shared by each of the group of patients in the cohort; 3) aligning, for each patient of the group of patients, a timeline associated with each patient of the group of patients to the common anchor point; 4) identifying an outcome target; 5) retrieving, for each patient of the group of patients and for each of the plurality of forward features and the plurality of prior features, the generated plurality of sets of predictions each including a predicted target value; 6) generating a plurality of decision trees, including, for decision each tree of the plurality of decision trees: a) for each feature of the plurality of forward features and the plurality of prior features: i) dividing the group of patients into a first subgroup and a second subgroup based on a difference between the predicted target value and an actual target value, ii) determining a difference between a number of patients in the first subgroup and the second subgroup, and iii) selecting a feature that results in the difference that is a largest difference between a number of patients in the first subgroup and the second subgroup; 7) creating a new node of a tree structure based on the feature that results in the largest difference between the number of patients in the first subgroup and the second subgroup; 8) creating a first branch from the new node based on the first subgroup; 9) creating a second branch from the new node based on the second subgroup; and 10) for each of the first branch and the second branch, repeat steps of 6) a) i-iii) and 7) based on patients in the first subgroup and the second subgroup, respectively, until either: a maximum number of nodes or branches has been created, or a node contains fewer than a minimum number of patients.

In other embodiments the method may further include: receiving the plurality of predictions, an outcome target, a subset of the plurality of forward features corresponding to the outcome target, and a cohort of patients including a subset of the plurality of patients; receiving an anchor point; for each patient in the cohort having the anchor point, providing the prediction model with the selected subset of the plurality of forward features and a difference between each of the plurality of predictions and the outcome target; and for each feature of the selected subset of the plurality of forward features, generating a decision tree based on determining a greatest difference between each of the plurality of predictions and the outcome target, wherein the decision tree includes a plurality of leaf nodes and one or more branch nodes, wherein each of the one or more branch nodes includes a pair of branches each of which includes a leaf node or a branch node, and wherein each of the plurality of leaf nodes of the decision tree includes a number of patients from the cohort of patients.

The foregoing and other aspects and advantages of the invention will appear from the following description. In the description, reference is made to the accompanying drawings which form a part hereof, and in which there is shown by way of illustration preferred embodiments of the invention. Such embodiments do not necessarily represent the full scope of the invention, however, and reference is made therefore to the claims herein for interpreting the scope of the invention.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIG. 2 is one example of a patient cohort selection filtering interface;

FIGS. 27A and 27B show an example of adaptive feature ranking in accordance with embodiments of the SAFE algorithm;

FIG. 27C shows an example of handling of correlated features in accordance with embodiments of the SAFE algorithm;

FIG. 38 illustrates an example of a user interface of the Interactive Analysis Portal for generating a new cohort according to certain embodiments;

FIG. 45 illustrates an example of a user interface of the Interactive Analysis Portal for generating a cohort having patients that are similar to a target patient;

Figure 46:
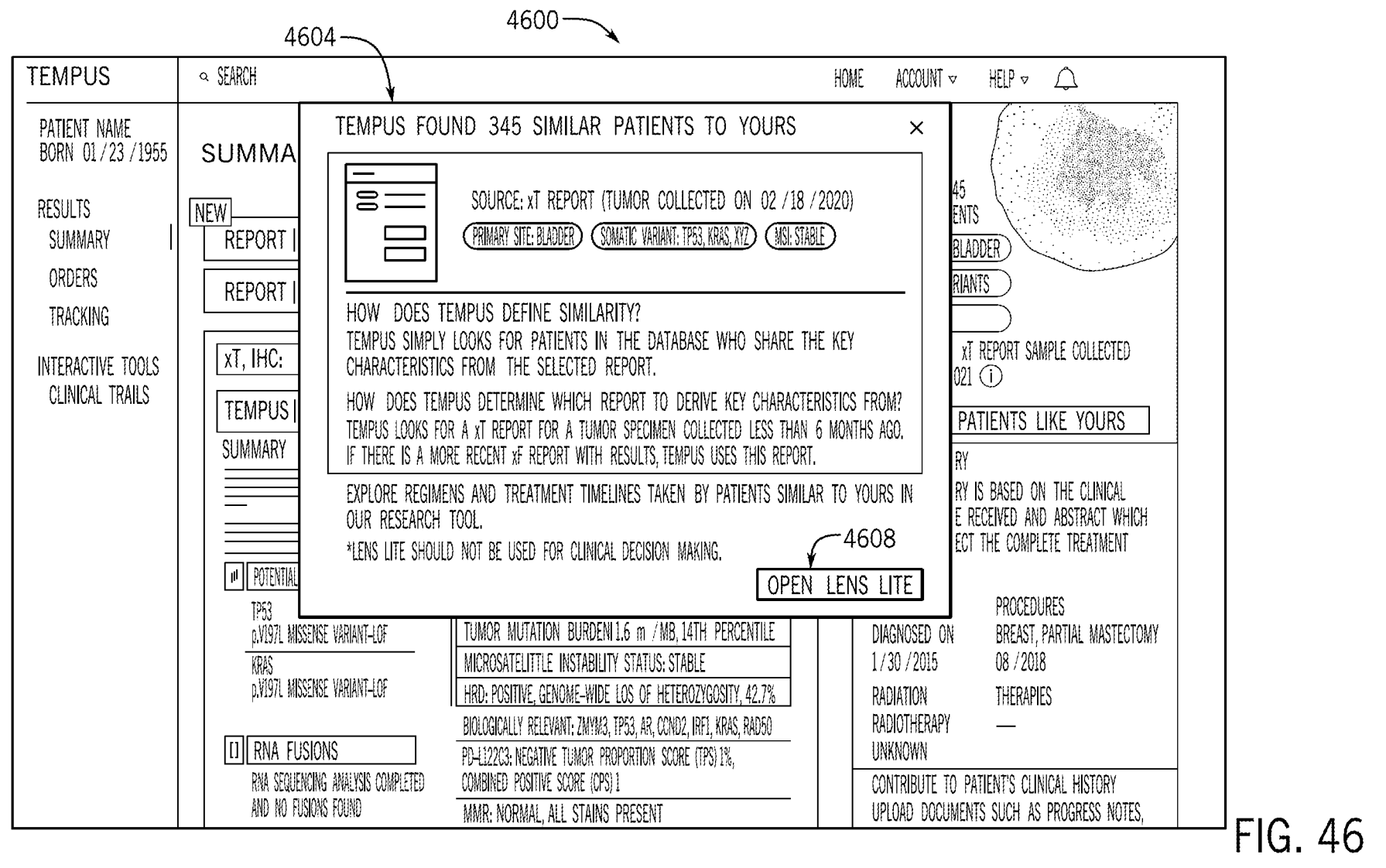

FIG. 46 illustrates another example of a user interface of the Interactive Analysis Portal for generating a cohort having patients that are similar to a target patient;

Figure 47:
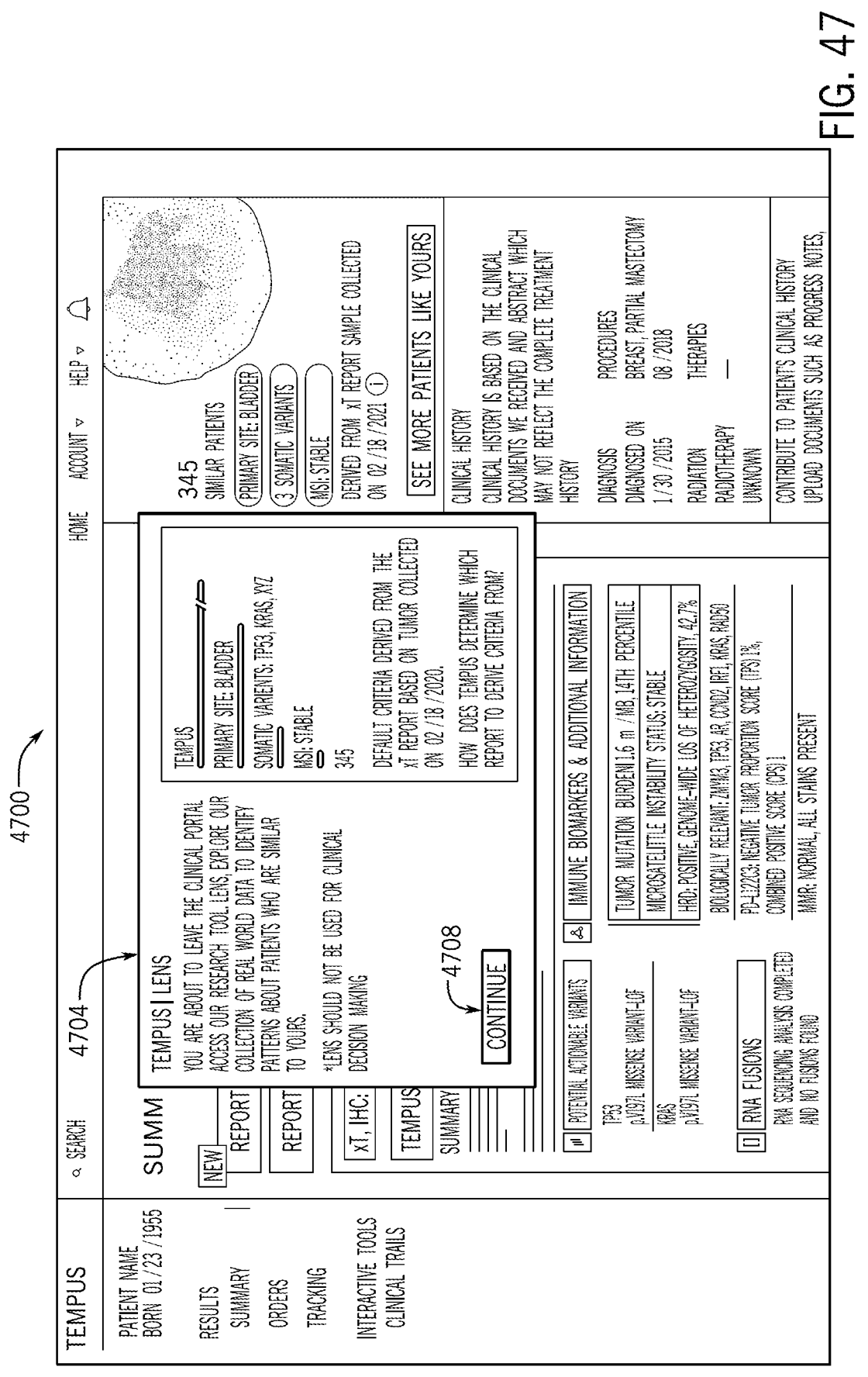

FIG. 47 illustrates yet another example of a user interface of the Interactive Analysis Portal for generating a cohort having patients that are similar to a target patient;

FIG. 48 illustrates still yet another example of a user interface of the Interactive Analysis Portal for generating a cohort having patients that are similar to a target patient;

Figure 49:
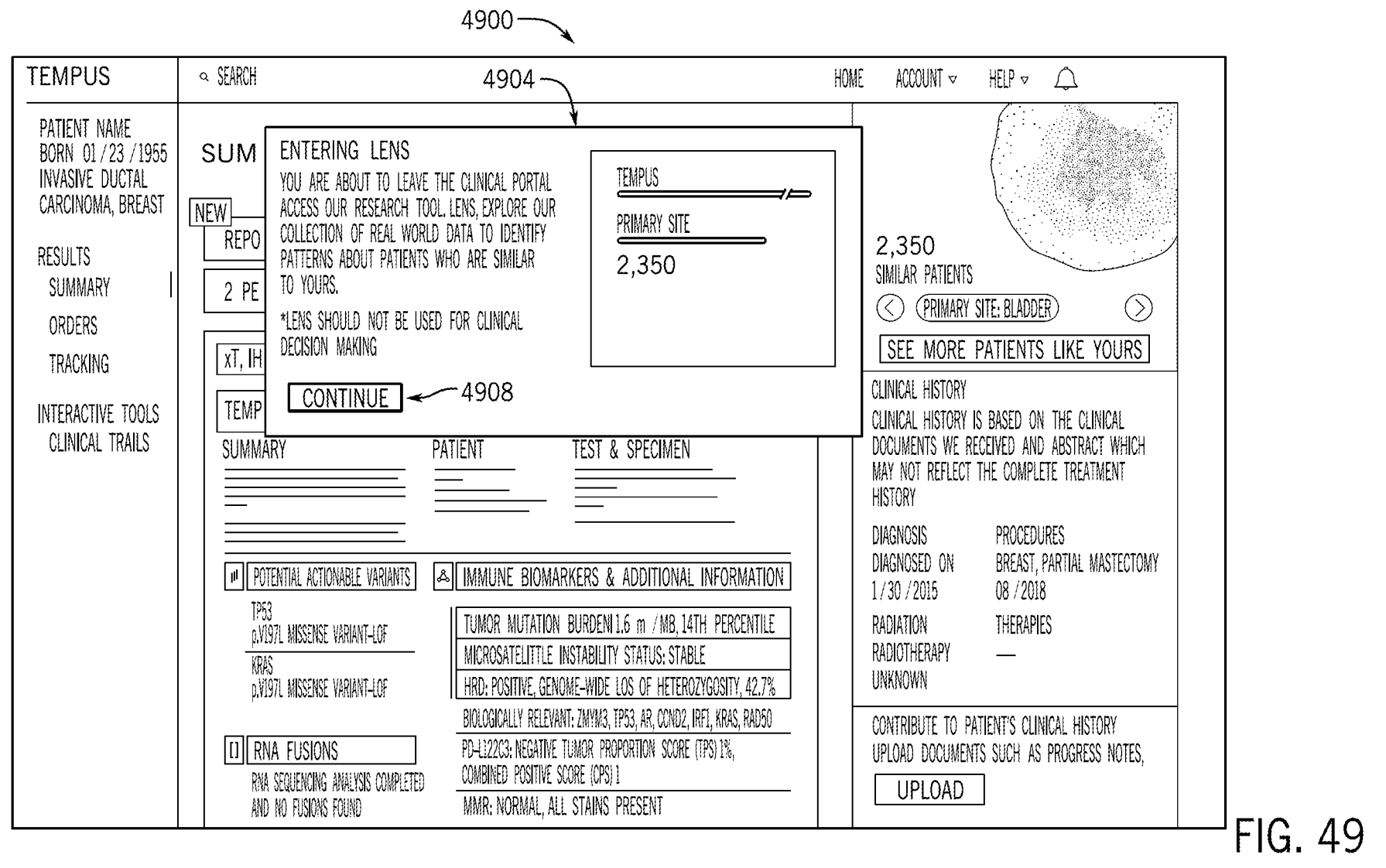

FIG. 49 illustrates a further example of a user interface of the Interactive Analysis Portal for generating a cohort having patients that are similar to a target patient;

FIG. 50 illustrates another further example of a user interface of the Interactive Analysis Portal for generating a cohort having patients that are similar to a target patient;

FIG. 51 illustrates yet another further example of a user interface of the Interactive Analysis Portal for generating a cohort having patients that are similar to a target patient;

FIG. 52 illustrates a still further example of a user interface of the Interactive Analysis Portal for generating a cohort having patients that are similar to a target patient;

DETAILED DESCRIPTION

Figure 1:
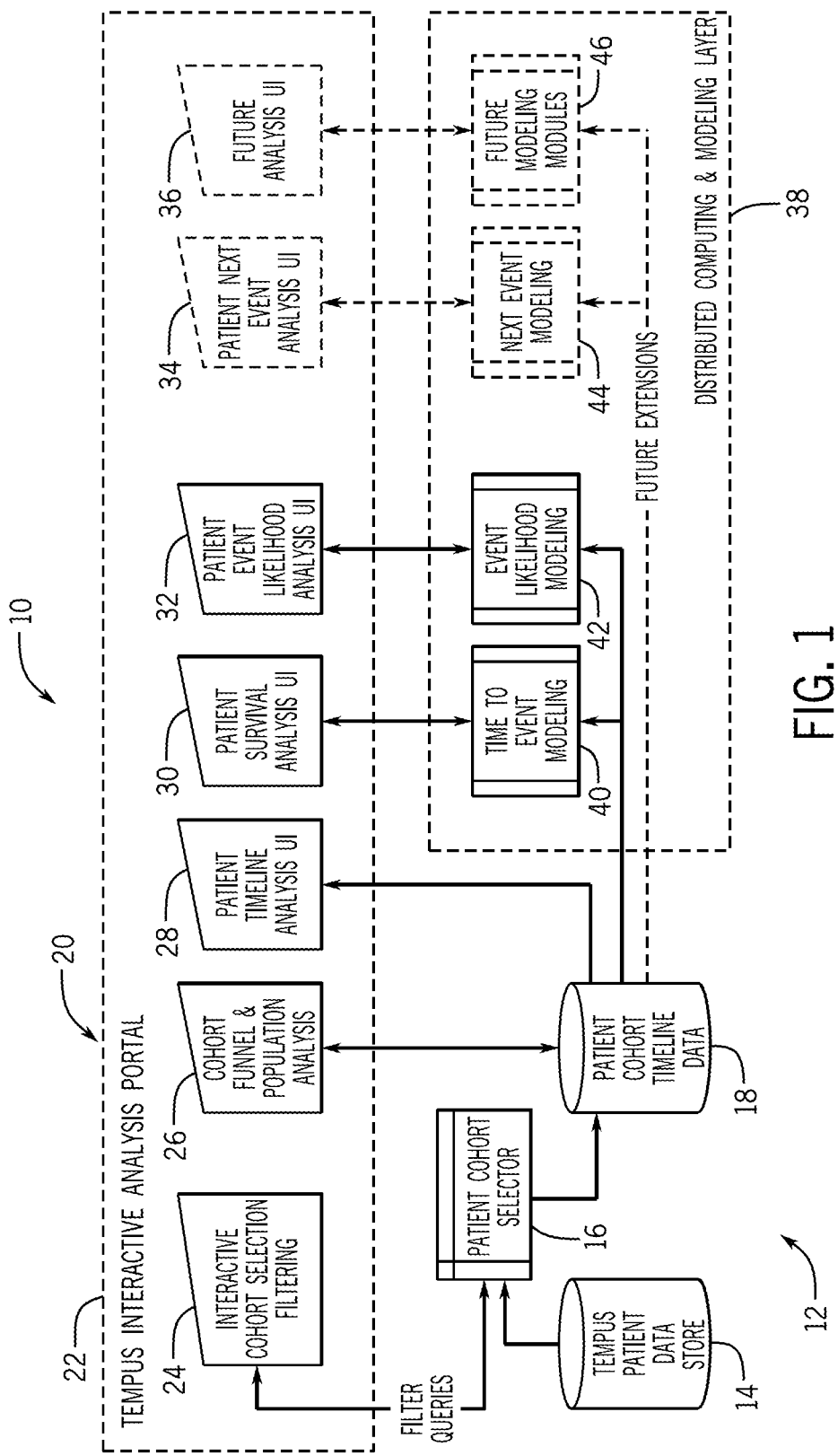
FIG. 1 is an exemplary system diagram of back end and front end components for predicting and analyzing patient cohort response, progression, and survival.
Figure 3:
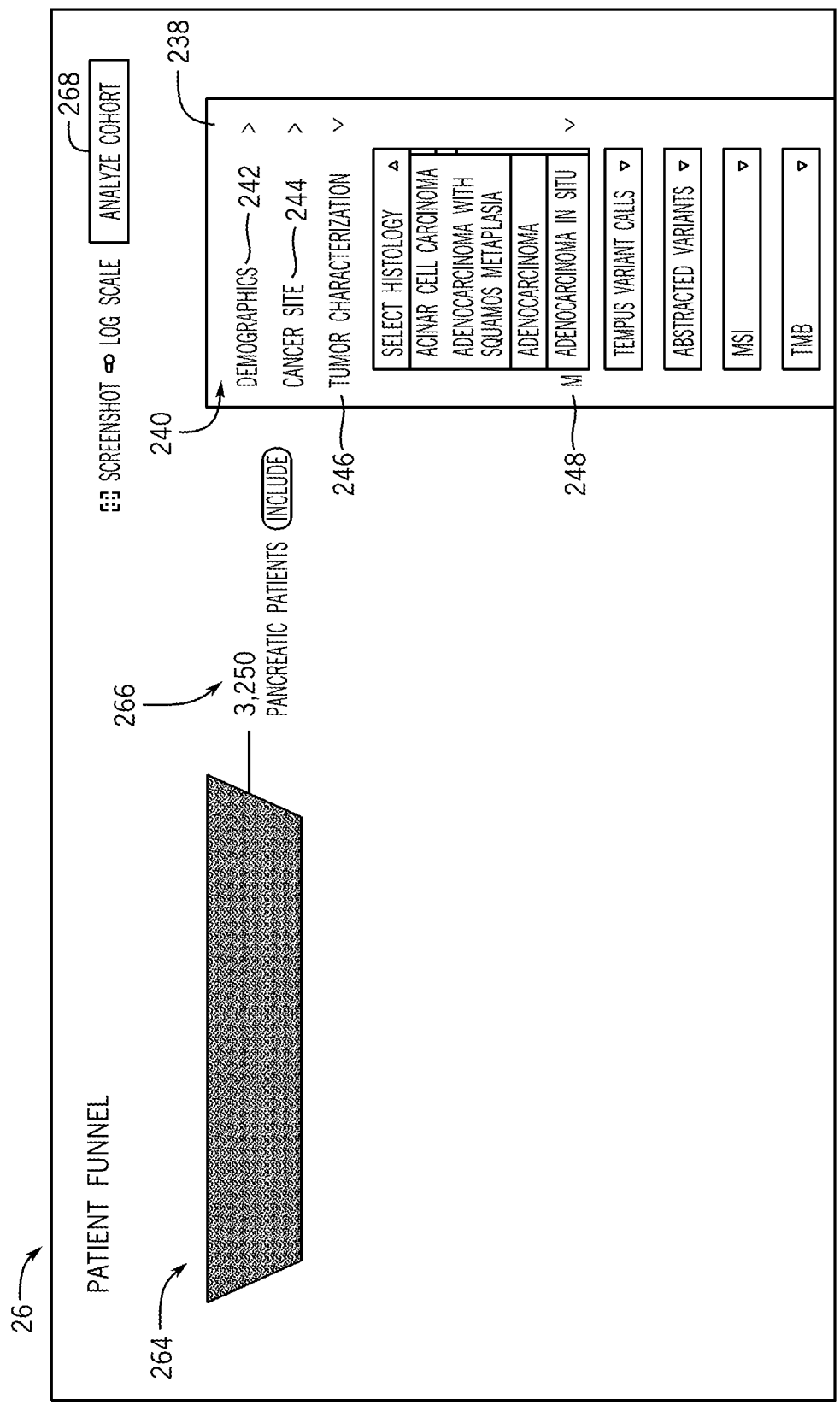
FIG. 3 is one example of a cohort funnel & population analysis user interface.
Figure 4:
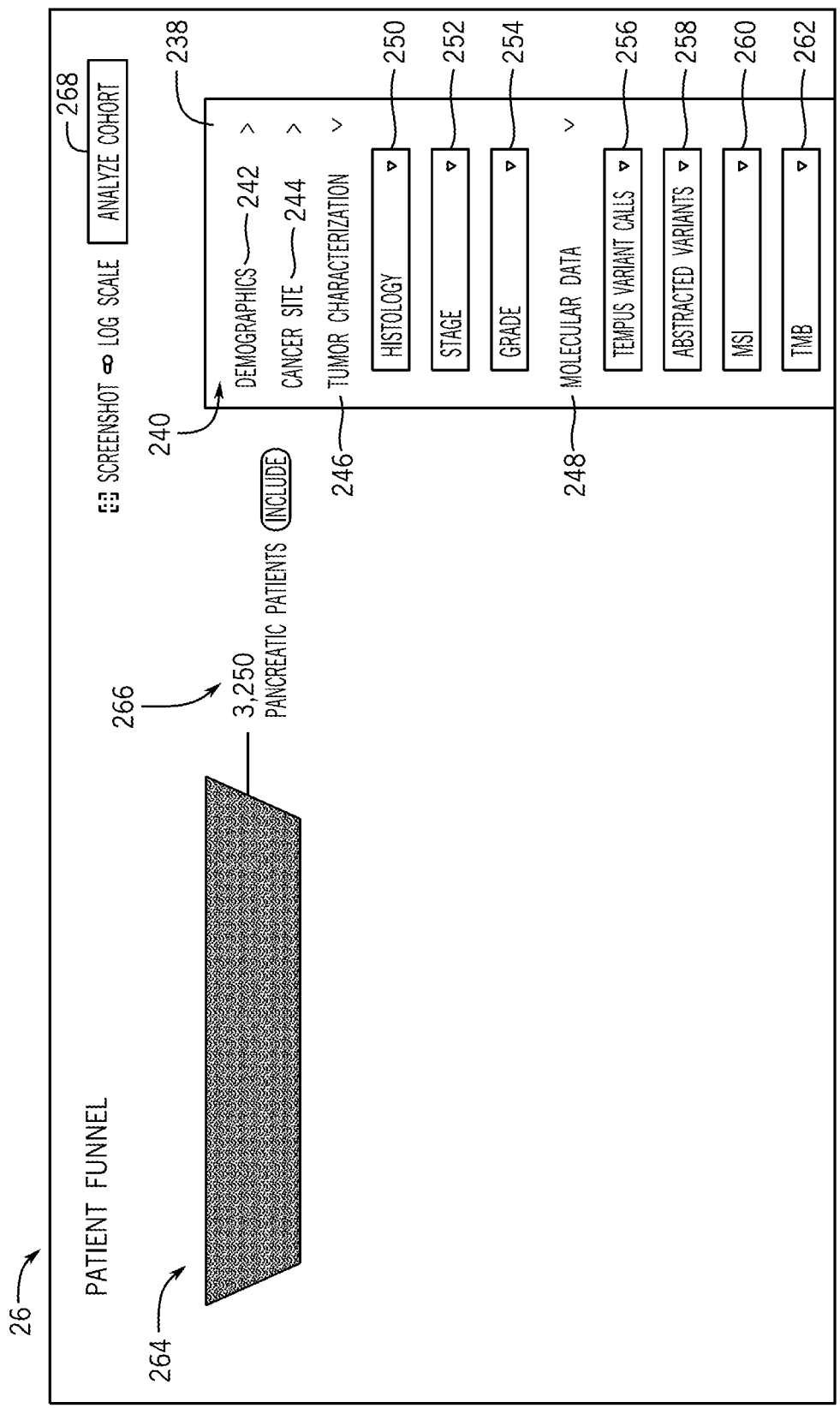
FIG. 4 is another example of a cohort funnel & population analysis user interface.
Figure 5:
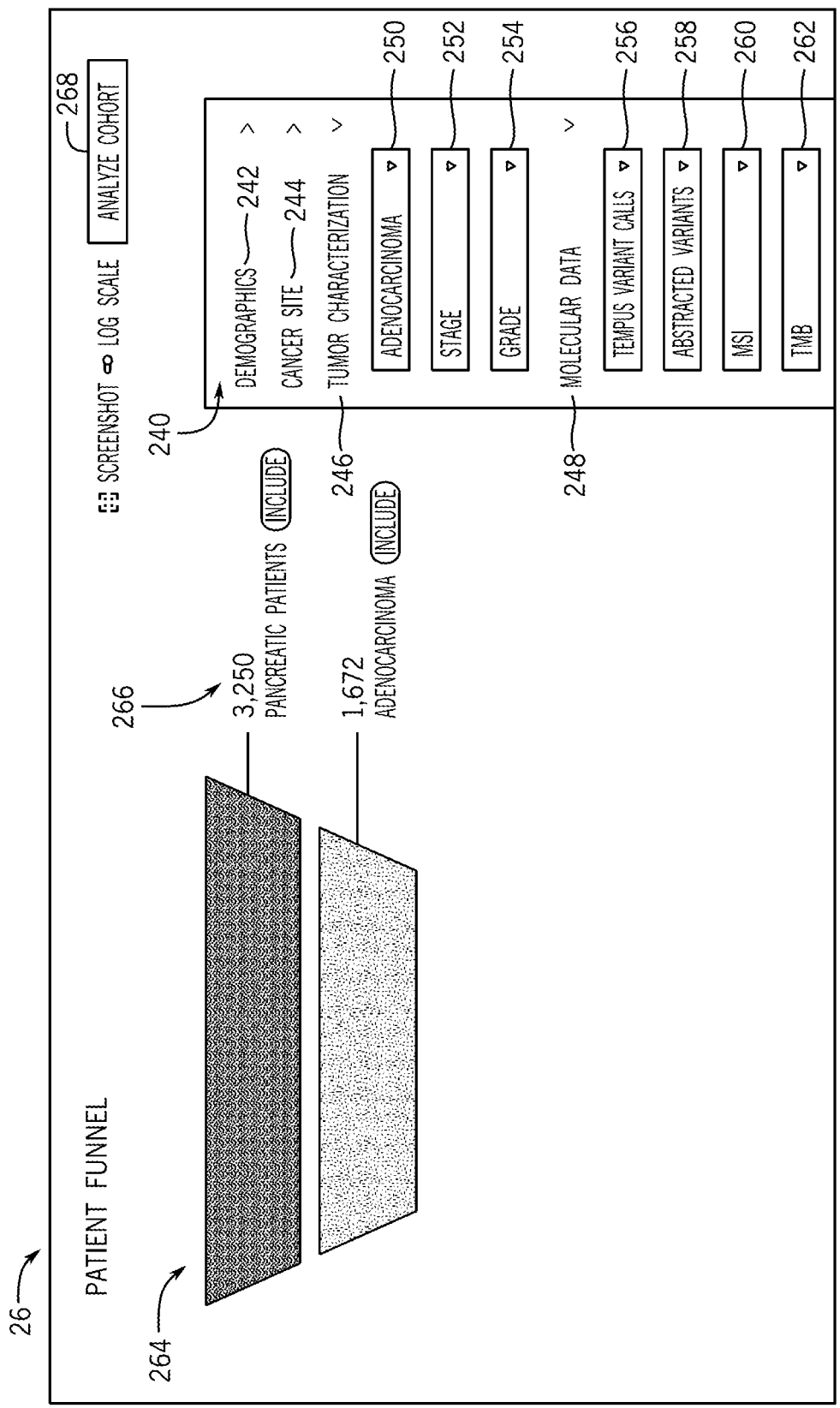
FIG. 5 is another example of a cohort funnel & population analysis user interface.
Figure 6:
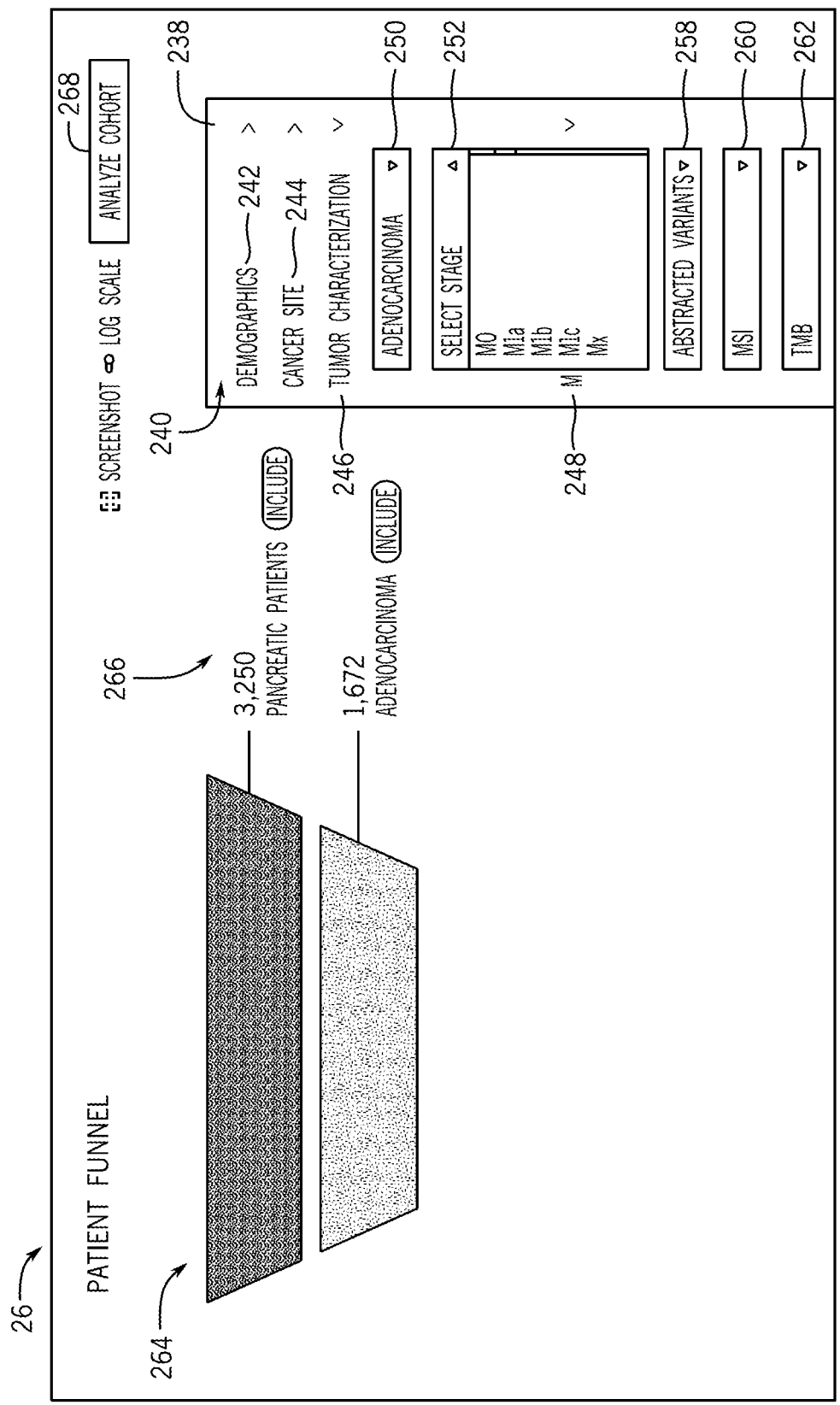
FIG. 6 is another example of a cohort funnel & population analysis user interface.
Figure 7:
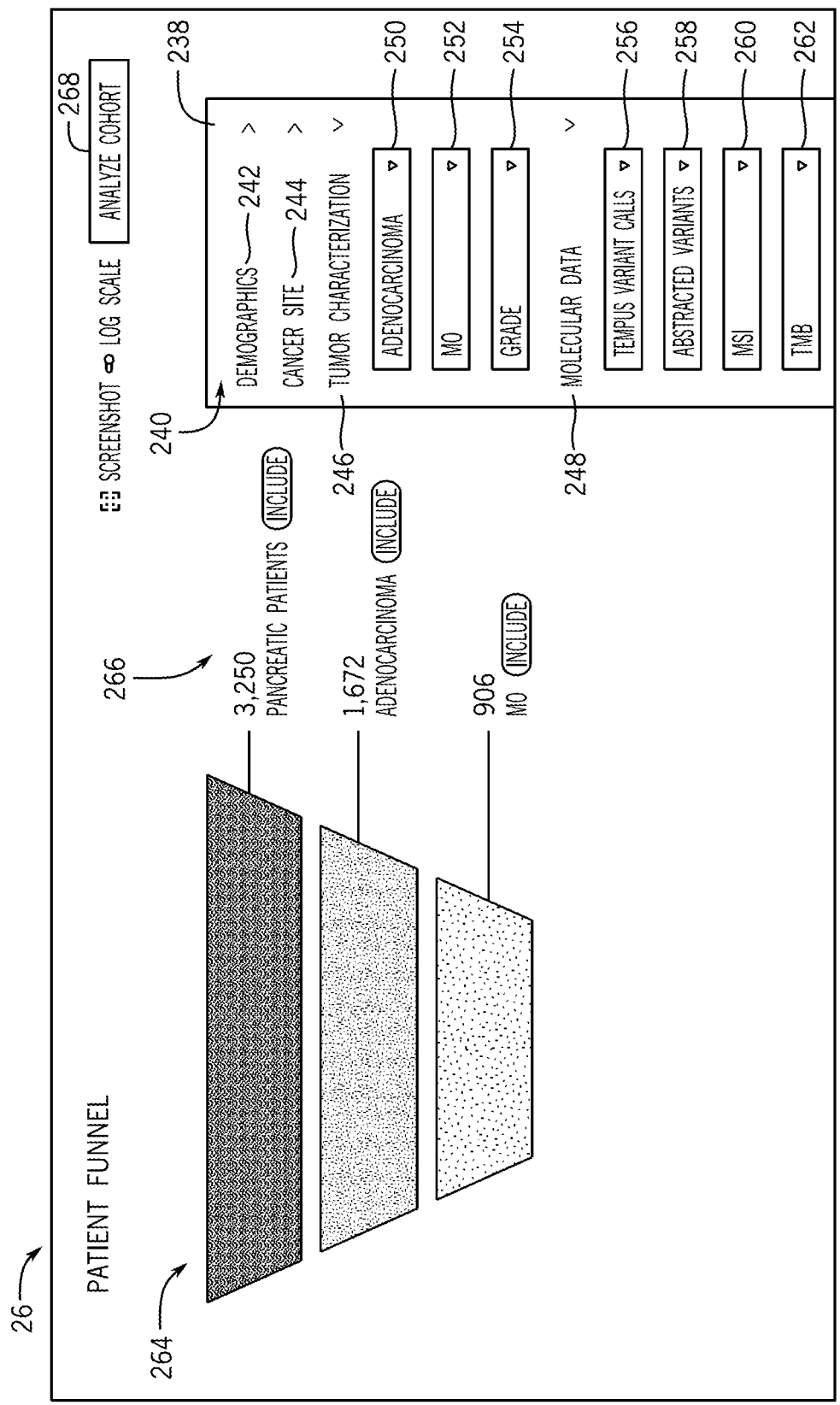
FIG. 7 is another example of a cohort funnel & population analysis user interface.
Figure 8:
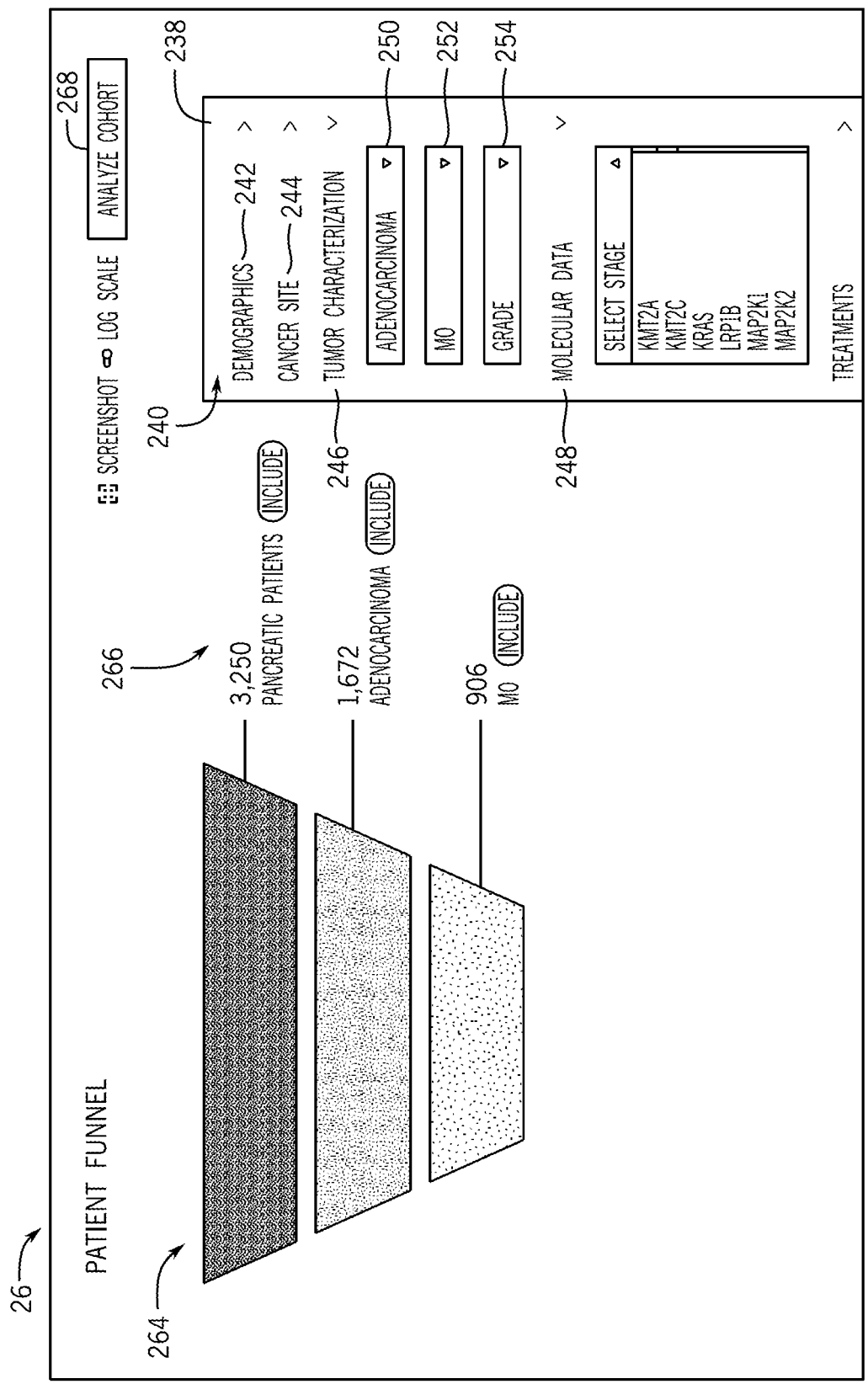
FIG. 8 is another example of a cohort funnel & population analysis user interface.
Figure 9:
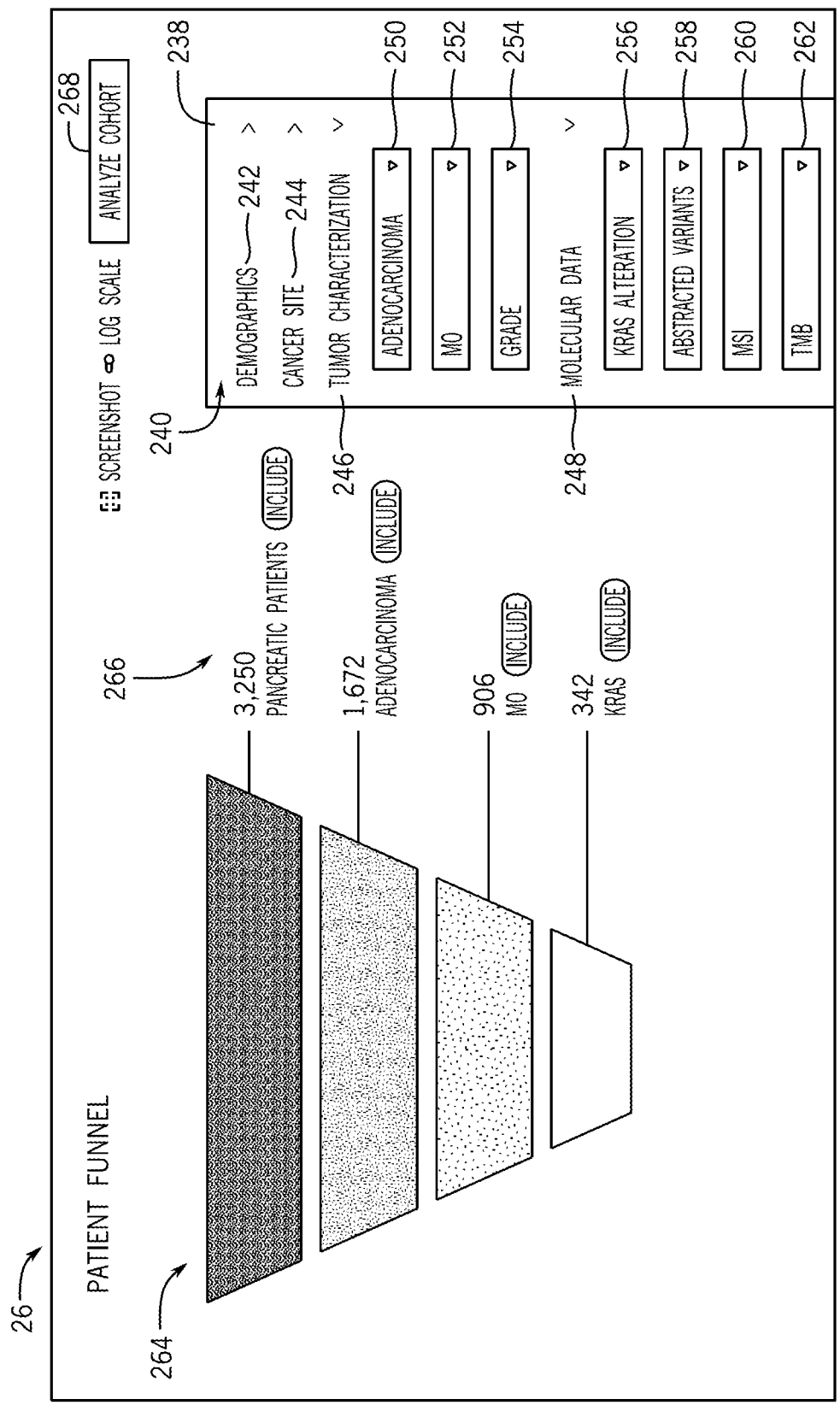
FIG. 9 is another example of a cohort funnel & population analysis user interface.

With reference to the accompanying figures, and particularly with reference to FIG. 1, a system 10 for predicting and analyzing patient cohort response, progression, and survival may include a back end layer 12 that includes a patient data store 14 accessible by a patient cohort selector module 16 in communication with a patient cohort timeline data storage 18. The patient cohort selector module 16 interacts with a front end layer 20 that includes an interactive analysis portal 22 that may be implemented, in one instance, via a web browser to allow for on-demand filtering and analysis of the data store 14.

The interactive analysis portal 22 may include a plurality of user interfaces including an interactive cohort selection filtering interface 24 that, as discussed in greater detail below, permits a user to query and filter elements of the data store 14. As discussed in greater detail below, the portal 22 also may include a cohort funnel and population analysis interface 26, a patient timeline analysis user interface 28, a patient survival analysis user interface 30, and a patient event likelihood analysis user interface 32. The portal 22 further may include a patient next analysis user interface 34 and one or more patient future analysis user interfaces 36.

Returning to FIG. 1, the back end layer 12 also may include a distributed computing and modeling layer 38 that receives data from the patient cohort timeline data storage 18 to provide inputs to a plurality of modules, including, a time to event modeling module 40 that powers the patient survival analysis user interface 30, an event likelihood module 42 that calculates the likelihood of one or more events received at the patient event likelihood analysis user interface 32 for subsequent display in that user interface, a next event modeling module 44 that generates models of one or more next events for subsequent display at the patient next event analysis user interface 34, and one or more future modeling modules 46 that generate one or more future models for subsequent display at the one or more patient future analysis user interfaces 36.

The patient data store 14 may be a pre-existing dataset that includes patient clinical history, such as demographics, comorbidities, diagnoses and recurrences, medications, surgeries, and other treatments along with their response and adverse effects details. The Patient Data Store may also include patient genetic/molecular sequencing and genetic mutation details relating to the patient, as well as organoid modeling results. In one aspect, these datasets may be generated from one or more sources. For example, institutions implementing the system may be able to draw from all of their records; for example, all records from all doctors and/or patients connected with the institution may be available to the institutions agents, physicians, research, or other authorized members. Similarly, doctors may be able to draw from all of their records; for example, records for all of their patients. Alternatively, certain system users may be able to buy or license aspect to the datasets, such as when those users do not have immediate access to a sufficiently robust dataset, when those users are looking for even more records, and/or when those users are looking for specific data types, such as data reflecting patients having certain primary cancers, metastases by origin site and/or diagnosis site, recurrences by origin, metastases, or diagnosis sites, etc.

Features and Feature Modules

A patient data store may include one or more feature modules which may comprise a collection of features available for every patient in the system 10. These features may be used to generate and model the artificial intelligence classifiers in the system 10. While feature scope across all patients is informationally dense, a patient's feature set may be sparsely populated across the entirety of the collective feature scope of all features across all patients. For example, the feature scope across all patients may expand into the tens of thousands of features while a patient's unique feature set may only include a subset of hundreds or thousands of the collective feature scope based upon the records available for that patient.

Feature collections may include a diverse set of fields available within patient health records. Clinical information may be based upon fields which have been entered into an electronic medical record (EMR) or an electronic health record (EHR) by a physician, nurse, or other medical professional or representative. Other clinical information may be curated from other sources, such as molecular fields from genetic sequencing reports. Sequencing may include next-generation sequencing (NGS) and may be long-read, short-read, or other forms of sequencing a patient's somatic and/or normal genome. A comprehensive collection of features in additional feature modules may combine a variety of features together across varying fields of medicine which may include diagnoses, responses to treatment regimens, genetic profiles, clinical and phenotypic characteristics, and/ or other medical, geographic, demographic, clinical, molecular, or genetic features. For example, a subset of features may comprise molecular data features, such as features derived from an RNA feature module or a DNA feature module sequencing.

Another subset of features, imaging features from imaging feature module, may comprise features identified through review of a specimen through pathologist review, such as a review of stained H&E or IHC slides. As another example, a subset of features may comprise derivative features obtained from the analysis of the individual and combined results of such feature sets. Features derived from DNA and RNA sequencing may include genetic variants from variant science module which are present in the sequenced tissue. Further analysis of the genetic variants may include additional steps such as identifying single or multiple nucleotide polymorphisms, identifying whether a variation is an insertion or deletion event, identifying loss or gain of function, identifying fusions, calculating copy number variation, calculating microsatellite instability, calculating tumor mutational burden, or other structural variations within the DNA and RNA. Analysis of slides for H&E staining or IHC staining may reveal features such as tumor infiltration, programmed death-ligand 1 (PD-L1) status, human leukocyte antigen (HLA) status, or other immunology features.

Features derived from structured, curated, or electronic medical or health records may include clinical features such as diagnosis, symptoms, therapies, outcomes, patient demographics such as patient name, date of birth, gender, ethnicity, date of death, address, smoking status, diagnosis dates for cancer, illness, disease, diabetes, depression, other physical or mental maladies, personal medical history, family medical history, clinical diagnoses such as date of initial diagnosis, date of metastatic diagnosis, cancer staging, tumor characterization, tissue of origin, treatments and outcomes such as line of therapy, therapy groups, clinical trials, medications prescribed or taken, surgeries, radiotherapy, imaging, adverse effects, associated outcomes, genetic testing and laboratory information such as performance scores, lab tests, pathology results, prognostic indicators, date of genetic testing, testing provider used, testing method used, such as genetic sequencing method or gene panel, gene results, such as included genes, variants, expression levels/ statuses, or corresponding dates to any of the above.

Features may be derived from information from additional medical or research based Omics fields including proteome, transcriptome, epigenome, metabolome, microbiome, and other multi-omic fields. Features derived from an organoid modeling lab may include the DNA and RNA sequencing information germane to each organoid and results from treatments applied to those organoids. Features derived from imaging data may further include reports associated with a stained slide, size of tumor, tumor size differentials over time including treatments during the period of change, as well as machine learning approaches for classifying PDL1 status, HLA status, or other characteristics from imaging data. Other features may include the additional derivative features sets from other machine learning approaches based at least in part on combinations of any new features and/or those listed above. For example, imaging results may need to be combined with MSI calculations derived from RNA expressions to determine additional further imaging features. In another example a machine learning model may generate a likelihood that a patient's cancer will metastasize to a particular organ or a patient's future probability of metastasis to yet another organ in the body. Other features that may be extracted from medical information may also be used. There are many thousands of features, and the above listing of types of features are merely representative and should not be construed as a complete listing of features.

An alteration module may be one or more microservices, servers, scripts, or other executable algorithms which generate alteration features associated with de-identified patient features from the feature collection. Alterations modules may retrieve inputs from the feature collection and may provide alterations for storage. Exemplary alterations modules may include one or more of the following alterations as a collection of alteration modules. A SNP (single-nucleotide polymorphism) module may identify a substitution of a single nucleotide that occurs at a specific position in the genome, where each variation is present to some appreciable degree within a population (e.g. >1%). For example, at a specific base position, or loci, in the human genome, the C nucleotide may appear in most individuals, but in a minority of individuals, the position is occupied by an A. This means that there is a SNP at this specific position and the two possible nucleotide variations, C or A, are said to be alleles for this position. SNPs underline differences in our susceptibility to a wide range of diseases (e.g. —sickle-cell anemia, β-thalassemia and cystic fibrosis result from SNPs). The severity of illness and the way the body responds to treatments are also manifestations of genetic variations. For example, a single-base mutation in the APOE (apolipoprotein E) gene is associated with a lower risk for Alzheimer's disease. A single-nucleotide variant (SNV) is a variation in a single nucleotide without any limitations of frequency and may arise in somatic cells. A somatic single-nucleotide variation (e.g., caused by cancer) may also be called a single-nucleotide alteration. An MNP (Multiple-nucleotide polymorphisms) module may identify the substitution of consecutive nucleotides at a specific position in the genome. An InDels module may identify an insertion or deletion of bases in the genome of an organism classified among small genetic variations. While usually measuring from 1 to 10 000 base pairs in length, a microindel is defined as an indel that results in a net change of 1 to 50 nucleotides. Indels can be contrasted with a SNP or point mutation. An indel inserts and deletes nucleotides from a sequence, while a point mutation is a form of substitution that replaces one of the nucleotides without changing the overall number in the DNA. Indels, being either insertions, or deletions, can be used as genetic markers in natural populations, especially in phylogenetic studies. Indel frequency tends to be markedly lower than that of single nucleotide polymorphisms (SNP), except near highly repetitive regions, including homopolymers and microsatellites. An MSI (microsatellite instability) module may identify genetic hypermutability (predisposition to mutation) that results from impaired DNA mismatch repair (MMR). The presence of MSI represents phenotypic evidence that MMR is not functioning normally. MMR corrects errors that spontaneously occur during DNA replication, such as single base mismatches or short insertions and deletions. The proteins involved in MMR correct polymerase errors by forming a complex that binds to the mismatched section of DNA, excises the error, and inserts the correct sequence in its place. Cells with abnormally functioning MMR are unable to correct errors that occur during DNA replication and consequently accumulate errors. This causes the creation of novel microsatellite fragments. Polymerase chain reaction-based assays can reveal these novel microsatellites and provide evidence for the presence of MSI. Microsatellites are repeated sequences of DNA. These sequences can be made of repeating units of one to six base pairs in length. Although the length of these microsatellites is highly variable from person to person and contributes to the individual DNA "fingerprint", each individual has microsatellites of a set length. The most common microsatellite in humans is a dinucleotide repeat of the nucleotides C and A, which occurs tens of thousands of times across the genome. Microsatellites are also known as simple sequence repeats (SSRs). A TMB (tumor mutational burden) module may identify a measurement of mutations carried by tumor cells and is a predictive biomarker being studied to evaluate its association with response to Immuno-Oncology (I-O) therapy. Tumor cells with high TMB may have more neoantigens, with an associated increase in cancer-fighting T cells in the tumor microenvironment and periphery. These neoantigens can be recognized by T cells, inciting an anti-tumor response. TMB has emerged more recently as a quantitative marker that can help predict potential responses to immunotherapies across different cancers, including melanoma, lung cancer and bladder cancer. TMB is defined as the total number of mutations per coding area of a tumor genome. Importantly, TMB is consistently reproducible. It provides a quantitative measure that can be used to better inform treatment decisions, such as selection of targeted or immunotherapies or enrollment in clinical trials. A CNV (copy number variation) module may identify deviations from the normal genome and any subsequent implications from analyzing genes, variants, alleles, or sequences of nucleotides. CNV are the phenomenon in which structural variations may occur in sections of nucleotides, or base pairs, that include repetitions, deletions, or inversions. A Fusions module may identify hybrid genes formed from two previously separate genes. It can occur as a result of: translocation, interstitial deletion, or chromosomal inversion. Gene fusion plays an important role in tumorgenesis. Fusion genes can contribute to tumor formation because fusion genes can produce much more active abnormal protein than non-fusion genes. Often, fusion genes are oncogenes that cause cancer; these include BCR-ABL, TEL-AML1 (ALL with t(12; 21)), AML1-ETO (M2 AML with t(8; 21)), and TMPRSS2-ERG with an interstitial deletion on chromosome 21, often occurring in prostate cancer. In the case of TMPRSS2-ERG, by disrupting androgen receptor (AR) signaling and inhibiting AR expression by oncogenic ETS transcription factor, the fusion product regulates the prostate cancer. Most fusion genes are found from hematological cancers, sarcomas, and prostate cancer. BCAM-AKT2 is a fusion gene that is specific and unique to high-grade serous ovarian cancer. Oncogenic fusion genes may lead to a gene product with a new or different function from the two fusion partners. Alternatively, a proto-oncogene is fused to a strong promoter, and thereby the oncogenic function is set to function by an upregulation caused by the strong promoter of the upstream fusion partner. The latter is common in lymphomas, where oncogenes are juxtaposed to the promoters of the immunoglobulin genes. Oncogenic fusion transcripts may also be caused by trans-splicing or read-through events. Since chromosomal translocations play such a significant role in neoplasia, a specialized database of chromosomal aberrations and gene fusions in cancer has been created. This database is called Mitelman Database of Chromosome Aberrations and Gene Fusions in Cancer. An IHC (Immunohistochemistry) module may identify antigens (proteins) in cells of a tissue section by exploiting the principle of antibodies binding specifically to antigens in biological tissues. IHC staining is widely used in the diagnosis of abnormal cells such as those found in cancerous tumors. Specific molecular markers are characteristic of particular cellular events such as proliferation or cell death (apoptosis). IHC is also widely used in basic research to understand the distribution and localization of biomarkers and differentially expressed proteins in different parts of a biological tissue. Visualising an antibody-antigen interaction can be accomplished in a number of ways. In the most common instance, an antibody is conjugated to an enzyme, such as peroxidase, that can catalyse a color-producing reaction in immunoperoxidase staining. Alternatively, the antibody can also be tagged to a fluorophore, such as fluorescein or rhodamine in immunofluorescence. Approximations from RNA expression data, H&E slide imaging data, or other data may be generated. A Therapies module may identify differences in cancer cells (or other cells near them) that help them grow and thrive and drugs that "target" these differences. Treatment with these drugs is called targeted therapy. For example, many targeted drugs go after the cancer cells' inner 'programming' that makes them different from normal, healthy cells, while leaving most healthy cells alone. Targeted drugs may block or turn off chemical signals that tell the cancer cell to grow and divide; change proteins within the cancer cells so the cells die; stop making new blood vessels to feed the cancer cells; trigger your immune system to kill the cancer cells; or carry toxins to the cancer cells to kill them, but not normal cells. Some targeted drugs are more "targeted" than others. Some might target only a single change in cancer cells, while others can affect several different changes. Others boost the way your body fights the cancer cells. This can affect where these drugs work and what side effects they cause. Matching targeted therapies may include identifying the therapy targets in the patients and satisfying any other inclusion or exclusion criteria. A VUS (variant of unknown significance) module may identify variants which are called but cannot be classify as pathogenic or benign at the time of calling. VUS may be catalogued from publications regarding a VUS to identify if they may be classified as benign or pathogenic. A Trial module may identify and test hypotheses for treating cancers having specific characteristics by matching features of a patient to clinical trials. These trials have inclusion and exclusion criteria that must be matched to enroll which may be ingested and structured from publications, trial reports, or other documentation. An Amplifications module may identify genes which increase in count disproportionately to other genes. Amplifications may cause a gene having the increased count to go dormant, become overactive, or operate in another unexpected fashion. Amplifications may be detected at a gene level, variant level, RNA transcript or expression level, or even a protein level. Detections may be performed across all the different detection mechanisms or levels and validated against one another. An Isoforms module may identify alternative splicing (AS), the biological process in which more than one mRNA (isoforms) is generated from the transcript of a same gene through different combinations of exons and introns. It is estimated by large-scale genomics studies that 30-60% of mammalian genes are alternatively spliced. The possible patterns of alternative splicing for a gene can be very complicated and the complexity increases rapidly as number of introns in a gene increases. In silico alternative splicing prediction may find large insertions or deletions within a set of mRNA sharing a large portion of aligned sequences by identifying genomic loci through searches of mRNA sequences against genomic sequences, extracting sequences for genomic loci and extending the sequences at both ends up to 20 kb, searching the genomic sequences (repeat sequences have been masked), extracting splicing pairs (two boundaries of alignment gap with GT-AG consensus or with more than two expressed sequence tags aligned at both ends of the gap), assembling splicing pairs according to their coordinates, determining gene boundaries (splicing pair predictions are generated to this point), generating predicted gene structures by aligning mRNA sequences to genomic templates, and comparing splicing pair predictions and gene structure predictions to find alternative spliced isoforms. A Pathways module may identify defects in DNA repair pathways which enable cancer cells to accumulate genomic alterations that contribute to their aggressive phenotype. Cancerous tumors rely on residual DNA repair capacities to survive the damage induced by genotoxic stress which leads to isolated DNA repair pathways being inactivated in cancer cells. DNA repair pathways are generally thought of as mutually exclusive mechanistic units handling different types of lesions in distinct cell cycle phases. Recent preclinical studies, however, provide strong evidence that multifunctional DNA repair hubs, which are involved in multiple conventional DNA repair pathways, are frequently altered in cancer. Identifying pathways which may be affected may lead to important patient treatment considerations. A Raw Counts module may identify a count of the variants that are detected from the sequencing data. For DNA, this may be the number of reads from sequencing which correspond to a particular variant in a gene. For RNA, this may be the gene expression counts or the transcriptome counts from sequencing.

Structural variant classification may include evaluating features from the feature collection, alterations from the alteration module, and other classifications from within itself from one or more classification modules. Structural variant classification may provide classifications to a stored classifications storage. An exemplary classification module may include a classification of a CNV as "Reportable" may mean that the CNV has been identified in one or more reference databases as influencing the tumor cancer characterization, disease state, or pharmacogenomics, "Not Reportable" may mean that the CNV has not been identified as such, and "Conflicting Evidence" may mean that the CNV has both evidence suggesting "Reportable" and "Not Reportable." Furthermore, a classification of therapeutic relevance is similarly ascertained from any reference datasets mention of a therapy which may be impacted by the detection (or non-detection) of the CNV. Other classifications may include applications of machine learning algorithms, neural networks, regression techniques, graphing techniques, inductive reasoning approaches, or other artificial intelligence evaluations within modules. A classifier for clinical trials may include evaluation of variants identified from the alteration module which have been identified as significant or reportable, evaluation of all clinical trials available to identify inclusion and exclusion criteria, mapping the patient's variants and other information to the inclusion and exclusion criteria, and classifying clinical trials as applicable to the patient or as not applicable to the patient. Similar classifications may be performed for therapies, loss-of-function, gain-of-function, diagnosis, microsatellite instability, tumor mutational burden, indels, SNP, MNP, fusions, and other alterations which may be classified based upon the results of the alteration modules.

Each of the feature collection, alteration module(s), structural variant and feature store may be communicatively coupled to a data bus to transfer data between each module for processing and/or storage. In another embodiment, each of the feature collection, alteration module(s), structural variant and feature store may be communicatively coupled to each other for independent communication without sharing the data bus.

In addition to the above features and enumerated modules, feature modules may further include one or more of the following modules within their respective modules as a sub-module or as a standalone module.

Germline/somatic DNA feature module may comprise a feature collection associated with the DNA-derived information of a patient or a patient's tumor. These features may include raw sequencing results, such as those stored in FASTQ, BAM, VCF, or other sequencing file types known in the art; genes; mutations; variant calls; and variant characterizations. Genomic information from a patient's normal sample may be stored as germline and genomic information from a patient's tumor sample may be stored as somatic.

An RNA feature module may comprise a feature collection associated with the RNA-derived information of a patient, such as transcriptome information. These features may include raw sequencing results, transcriptome expressions, genes, mutations, variant calls, and variant characterizations.

A metadata module may comprise a feature collection associated with the human genome, protein structures and their effects, such as changes in energy stability based on a protein structure.

A clinical module may comprise a feature collection associated with information derived from clinical records of a patient and records from family members of the patient. These may be abstracted from unstructured clinical documents, EMR, EHR, or other sources of patient history. Information may include patient symptoms, diagnosis, treatments, medications, therapies, hospice, responses to treatments, laboratory testing results, medical history, geographic locations of each, demographics, or other features of the patient which may be found in the patient's medical record. Information about treatments, medications, therapies, and the like may be ingested as a recommendation or prescription and/or as a confirmation that such treatments, medications, therapies, and the like were administered or taken.

An imaging module may comprise a feature collection associated with information derived from imaging records of a patient. Imaging records may include H&E slides, IHC slides, radiology images, and other medical imaging which may be ordered by a physician during the course of diagnosis and treatment of various illnesses and diseases. These features may include TMB, ploidy, purity, nuclear-cytoplasmic ratio, large nuclei, cell state alterations, biological pathway activations, hormone receptor alterations, immune cell infiltration, immune biomarkers of MMR, MSI, PDL1, CD3, FOXP3, HRD, PTEN, PIK3CA; collagen or stroma composition, appearance, density, or characteristics; tumor budding, size, aggressiveness, metastasis, immune state, chromatin morphology; and other characteristics of cells, tissues, or tumors for prognostic predictions.

An epigenome module, such as epigenome module from Omics, may comprise a feature collection associated with information derived from DNA modifications which are not changes to the DNA sequence and regulate the gene expression. These modifications are frequently the result of environmental factors based on what the patient may breathe, eat, or drink. These features may include DNA methylation, histone modification, or other factors which deactivate a gene or cause alterations to gene function without altering the sequence of nucleotides in the gene.

A microbiome module, such as microbiome module from Omics, may comprise a feature collection associated with information derived from the viruses and bacteria of a patient. These features may include viral infections which may affect treatment and diagnosis of certain illnesses as well as the bacteria present in the patient's gastrointestinal tract which may affect the efficacy of medicines ingested by the patient.

A proteome module, such as proteome module from Omics, may comprise a feature collection associated with information derived from the proteins produced in the patient. These features may include protein composition, structure, and activity; when and where proteins are expressed; rates of protein production, degradation, and steady-state abundance; how proteins are modified, for example, post-translational modifications such as phosphorylation; the movement of proteins between subcellular compartments; the involvement of proteins in metabolic pathways; how proteins interact with one another; or modifications to the protein after translation from the RNA such as phosphorylation, ubiquitination, methylation, acetylation, glycosylation, oxidation, or nitrosylation.

Additional Omics module(s) may also be included in Omics, such as a feature collection associated with all the different field of omics, including: cognitive genomics, a collection of features comprising the study of the changes in cognitive processes associated with genetic profiles; comparative genomics, a collection of features comprising the study of the relationship of genome structure and function across different biological species or strains; functional genomics, a collection of features comprising the study of gene and protein functions and interactions including transcriptomics; interactomics, a collection of features comprising the study relating to large-scale analyses of gene-gene, protein-protein, or protein-ligand interactions; metagenomics, a collection of features comprising the study of metagenomes such as genetic material recovered directly from environmental samples; neurogenomics, a collection of features comprising the study of genetic influences on the development and function of the nervous system; pangenomics, a collection of features comprising the study of the entire collection of gene families found within a given species; personal genomics, a collection of features comprising the study of genomics concerned with the sequencing and analysis of the genome of an individual such that once the genotypes are known, the individual's genotype can be compared with the published literature to determine likelihood of trait expression and disease risk to enhance personalized medicine suggestions; epigenomics, a collection of features comprising the study of supporting the structure of genome, including protein and RNA binders, alternative DNA structures, and chemical modifications on DNA; nucleomics, a collection of features comprising the study of the complete set of genomic components which form the cell nucleus as a complex, dynamic biological system; lipidomics, a collection of features comprising the study of cellular lipids, including the modifications made to any particular set of lipids produced by a patient; proteomics, a collection of features comprising the study of proteins, including the modifications made to any particular set of proteins produced by a patient; immunoproteomics, a collection of features comprising the study of large sets of proteins involved in the immune response; nutriproteomics, a collection of features comprising the study of identifying molecular targets of nutritive and non-nutritive components of the diet including the use of proteomics mass spectrometry data for protein expression studies; proteogenomics, a collection of features comprising the study of biological research at the intersection of proteomics and genomics including data which identifies gene annotations; structural genomics, a collection of features comprising the study of 3-dimensional structure of every protein encoded by a given genome using a combination of modeling approaches; glycomics, a collection of features comprising the study of sugars and carbohydrates and their effects in the patient; foodomics, a collection of features comprising the study of the intersection between the food and nutrition domains through the application and integration of technologies to improve consumer's well-being, health, and knowledge; transcriptomics, a collection of features comprising the study of RNA molecules, including mRNA, rRNA, tRNA, and other non-coding RNA, produced in cells; metabolomics, a collection of features comprising the study of chemical processes involving metabolites, or unique chemical fingerprints that specific cellular processes leave behind, and their small-molecule metabolite profiles; metabonomics, a collection of features comprising the study of the quantitative measurement of the dynamic multiparametric metabolic response of cells to pathophysiological stimuli or genetic modification; nutrigenetics, a collection of features comprising the study of genetic variations on the interaction between diet and health with implications to susceptible subgroups; cognitive genomics, a collection of features comprising the study of the changes in cognitive processes associated with genetic profiles; pharmacogenomics, a collection of features comprising the study of the effect of the sum of variations within the human genome on drugs; pharmacomicrobiomics, a collection of features comprising the study of the effect of variations within the human microbiome on drugs; toxicogenomics, a collection of features comprising the study of gene and protein activity within particular cell or tissue of an organism in response to toxic substances; mitointeractome, a collection of features comprising the study of the process by which the mitochondria proteins interact; psychogenomics, a collection of features comprising the study of the process of applying the powerful tools of genomics and proteomics to achieve a better understanding of the biological substrates of normal behavior and of diseases of the brain that manifest themselves as behavioral abnormalities, including applying psychogenomics to the study of drug addiction to develop more effective treatments for these disorders as well as objective diagnostic tools, preventive measures, and cures; stem cell genomics, a collection of features comprising the study of stem cell biology to establish stem cells as a model system for understanding human biology and disease states; connectomics, a collection of features comprising the study of the neural connections in the brain; microbiomics, a collection of features comprising the study of the genomes of the communities of microorganisms that live in the digestive tract; cellomics, a collection of features comprising the study of the quantitative cell analysis and study using bioimaging methods and bioinformatics; tomomics, a collection of features comprising the study of tomography and omics methods to understand tissue or cell biochemistry at high spatial resolution from imaging mass spectrometry data; ethomics, a collection of features comprising the study of high-throughput machine measurement of patient behavior; and videomics, a collection of features comprising the study of a video analysis paradigm inspired by genomics principles, where a continuous image sequence, or video, can be interpreted as the capture of a single image evolving through time of mutations revealing patient insights.

A feature set for DNA related (molecular) features may include a proprietary calculation of the maximum effect a gene may have from sequencing results for the following genes: ABCB1, ACTA2, ACTC1, ALK, ALK, ALK, ALK, AMER1, APC, APC, APC, APOB, APOB, AR, ARHGAP35, ARID1A, ARID1B, ARID2, ASXL1, ATM, ATM, ATM, ATP7B, ATR, ATRX, AXIN2, BACH1, BCL11B, BCLAF1, BCOR, BCORL1, BCR, BMPR1A, BRAF, BRAF, BRAF, BRCA1, BRCA1, BRCA2, BRCA2, BRD4, BRIP1, CACNA1S, CARD11, CASR, CD274, CD274, CDH1, CDH1, CDK12, CDKN2A, CDKN2A, CDKN2A, CEBPA, CEBPA, CFTR, CHD2, CHD4, CHEK2, CIC, COL3A1, CREBBP, CTNNB1, CUX1, DICER1, DOT1L, DPYD, DSC2, DSG2, DSP, DYNC2H1, EGFR, EGFR, EGFR, EGFR, EGFR, EP300, EPCAM, EPHA2, EPHA7, EPHB1, ERBB2, ERBB2, ERBB2, ERBB2, ERBB3, ERBB4, ESR1, ESR1, ETV6, FANCA, FANCA, FANCD2, FANCI, FANCL, FANCM, FAT1, FBN1, FBXW7, FGFR3, FH, FLCN, FLG, FLT1, FLT4, GATA2, GATA3, GATA4, GATA6, GLA, GNAS, GRIN2A, GRM3, HDAC4, HGF, IDHL IKZF1, IRS2, JAK3, KCNH2, KCNQ1, KDMSA, KDMSC, KDM6A, KDR, KEAP1, KEL, KIF1B, KMT2A, KMT2A, KMT2B, KMT2C, KMT2D, KRAS, KRAS, KRAS, LDLR, LMNA, LRP1B, MAP3K1, MED12, MEN1, MET, MET, MKI67, MKI67, MLH1, MSH2, MSH3, MSH6, MSH6, MTOR, MUTYH, MYBPC3, MYCN, MYH11, MYH11, MYH7, MYL2, MYL3, NBN, NCOR1, NCOR2, NF1, NF2, NOTCH1, NOTCH2, NOTCH3, NRG1, NSD1, NTRK1, NTRK3, NUP98, OTC, PALB2, PALLD, PBRM1, PCSK9, PDGFRA, PDGFRB, PGR, PIK3C2B, PIK3CA, PIK3CG, PIK3R1, PIK3R2, PKP2, PLCG2, PML, PMS2, POLD1, POLD1, POLE, POLE, PREX2, PRKAG2, PTCH1, PTEN, PTEN, PTEN, PTEN, PTPN13, PTPRD, RAD51B, RAD51C, RAD51D, RAD52, RAD54L, RANBP2, RB1, RB1, RBM10, RECQL4, RET, RET, RET, RICTOR, RNF43, ROS1, ROS1, ROS1, RPTOR, RUNX1, RUNX1T1, RYR1, RYR2, SCN5A, SDHAF2, SDHB, SDHC, SDHD, SETBP1, SETD2, SH2B3, SLIT2, SLX4, SMAD3, SMAD4, SMAD4, SMARCA4, SOX9, SPEN, STAG2, STK11, STK11, STK11, TAF1, TBX3, TCF7L2, TERT, TET2, TGFBR1, TGFBR2, TGFBR2, TMEM43, TNNI3, TNNT2, TP53, TP53, TP53, TP53, TP53, TPM1, TSC1, TSC1, TSC2, TSC2, VHL, WT1, WT1, XRCC3, and ZFHX3.

A sufficiently robust collection of features may include all of the features disclosed above; however, models and predictions based from the available features may include models which are optimized and trained from a selection of features that are much more limiting than the exhaustive feature set. Such a constrained feature set may include as few as tens to hundreds of features. For example, a model's constrained feature set may include the genomic results of a sequencing of the patient's tumor, derivative features based upon the genomic results, the patient's tumor origin, the patient's age at diagnosis, the patient's gender and race, and symptoms that the patient brought to their physicians attention during a routine checkup.

A feature store may enhance a patient's feature set through the application of machine learning and analytics by selecting from any features, alterations, or calculated output derived from the patient's features or alterations to those features. Such a feature store may generate new features from the original features found in feature module or may identify and store important insights or analysis based upon the features. The selections of features may be based upon an alteration or calculation to be generated, and may include the calculation of single or multiple nucleotide polymorphisms insertion or deletions of the genome, a tumor mutational burden, a microsatellite instability, a copy number variation, a fusion, or other such calculations. An exemplary output of an alteration or calculation generated which may inform future alterations or calculations includes a finding of hypertrophic cardiomyopathy (HCM) and variants in MYH7. Wherein previous classified variants may be identified in the patient's genome which may inform the classification of novel variants or indicate a further risk of disease. An exemplary approach may include the enrichment of variants and their respective classifications to identify a region in MYH7 that is associated with HCM. Any novel variants detected from a patient's sequencing localized to this region would increase the patient's risk for HCM. Features which may be utilized in such an alteration detection include the structure of MYH7 and classification of variants therein. A model which focuses on enrichment may isolate such variants.

Artificial Intelligence Models

Artificial intelligence models referenced herein may be gradient boosting models, random forest models, neural networks (NN), regression models, Naive Bayes models, or machine learning algorithms (MLA). A MLA or a NN may be trained from a training data set. In an exemplary prediction profile, a training data set may include imaging, pathology, clinical, and/or molecular reports and details of a patient, such as those curated from an EHR or genetic sequencing reports. MLAs include supervised algorithms (such as algorithms where the features/classifications in the data set are annotated) using linear regression, logistic regression, decision trees, classification and regression trees, Naïve Bayes, nearest neighbor clustering; unsupervised algorithms (such as algorithms where no features/classification in the data set are annotated) using Apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines. NNs include conditional random fields, convolutional neural networks, attention based neural networks, deep learning, long short term memory networks, or other neural models where the training data set includes a plurality of tumor samples, RNA expression data for each sample, and pathology reports covering imaging data for each sample. While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in patient records, and training the MLA to predict or classify based on new inputs. Artificial NNs are efficient computing models which have shown their strengths in solving hard problems in artificial intelligence. They have also been shown to be universal approximators (can represent a wide variety of functions when given appropriate parameters). Some MLA may identify features of importance and identify a coefficient, or weight, to them. The coefficient may be multiplied with the occurrence frequency of the feature to generate a score, and once the scores of one or more features exceed a threshold, certain classifications may be predicted by the MLA. A coefficient schema may be combined with a rule based schema to generate more complicated predictions, such as predictions based upon multiple features. For example, ten key features may be identified across different classifications. A list of coefficients may exist for the key features, and a rule set may exist for the classification. A rule set may be based upon the number of occurrences of the feature, the scaled weights of the features, or other qualitative and quantitative assessments of features encoded in logic known to those of ordinary skill in the art. In other MLA, features may be organized in a binary tree structure. For example, key features which distinguish between the most classifications may exist as the root of the binary tree and each subsequent branch in the tree until a classification may be awarded based upon reaching a terminal node of the tree. For example, a binary tree may have a root node which tests for a first feature. The occurrence or non-occurrence of this feature must exist (the binary decision), and the logic may traverse the branch which is true for the item being classified. Additional rules may be based upon thresholds, ranges, or other qualitative and quantitative tests. While supervised methods are useful when the training dataset has many known values or annotations, the nature of EMR/EHR documents is that there may not be many annotations provided. When exploring large amounts of unlabeled data, unsupervised methods are useful for binning/bucketing instances in the data set. A single instance of the above models, or two or more such instances in combination, may constitute a model for the purposes of models, artificial intelligence, neural networks, or machine learning algorithms, herein.

A set of transformation steps may be performed to convert the data from the Patient Data Store into a format suitable for analysis. Various modern machine learning algorithms may be utilized to train models targeting the prediction of expected survival and/or response for a particular patient population. An exemplary data store 14 is described in further detail in U.S. Provisional Patent Application No. 62/746,997, titled "Data Based Cancer Research and Treatment Systems and Methods," filed Oct. 17, 2018; U.S. patent application Ser. No. 16/289,027, titled "Mobile Supplementation, Extraction, and Analysis of Health Records" and filed Feb. 28, 2019, and issued Aug. 27, 2019, as U.S. Pat. No. 10,395,772; and PCT International Application No. PCT/US19/56713 filed Oct. 17, 2019 and titled "Data Based Cancer Research and Treatment Systems and Methods," each of which is incorporated herein by reference in its entirety.

The system may include a data delivery pipeline to transmit clinical and molecular de-identified records in bulk. The system also may include separate storage for de-identified and identified data to maintain data privacy and compliance with applicable laws or guidelines, such as the Health Insurance Portability and Accountability Act.

The raw input data and/or any transformed, normalized, and/or predictive data may be stored in one or more relational databases for further access by the system in order to carry out one or more comparative or analytical functions, as described in greater detail herein. The data model used to construct the relational database(s) may be used to store, organize, display, and/or interpret a significant amount and variety of data, e.g., dozens of tables that comprise hundreds of different columns. Unlike standard data models such as OMOP or QDM, the data model may generate unique linkages within a table or across tables to directly relate various clinical attributes, thereby making complex clinical attributes easier to ingest, interpret and analyze.

Once the relevant data has been received, transformed, and manipulated, as discussed above, the system may include a plurality of modules in order to generate the desired dynamic user interfaces, as discussed above with regard to the system diagram of FIG. 1.

Patient Cohort Filtering User Interface

Turning to FIG. 2, a first embodiment of a patient cohort selection filtering interface 24 may be provided as a side pane 200 provided along a height (or, alternatively, a length) of a display screen, through which attribute criteria 202 (such as clinical, molecular, demographic etc.) can be specified by the user, defining a patient population of interest for further analysis. The side pane 200 may be hidden or expanded by selecting it, dragging it, double-clicking it, etc.

Additionally, or alternatively, the system may recognize one or more attributes defined for tumor data stored by the system, where those attributes may be, for example, genotypic, phenotypic, genealogical, or demographic. The various selectable attribute criteria may reflect patient-related metadata stored in the patient data store 14, where exemplary metadata may include, for instance: Project Name (which may reflect a database storing a list of patients) 204, Gender 206, Race 208; Cancer, Cancer Site 210, Cancer Name 212; Metastasis, Cancer Name 214; Tumor Site 216 (which may reflect where the tumor was located), Stage 218 (such as I, II, III, IV, and unknown), M Stage 220 (such as m0, m1, m2, m3, and unknown); Medication (such as by Name 222 or Ingredient 224); Sequencing 226 (such as gene name or variant), MSI (Microsatellite Instability) status 228, TMB (Tumor Mutational Burden) status (not shown); Procedure 230 (such as, by Name); or Death (such as, by Event Name 232 or Cause of Death 234).

The system also may permit a user to filter patient data according to any of the criteria listed herein including those listed under the heading "Features and Feature Modules," and include one or more of the following additional criteria:

institution, demographics, molecular data, assessments, diagnosis site, tumor characterization, treatment, or one or more internal criteria. The institution option may permit a user to filter according to a specific facility. The demographics option may permit a user to sort, for example, by one or more of gender, death status, age at initial diagnosis, or race. The molecular data option may permit a user to filter according to variant calls (for example, when there is molecular data available for the patient, what the particular gene name, mutation, mutation effect, and/or sample type is), abstracted variants (including, for example, gene name and/or sequencing method), MSI status (for example, stable, low, or high), or TMB status (for example, selectable within or outside of a user-defined ranges). Assessments may permit a user to filter according to various system-defined criteria such as smoking status and/or menopausal status. Diagnosis site may permit a user to filter according to primary and/or metastatic sites. Tumor characterization may permit the user to filter according to one or more tumor-related criteria, for example, grade, histology, stage, TNM Classification of Malignant Tumours (TNM) and/or each respective T value, N value, and/or M value. Treatment may permit the user to select from among various treatment-related options, including, for instance, an ingredient, a regimen, a treatment type, etc.

Certain criteria may permit the user to select from a plurality of sub-criteria that may be indicated once the initial criteria is selected. Other criteria may present the user with a binary option, for example, deceased or not. Still other criteria may present the user with slider or range-type options, for example, age at initial diagnosis may presented as a slider with user-selectable lower and upper bounds. Still further, for any of these options, the system may present the user with a radio button or slider to alternate between whether the system should include or exclude patients based on the selected criterion. It should be understood that the examples described herein do not limit the scope of the types of information that may be used as criteria. Any type of medical information capable of being stored in a structured format may be used as a criteria.

In another embodiment, the user interface may include a natural language search style bar to facilitate filter criteria definition for the cohort, for example, in the "Ask Gene" tab 236 of the user interface or via a text input of the filtering interface. In one aspect, an ability to specify a query, either via keyboard-type input or via machine-interpreted dictation, may define one or more of the subsequent layers of a cohort funnel (described in greater detail in the next section). Thus, for example, when employing traditional natural language processing software or techniques, an input of "breast cancer patients" would cause the system to recognize a filter of "cancer_site==breast cancer" and add that as the next layer of filtering. Similarly, the system would recognize an input of "pancreatic patients with adverse reactions to gemcitabine" and translate it into multiple successive layers of filtering, for example, "cancer_site==pancreatic cancer" AND "medication==gemcitabine" AND "adverse reaction==not null."

In a second aspect, the natural language processing may permit a user to use the system to query for general insights directly, thereby both narrowing down a cohort of patients via one or more funnel levels and also causing the system to display an appropriate summary panel in the user interface. Thus, in the situation that the system receives the query "What is the 5 years progression-free survival rate for stage III colorectal cancer patients, after radiotherapy?," it would translate it into a series of filters such as "cancer_site==colorectal" AND "stage==III" AND "treatment==radiotherapy" and then display five-year progression-free survival rates using, for example, the patient survival analysis user interface 30. Similarly, the query "What percentage of female lung cancer patients are post-menopausal at a time of diagnosis?" would translate it into a series of patients such as "gender==female," "cancer_site==lung," and "temporal==at diagnosis," determine how many of the resulting patients had data reflecting a post-menopause situation, and then determine the relevant percentage, for example, displaying the results through one or more statistical summary charts.

Cohort Funnel and Population Analysis User Interface

Turning now to FIGS. 3-9, the cohort funnel and population analysis user interface 26 may be configured to permit a user to conduct analysis of a cohort, for the purpose of identifying key inflection points in the distribution of patients exhibiting each attribute of interest, relative to the distributions in the general patient population or a patient population whose data is stored in the patient data store 14. In one aspect, the filtering and selection of additional patient-related criteria discussed above with regard to FIG. 2 may be used in connection with the cohort funnel and population analysis user interface 26.

In another embodiment, the system may include a selectable button or icon that opens a dialogue box 238 which shows a plurality of selectable tabs, each tab representing the same or similar filtering criteria discussed above (Demographics, Molecular Data, Assessments, Diagnosis Site, Tumor Characterization, and Treatment). Selection of each tab may present the user with the same or similar options for each respective filter as discussed above (for example, selecting "Demographics" may present the user with further options relating to: Gender, Death Status, Age at Initial Diagnosis, or Race). The user then may select one or more options, select "next," and then select whether it is an inclusion or exclusion filter, and the corresponding selection is added to the funnel (discussed in greater detail below), with an icon moving to be below a next successively narrower portion of the funnel.

Additionally, or alternatively, looking at the cohort, or set of patients in a database, the system permits filtering by a plurality of clinical and molecular factors via a menu 240. For example, and with regard to clinical factors, the system may include filters based on patient demographics 242, cancer site 244, tumor characterization 246, or molecular data 248 which further may include their own subsets of filterable options 242, such as histology 250, stage 252, and/or grade-based options 254 (see FIG. 4) for tumor characterization. With regard to molecular factors, the system may permit filtering according to variant calls 256, abstracted variants 258, MSI 260, and/or TMB 262.

Although the examples discussed herein provide analysis with regard to various cancer types, in other embodiments, it will be appreciated that the system may be used to indicate filtered display of other disease conditions, and it should be understood that the selection items will differ in those situations to focus particularly on the relevant conditions for the other disease.

The cohort funnel and population analysis user interface 26 visually may depict the number of patients in the data set, either all at once or progressively upon receiving a user's selection of multiple filtering criteria. In one aspect, the display of patient frequencies by filter attribute may be provided using an interactive funnel chart 264. As seen in FIGS. 3-9, with each selection, the user interface 26 updates to illustrate the reduction in results matching the filter criteria; for example, as more filter criteria are added, fewer patients matching all of the selected criteria exist, upon receiving each of a user's filtering factors.

The above filtering can be performed upon receiving each user selection of a filter criterion, the funnel 264 updating to show the narrowing span of the dataset upon each filter selection. In that situation a filtering menu 240 such as the one discussed above may remain visible in each tab as they are toggled, or may be collapsed to the side, or may be represented as a summary 266 of the selected filtered options to keep the user apprised of the reduced data set/size.

With regard to each filtering method discussed above, the combination of factors may be based on Boolean-style combinations. Exemplary Boolean-style combinations may include, for filtering factors A and B, permitting the user to select whether to search for patients with "A AND B," "A OR B," "A AND NOT B," "B AND NOT A," etc.

The final filtered cohort of interest may form the basis for further detailed analysis in the modules or other user interfaces described below. The population of interest is called a "cohort". The user interface can provide fixed functional attribute selectors pre-populated appropriately based on the available data attributes in a Patient Data Store.

The display may further indicate a geographic location clustering plot of patients and/or demographic distribution comparisons with publicly reported statistics and/or privately curated statistics.

Patient Timeline Analysis Module

Additionally, the system may include a patient timeline analysis module 28 that permits a user to review the sequence of events in the clinical life of each patient. It will be appreciated that this data may be anonymized, as discussed above, in order to protect confidentiality of the patient data.

Once a user has provided all of his or her desired filter criteria, e.g., via the cohort funnel & population analysis user interface 26, the system permits the user to analyze the filtered subset of patients. With respect to the user interface depicted in the figures, this procedure may be accomplished by selecting the "Analyze Cohort" option 268 presented in the upper right-hand corner of the interface 26.

Figure 10:
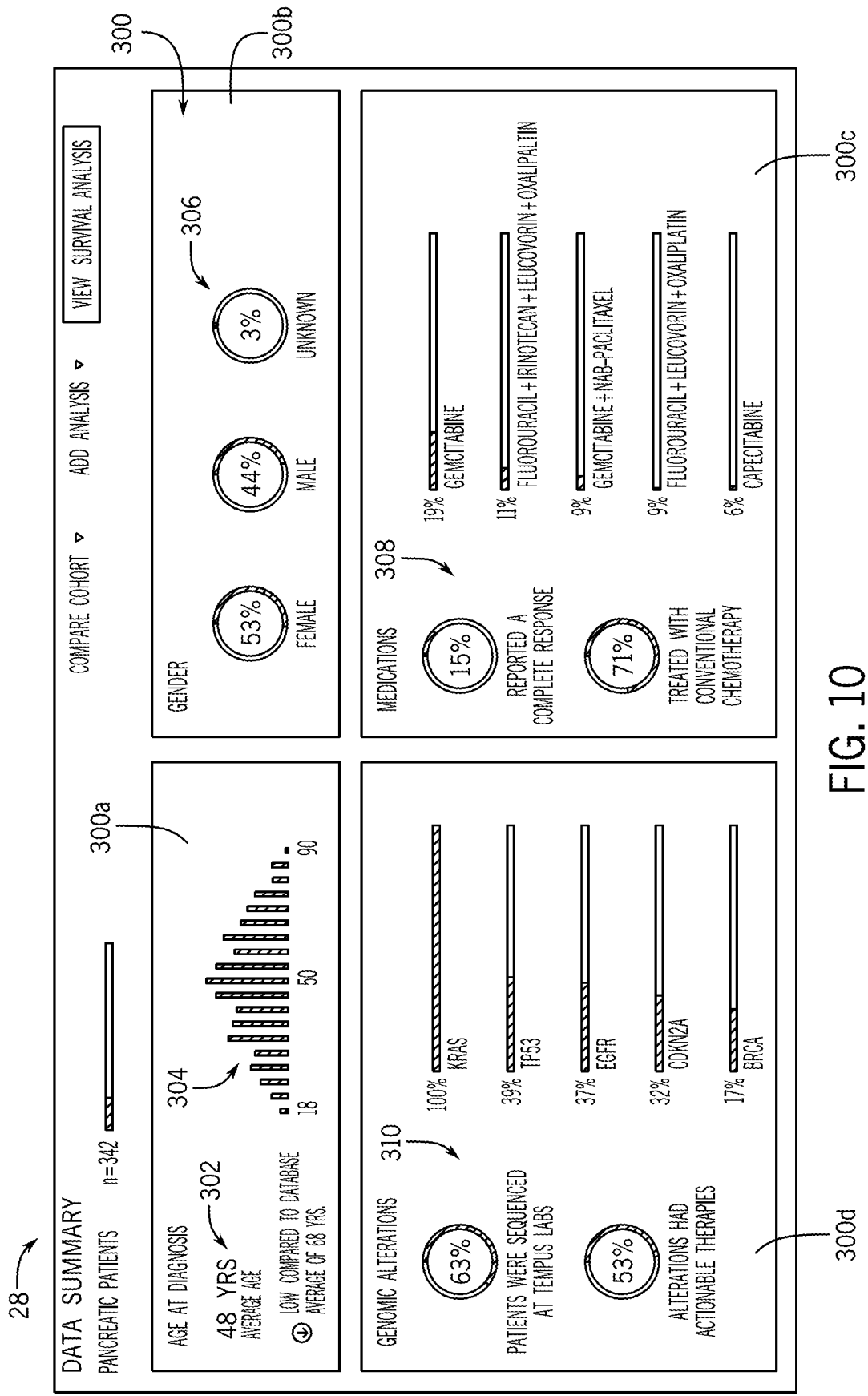
FIG. 10 is one example of a data summary window in a patient timeline analysis user interface.

Turning now to FIG. 10, after requesting analysis of the filtered subset of patients, the user interface may generate a data summary window in the patient timeline analysis user interface 28, with one or more regions 300 providing information about the selected patient subset, for example, a number of other distributions across clinical and molecular features. In one aspect, a first region 300*a* may include demographic information such as an average patient age 302 and/or a plot of patient ages 304. A second region 300*b* may include additional demographic information, such as gender information 306, for the subset of patients. A third region 300*c* may include a summary of certain clinical data, including, for example, an analysis of the medications 308 taken by each of the patients in the subset. Similarly, a fourth region 300*d* may include molecular data about each of the patients, for example, a breakdown of each genomic variant or alteration 310 possessed by the patients in the subset.

Figure 11:
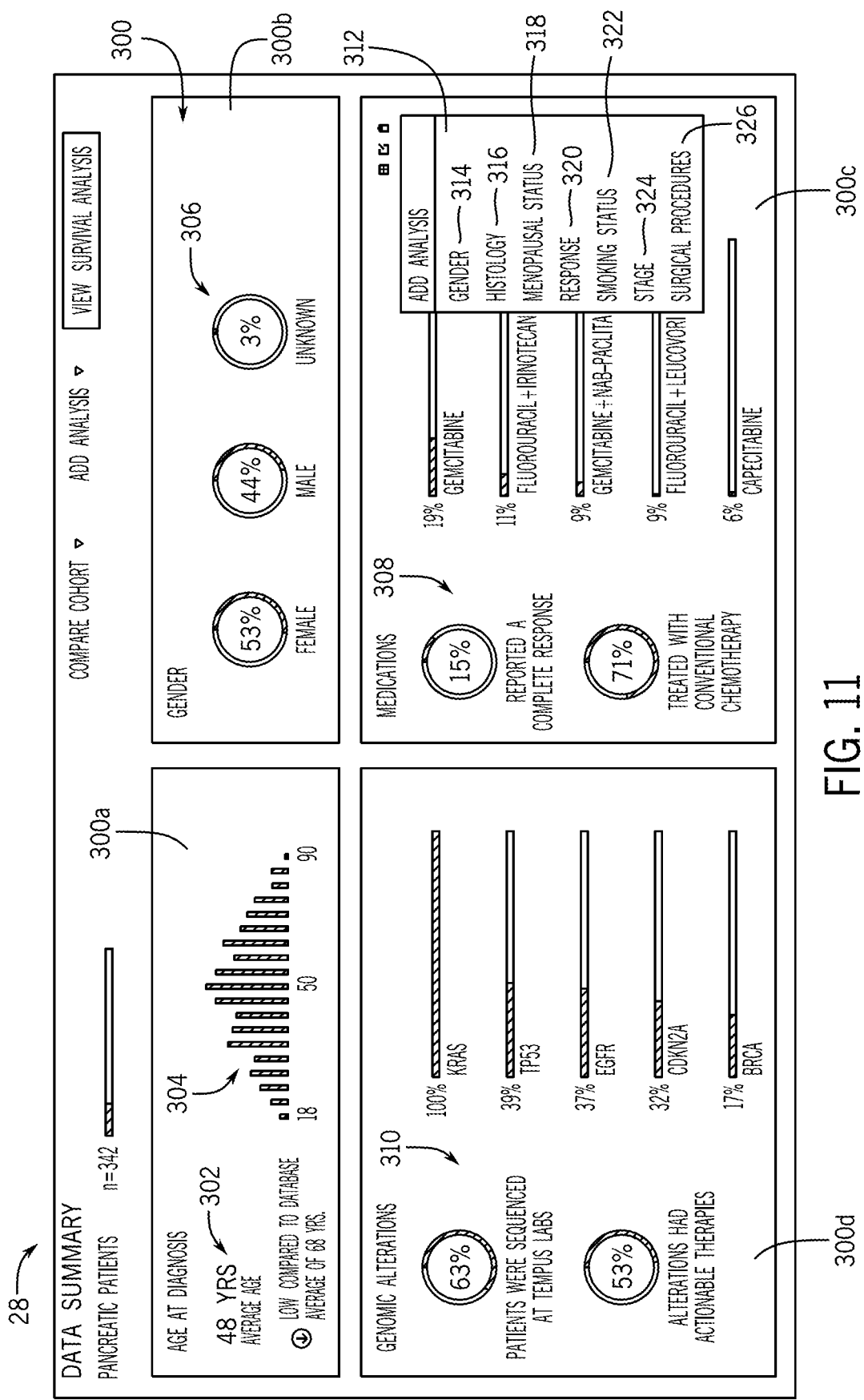
FIG. 11 is another example of a data summary window in a patient timeline analysis user interface.
Figure 12:
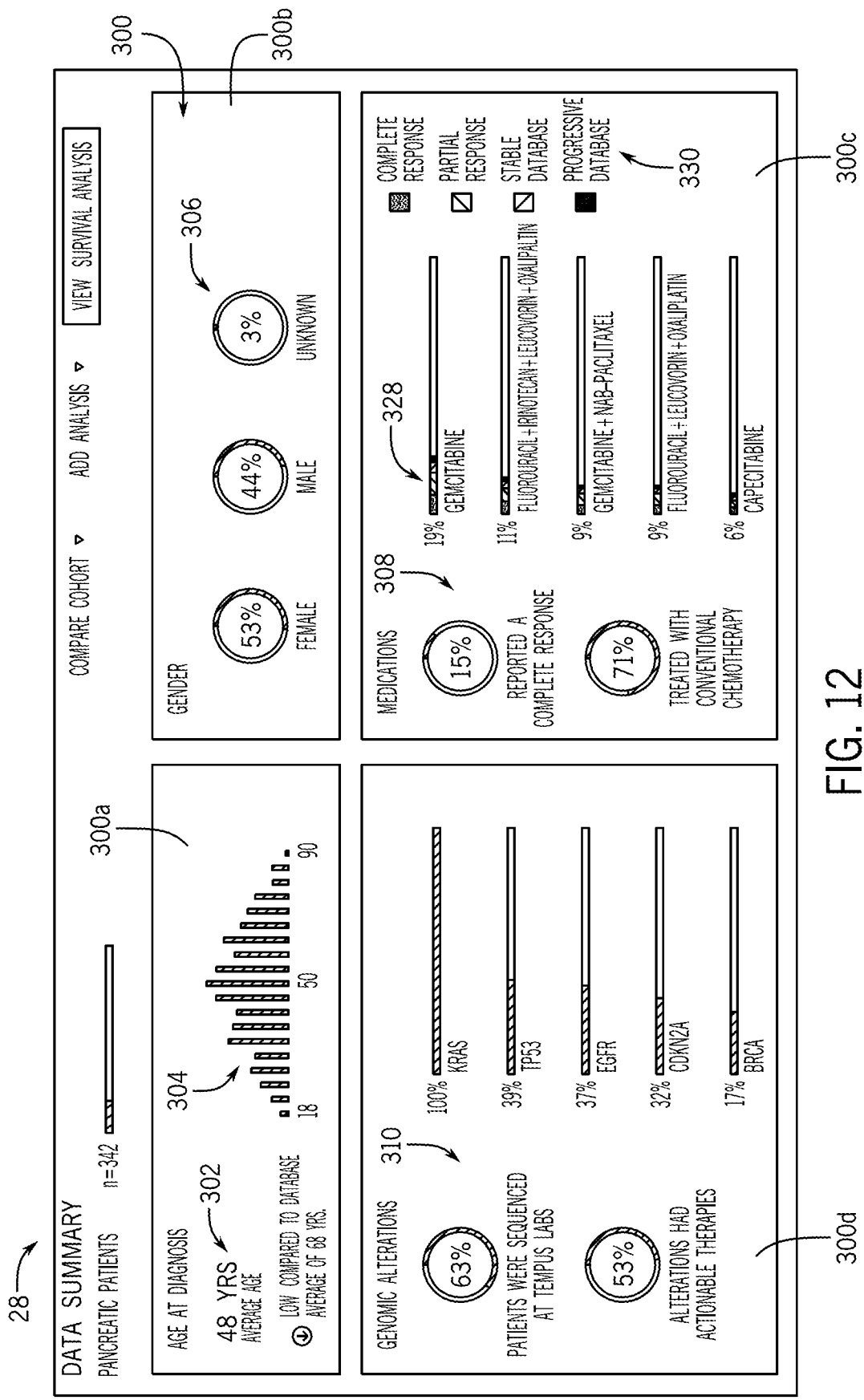
FIG. 12 is another example of a data summary window in a patient timeline analysis user interface.

The user interface 28 also permits a user to query the data summary information presented in the data summary window or region 300 in order to sort that data further, e.g., using a control panel 312. For example, as seen in FIGS. 11-14, the system may be configured to sort the patient data based on one or more factors including, for example, gender 314, histology 316, menopausal status 318, response 320, smoking status 322, stage 324, and surgical procedures 326. Selecting one or more of these options may not reduce the sample size of patients, as was the case above when discussing filtering being summarized in the data summary window. Instead, the sort functions may subdivide the summarized information into one or more subcategories. For example, FIGS. 11 and 12 depict medication information 308 being sorted by having additional response data 328 layered over it within the data summary window 300*c*, along with a legend 330 explaining the layered response data.

Figure 13:
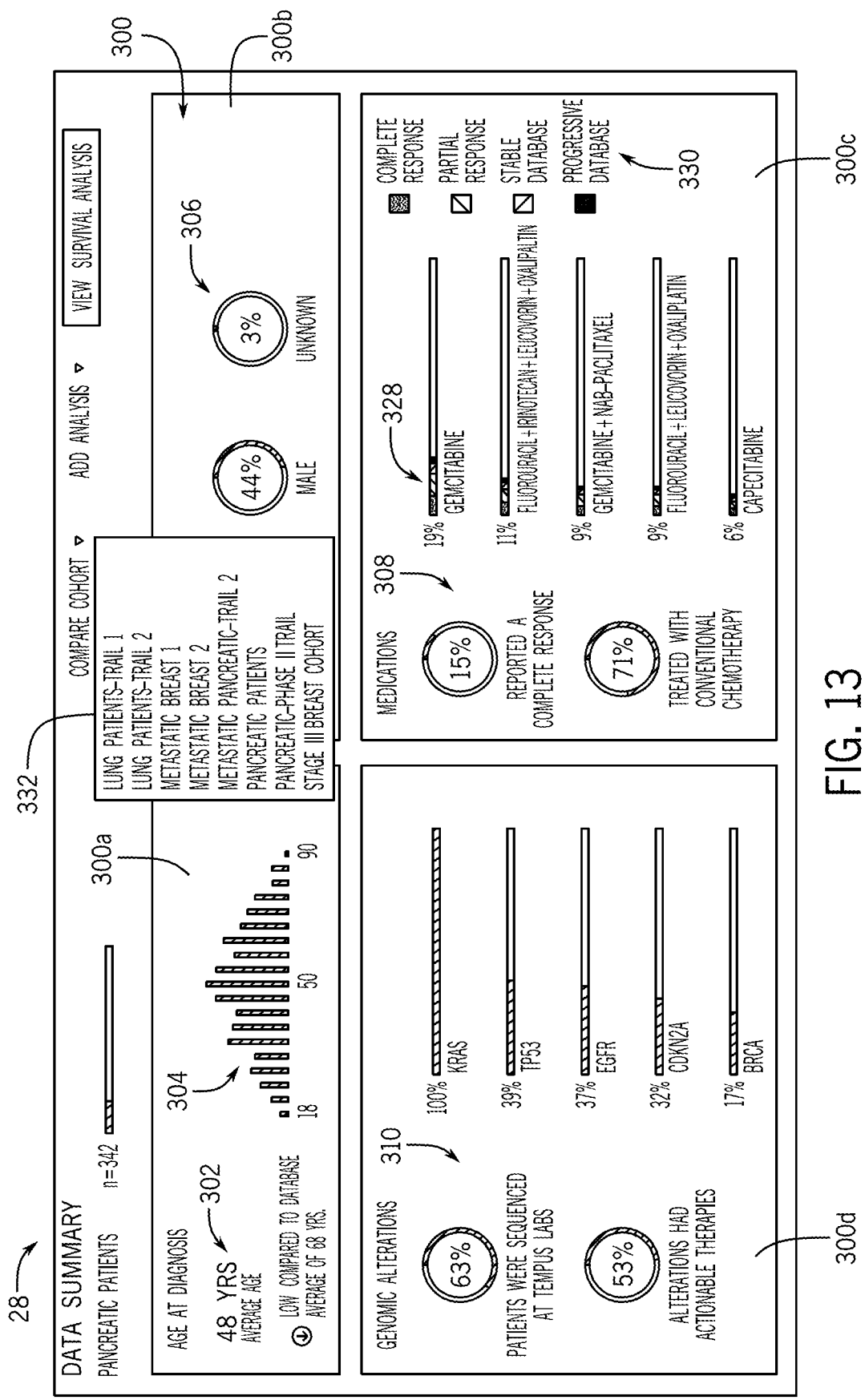
FIG. 13 is another example of a data summary window in a patient timeline analysis user interface.
Figure 14:
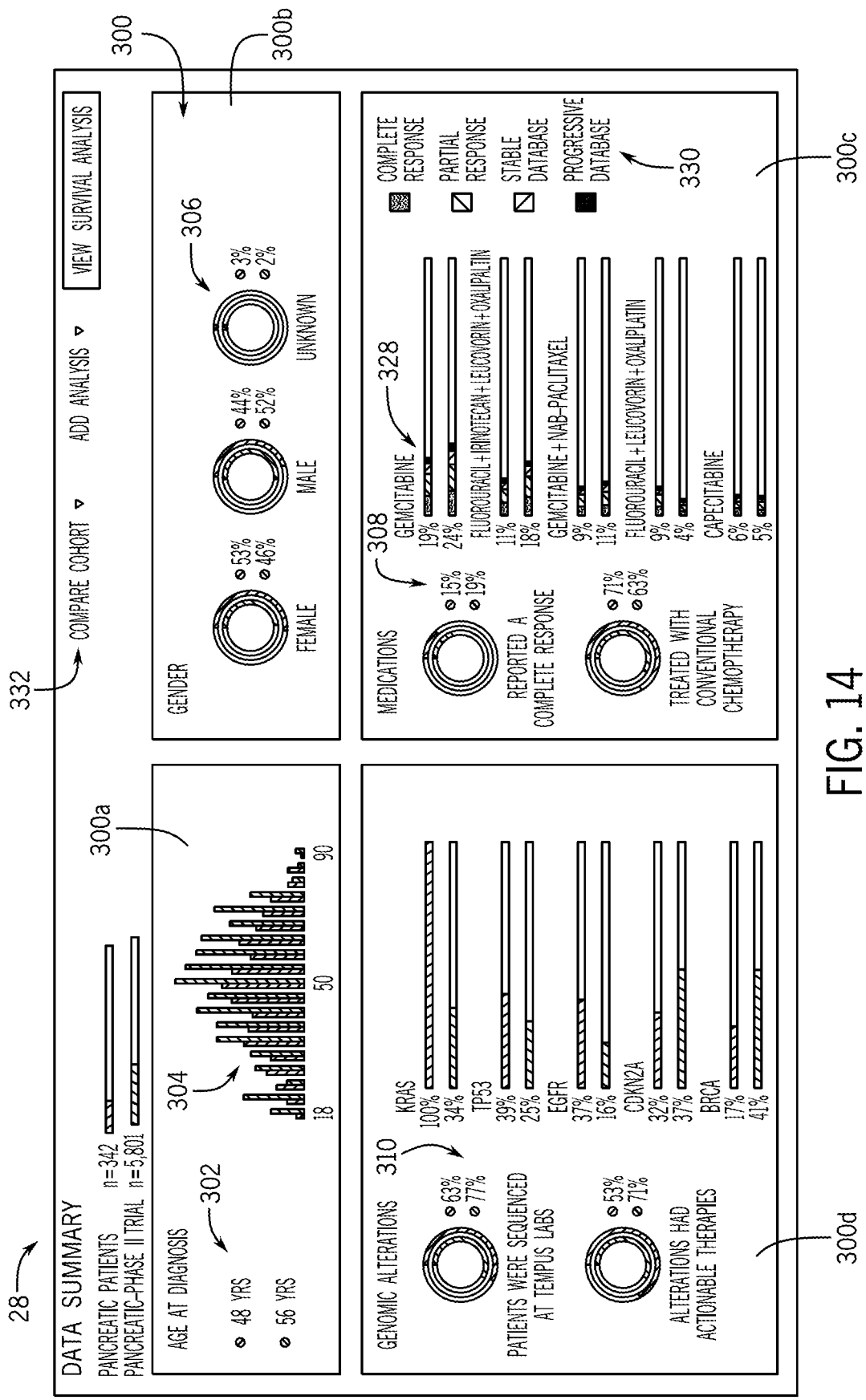
FIG. 14 is another example of a data summary window in a patient timeline analysis user interface.

Turning now to FIGS. 13-14, the subset of patients selected by the user also may be compared against a second subset (or "cohort") of patients, e.g., via a drop-down menu 332, thereby facilitating a side-by-side analysis of the groups. Doing so may permit the user to quickly and easily see any similarities, as well as any noticeable differences, between the subsets.

In one embodiment, an event timeline Gantt style chart is provided for a high-level overview, coupled with a tabular detail panel. The display may also enable the visualization and comparison of multiple patients concurrently on a normalized timeline, for the purposes of identifying both areas of overlap, and potential discontinuity across a patient subset.

Patient "Survival" Analysis Module

The system further may provide survival analysis for the subset of patients through use of the patient survival analysis user interface 30, as seen in FIGS. 15-20. This modeling and visualization component may enable the user to interactively explore time until event (and probability at time) curves and their confidence intervals, for sub-groups of the filtered cohort of interest. The time series inception and target events can be selected and dynamically modified by the user, along with attributes on which to cluster patient groups within the chosen population, all while the curve visualizer reactively adapts to the provided parameters.

In order to provide the user with flexibility to define the metes and bounds of that analysis, the system may permit the user to select one or both of the starting and ending events upon which that analysis is based. Exemplary starting events include an initial primary disease diagnosis, progression, metastasis, regression, identification of a first primary cancer, an initial prescription of medication, etc. Conversely, exemplary ending events may include progression, metastasis, recurrence, death, a period of time, and treatment start/end dates. Selecting a starting event sets an anchor point for all patients from which the curve begins, and selecting an end event sets a horizon for which the curve is predicting.

Figure 15:
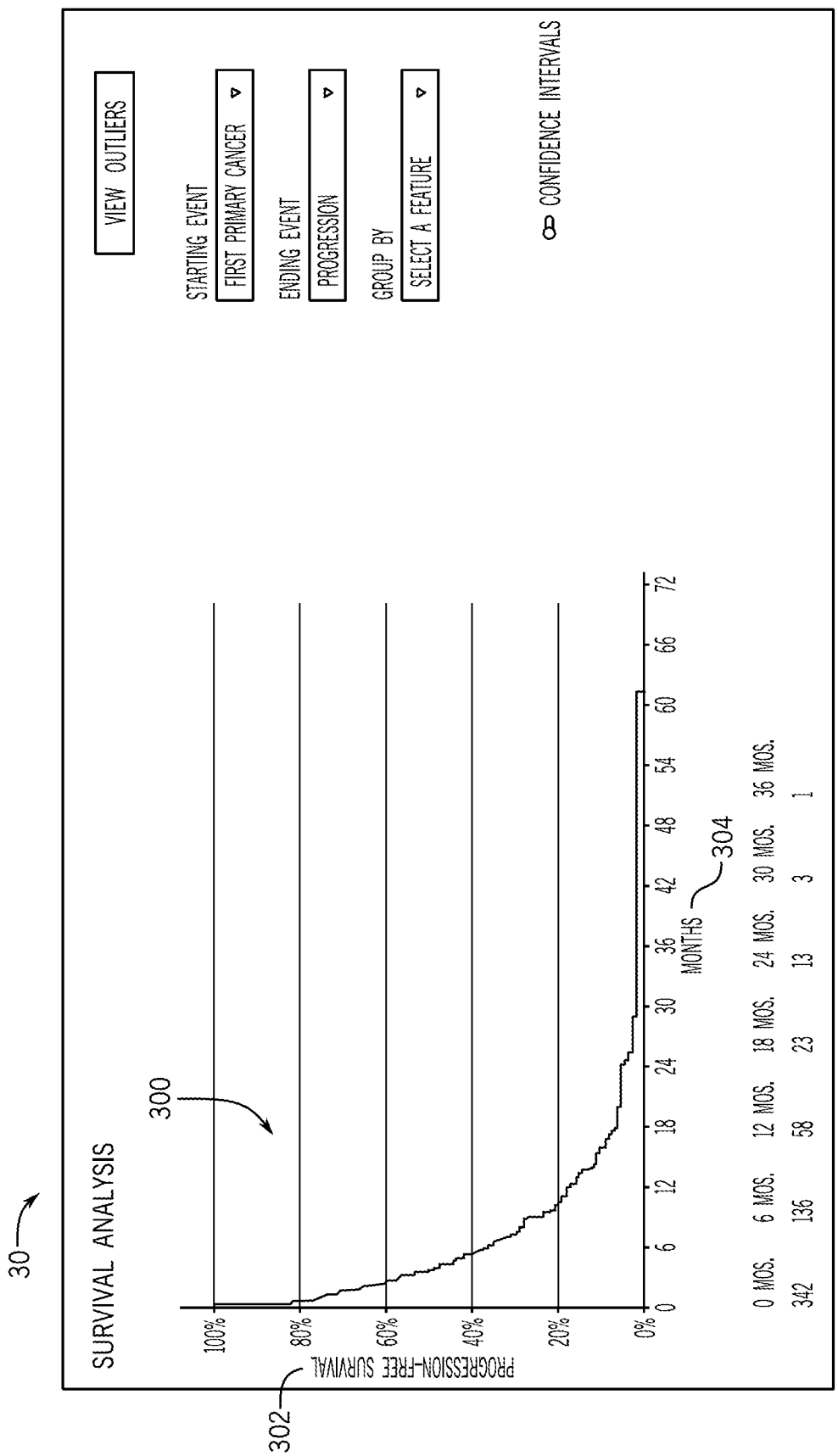
FIG. 15 is one example of a patient survival analysis user interface.

As seen in FIG. 15, the analysis may be presented to the user in the form of a plot 300 of ending event 302, for example, progression free survival or overall survival, versus time 304. Progression for these purposes may reflect the occurrence of one or more progression events, for example, a metastases event, a recurrence, a specific measure of progression for a drug or independent of a drug, a certain tumor size or change in tumor size, or an enriched measurement (such as measurements which are indirectly extracted from the underlying clinical data set). Exemplary enriched measurements may include detecting a stage change (such as by detecting a stage 2 categorization changed to stage 3), a regression, or via an inference (such as both stage 3 and metastases are inferred from detection of stages 2 and 4, but no detection of stage 3).

Figure 16:
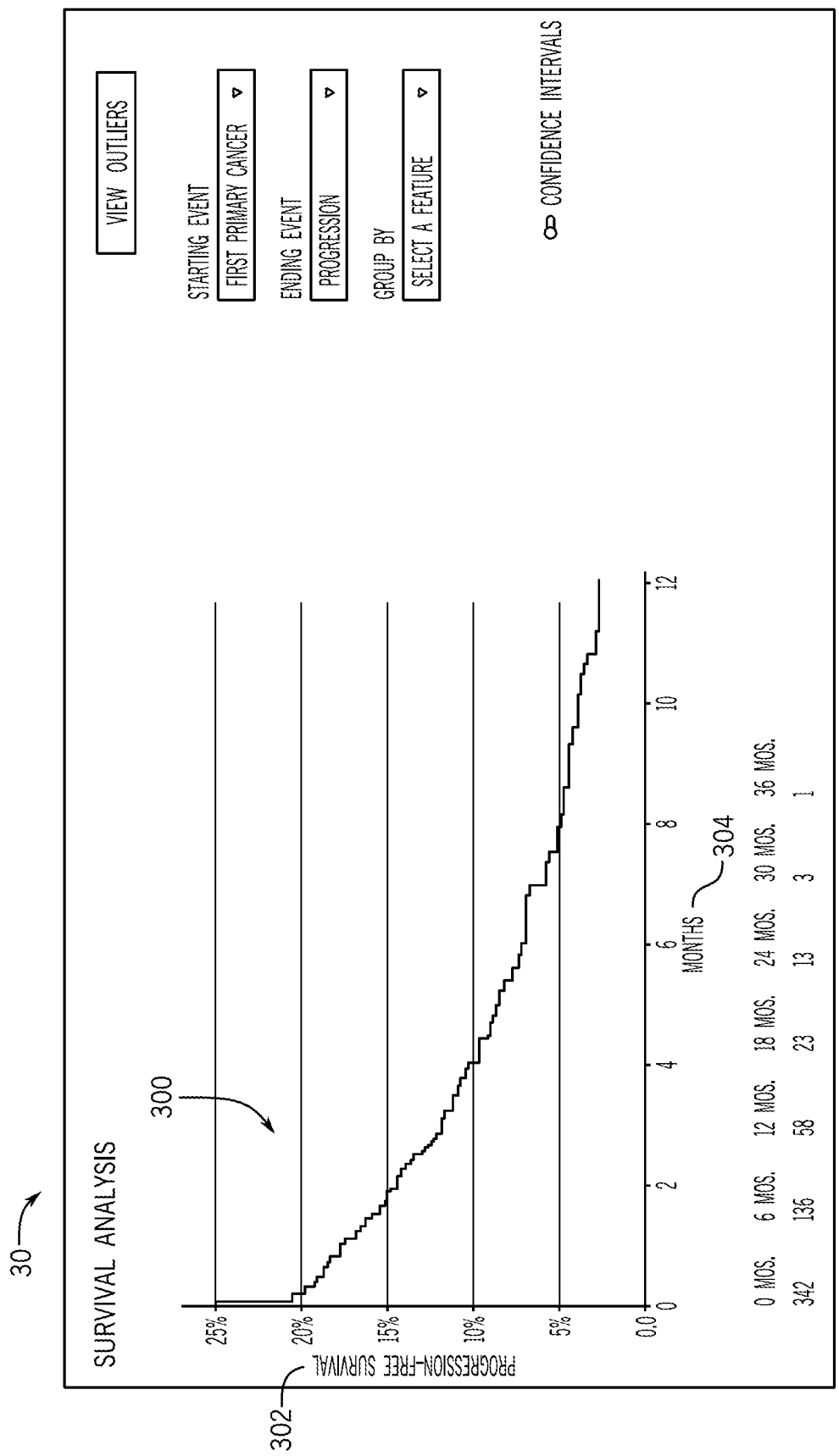
FIG. 16 is another example of a patient survival analysis user interface.
Figure 17:
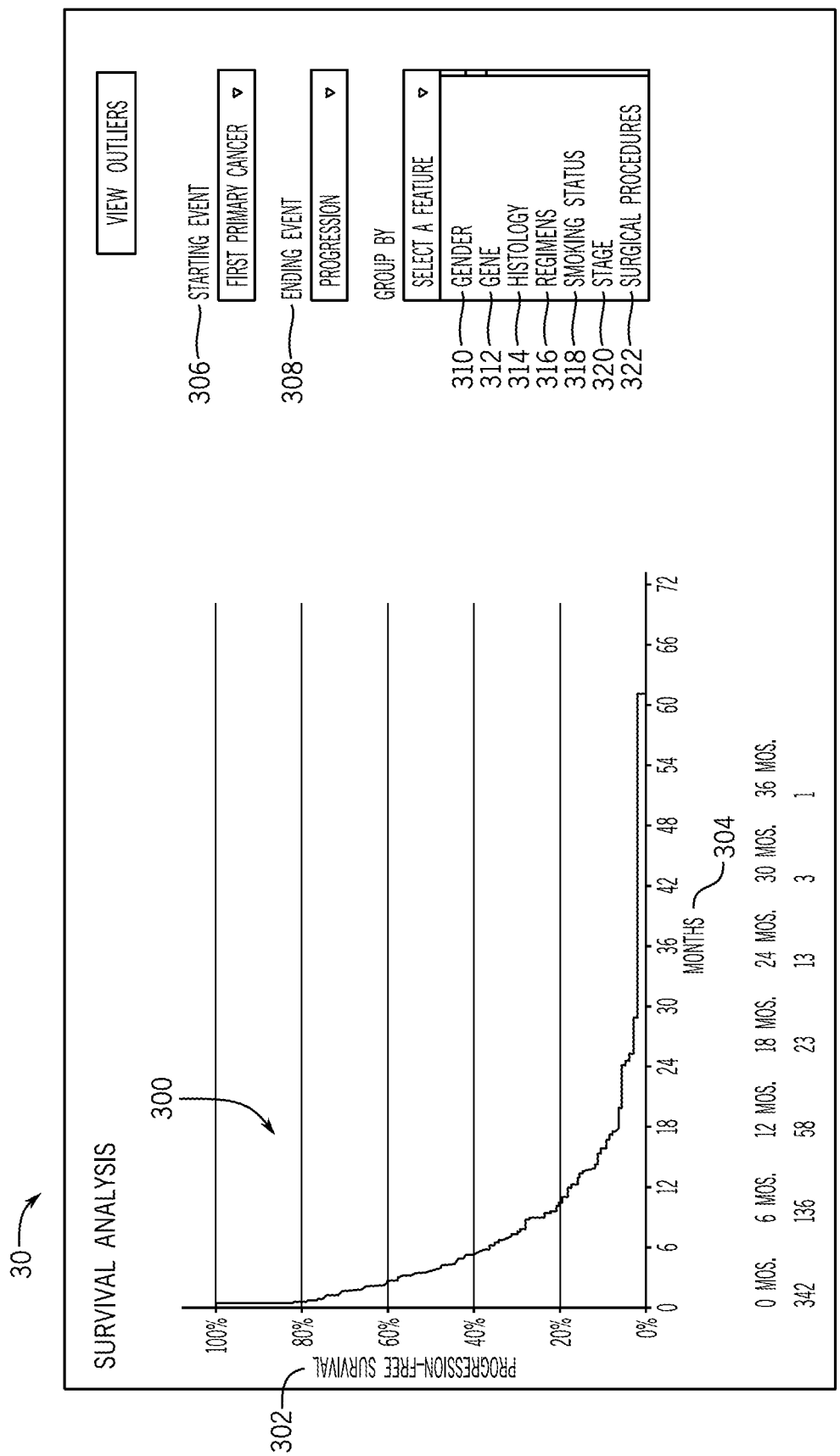
FIG. 17 is another example of a patient survival analysis user interface.

Additionally, the system may be configured to permit the user to focus or zoom in on a particular time span within the plot, as seen in FIG. 16. In particular, the user may be able to zoom in the x-axis only, the y-axis only, or both the x- and y-axes at the same time. This functionality may be particularly useful depending on the type of disease being analyzed, as certain, aggressive diseases may benefit from analyzing a smaller window of time than other diseases. For example, survival rates for patients with pancreatic cancer tend to be significantly lower than for other types of cancer; thus, when analyzing pancreatic cancer, it may be useful to the user to zoom in to a shorter time period, for example, going from about a 5-year window to about a 1-year window.

Turning now to FIGS. 17-20, the user interface 30 also may be configured to modify its display and present survival information of smaller groups within the subset by receiving user inputs corresponding to additional grouping or sorting criteria. Those criteria may be clinical or molecular factors, and the user interface 30 may include a selector such as one or more drop-down menus permitting the user to select, e.g., any of the beginning event 306 or ending event 308, as well as gender 310, gene 312, histology 314, regimens 316, smoking status 318, stage 320, surgical procedures 322, etc.

Figure 18:
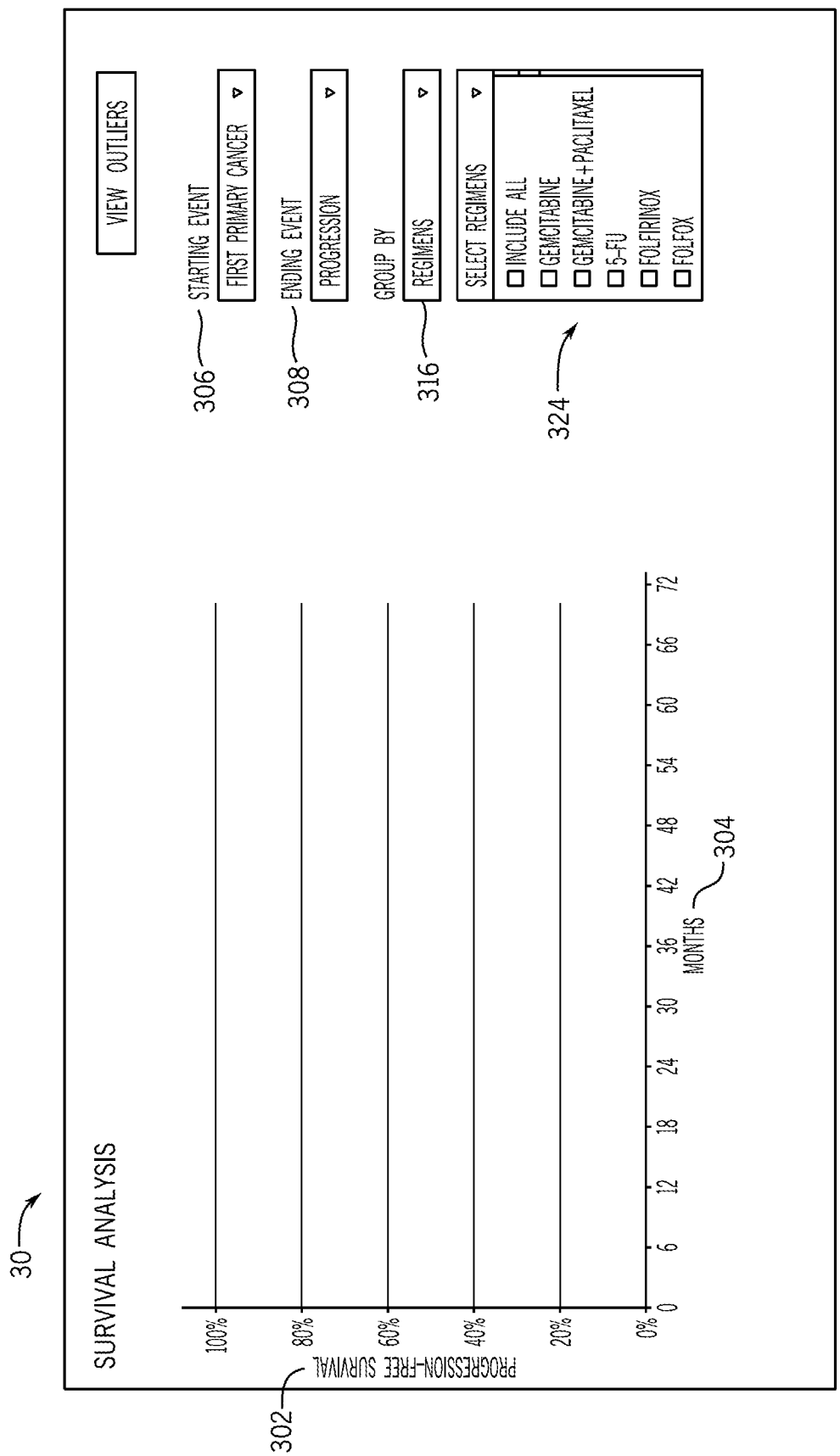
FIG. 18 is another example of a patient survival analysis user interface.
Figure 19:
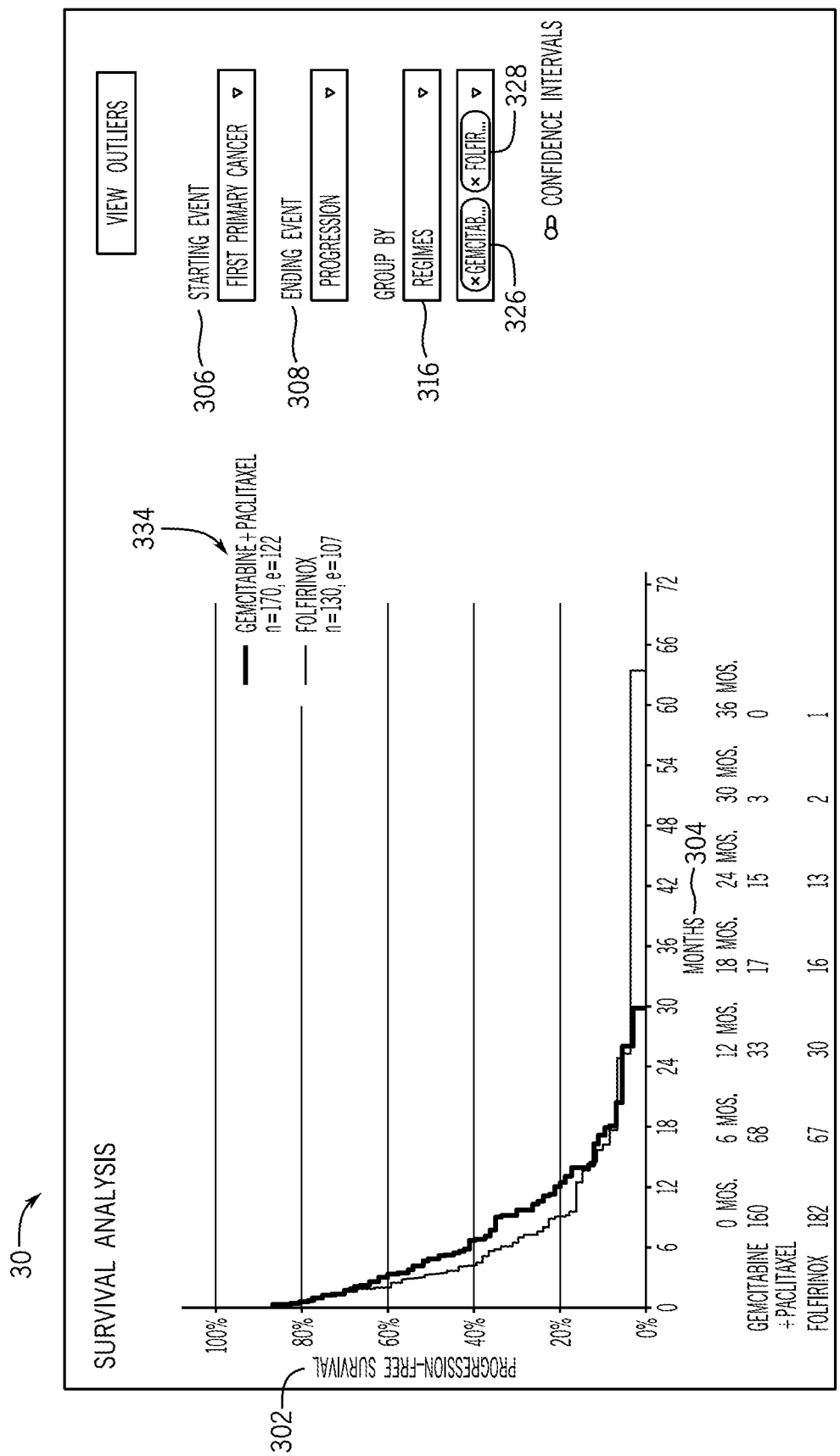
FIG. 19 is another example of a patient survival analysis user interface.

As shown in FIG. 18, selecting one of the criteria then may present the user with a plurality of options relevant to that criterion. For example, selecting "regimens" may cause the system to use one or more value sets to populate a selectable field generated within the user interface to prompt the user to select one or more of the specific medication regimens 324 undertaken by one or more of the patients within the subset. Thus, as FIG. 19 depicts, selecting the "Gemcitabine+Paclitaxel" option 326, followed by the "FOLFIRINOX" option 328, results in the system analyzing the patient subset data, determining which patients' records include data corresponding to either of the selected regimens, recalculating the survival statistics for those separate groups of patients, and updating the user interface to include separate survival plots 330, 332 for each regimen. Adding a group/adding two or more selections may result in the system plotting them on the same chart to view them side by side, and the user interface may generate a legend 334 with name, color, and sample size to distinguish each group.

Figure 20:
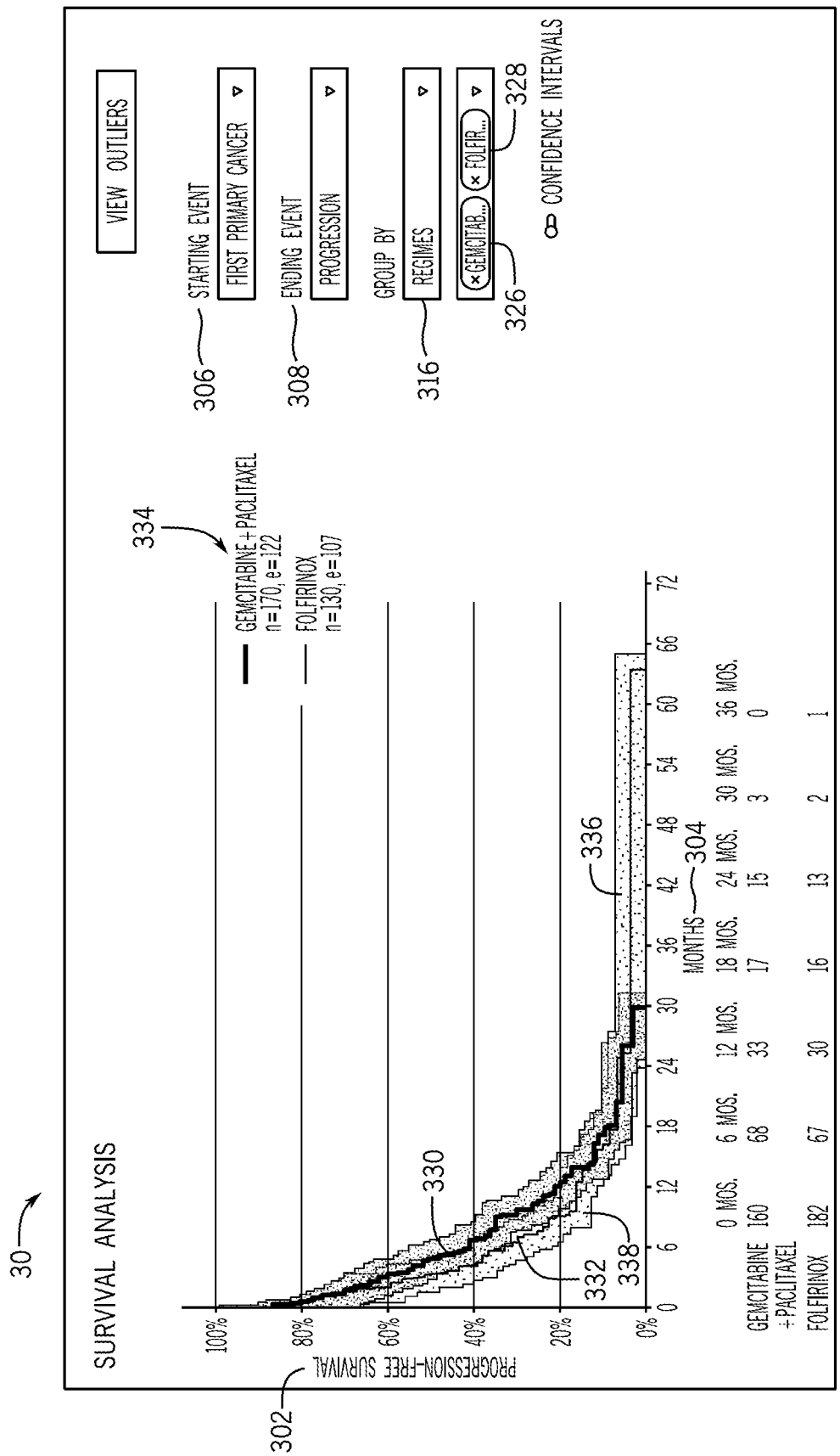
FIG. 20 is another example of a patient survival analysis user interface.

As seen in FIG. 20, the system may permit a greater level of analysis by calculating and overlaying statistical ranges with respect to the survival analysis. In particular, the system may calculate confidence intervals with regard to each dataset requested by the user and display those confidence intervals 336, 338 relative to the survival plots 330, 332. In one instance, the desired confidence interval may be user-established. In another instance, the confidence interval may be pre-established by the system and may be, for example, a 68% (one standard deviation) interval, a 95% (two standard deviations) interval, or a 99.7% (three standard deviations) interval. Confidence intervals may be calculated as Kaplan Meier confidence intervals or using another type of statistical analysis, as would be appreciated by one of ordinary skill in the relevant art.

As will be appreciated from the previous discussion, underpinning the utility of the system is the ability to highlight features and interaction pathways of high importance driving these predictions, and the ability to further pinpoint cohorts of patients exhibiting levels of response that significantly deviate from expected norms. In this context, high importance may be understood to be based upon feature importance to an outcome of a prediction. In particular, features that provide the greatest weight to the prediction may be designated as those of high importance. The present system and user interface provide an intuitive, efficient method for patient selection and cohort definition given specific inclusion and/or exclusion criteria. The system also provides a robust user interface to facilitate internal research and analysis, including research and analysis into the impact of specific clinical and/or molecular attributes, as well as drug dosages, combinations, and/or other treatment protocols on therapeutic outcomes and patient survival for potentially large, otherwise unwieldy patient sample sizes.

The modeling and visualization framework set forth herein may enable users to interactively explore auto-detected patterns in the clinical and genomic data of their filtered patient cohort, and to analyze the relationship of those patterns to therapeutic response and/or survival likelihood. That analysis may lead a user to more informed treatment decisions for patients, earlier in the cycle than may be the case without the present system and user interface. The analysis also may be useful in the context of clinical trials, providing robust, data-backed clinical trial inclusion and/or exclusion analysis. Backed by an extensive library of clinical and molecular data, the present system unifies and applies various algorithms and concepts relating to clinical analysis and machine learning to generate a fully integrated, interactive user interface.

Outlier Analysis Module

Turning now to FIGS. 21-24, in another aspect, the system may include an additional user interface such as patient event likelihood analysis user interface 32 to quickly and effectively determine the existence of one or more outliers within the group of patients being analyzed. For example, the interface in FIG. 21 permits a user to visually determine how one or more groups of patients separate naturally in the data based on progression-free survival. This user interface includes a first region 400 including a plurality of indicators 402 representing a plurality of patient groups, where each patient in a given group has commonality with other patients in that group; for example, commonality may be based on one or more of the above mentioned attributes, additional, system-defined, and tumor-related criteria used for filtering, and other medical information capable of being stored in a structured format that may be identified by the system. Additionally, groups may be formed from the absence of any attribute. For example, a commonality may be found by a group that never took a medication, never received a treatment, or otherwise share an absence of one or more attributes. This region may resemble a radar plot 406, in that the indicators are plotted radially away from a central indicator 408, as well as circumferentially about that indicator, where the radial distance from the central indicator 408 is reflective of a similarity between the patients represented by the central and radially-spaced indicators, and where circumferential distances between radially-spaced indicators is reflective of a similarity between the patients represented by those indicators. In this instance, similarity with regard to radial distances may be based primarily or solely on the criterion/criteria governing the outlier analysis. For example, when analyzing patient groups with regard to progression-free survival ("PFS"), the central point or indicator 408 may be based on a particular fraction or percentage of the PFS (e.g. 10%, 25%, 50%, 75%, or other percentage) of the entire cohort over the time period evaluated, the radial distance from the central point or indicator 408 may be indicative of the progression-free survival rate of the groups of patients reflected by the respective indicators 402 such that groups of patients with better than the particular percentage PFS are plotted above the central point or indicator 408 and that groups of patients with worse than the particular percentage PFS are plotted below the central point or indicator 408, and the distance from the central point on the X axis may be derived based upon the size of the population, a difference between an observed and expected PFS, or similar metric.

Figure 21:
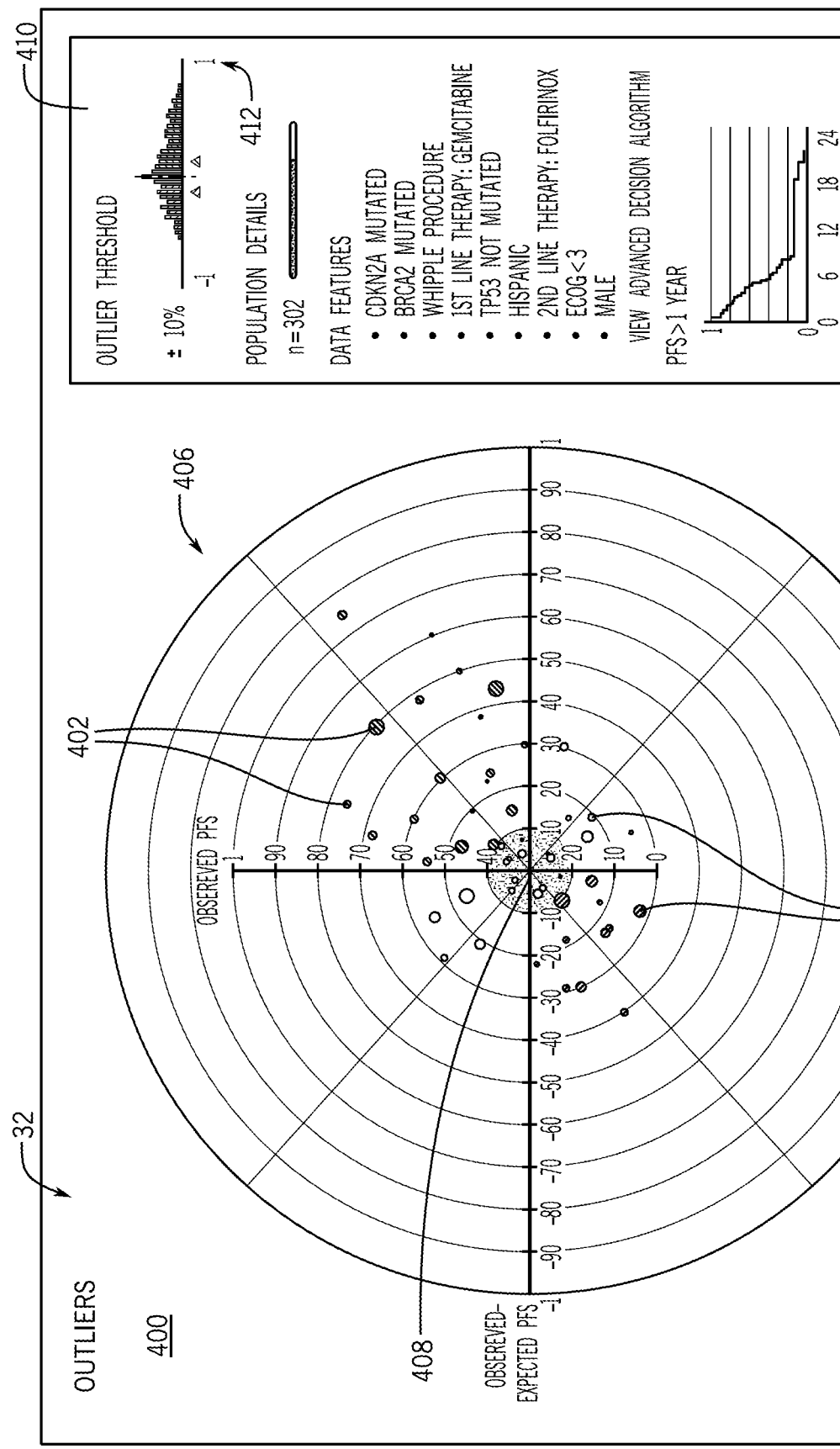
FIG. 21 is an example of a patient event likelihood analysis user interface.
Figure 22:
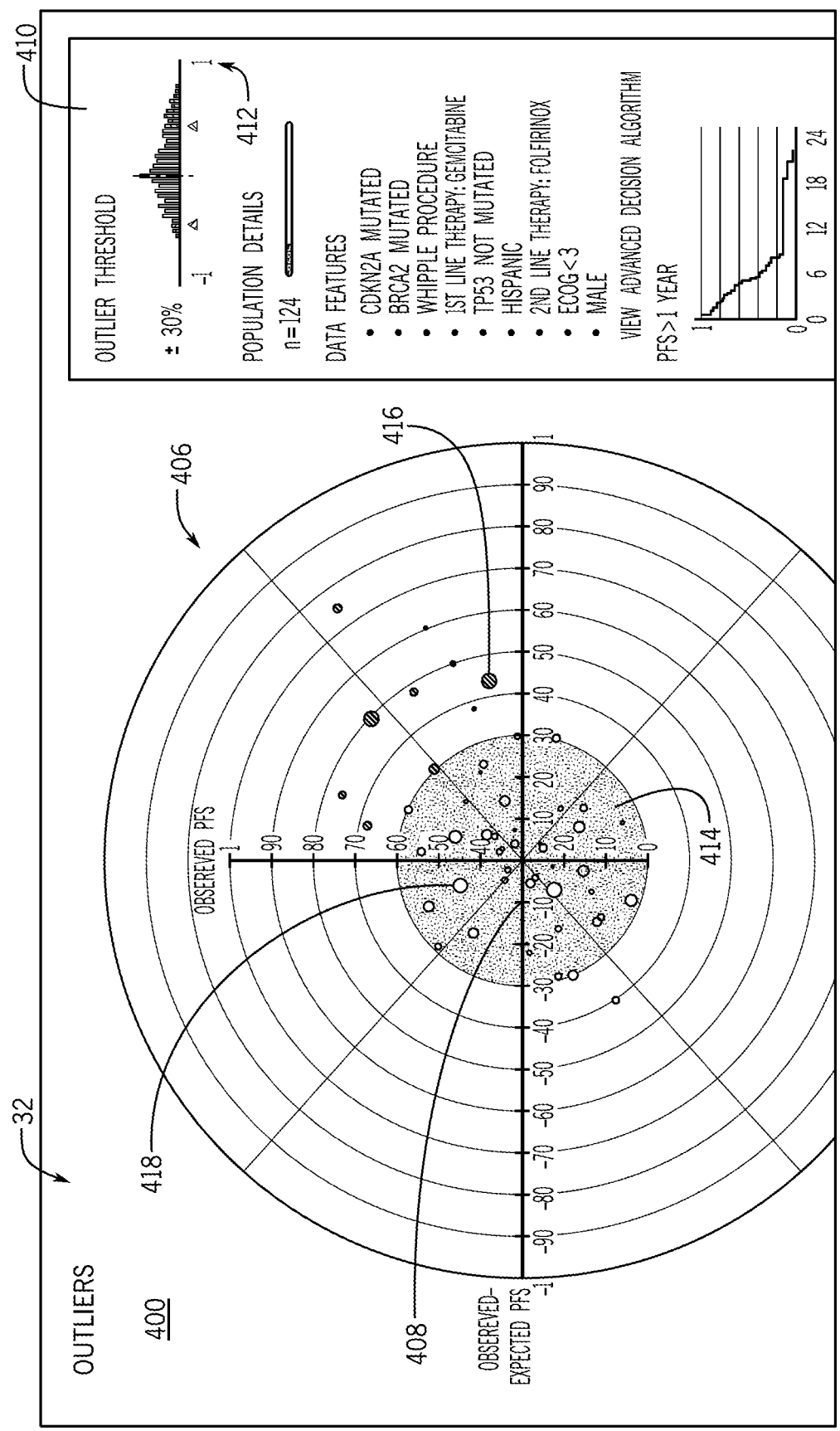
FIG. 22 is another example of a patient event likelihood analysis user interface.

Additionally, the user interface may include a second region 410 including a control panel 412 for filtering, selecting, or otherwise highlighting in the first region a subset of the patients as outliers. Setting a value or range in the control panel may generate an overlay 414 on the radar plot (see FIG. 22), where the overlay may be in the form of a circle centered on the central indicator 408 and the radius of the circle may be related to the value or range received from the user in the second region 410. In this aspect, the user may select a value that is applied equally in both directions relative to the reference patient. For example, the user may select "25%," which may be reflected as a range from −25% to +25% such that the overlay may be a uniform circle surrounding the central point or indicator 408. Alternatively, the system may receive multiple values from the user, for example, one representing a positive range and a second representing a negative range, such as "−20% to +25%." The values may be received via a text input, drop down, or may be selected by clicking a respective position on a graph. In that case, the overlay may take the form of two separate hemispheres having different radii, the radii reflective of the values received from the user. As seen in FIGS. 21 and 22, the values may indicate the percent deviation from whatever value is related to the central point or indicator 408. For example, FIGS. 21 and 22 are displaying progression-free survival (PFS) percentages for various clusters of patients centered around a patient with a 0% PFS value. FIG. 21 includes an overlay 414 at the +/−10% range, while FIG. 22 shows how the overlay is adjusted when the range is modified to +/−30%. It will be appreciated that the central point or indicator 408 could be associated with a patient at a non-zero value, e.g., 20% PFS. In that case, the +/−10% range would encapsulate clusters of patients in a 10-30% PFS range, while the +/−30% range would encapsulate clusters of patients in the −10-50% range. In either case, once the system has received a user input, the indicators covered by the overlay may change in visual appearance, for example, to a grayed-out or otherwise less conspicuous form, as is shown in FIG. 22 in which values 416 that are outside the outlier threshold 414 (shown in a histogram format in the upper right corner of FIG. 22) are a darker color (e.g. blue or shaded) and the values 418 within the outlier threshold 414 are displayed in a lighter color (e.g. pale gray or unshaded). That is, indicators outside of the overlay may remain highlighted or otherwise more readily visually distinguishable, thereby identifying those indicators as representing outliers.

Figure 23:
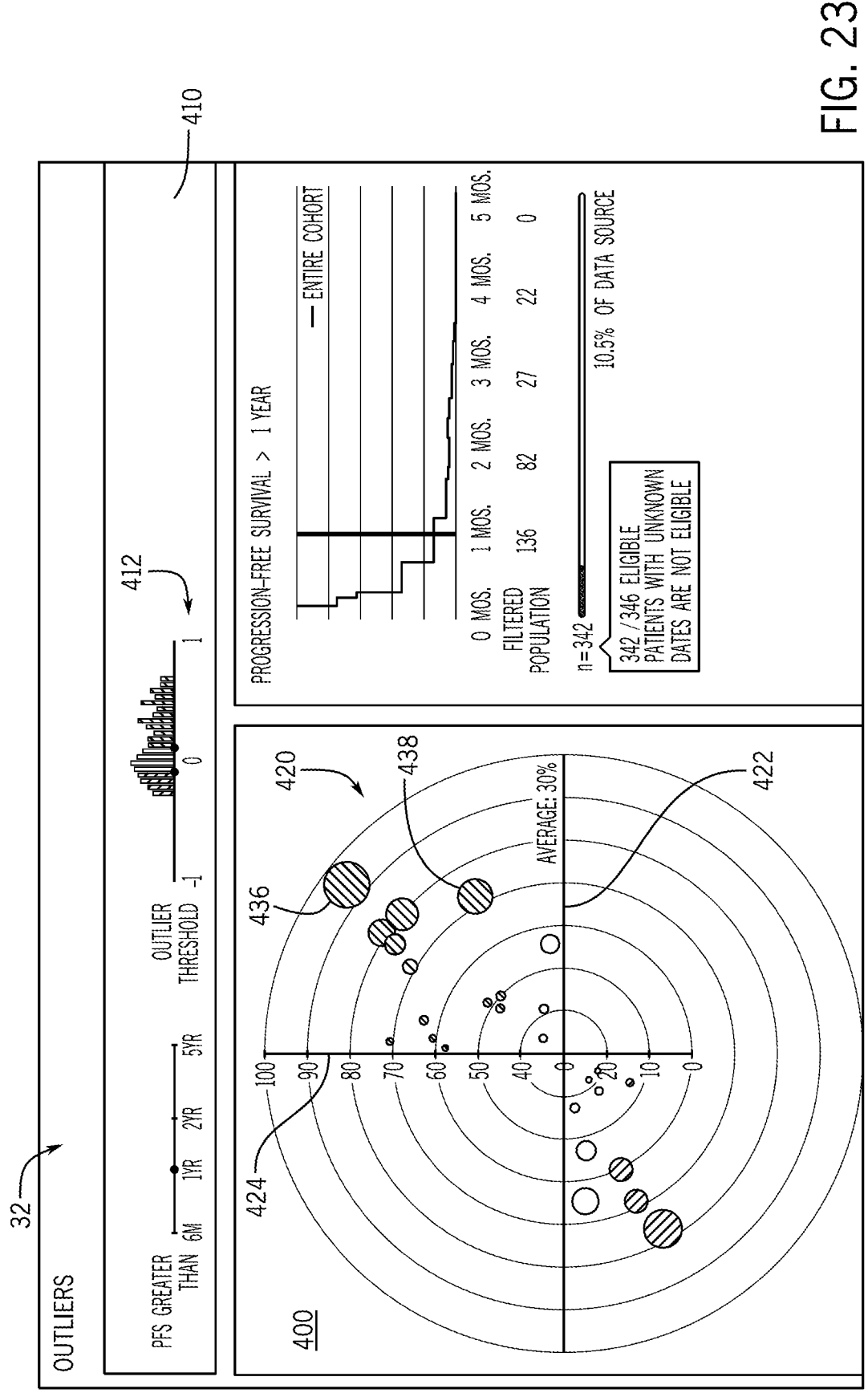
FIG. 23 is another example of a patient event likelihood analysis user interface.
Figure 24:
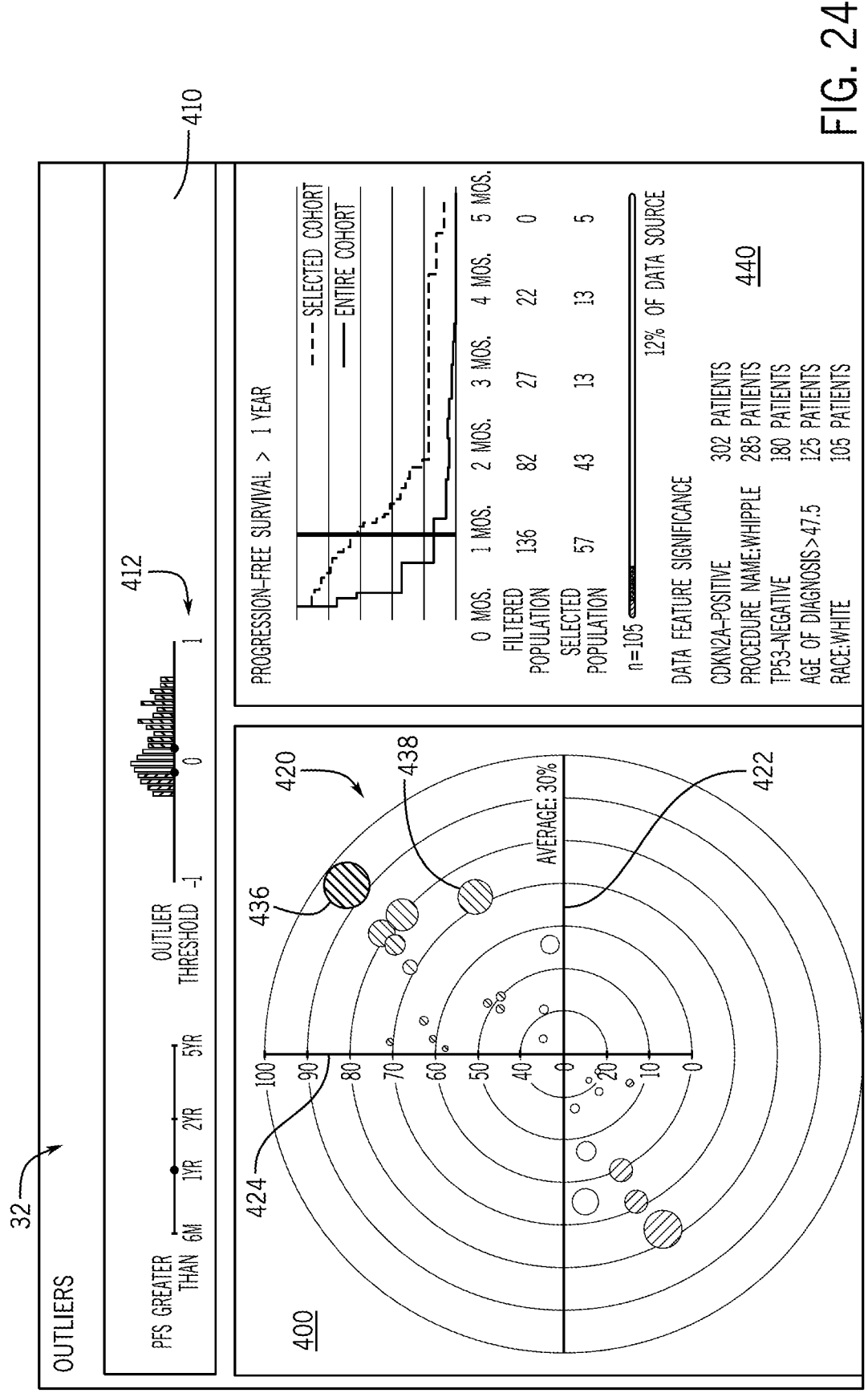
FIG. 24 is another example of a patient event likelihood analysis user interface.

In another aspect, as seen in FIGS. 23-24, the first region 400 of the user interface may include a different type of plot 420 of the plurality of patient groups than the radar-type plot just discussed. In this aspect, an x-axis 422 may represent the number of patients in a given group represented by an indicator and a y-axis 434 may represent a degree of deviation from the criterion/criteria being considered. As a result of these display parameters, this user interface 32 will present the largest patient groups 436 farthest away from the y-axis and the largest outlier groups 438 farthest away from the x-axis 422. (For both this user interface and the one previously described, it should be appreciated that the origin may not reflect a value of 0 for either the y-axis or the radial dimension, respectively. Instead, the origin may reflect a base level of the criterion/criteria being analyzed. For example, in the case of progression-free survival, the base group may have a 2-year rate of 15%. In that case, deviations may be determined with regard to that 15% value to assess the existence of outliers. Such deviations may be additive, +/−20% may be 0% to 35% (0% instead of −5% because negative survival rates are not possible), or multiplicative, +/−20% may be 12% to 18%).

As with the previously described user interface, the interface of FIGS. 23-24 may include a second region 410 including a control panel 412 for modifying the presentation of identifiers in the first panel 400. Again, as with that interface, the control panel may permit the user to make uniform or independent selections to the positive and negative sides of a scale. In particular, as seen in FIG. 24, the control panel 412 in this instance permits the user to independently select the positive and negative ranges in the search for outliers. Upon making each selection, the user interface 32 may adjust dynamically to cover, obscure, un-highlight, remove, or otherwise distinguish the indicators falling within the zone(s) selected by the user from the outlying indicators falling outside of that zone. Due to the configuration of the x- and y-axes, as discussed above, this user interface 32 may be configured to make it possible for the user to quickly identify which outlier group is the farthest removed from the representative patient/group, since that outlier group will be the farthest spaced from the x-axis, in the positive direction, the negative direction, or in both directions. Similarly, the user interface 32 may be configured to make it easy for the user to quickly, visually determine which patient group has the largest number of patients, since that group will be the farthest spaced from the y-axis, in the positive direction, the negative direction, or in both directions. Still further, the combination of axes may permit the user to make a quick visual determination as to which indicator(s) warrant(s) further inspection, for example, by permitting the user to visually determine which indicator(s) strike an ideal balance between degree of deviation/outlier and patient size.

With regard to either outlier user interface described above, the interface further may include a third region 440 providing information specific to a selected node when the system receives a user input corresponding to a given indicator, for example, by clicking on that indicator 436 in the first region of the interface, as seen in FIG. 24. In one aspect, that additional information may include a comparison of the criterion/criteria being evaluated as compared to the values of the overall population used to generate the interface of the first region. Information in this region also may include an identification of a total number of patients in a record set, a number of patients that record set was filtered down to based on one or more different criteria, and then the population size of the selected node as part of an in-line plot, which size comparisons may help inform the user as to the potential significance of the outlier group.

Figure 25A:
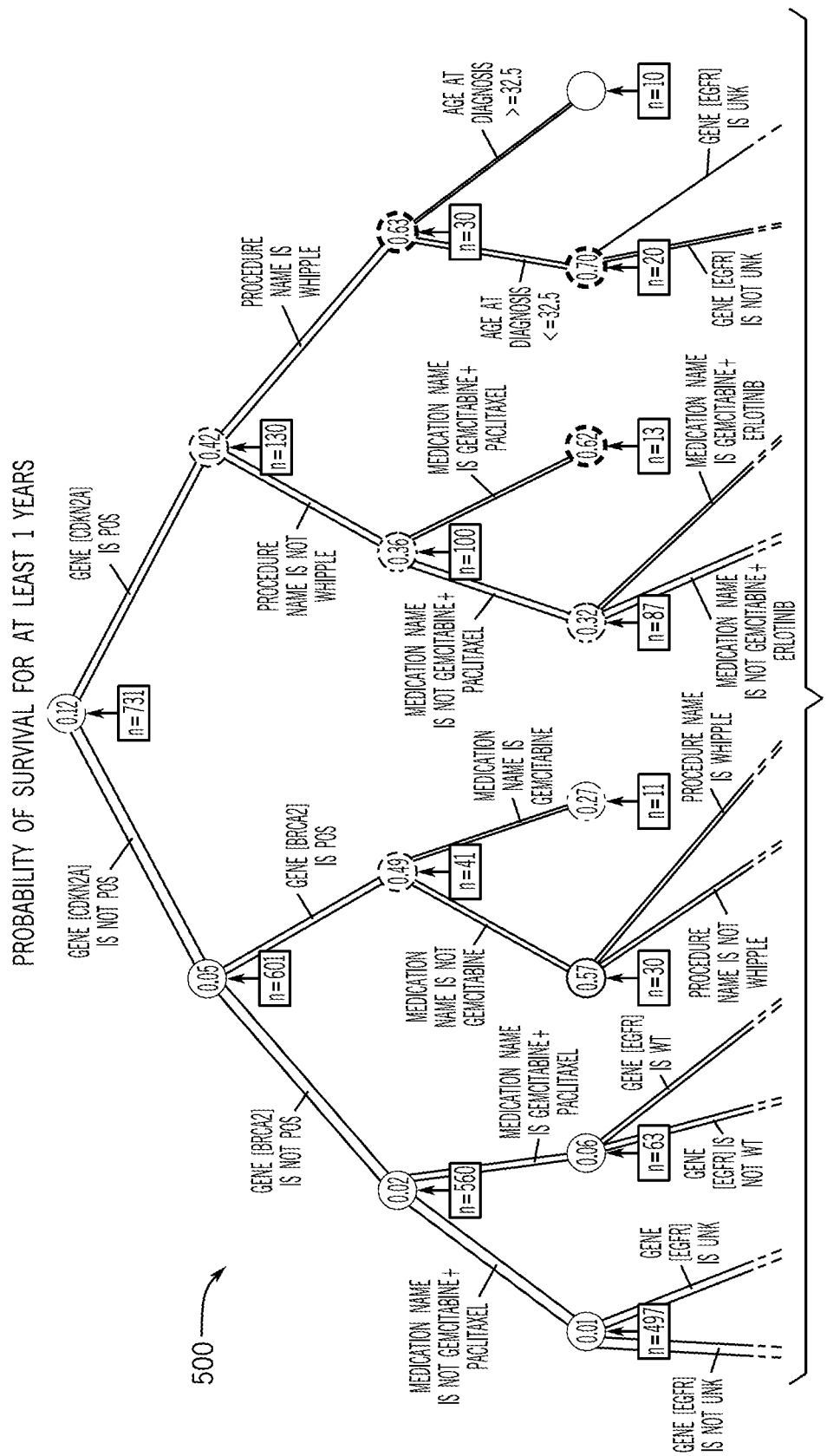
FIGS. 25A and 25B show an example of a binary decision tree for determining outliers usable with respect to the patient event likelihood analysis user interface.
Figure 25B:
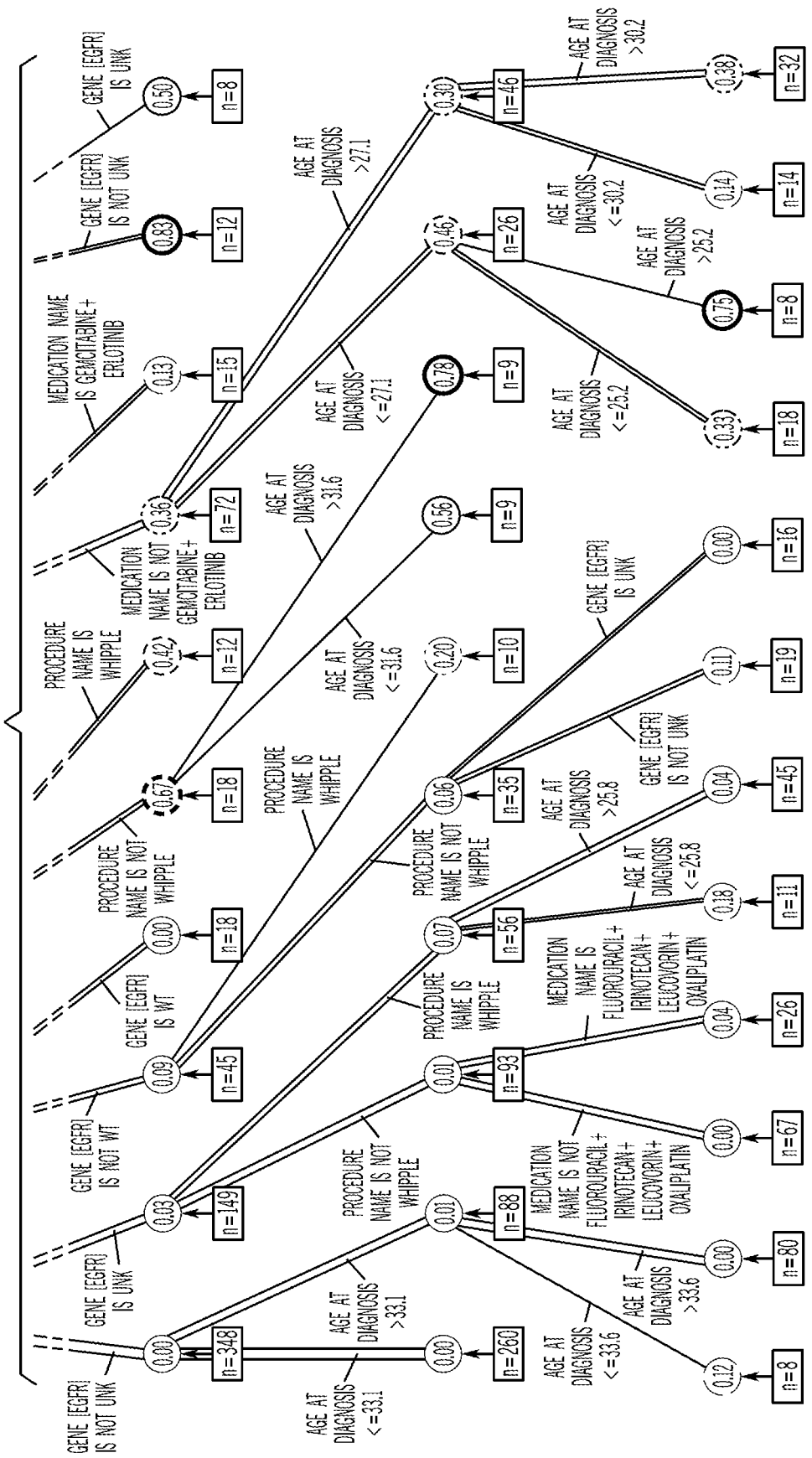

Additionally, with regard to either outlier user interface described above, the algorithm to determine the existence of an outlier may be based on a binary tree 500 such as the one seen in FIGS. 25A and 25B. In order to generate such a tree, the system may separate each feature into its own category. For each category, the system then may determine which subset of the cohort have a largest spread of progression free survival vs. non-survival and treat the feature split which generated the largest spread as an edge between nodes and the features themselves as nodes. The system may continue with this analysis until it encounters a leaf. For example a mutation column may be separated into either "mutated" or "not mutated," and an age option may be set by the user to be "over 50" vs. "under 50." The system then may determine what the biggest cutoff age for survival is, and use that as the binary decision point. Within all of these categories, each having a binary selection that split it into two groups, the system may determine which has the better survival and which has the worse survival, and compare those determinations across all columns to find the group having the biggest difference. A category with the biggest difference is the first node split in a tree that continues to split at additional nodes, forming a plurality of branches where the category criterion for the group is the edge between each node. Each of the branches terminates in a leaf, which is just a split of all the features that came before to identify a group of people with the highest PFS within the cohort according to the divisions above it. In one aspect, the system may treat each leaf as an outlier. Alternatively, outliers may be certain, particularly divergent features. For example, outlier leafs may be those that deviate from a user-input or an expected value by some threshold, e.g., one standard deviation or more away from the expected threshold.

In some instances, data in a branch may be lost when the system fully extrapolates out to a leaf. In such instances, the system may scan features that a current patient has in common with outlier patients, and suggest changes to clinical process that may place them in a new bucket (leaf/node) of patients that have a higher outlier. For example, if a branch has a high PFS in a node, but loses the distinction by the time the branch resolves in a leaf, the system may identify the node with the highest PFS as a leaf.

In order to generate an expected survival rate for a population, the system may rely upon a predictive algorithm built on the survival rates of the patients in the data set 14. Alternatively, the system may use an external source for a PFS prediction, such as an FDA published PFS for certain cancers or treatments. The system then may compare the expected survival rate with an observed PFS rate for a population in order to determine outliers.

In one particular embodiment, a method for identifying one or more outlier groups of patients are provided. The method includes steps of selecting a cohort of patients, where the cohort includes a plurality of patients. Selection of the cohort may be based on identifying a group of patients having a particular condition such as a particular disease. In one particular embodiment, the cohort may include a group of patients (e.g. several tens, hundreds, thousands, or more) who have non-small cell lung cancer or breast cancer. Other groupings based on other criteria are also possible.

In various embodiments, a next step of the method may include calculating an average survival rate for the cohort of patients. For example, based on available data it may be determined that these patients on average survive for a particular time (e.g. a number of months such as 63 months).

In certain embodiments, another step of the method may include selecting a plurality of clinical or molecular characteristics associated with the cohort of patients. The clinical or molecular characteristics associated with the cohort of patients may include one or more of a genetic marker, a procedure performed on a patient, a pharmaceutical treatment given to a patient, an age at which a patient receives a diagnosis, an age at which a patient receives a treatment, or a lifestyle indicator. In particular embodiments, the clinical or molecular characteristics for a patient may include a smoking status of the patient (e.g. yes, no, unknown), a DNA mutation associated with the patient (e.g. KRAS, BRAF, EGFR, etc.), an age of the patient at a time of diagnosis or treatment (e.g. one or more integers in a particular age range such as 18-115 years old), or one or more treatment procedures or pharmaceuticals received by the patient.

In some embodiments, information regarding the cohort of patients may be used to generate a tree structure, where a node of the tree structure may contain one or more patients who are outliers, that is, patients who have shown a significantly different survival (shorter or longer) for a given set of conditions. Thus to generate the tree structure, for each characteristic of the plurality of characteristics the method may include identifying a plurality of data values associated with the characteristic. For each data value of the plurality of data values associated with the characteristic, the method may include: dividing the cohort of patients into a first subgroup and a second subgroup of the plurality of patients based on a criterion such as whether each patient of the plurality of patients survived during an outlier time period; determining a difference between a number of patients in the first subgroup and the second subgroup; and selecting a data value that results in the difference that is a largest difference between a number of patients in the first subgroup and the second subgroup.

This procedure may be repeated for each data value of each characteristic. For example, for embodiments in which the characteristic relates to an age then the data values include a range of ages, beginning with a lower age range such as age 18, 19, 20, 21, . . . to an upper limit such as age 115 (or another suitable value). In one particular example, if age=20 and the time period is x years (e.g. 5 years), then a first cohort of patients may be those who died x years after an age 20 diagnosis and a second cohort of patients may be those who did not die within x years of an age 20 diagnosis.

To determine the difference, the number of patients who did not survive within the particular time is considered a first subgroup of patients and the number of patients who did survive during the particular time is considered a second subgroup of patients. A difference is then determined between the number of patients in the first and second subgroups for each data value associated with each characteristic. The difference may be divided by the total number of patients in the first and second subgroups and expressed as a decimal value between 0 and 1 (e.g. if 400 patients died x years after age 20 diagnosis and 100 patients did not die x years after age 20 diagnosis, then the difference 400−100=300, which is divided by the total number in the two groups, 500, to get a difference of 0.6). The particular data value having the largest such difference may be retained while the procedure is being performed in order to determine a node for the tree structure (e.g. the largest difference may be a difference of 0.7 at age=44).

The method may further include creating a new node of the tree structure based on the data value that results in the largest difference between the number of patients in the first subgroup and the second subgroup (e.g. a node may be created for age=44). Once the particular data value has been identified as having the largest difference, the method may then include creating branches from the node, including creating a first branch from the new node based on the first subgroup, and creating a second branch from the new node based on the second subgroup. Several examples of potential nodes may include the following: Smoking=Yes, Difference=0.8; DNA mutation=KRAS, Difference=0.78; Age=82, Difference=0.9; Gender=Male, Difference=0.6. Based on this information, the "Age" characteristic has the greatest difference and is selected, where branches may be created that are based on Age greater than or equal to 82 and Age less than 82.

The tree structure may continue to be built by repeating steps above, including steps of dividing the cohort into subgroups for each characteristic and each data value of each characteristic. The starting cohort in each subsequent repeated step is the group of patients in the particular node that is the starting point. This procedure is repeated at each node based on the patients in the first subgroup and the second subgroup, respectively. The procedure continues until one or both of the following conditions are met: (1) a maximum number of nodes or branches has been created, or (2) a node contains fewer than a minimum number of patients. When the procedure is complete, the method may include identifying at least one node from the tree structure which contains an outlier group of patients.

Smart Cohorts

In various embodiments, a prediction model may be developed which facilitates identification of one or more cohorts of patients whose disease progression and/or likelihood of survival is substantially different from expectation, for example significantly longer or shorter than would be expected. Information from these cohorts may then be examined to identify one or more primary factors that could potentially contribute to the survival profile of the cohorts. Identification of smart cohorts may be used to provide precision medicine results for a particular patient, aid in the identification of potential areas of interest to target medication research, and/or identification of unexpected potential to expand medication patient targeting.

Given a set of patient timelines, in various embodiments the objective of the smart cohorts module will be three-fold, attempting to answer one or more of the following questions:

1. What is the likelihood of each patient surviving longer than Y years (or living progression-free for at least Y years) (i.e. "Survival"), measured at each event point in the patient's timeline;
2. What are the primary factors that most influence the expected survival outcome;
3. Which subsets of patients exhibit combinations of these factors such that they stand out as an outlier cohort in terms of their survival profile, relative to expectation, at a user specified anchor timeline event (e.g. at stage IV diagnosis), and what are these patients' characteristics;

This problem may be approached from a time series modeling perspective, with point in time snapshots of feature states, and a binary classification objective. In certain embodiments a tree-based supervised-clustering approach may be used to help identify patient groups of interest, although in other embodiments other analysis and visualization methods are also included.

The inherent temporal nature of the problem is complicated by the fact that target survival at anchor point T may be just as dependent on what happens to the patient after point T as it is on what happened prior to point T. As such, expected future survival cannot simply be modeled using event history alone and future events cannot be included in the model without invalidating the model as a recommender or accidentally introducing information leakage into the features, which could result in overfitting.

In certain embodiments a hybrid two-model approach may be taken. In one part of the approach, a historic only model is trained to derive "expectation" at each time point, and in another part of the approach a forward-looking clustering model is developed to isolate divergences between expected and observed survival, along with associated features.

Thus, in certain embodiments, the hybrid approach may include:

1. Building a dataset that only utilizes backward-looking features, derived at each event point on the timeline;
2. Training a model on such a dataset, to derive predictions for expected future survival at each time point;
3. Tagging these expected survival predictions at each time point to act as best-guess priors using all historic information content;
4. Building a "forward looking" feature set at each time point, ensuring not to permit implicit survival duration information be incorporated into the features (in some cases the historic priors may be included as features in this set as well); and
5. Training a "Summarization/Clustering" model using the forward looking feature set.

At this point, following the "training" step, a determination may be made regarding whether to limit how forward-looking the features for this part may be. For example it may not make sense to include a feature that is observed 2 years in the future if you are trying to predict 1 year survival likelihood. In addition one could also consider giving less importance to features that happen further away from the anchor event. Finally, one may consider excluding event points that are observed after the outcome event of interest, even if such events occur within the X-year boundary. For example, if the first progression event observed is within 6 months, and we are predicting 2 year PFS, then for that patient should exclude all events between 6 months and 2 years.

6. Comparing the expected survival predictions to the actual survival based on the forward looking model, for each of the forward-looking clusters, and identify clusters of high divergence from the expected survival predictions, along with their constituent forward-looking feature set.

Thus the model is directed to determining how future events may impact an expected survival that is predicted by prior events, agnostic to whether the expected survival prediction for a particular sub-cluster is higher than the expected survival prediction for a different cluster (although the root cause of a divergence in expected survival predictions would also be of interest). That is, it is of interest to know whether the next actions have an impact on the patient's survival, or whether patient survival is mainly determined by their already-experienced events.

Figure 26:
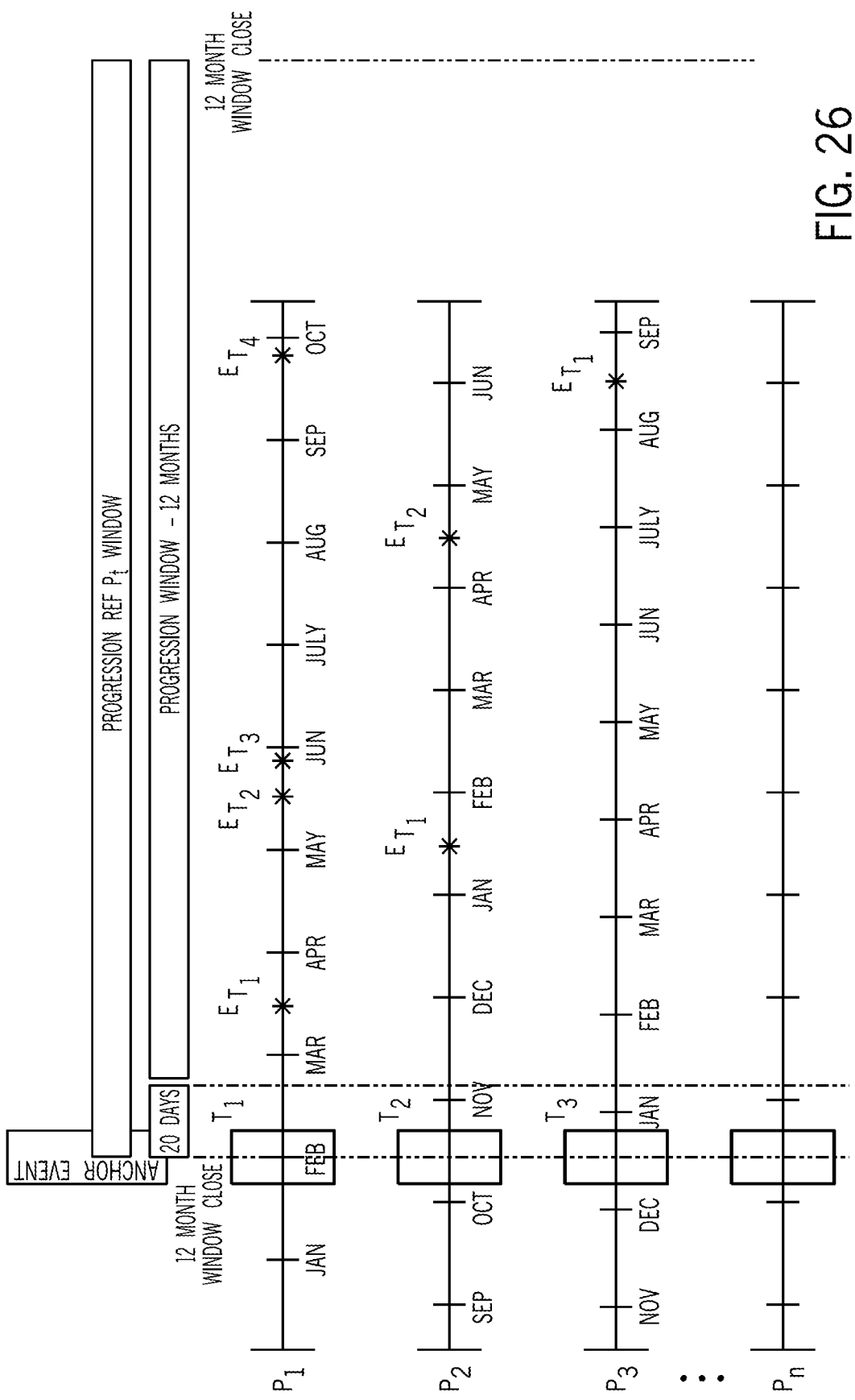
FIG. 26 shows a sample timeline of an anchor event with an associated progression window.

The prediction model may be implemented based on data from a large number of patients, using information about the patients' medical history and treatments along with information about their survival. In order to chronologically align the data from numerous patients, one or more anchor points (also referred to as "patient timepoints") may be identified within the data (FIG. 26). The anchor points identify points in time that may be common to all or at least many of the patients and which may help to standardize the time course of the data relative to events such as disease progression. The anchor points may include events such as time of first diagnosis, time of first metastasis, or time of first treatment, although other anchor point events are also possible. FIG. 26 shows an alignment of timelines for patients $P_1$, $P_2$, $P_3$, . . . , $P_n$ based on a common anchor event.

There may be some imprecision with regard to the time of certain anchor point events, for example a date of first diagnosis may occur several weeks earlier or later for a given patient (e.g. relative to when the disease began) due to the time that the patient first notices symptoms or sees a clinician to receive the diagnosis to account for the lack of precision. Therefore, in certain embodiments the anchor points may include a tolerance window before and/or after the date of the anchor point which can provide flexibility in the modeling procedure. In various embodiments, the tolerance window may be +/−1 day, 3 days, 1 week, 2 weeks, 1 month, 2 months, 3 months, or other suitable time period.

FIG. 26 shows a diagram of an anchor event (set to January 1) followed by a progression window of 12 months. The anchor event may have a tolerance window of +/−15 days associated with it. In addition, the progression window may have a 3 month tolerance window and thus a progression reference point window may extend backward in time 3 months prior to January 1, to October 1.

With regard to the predictive model, in various embodiments a plurality of data is obtained or received for a plurality of patients, covering a period of time (e.g. a time span covering each of the patients' medical history from the time of their diagnosis until the current time or a time of death, medical history may also begin before diagnosis).

The data may be processed to identify a plurality of patient timepoints (anchor points) that occur within the period of time covered by each patient's data. As discussed above, the anchor points or patient timepoints may include timepoints associated with any patient interaction with the medical system, including any interaction with an individual or facility that provides medical care or obtains medical information such as a care provider, a genetic sequencing organization, a hospital outpatient or inpatient facility, etc. The patient timepoints may be identified by a date attached to or associated with each piece of data in the received set of patient data.

In general both temporal and static features may be derived from the patient data but the analysis at this stage is purely backward-looking to avoid leaking future information. Different categories or classes of features include: "time since last/first XXX"; "number of XXX"; or "demographics." Extracting features may include multiple look-back horizons, for example features may be bounded to the trailing 12 months or may be based on continuous historic analysis.

In one particular example, four timepoints may be identified for a hypothetical patient A: date of biopsy collection, Jul. 1, 2018 (KRAS PL1S147GLU mutation with high SNP effect identified); start anastrozal and lotinib administration, Aug. 1, 2018; radiation therapy performed, Nov. 1, 2018; therapy outcome reported: progression of disease from stage 1 to stage 2, Jan. 1, 2019; imaging performed, Jul. 1, 2018 and Nov. 1, 2018. Other patients B, C, D . . . will each have their own sets of timepoints which may correspond to some of the same events (e.g. diagnosis, start medication, imaging, etc.) or to different events, or to a combination of some of the same events and some different events.

Based on the data for each of the patients and for each patient timepoint, an outcome target for an outcome event may be calculated within a horizon time window; a plurality of prior features may be identified; and a state of each of the plurality of prior features at the patient timepoint may be determined. An outcome event may include a state of the patient and/or the disease, such as progression or death, and the outcome target may be described with a target label such as a yes or no indication of whether the outcome will occur within a particular horizon time window from the patient timepoint/anchor point, along with a date of the endpoint. The horizon time window may include any suitable periods of time such as 3 months, 6 months, 9 months, 12 months, 24 months, 36 months, 48 months, or 60 months, or other periods of time.

In the case of hypothetical patient A, the analysis of a progression event occurring within 6 months of a timepoint is as follows:
   Patient A: Jul. 1, 2018—Progression within 12 mo. —Yes, Jan. 1, 2019
   Patient A: Aug. 1, 2018—Progression within 12 mo. —Yes, Jan. 1, 2019
   Patient A: Nov. 1, 2018—Progression within 12 mo. —Yes, Jan. 1, 2019
   Patient A: Jan. 1, 2019—Progression within 12 mo. —null Since the data for patient A included information of a report of progression from stage 1 to stage 2 on Jan. 1, 2019, there is a valid outcome target for "progression within 12 months" for each of the first three time points: "yes." However, the analysis for the final time point is indicated as "null" because no patient information is available after this date from which to inform the model. Although progression was reported on this date, no further information is available for patient A after this date.

The prior features may include various features related to a patient's medical condition and/or treatment. In various embodiments the prior features may include temporal/time-based events or features, structural or biological features, or molecular/genetic features, among other categories. In particular embodiments the prior features may include one or more of: time since starting a particular medication; time since taking a particular medication; time since last progressive therapy outcome (e.g. patient response to drug); time since metastasis; largest tumor size to date/last recorded tumor size; most severe effect of identified SNP (e.g. low effect, high effect); or RNA features (e.g. expression level per gene/transcript). In some embodiments the data may require additional processing, such as using an autoencoder, to reduce dimensionality of the feature space.

A state of each prior feature may be determined at each of the patient timepoints. For hypothetical patient A, the state of three features (time since starting medication A, time since last imaging, and highest SNP effect as identified by lab A) for each of the four patient timepoints is shown below (note that the value for "time since taking medication A" at the first patient timepoint is "null" since patient A did not take medication A until the next timepoint):
   Patient A: Jul. 1, 2018
   Time since starting medication A: null
   Time since last imaging: 0 days
   Highest SNP effect as identified by lab A: Germline: KRAS: High (5)
   Patient A: Aug. 1, 2018
   Time since starting medication A: 0 days
   Time since last imaging: 1 month
   Highest SNP effect as identified by lab A: Germline: KRAS: High (5)
   Patient A: Nov. 1, 2018
   Time since starting medication A: 3 months
   Time since last imaging: 0 days
   Highest SNP effect as identified by lab A: Germline: KRAS: High (5)
   Patient A: Jan. 1, 2019
   Time since starting medication A: 5 months
   Time since last imaging: 2 months
   Highest SNP effect as identified by lab A: Germline: KRAS: High (5)

Next a plurality of forward features may be identified for each patient timepoint of the plurality of timepoints which has a valid outcome target and for each combination of horizon time window and outcome event. The combinations of horizon time windows and outcome events may include "progression within 6 months," "progression within 12 months," "progression within 24 months," progression within 60 months," "death within 6 months," "death within 12 months," "death within 24 months," death within 60 months," etc.

For patient A, using a horizon time window/outcome event combination of "progression within 12 months," the forward features may include:

Patient A: Jul. 1, 2018
 Will patient take medication A after timepoint and before date of endpoint (YES)
 Did patient take medication A before timepoint (NO)
 Highest SNP Effect As Identified by Lab A: Germline: KRAS: High (5)
Patient A: Aug. 1, 2018
 Will patient take medication A after timepoint and before date of endpoint (NO)
 Highest SNP Effect As Identified by Lab A: Germline: KRAS: High (5)
 Did patient take medication A before timepoint (YES)
Patient A: Nov. 1, 2018
 Will patient take medication A after timepoint and before date of endpoint (NO)
 Highest SNP Effect As Identified by Lab A: Germline: KRAS: High (5)
 Did patient take medication A before timepoint (YES)

At this point a plurality of sets of predictions for the plurality of patients may be generated based on the plurality of prior features and the plurality of forward features, and a prediction model may be generated based on the sets of predictions using machine learning. In some embodiments the prediction model may be generated using gradient boosting.

Figure 28:
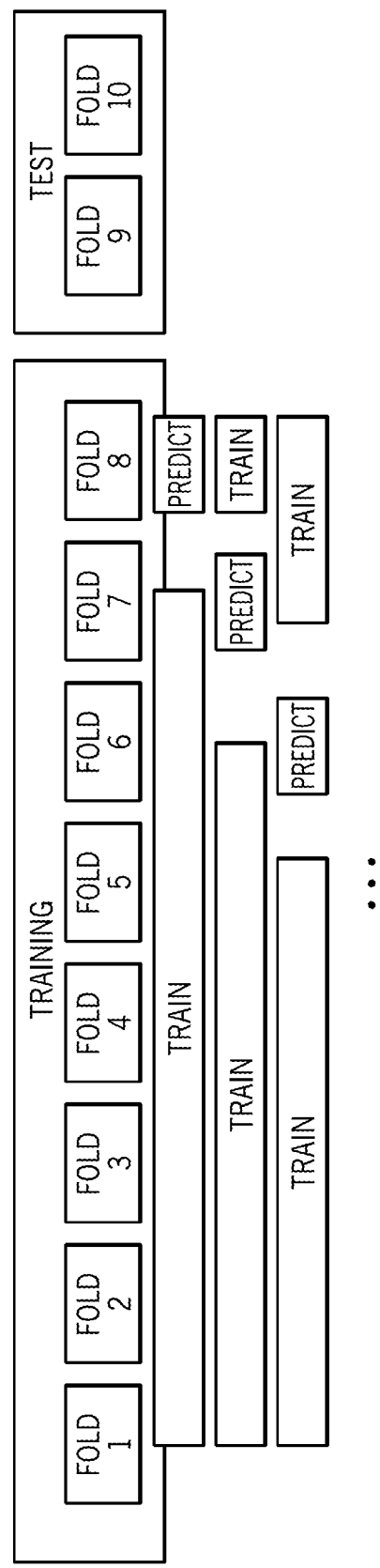
FIG. 28 shows an example of using patient folds for cross-validation.

The plurality of sets of predictions may be divided into several folds, where each fold includes data corresponding to a subset or subgroup of the plurality of patients such that the data for each patient is kept within the same fold (FIG. 28). Thus the machine learning procedure such as gradient boosting may be trained using a subset of the folds. For example, if there are 8 folds, the gradient boosting algorithm may be performed on 7 of the 8 folds. The remaining fold(s) that are not used for training are then run through the model for predictive purposes and the difference between the predicted and actual results may be used to adjust the model before a subsequent round of training is performed. This may be repeated with different folds being omitted from the training step and used for prediction and/or adjustment of the model. More generally, if there are N folds training may be performed on X<N folds and predictions may be performed using N-X folds. In generating the prediction model, various parameters may be adjusted or tuned (depending on the type of model), including learning rate, maximum depth of tree, minimum leaf size, etc. The goal is a model which learns the relationships between the prior features across all patients that lead to the target results. Predictions are received from each patient timepoint from the model and are tied or associated with a corresponding outcome target. In some embodiments, 8 folds may be cross-validated while an additional 2 folds may be complete holdouts for separate testing purposes. Folds may be stratified by a combination of multiple features such as target, gender, cancer, patient event count, etc.

Having generated the plurality of predictions, this information may be used to identify one or more "smart cohorts," that is, one or more cohorts of patients whose disease progression and/or likelihood of survival is substantially different from expectation, for example significantly longer or shorter than would be expected. In general, a decision tree may be constructed using the prediction information to identify various potential smart cohorts, which end up being grouped in various leaf nodes of the decision tree. Disclosed herein are two approaches for constructing decision trees which are referred to as Offline Smart Cohorts and Online Smart Cohorts.

Offline Smart Cohorts

In certain embodiments, a method for identifying a cohort of patients may be developed. The method may include selecting a cohort of patients including a plurality of patients, for example a cohort of 500 breast cancer patients. In general, the cohort may be selected based on the patients having a particular condition in common, e.g. a particular disease.

The method may also include identifying a common anchor point in time from a set of anchor points associated with each of the group of patients, where the common anchor point is shared by each of the group of patients in the cohort. Selecting a common point between all patients facilitates visualization of the data and also makes it possible to prevent the same patient from appearing in the model multiple times at each of the patient's available anchors. The possible anchor points include time of diagnosis, times of treatments, time of metastasis, and others. In one particular embodiment, the time of diagnosis may be selected as the anchor point.

For each patient in the group of patients, a timeline associated with each of the group of patients may be aligned to the common anchor point. Next an outcome target may be identified, such as disease progression within 12 months. Subsequently, the plurality of sets of predictions that were previously generated, each of which includes a predicted target value, may be retrieved for each patient of the group of patients and for each of the plurality of forward features and the plurality of prior features. The predictions may include information such as that shown in Table 1:

TABLE 1

| Patient | Target Prediction | Target Actual | Feature Sets |
|---|---|---|---|
| A | 0.95 | 1 | A B C D |
| B | 0.93 | 1 | A C D F G |
| C | 0.25 | 0 | B D F |
| D | 0.1 | 0 | A C D G |

More generally, the "target prediction" may take the form of: "Probability for Survival (PFS) in X months," "Death in X months," "Likelihood of taking medication in X months," "Likelihood of other targets in X months," etc. and may be in the form of a decimal value between 0 and 1. The "target actual" value is essentially a binary, yes/no value that is shown as a 1 or a 0 and represents the occurrence or non-occurrence of the event within X months. In various embodiments the feature sets may include prior features and/or forward features, for example any of the features disclosed herein including those listed under the heading of "Features and Feature Models." The prior features may include one or more of Age, Gender, Treatments (e.g. medications, procedures, therapies, etc.), Sequencing/Lab/Imaging results. The forward features, which are discussed further below, may include events, treatments, etc. that happen in the future between the anchor point and the observed target.

In various embodiments, hundreds or thousands (or other, greater numbers) of decision trees may be generated using this information, for example using a procedure similar to that described above for the Outliers procedure. For each of the decision trees that is constructed, for each feature of the plurality of forward features and the plurality of prior features, the following steps may be carried out.

The group of patients may be divided into a first subgroup and a second subgroup based on a difference between the predicted target value and an actual target value;

A difference between a number of patients in the first subgroup and a number in the second subgroup may be determined, and A feature which results in the difference that is a largest difference between a number of patients in the first subgroup and the second subgroup may be selected.

A new node of the tree structure may be created based on the feature that results in the largest difference between the number of patients in the first subgroup and the second subgroup. A first branch may be created from the new node based on the first subgroup, and a second branch may be created from the new node based on the second subgroup. The steps of building the decision tree may then be repeated for each of the first branch and the second branch based on patients in the first subgroup and the second subgroup, respectively. This may continue as the tree is completed as defined by either: a maximum number of nodes or branches has been created, or a particular node contains fewer than a minimum number of patients for all nodes and branches.

The goal of constructing the decision trees is, for each patient and based on the features in the feature set, to predict the difference between the prediction and the actual outcome for the target by clustering the patients based on which features most accurately predict the difference between the prediction and the actual outcomes.

In certain embodiments, the method may include determining a similarity metric by determining how often a given patient ends up in a same leaf node of the trees with other patients across the hundreds or thousands of decision trees. Thus, for each patient of the group of patients, the method may include identifying a co-incidence of the given patient occurring within each of the plurality of leaf nodes, across the hundreds or thousands of decision trees, with each of the other of the plurality of patients. The similarity metric may be determined for the given patient based on a sum of the co-incidence divided by a total number of nodes the given patient is in across all of the hundreds or thousands of decision trees that are constructed and analyzed. In some embodiments a database of patient-patient similarity metrics may be generated based on determining the similarity metric for each of the plurality of patients. In other embodiments the similarity metric may be displayed, e.g. as a cohort radar plot. Further, data may be displayed in association with one or more of the steps outlined above to identify at least one of the plurality of features.

The method may further include determining a similarity metric for a new patient, i.e. a patient different from the initial group of patients. The new patient may be matched with a subgroup of patients corresponding to a particular leaf node of the plurality of leaf nodes based on determining the similarity metric. A treatment may then be identified for the new patient based on matching the new patient with the subgroup of patients. Further, the database of patient-patient similarity metrics may be processed using a dimensionality reducing algorithm to identify a particular cohort of patients having a shared feature such as a shared prior feature or a shared forward feature. In general, dimensionality reduction identifies a certain subgrouping (such as K subgroups) where each of the subgroups 1-k has certain characteristics in common across the grouping that is identified from the entire patient cohort (standard population grouping).

Online Smart Cohorts

In addition to the plurality of predictions, the system may receive an outcome target, a subset of the plurality of forward features corresponding to the outcome target, and a cohort of patients including a subset of the plurality of patients. The cohort may be a group that shares a condition or trait of interest, for example the cohort may be a group of 20,000 breast cancer patients. This group will then be subdivided using the decision tree to find one or more particular subgroups of interest for further investigation.

Table 2 shows an example of the type of prediction data that might be received:

TABLE 2

| Patient | Timepoint | Prediction | Target | Feature Sets |
| --- | --- | --- | --- | --- |
| A | T1 | .95 | 1 | C D |
| A | T2 | .75 | 1 | B C |
| A | T3 | .66 | 0 | A B C D |
| B | T4 | .92 | 1 | A E F G |

The forward features may include various future actions or conditions that relate to the patients and in certain embodiments could be used to advise patients who have a particular condition. Some of the forward features may be "actionable," that is, they may include things that a given patient could do to possibly change their prognosis or outcome. For example, a doctor or other clinician could take certain steps or actions (e.g. prescribe a medication or combination of medications; prescribe a particular treatment such as surgery, chemotherapy, or radiation; or send a tumor sample for sequencing to receive molecular information such as a test for a DNA marker) to improve the patient's prognosis. Certain molecular features may or may not be considered actionable, based on whether the molecular information that is obtained is associated with a subsequent action or step. In various embodiments, features such as lab results, imaging results, tumor characterization (e.g. histology, grade, TNM stage, etc.) may not be included as forward features in order to avoid making a suggestion to a patient to take an action that is not within their control such as "lower N stage", "increase hemoglobin density", etc.

In various embodiments, this information could be used to counsel a particular patient group, e.g. for N Stage patients with X mutation, treatment A and B taken together improve probability for survival (PFS) within 12 months. For example, Stage 4 Breast cancer patients with the KRAS mutation are expected to progress based on their placement in a cohort (90% progression prediction) and should take anastrozal and lotinib together as an intervening therapy to improve PFS within 12 months (60% progression prediction) based on predictions after the selected anchor point of time of first metastasis. Other specific courses of action could be determined based on the data.

Examples of predictions include predictions of probability for survival within 12 months, for Patient A and B and timepoints T1 (Jan. 1, 2018) and T2 (May 1, 2018), expressed as a probability value between 0 and 1, as shown in Table 3:

TABLE 3

| Patient | Timepoint | Prediction |
| --- | --- | --- |
| A | Jan. 1, 2018 | .95 |
| A | May 1, 2018 | .75 |
| B | Jan. 1, 2018 | .92 |

The outcome target may be a probability for survival within 12 months, given as a 0 or 1, as shown in Table 4:

TABLE 4

| Patient | Timepoint | Prediction |
|---|---|---|
| A | Jan. 1, 2018 | 1 |
| A | May 1, 2018 | 1 |
| B | Jan. 1, 2018 | 1 |

Below is an example of a subset of the plurality of forward features (FD1, FD2, FD3, each indicated below) corresponding to the outcome target including forward data corresponding to probability for survival within 12 months:

Jan. 1, 2018:
  FD1 (Patient will take anastrozal and lotinib): (YES)
  FD2 (Patient will have radiation therapy): . . . .
  FD3 (Patient will have surgery): . . . .
May 1, 2018:
  FD1 (Patient will take anastrozal and lotinib): (YES)
  FD2 (Patient will have radiation therapy): . . . .
  FD3 (Patient will have surgery): . . . .

The system may also receive an anchor point or patient timepoint, e.g. a time of first diagnosis, a time of first metastasis, a time of first treatment, etc.

A subset of the plurality of forward features may be selected. These features may include medications (future and historic) as well as sequencing (somatic sequencing (future or historic), germline sequencing, etc.). For each patient in the cohort having the anchor point, the prediction model may be provided with the selected subset of the plurality of forward features and a difference may be determined between each of the plurality of predictions and the outcome target.

For example, the model may receive data such as:
Patient A: [.95-1], [Medications and sequencing data sets]
Patient B: [.92-1], [Medications and sequencing data sets]
Patient C: [.63-0], [Medications and sequencing data sets]

The data may include information such as "medications and sequencing data sets at the anchor point" which may include an N×M table of patients and respective features. The respective features may include information such as:

Patient A: Jul. 1, 2018 (date of anchor point)
  Col. 1: Will patient take medication A after timepoint and before date of endpoint (YES)
  Col. 2: Did patient take medication A before timepoint (NO)
  Col. 3: Highest SNP Effect As Identified by Lab A: Germline: KRAS: High (5)

Subsequently, for each feature of the selected subset of the plurality of forward features, a decision tree may be generated based on determining a greatest difference between each of the plurality of predictions and the outcome target. The decision tree may include a plurality of leaf nodes and one or more branch nodes, and each of the one or more branch nodes may include a pair of branches each of which includes a leaf node or a branch node, where the branches are formed based on a feature selected from the subset of the plurality of forward features.

Each of the plurality of leaf nodes of the decision tree may include a number of patients from the cohort of patients. In some embodiments, the decision tree may continue to split based on the difference between each of the plurality of predictions and the outcome target until the number of patients in a particular leaf node of the plurality of leaf nodes is less than a minimum number of patients. In other embodiments, the decision tree may continue to split based on the difference between each of the plurality of predictions and the outcome target until the number of levels of the decision tree has reached a particular number, that is, is equal to a maximum number of levels. In one specific example, each patient's status with regard to a feature "KRAS Somatic: Historical >3" may be used to split a branch node to two branches based on whether each patient's historical importance value for this marker is greater than 3 (high importance).

The leaf nodes of the decision tree provide information that may be used to identify cohorts of interest. In some cases leaf nodes may have high values for the prediction target since prediction values are on average much higher than target values. For patient C in the examples above, the prediction indicated that it was likely that patient C's condition would progress but in fact it did not. In other cases leaf nodes may also generate low negative values for the difference of "prediction minus target"; for example, a prediction minus target may be [0.05-1]=−0.95, which would indicate that the patient's condition would be unlikely to progress but in some instances it may still progress. However in certain cases the leaf nodes may have a value of approximately zero, which indicates that the model has made an accurate prediction. The Smart Cohorts procedure focuses on the instances where patients' actual outcomes have greatly deviated from the expected result because these groups of patents can provide information as to what can be done to change the trajectory of a disease progression, whereas the cohorts where the prediction-target differences are closest to zero inform the model on what features are most important to a reliable prediction.

In some embodiments, analytics may be performed on one or more of the leaf nodes of the decision tree, where the analytics parse the branches of the leaf to render them meaningful. Only subsets of features that are sent to the model will be considered for creating splits. In one embodiment in which the subset of features includes "medication" and "molecular," a particular leaf may show "Variant effect on KRAS (somatic) protein (post-anchor): >1" (a molecular feature) and "Will not take medication: Pembrolizumab" (a medical feature). Thus, analytics may be performed on the data to improve the overall quality and to improve the accuracy of the splitting and the resulting leaf nodes. In a particular case (although not relevant to the case in which medication and molecular features are used for splitting), analytics may be used to parse branching information to make otherwise ambiguous information meaningful: information indicating "Gender not male" may be set to "gender female."

In another instance, which relates to the model in which splitting is based on medication and molecular features, the analytics may be used to map data to particular categories and/or ranges to render the data meaningful. For example, a range may be presented as:

Variant effect on KRAS (somatic) protein (post-anchor):
  =>1,
which may map to:
Variant effect on KRAS (somatic) protein (post-anchor):
  =1 ('negative',
where the term 'negative' indicates 'tested and confirmed not to be mutated' (as opposed to unknown status).

In certain embodiments the analysis which leads to generating branches from a node requires that all of the patients in the resulting leaf nodes meet the particular requirements, that is, the procedure may require 100% cohort participation to form branches. In some cases, however, features derived from the tree may miss statistically relevant cohort features due to this requirement for 100% cohort participation. Therefore in certain embodiments a Subset Aware Feature Effect (SAFE) algorithm may be run to allow features which are shared by fewer than all of the patients (e.g. shared by 95%) of the leaf cohort but not all (e.g. 95%) of patients in the whole cohort to be included in a particular leaf.

In various embodiments the smart cohorts algorithm may be run in an observational mode (which does not use predictions and uses targets only, e.g. 0 or 1) or an algorithmic mode (which uses predictions, e.g. prediction—target [0.95-1]).

The SAFE algorithm has been developed to return viable feature importance ranks based on the selected sub-population of patients, without a need for re-training of the underlying models. Given the predictions from a pre-trained global multi cancer type model on the patient population, the SAFE algorithm may derive approximate high level importance ranks interactively and quickly. In addition, the feature importance ranks may be intelligently and dynamically adjusted to be relevant given a selected subset cohort of the population, without needing to re-train the global model. To optimize interpretability, in certain embodiments the SAFE feature importance algorithm may be agnostic of the underlying machine learning model that was used and may be made to cleanly handle assigning appropriate importance to correlated features. The SAFE algorithm may also provide the ability to explore feature importance on "feature+prediction" datasets for which targets may not necessarily have been defined. Finally, for more continuous features, the SAFE algorithm may enable deeper exploration of the change in feature importance with varying feature value.

In one embodiment, the SAFE algorithm may include calculating a population mean prediction. The algorithm may then include encoding categorical feature levels as the delta between the predicted value and the population mean prediction, where infrequent levels may be grouped together. The algorithm may further include clustering or bucketing of continuous features and processing these features as in the previous step. Next the algorithm may include, for each feature, aggregating an average (p-E(p)) per categorical level. Finally, the algorithm may include, for each feature, assigning an overall feature importance as the frequency-weighted sum of an absolute value of all values.

As can be seen using the above-described approach, the algorithm does not rely explicitly on the presence of a target variable for deriving an importance ranking and instead only requires features and predictions. As such, it can effectively be applied to predictions made on unlabeled datasets, as well generalizing to predictions obtained from different types of machine learning (ML) algorithms.

FIGS. 27A and 27B show an example of adaptive feature ranking in accordance with embodiments of the SAFE algorithm. FIG. 27A shows a list of top 10 features from an overall model, which is based predominantly on breast cancer patients. FIG. 27B shows a list of top 10 features from the dataset from FIG. 27A after creating a subset directed to colorectal stage 4 patients. As can be seen in FIG. 27B, certain features that are more likely to be associated with colorectal patients (e.g. "historical-took_medication: irinotecan" and "historical-took_medication: bevacizumab") have a higher ranking and higher value in the subset directed to colorectal stage 4 patients. On the other hand, features that are not related to colorectal stage 4 patients (e.g. "cancer: lung_cancer" and "cancer: pancreatica_cancer") do not show up in the list in FIG. 27B. FIG. 27C continues with the example of FIGS. 27A and 27B and shows an example of handling of correlated features. Continuing with the colorectal example from FIG. 27B, FIG. 27C shows that, upon addition of duplicated dummy columns based on the following two features: "historical-took_medication: irinotecan" and "historical-took_medication: capecitabine," these duplicated columns properly sort with the other values associated with colorectal stage 4 as would be expected.

Figure 27D:
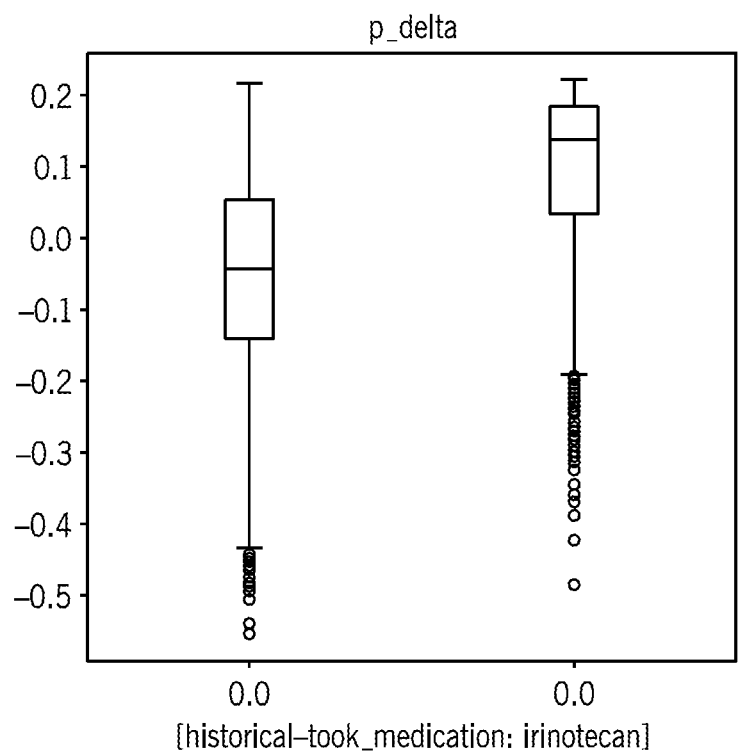
FIGS. 27D and 27E show an example of sample-level importance assignment in accordance with embodiments of the SAFE algorithm.
Figure 27E:
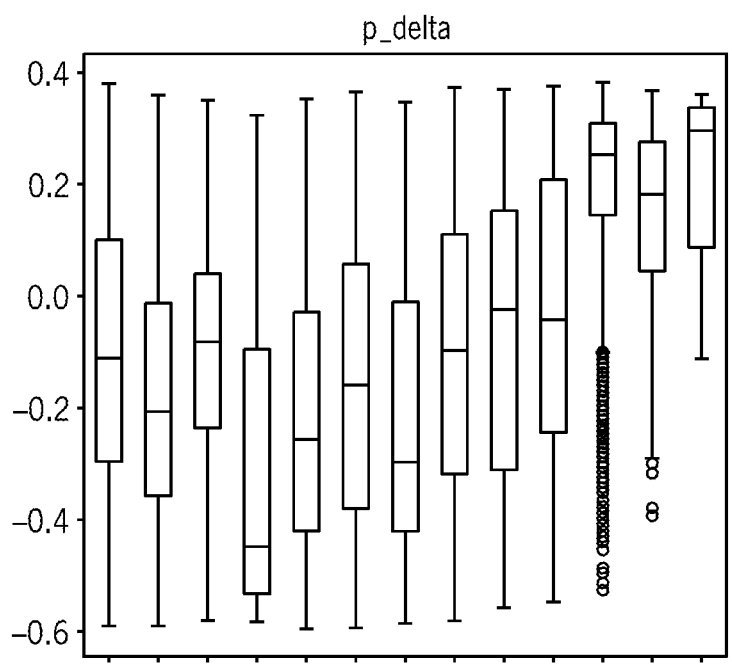

FIGS. 27D and 27E show an example of sample-level importance assignment in accordance with embodiments of the SAFE algorithm. Given the derivation of the SAFE algorithm, one benefit is that each instance of each feature value gets assigned an "impact" value representing its co-occurrence with an observed deviation from prediction mean, which in turn allows one to explore the variation in impact per change in feature value. FIG. 27D shows a boxplot grouped according to the feature of "historical-took_medication: irinotecan." FIG. 27E shows a boxplot grouped according to last stage. FIG. 27D shows that features that co-occur with a "historical-took_medication: irinotecan" value of 1 have a greater impact than those associated with a value of 0, as would be expected for the colorectal stage 4 subset. FIG. 27E shows a greater impact associated with later stages.

Although the SAFE algorithm does not directly factor in feature interactions, these values may be derived from manually constructed composite features. In addition, the SAFE algorithm is geared towards conveying how each feature impacts the predicted values from the underlying model, which is used as an indirect proxy for feature importance to predicting the target, although this will be subject to the efficacy of the model.

Notebooks

In various embodiments, one or more statistical models and analyses may be combined to accommodate a particular purpose and, through a variation of the initial analysis, may be used to solve a number of problems. Such a combination of statistical models and analyses may be stored as a notebook in the Interactive Analysis Portal 22. Notebook is a feature in the Interactive Analysis Portal 22 which provides an easily accessible framework for building statistical models and analyses. Once the statistical models and analyses have been developed, they may then be shared with different users to analyze and find answers to scientific and business questions other than those for which they were initially developed.

1) The Interactive Analysis Portal 22 allows input customization through a simple, intuitive point-and-click/drag-and-drop interface to narrow down the cohort for analysis. Cohorts which have been selected, either through the Interactive Analysis Portal 22, Outliers, Smart Cohorts, or other portals of the Interactive Analysis Portal 22, may be provided to a notebook for processing.

2) A custom application interface (API) having a library of function calls which interface with the Interactive Analysis Portal 22, underlying authorized databases, and any supported statistical models, visualizations, arithmetic models, and other provided operations may be provided to the user to integrate a notebook or workbook with the Interactive Analysis Portal 22 data, function calls, and other resources. Exemplary function calls may include listing authorized sources of data, selecting a datasource, filtering the datasource, listing clinical events of the patients in the current filtered cohort, identification of fusions from RNA or DNA, identification of genes from RNA or DNA, identifying matching clinical trials, DNA variants, identifying immunohistochemistry (IHC), identifying RNA expressions, identifying therapies in the cohort, identifying potential therapies that are applicable to treat patients in the cohort, and other cohort or dataset processing.

3) The Interactive Analysis Portal 22 allows the Notebook generation to perform one or more statistical models, analysis, and visualization or reporting of results to the narrowed down cohort without having the user code anything in the notebook as the selected models, analysis, visualizations, or reports of the notebook itself are configured to accept the cohort from the Interactive Analysis Portal 22 and provide the analysis on the cohort as is, without user intervention at the code level. Some models may have hyperparameters or tuning parameters which may be selected, or the models themselves may identify the optimal parameters to be applied based on the cohort and/or other models, analysis, visualizations, or reports during run-time.

4) The Interactive Analysis Portal 22 displays the prepared results to the user based on the selected notebook.

5) An associated user may then select a previously generated notebook which applies selected analysis to the narrowed down cohort without having the user code or recode anything in the notebook as the notebook itself is configured to accept the cohort from the Interactive Analysis Portal 22 and provide the notebook results without user intervention.

6) Users may track the computation resources used by their notebooks for understanding the costs for cloud computing or hardware resources over the network and may track the popularity of their notebook to judge the effectiveness of the statistical analysis that they provide through the notebook.

In certain embodiments, notebooks provide a benefit to users by allowing the Interactive Analysis Portal 22 to provide custom templates to their selected data and leverage pre-built healthcare statistical models to provide results to users who are not sophisticated in programming. Internal teams may analyze curated data in order to support new healthcare insights that both help improve patient care and improve life science research. Similarly, external users have easy access to this proprietary real-world data for analysis and access to proprietary statistical models.

A billing model for a user may be provided on a subscription basis or an on-demand basis. For example, a user may subscribe to one or more data sets for a period of time, such as a monthly or yearly subscription, or the user may pay on a per-access basis for data and notebook usage, such as for loading a specific cohort with corresponding notebook and paying a fee to generate the instant results for consumption. Users may desire a benchmarking and optimization portal through which they may view and optimize their storage and computing resources uses.

Generating a notebook may be performed with a GUI for notebook editing. A user may configure a reporting page for a notebook. A reporting page may include text, images, and graphs as selected and populated by the users. Preconfigured elements may be selected from a list, such as a dropdown list or a drag-and-drop menu. Preconfigured elements include statistical analysis modules and machine learning models. For example, a user may wish to perform linear regression on the data with respect to specific features. A user may select linear regression, and a menu with checkboxes may appear with features from their data set which should be supplied to the linear regression model. Once filled out, a template for reporting the linear regression results with respect to the selected features may be added to the reporting page at a location identified by the active cursor or the drop location for a drag-and drop-element. If a user wishes to solve a problem using a machine learning model, it may be added to the sheet. A header may be populated identifying the model, the hypertuning parameters, and the reported results. In some instances, a model that was previously trained may then be applied to the current cohort. In other instances, the model may be trained on the fly, for example by selecting annotated features and associated outcomes for which the model should be trained. In an unsupervised machine learning model, the model may not require selection of annotated features as the features will be identified during training. In some embodiments, if a selected statistical model requires results from a trained model which are not computed in the template, the template may automatically add the trained model to generate the required results prior to inserting the selected statistical model to the notebook.

Statistical analysis models may be predesigned for calculating the arithmetic mean of the cohort with respect to a selected feature, the standard deviation/distribution of the cohort for a selected feature, regression relationships between variables for selected features, sample size determining models for subsetting the cohort into the optimal sub-population for analysis, or t-testing modules for identifying statistically significant features and correlations in the cohort. Other precomputed statistical analysis modules may perform cohort analysis to identify significant correlations and/or features in the cohort, data mining to identify meaningful patterns, or data dredging to match statistical models to the data and report out which models may be applicable and add those models to the notebook.

Machine learning models may apply linear regression algorithms, non-linear regression, logistic regression algorithms, classification models, bootstrap resampling models, subset selection models, dimensionality reduction models, tree-based models (such as bagging, boosting, and random forest), and other supervised or unsupervised models. As each model is selected, a target output may be requested from the user specifying which feature(s) the model should identify, classify, and/or report. For example, a user may select for the model to identify which features most closely correlate to patient survival in the cohort, or which features most closely correlate with a positive treatment outcome in the cohort. The user may also select which classification labels from the classification labels of the model that they wish the model to classify. In an example where the model may classify the cohort according to five labels, the user may specify one or more labels as a binary classification (patient has label, patient does not have label) such as whether a patient with a tumor of unknown origin originated from the breast, lung, or brain. The user may select only breast to identify for any tumors of unknown origin whether the tumor may be classified as coming from the breast or not from the breast.

Figure 29:
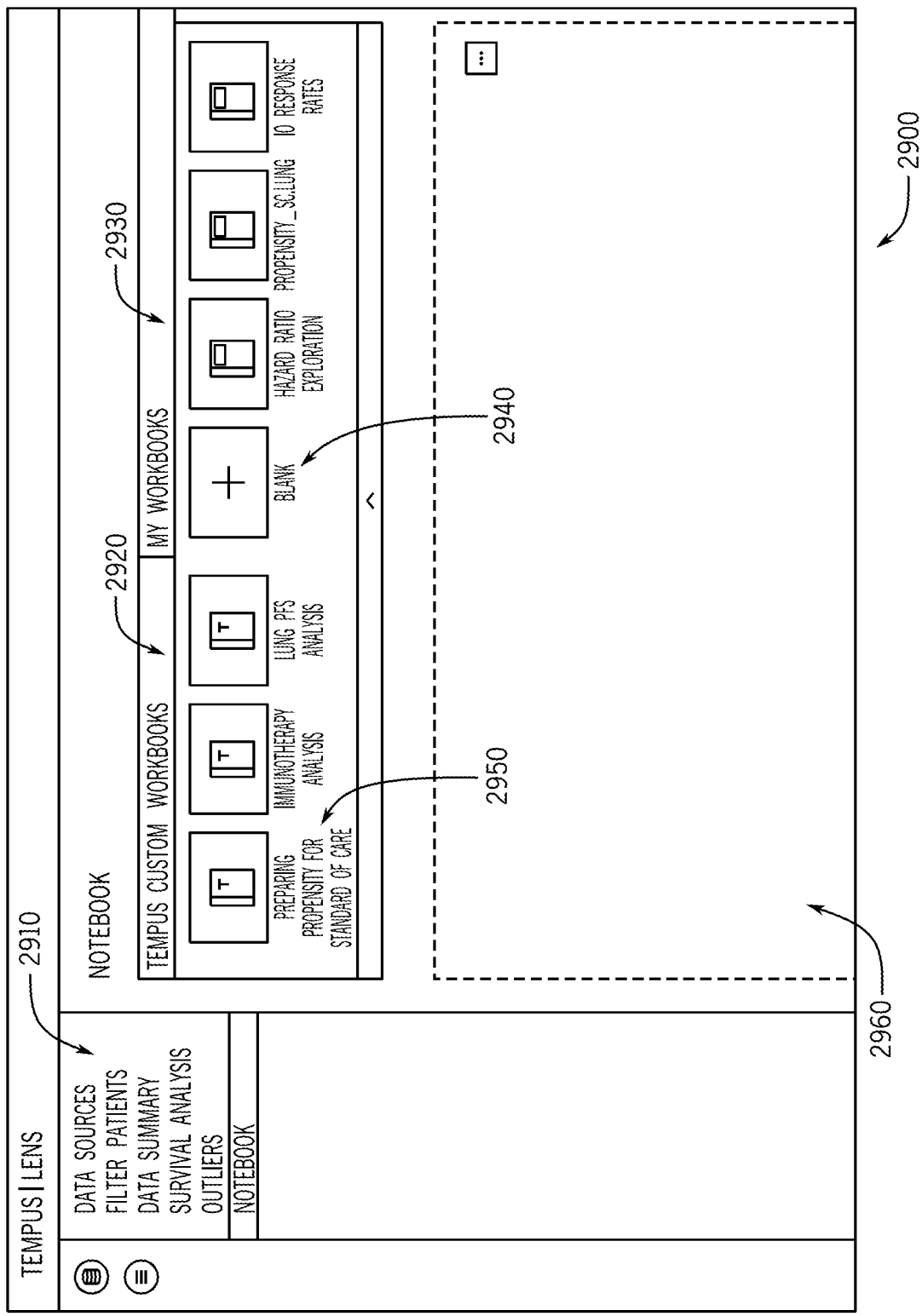
FIG. 29 illustrates an example of a user interface of the Interactive Analysis Portal for generating analytics via one or more notebooks according to certain embodiments.

FIG. 29 illustrates a user interface of the Interactive Analysis Portal 22 for generating analytics via one or more notebooks according to an embodiment.

The notebook user interface 2900 may be accessed by selecting Notebook from the Interactive Analysis Portal 22, such as via a sidebar menu 2910 either before or after filtering a database of patients to a desired cohort of patients via Interactive Cohort Selection Filtering 24.

Notebooks, or workbooks, may be internally curated at the company label by team members proficient in the fields of data science, machine learning, or other fields that routinely perform analytics on patient data and presented to the user via a custom workbooks widget 2920. The custom workbooks widget may be presented as a searchable list, searchable icons, a scrolling window which may scroll horizontally or vertically to display additional workbooks, or an expandable window which expands to provide access to all workbooks for which the user is authorized to access. A workbook may be represented by an icon and associated text, such as illustrated for workbook 2960. The user may also generate personalized workbooks which may be accessed via the my workbooks widget 2930. A workbook viewing window 2950 may be provided to view a workbook selected from widgets 2920 or 2930. New workbooks may be created by the user by selecting a blank workbook 2940. Upon selection of the blank workbook 2940, a workbook generation interface may open.

Figure 30:
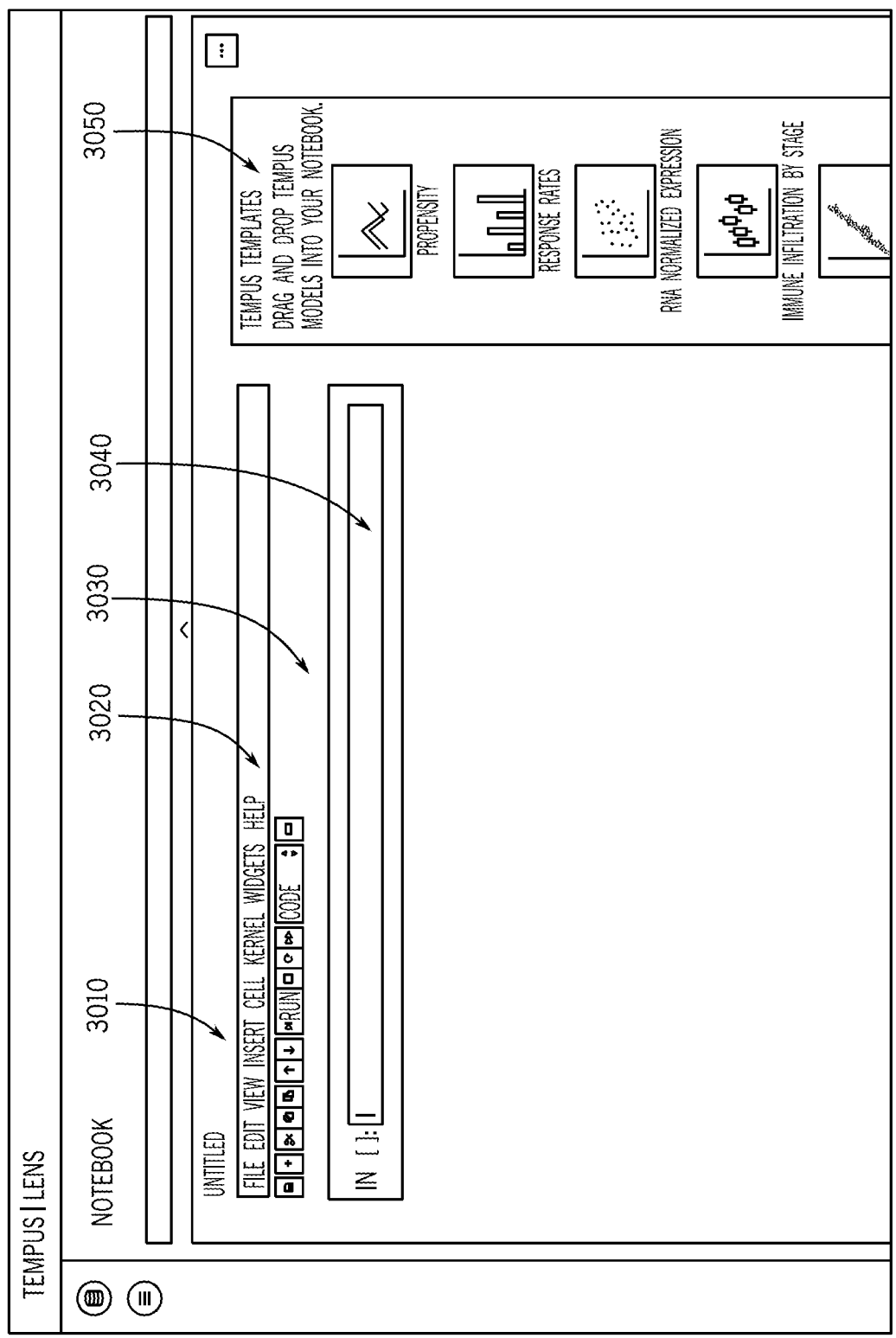
FIG. 30 illustrates a workbook generation interface of the Interactive Analysis Portal for creating a new workbook according to an embodiment.

FIG. 30 illustrates a workbook generation interface of the Interactive Analysis Portal 22 for creating a new workbook according to an embodiment.

Workbook generation interface 3000 may be provided to the user upon selection of a blank workbook from the notebook user interface. A text entry user interface element (UIE) 3010 may be provided to name the workbook for identification, searching, and indexing after generation. A series of button and drop down menu UIEs 3020 may be provided to compartmentalize grouped elements of the user interface. UIEs 3020 may assist the user in building and structuring the workbook's presentation. A cell UIE may provide selections pertaining to the currently selected cell of window 3040 having a block of code, such a commands for running the currently selected cell, terminating the currently selected cell, adding a cell, deleting a cell, running all cells, running all cells above, running all cells below, or terminating all cells. A kernel UIE may provide selections pertaining to one or more programming languages and/or available to the user such as Python, Structured Query Language (SQL), R, Spark, Haskell, Ruby, Typescript, Javascript, Perl, Lua, C, C++, Matlab, Java, Emu86, and other kernels. Selecting a kernel from the kernel UIE reloads the workbook so that the cells execute commands from the respective language. A widget UIE may provide selections pertaining to one or more supported code snippets for the active kernel. Code snippets may include code for creating visualizations such as a graph or a plot, code for simple arithmetic operations such as calculating a mean or a standard deviation, or code for more complex operations such as calculating a distribution and displaying a respective curve. A series of icon UIEs 3030 may be provided where each icon represents a popular command executed from the UIE 3020. Exemplary popular commands may include saving the document, adding a new cell, cutting or pasting code or cells, rearranging cells by moving them upwards or downwards down the page in relation to any other cells, or running/terminating the code in the active cell(s).

One or more cells may be present in window 3040 for a user to insert one or more lines of code for the active kernel. A user may enter code or commands into a cell which may operate on an active database or cohort of patients. Running the cell with execute the entered code or command. Outputs, such as stdout, error messages, or print statements may be displayed directly below the cell upon running. Additionally, a text widget may be inserted which will provide formatting and associated text based upon the code from one or more cells. Such a text widget may provide a simple, readable format for results from execute code. In one embodiment, a text widget may be presented as a markdown cell supporting HTML, indented lists, text formatting, TeX/LaTeX equations, and inline tables.

In one example, a code block may perform arithmetic on a matrix of values. An associated output, such as printing the matrix would result in a difficult to understand series of brackets, parentheticals, and commas. A visualization widget may receive a variable containing the matrix, and provide an image having the matrix values visible in a visible table format that represents a matrix instead of a potentially confusing text output. Cells accept all commands associated with each supported kernel and programming language. A cell may import a module or library from another source (such as dask, fastparaquet, pandas, or other libraries), support data structures, support conditional statements and logic loops, as well as establish and call functions. Cell output is generated asynchronously as the code runs so that the user may view the instantaneous output from the active code. If the output exceeds a preconfigured limit on the number of lines to display, the output may become scrollable text which may autoscroll with new entries or scroll upon user input.

One or more templates may be provided in template window 3050 for the user's convenience. Templates may include one or more cells preconfigured to operate on an input data such as the filtered patient cohort, run one or more cells of code to generate logical results, and run one or more cells of text or visualizations to report out the results of the performed logic on the input data in a convenient manner. Templates may exist for charts, graphs, regressions, dimension reductions, classifications, RNA or DNA normalization, and other commonly used features across templates available to the user. Templates may be provided with the dataset or custom created by a user to be shared with other users.

Figure 31:
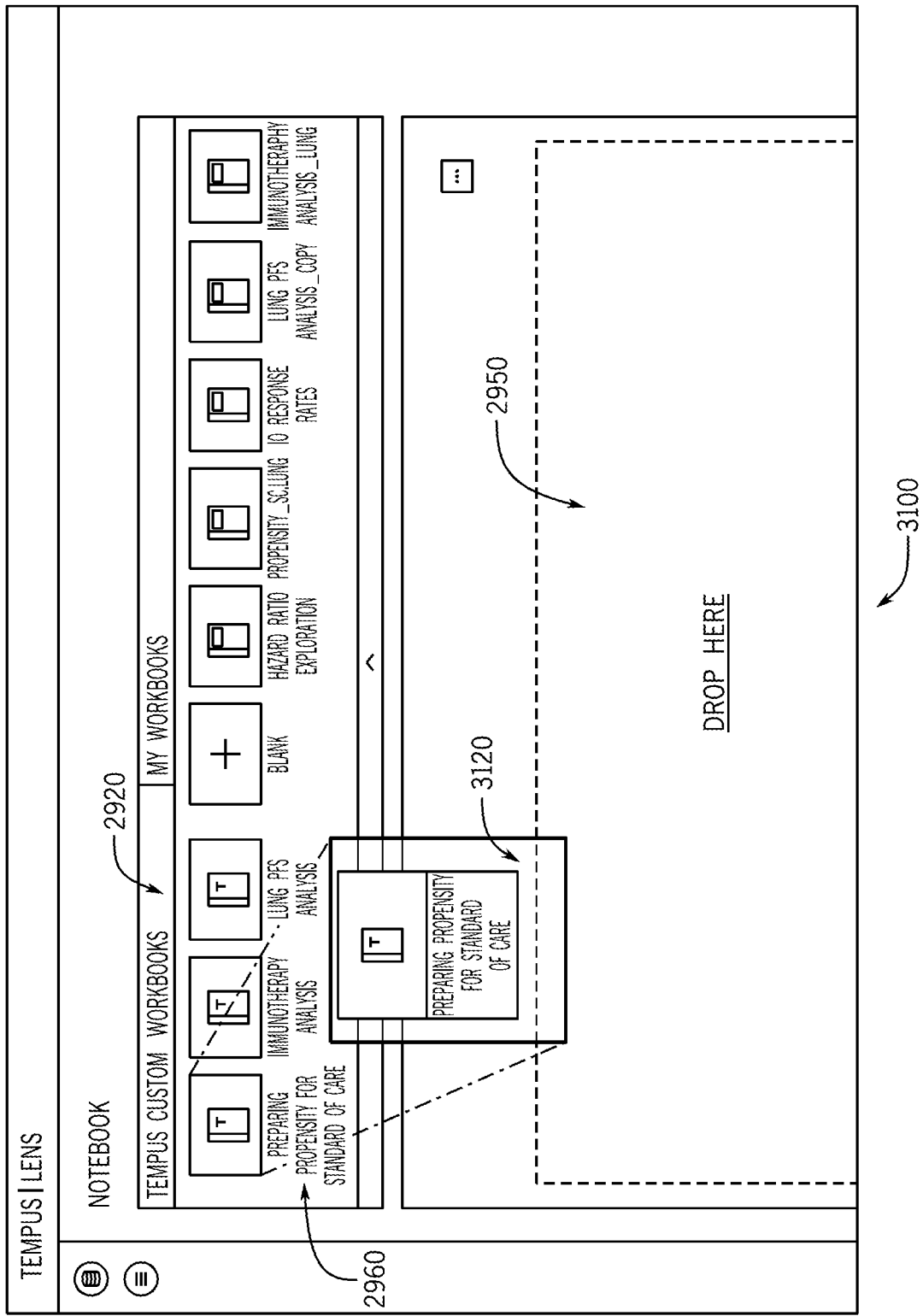
FIG. 31 illustrates opening a preconfigured template from the custom workbooks widget of the notebook user interface.

FIG. 31 illustrates opening a preconfigured template from the custom workbooks widget of the notebook user interface.

Returning to notebook user interface 2900, the user may populate workbook viewing window 2950 with a custom workbook from the custom workbook widget 2920 by clicking and dragging the desired workbook from the widget to the viewing window. In one example, the user may select workbook 2960 with the mouse cursor and drag the workbook to viewing window 2950 as illustrated at 3120. Other intuitive mouse, keyboard, or gesture commands may be implemented in place of, or in addition to, clicking and dragging.

Figure 32:
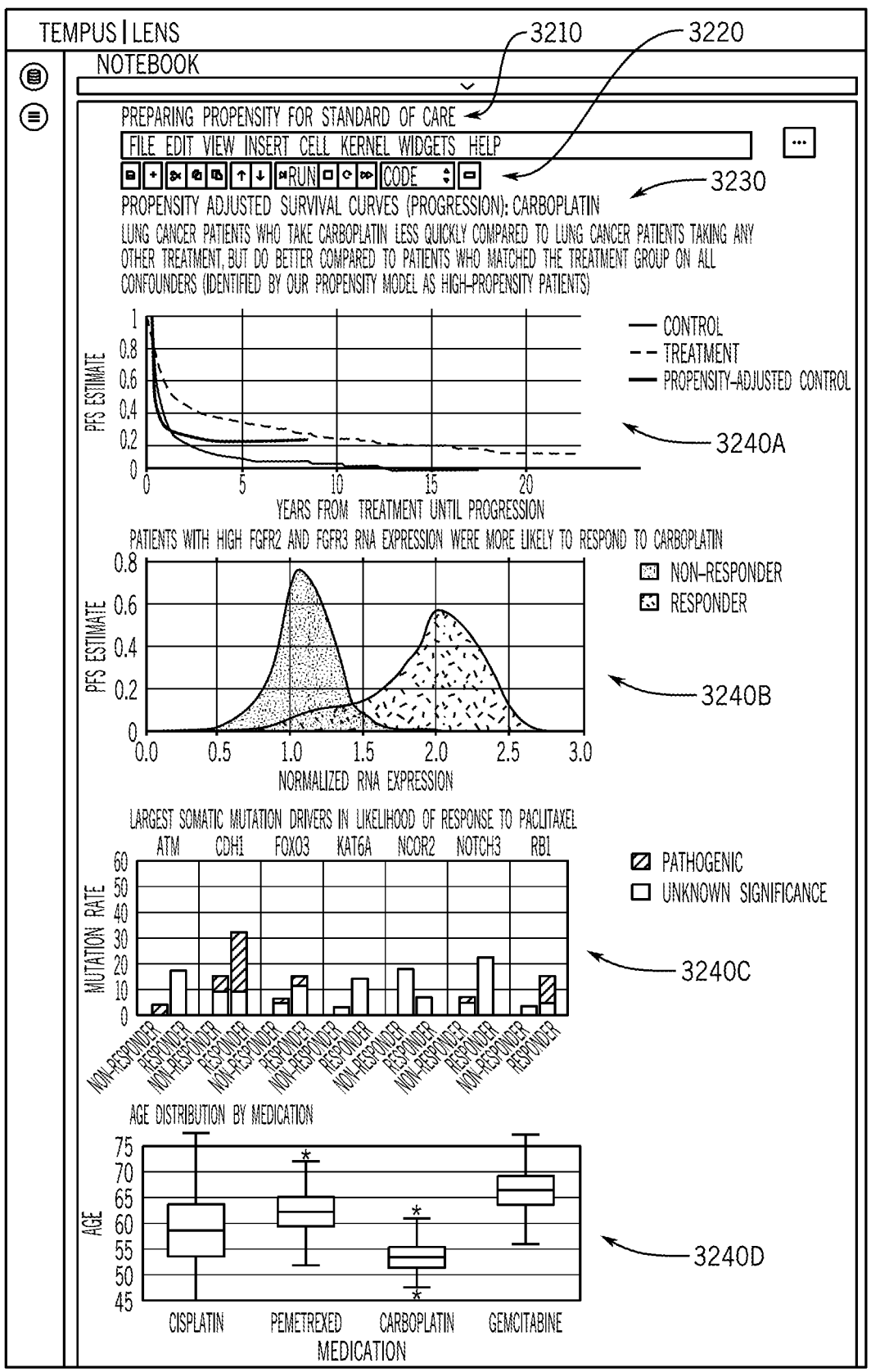
FIG. 32 illustrates a response from the notebook user interface when a user drags a workbook into the viewing window.

FIG. 32 illustrates a response from the notebook user interface when a user drags a workbook into the viewing window.

Notebook editor 3200 may auto-populate with Title 3210 and one or more cells 3240A-D based upon the user selected workbook. The user may rename the workbook using edit the workbook further using a text entry UIE 3220. The user may alter the configuration of the workbook via a series of button and drop down menu UIEs 3220 may be provided to compartmentalize grouped elements of the user interface. UIEs 3220 may assist the user in building and structuring the workbook's presentation. A cell UIE may provide selections pertaining to the currently selected cell 3240A-D having a block of code, such a commands for running the currently selected cell, terminating the currently selected cell, adding a cell, deleting a cell, running all cells, running all cells above, running all cells below, or terminating all cells. A kernel UIE may provide selections pertaining to one or more programming languages and/or available to the user such as Python, Structured Query Language (SQL), R, Spark, Haskell, Ruby, Typescript, Javascript, Perl, Lua, C, C++, Matlab, Java, Emu86, and other kernels. Selecting a kernel from the kernel UIE reloads the workbook so that the cells execute commands from the respective language. A widget UIE may provide selections pertaining to one or more supported code snippets for the active kernel. Code snippets may include code for creating visualizations such as a graph or a plot, code for simple arithmetic operations such as calculating a mean or a standard deviation, or code for more complex operations such as calculating a distribution and displaying a respective curve. The user may further alter the configuration of the workbook via a series of icon UIEs 3230 may be provided where each icon represents a popular command executed from the UIE 3220. Exemplary popular commands may include saving the document, adding a new cell, cutting or pasting code or cells, rearranging cells by moving them upwards or downwards down the page in relation to any other cells, or running/terminating the code in the active cell(s).

The user may also edit the source code for each of cells 3240A-D by selecting the cell and selecting the cell UIE option for edit or pressing an associated keyboard shortcut.

Figure 33:
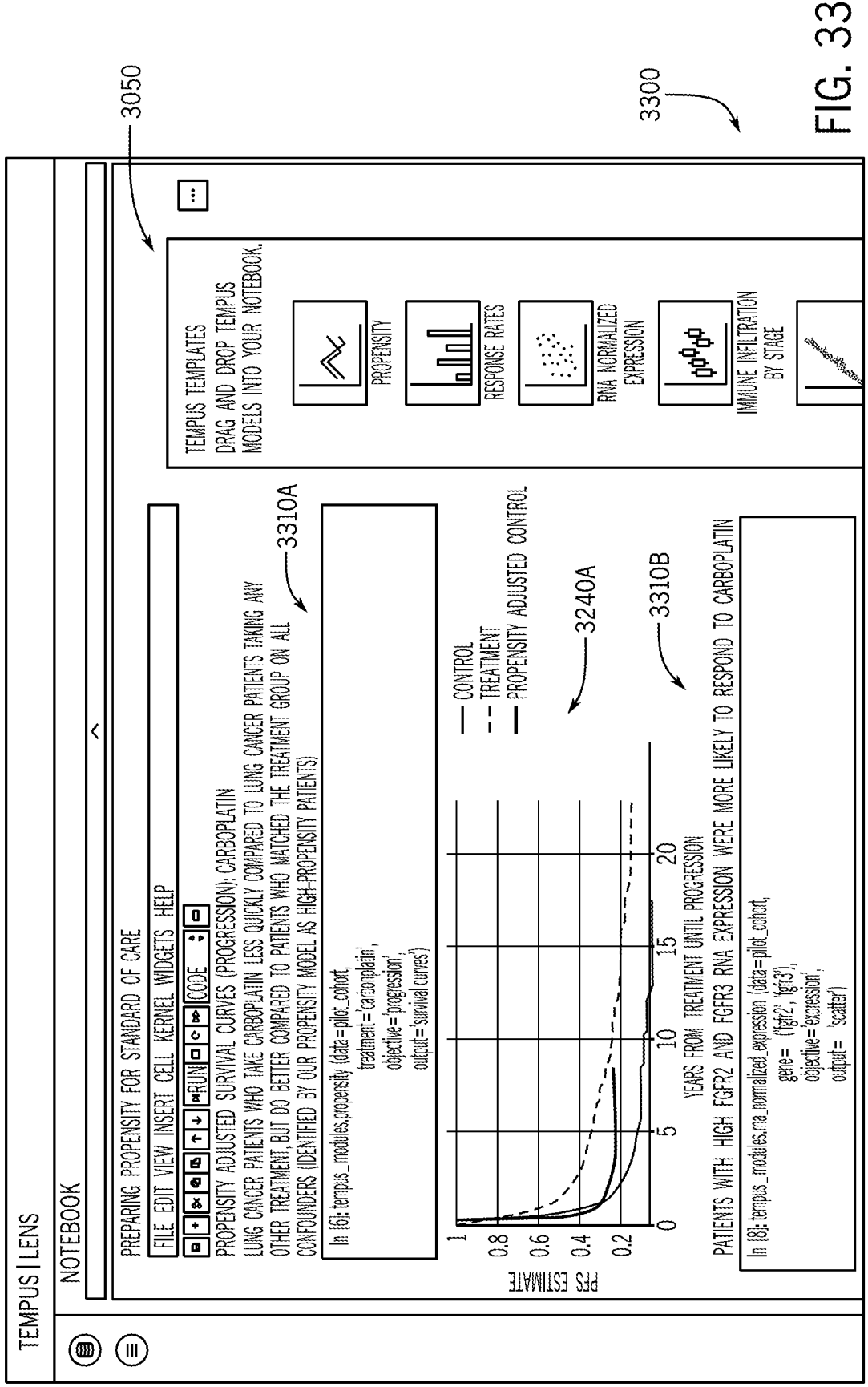
FIG. 33 illustrates an edit cell view of a custom workbook after the user loads a workbook into workbook editor and selects edit from the cell UIE.

FIG. 33 illustrates an edit cell view of a custom workbook after the user loads a workbook into workbook editor 3300 and selects edit from the cell UIE.

Cells 3310A and 3310B become visible (3310C-D not shown) upon entering an edit cell view of the workbook having cells 3240A-D. Cell 3310A displaying the code that generates a survival curve 3240A based on a propensity difference between a control cohort and a treatment cohort of patients. Cell 3310B displaying the code that generates a scatterplot 3240B (not shown) based on normalized RNA expressions for two selected RNA transcriptomes in the filtered cohort of patients. Similar cells 3310C-D (not shown) may be generated for scatter and box plots 3240C-D (not shown) respectively.

The user may edit the code to modify the workbook for their purposes as well as add or remove additional cells to create a new customized workbook.

During edit cell view, the user may also see one or more templates may be provided in template window 3050 for the user's convenience. Templates may include one or more cells preconfigured to operate on an input data such as the filtered patient cohort, run one or more cells of code to generate logical results, and run one or more cells of text or visualizations to report out the results of the performed logic on the input data in a convenient manner. Templates may exist for charts, graphs, regressions, dimension reductions, classifications, RNA or DNA normalization, and other commonly used features across templates available to the user. Templates may be provided with the dataset or custom created by a user to be shared with other users.

The user may drag any template into a cell to populate that cell with the code for generating the template's associated visualization or arithmetic.

Users may access the user interface for databases of patients which have been provisioned to the user by association with an institution or medical facility with a subscription to each patient database. Custom workbooks may also be provided on a database-by-database basis where workbooks are selected for their applicability to the patients within each database. Accessing the user interface may spawn resources in a cloud computing environment with access to any authorized databases and/or workbooks. User resource usage in the cloud computing environment may be monitored and tracked to supplement accurate billing for resources consumed by the user. User's may request and purchase other databases of patients. Databases of patients may be purchased based on characteristics of the patients within them. For example, a user may desire a database of patients who have been diagnosed with breast cancer. A look-up table (LUT) or cancer ontology may be referenced to provide alternative matchings for breast cancer, such as ductal carcinoma of the breast, cancer of the breast, mammary carcinoma, breast carcinoma, or other relevant terminology. Patients satisfying the requested diagnosis and any of the alternative terminologies from the LUT or cancer ontology may be combined into a database and delivered to the user. The user may then perform statistical analysis and research on the data in accordance with the disclosure herein.

Other web interfaces may be incorporated into the Interactive Analysis Portal 22 similar to the Outliers, Smart Cohorts, and Notebook portals above. One such other web interface may include identifying effects of a therapy, procedure, clinical trial, or other medical event on a disease state of a patient using propensity scoring. Propensity scoring and associated web interface is described in further detail in U.S. patent application Ser. No. 16/679,054, titled "Evaluating Effect of Event on Condition Using Propensity Scoring," filed Nov. 8, 2019, which is incorporated herein by reference in its entirety.

Data Completeness

Providing, in just once glance, relevant details about the suitability of a cohort of patients for one or more analytical methods may provide insight to a user regarding which analytics to pursue for ongoing research into treatment efficacy or potential outcomes associated with patients of a relevant cohort.

Data completeness metrics may be calculated from structured data. In the event unstructured data is presented, the data may be curated and structured. Protecting the confidentiality of patient data may be performed through a deidentification process prior to, during, or after data curation and structuring.

Data categorization into a plurality of categories may be performed as an aggregation process and the data then presented with respect to a metric of completeness across the patients in the cohort for one or more of the plurality of categories.

Figure 34:
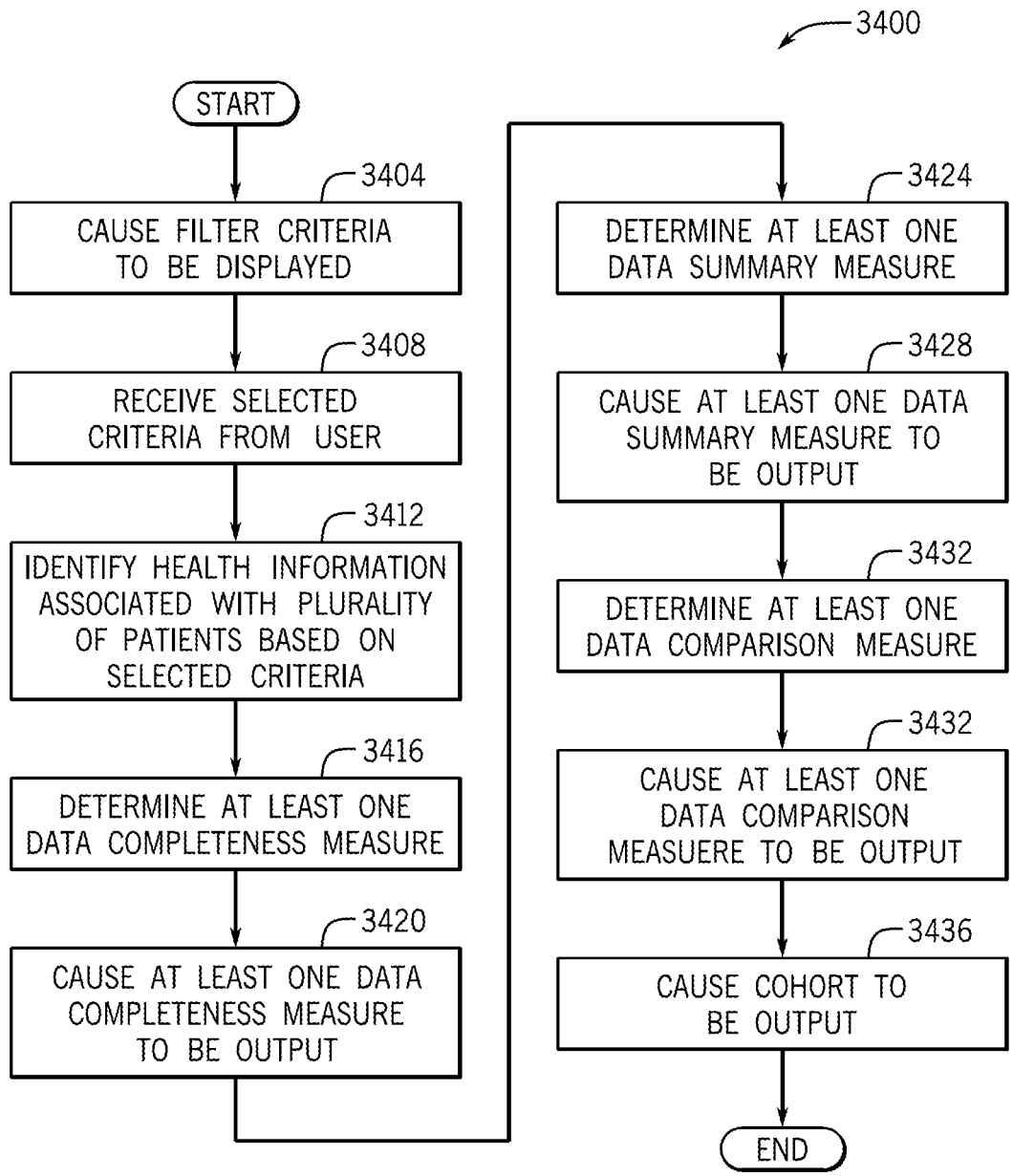
FIG. 34 illustrates an exemplary process for generating at least one data completeness measure, data summary measure, and/or data comparison measure according to some embodiments.

FIG. 34 illustrates an exemplary process 3400 for applying data which has been curated, deidentified, and aggregated to generate at least one data completeness measure, data summary measure, and/or data comparison measure according to some embodiments. The process 3400 can be implemented as computer readable instructions on one or more memories or other non-transitory computer readable media, and executed by one or more processors in communication with the one or more memories or other media.

At 3404, the process 3400 can cause filter criteria to be displayed. In some embodiments, the process 3400 can cause the filter criteria to be displayed at a user interface (e.g., using a display such as a computer monitor, a touchscreen, a television, a projector, etc.). The filter criteria can include a plurality of selectable criteria corresponding to the availability of patient data for a set of features. The patient data can include patient data associated with a cohort of patients selected from a plurality of patients associated with one or more health information sources (e.g., databases associated with hospitals, healthcare providers, etc.). In some embodiments, the plurality of patients can include at least one million patients.

The filter criteria can be used to narrow down which patients in the plurality of patients are associated with patient data having populated values for any of the features in the set of features. The set of features can include data fields such as diagnoses, responses to treatment regimens, genetic profiles, clinical characteristics, phenotypic characteristics, molecular data, imaging data, tumor infiltration, programmed death-ligand 1 (PD-L1) status, human leukocyte antigen (HLA) status, symptoms, therapies, outcomes, patient name, date of birth, gender, ethnicity, date of death, address, smoking status, diagnosis dates for cancer, illness, disease, diabetes, depression, other physical or mental maladies, personal medical history, family medical history, date of initial diagnosis, date of metastatic diagnosis, cancer staging, tumor characterization, tissue of origin, line of therapy, therapy groups, clinical trials, medication prescribed, medication taken, surgery, radiotherapy, imaging, adverse effects, associated outcomes, performance scores, lab tests, pathology results, prognostic indicators, date of genetic testing, testing provider used, testing method used, genetic sequencing method, gene panel, gene results, genes, variants, curated molecular data, and/or expression levels. For example, the filter criteria can be any of the features included in the set of features (e.g., cancer staging), and the filter criteria can be used to identify patients associated with patient data including populated values for a given feature (e.g., stage two cancer for the feature of cancer staging). Some patients may not be associated with populated values for a specific feature (e.g., tumor characterization), and a user may only wish to analyze patients that have one or more possible populated values for the specific feature (e.g., populated values of premalignant tumor for the specific feature of tumor characterization). In some embodiments, filters associated with the set of features can be hierarchically organized. In some embodiments, the filters can be grouped into categories of modality data, demographic data, assessment data, diagnosis data, next-generation sequencing (NGS) data, molecular data, treatment data, and/or outcome data.

In some embodiments, the filter criteria can include umbrella filters that can identify patients associated with one or more populated values for multiple features included in the set of features. In some embodiments, the modality data can include filters for clinical data (e.g., populated values for features including clinical characteristics, clinical trials, etc.), DNA data (e.g., populated values for features including DNA gene panels, DNA gene results, DNA genes, etc.), RNA data (populated values for features including RNA gene panels, RNA gene results, RNA genes, etc.), and/or imaging data (populated values for features including MRI data, 2D mammography data, digital breast tomosynthesis (DBT) data, etc.). In this way, a user can identify patients with similar analysis modality data. For example, an RNA data filter can be used to identify patients that have had any form of RNA testing and/or sequencing, which may assist a medical practitioner in identifying patients with RNA dysregulation, for example.

In some embodiments, the filter criteria can include one or more filters including one or more populated values for a feature. For example, a filter can include a "KRAS" populated value for a somatic variant data feature. As another example, a filter can include a "KRAS" populated value for a curated variant data feature. As yet another example, a filter can include a "male" populated value for a gender data feature. In this way, a user can identify all patients that have specific populated values for one or more features.

At 3408, the process 3400 can receive selected criteria from a user. The process 3400 can receive the selected criteria at the user interface. The selected criteria can include at least a portion of the filter criteria. In some embodiments, the selected criteria can include filters including one or more features and/or one or more specific populated values.

At 3412, the process 3400 can identify health information associated with a cohort of patients that meets the selected criteria. The cohort of patients can be a subset of the plurality of patients. The health information can be identified using at least one health information source. In some embodiments, the process 3400 can identify patients associated with patient information that satisfies the selected criteria. As described above, the selected criteria can include filters including one or more features and/or one or more specific populated values. The health information can include the patient information of all patients in the plurality of patients that satisfies the selected criteria. For example, if the selected criteria includes a first filter for imaging data and a second filter for a "KRAS" populated value for a curated variant data feature, the process 3400 can identify all patients associated with patient information that includes at least one form of imaging data as well as a "KRAS" populated value for the curated variant data feature. In addition to, or instead of being inclusionary, one or more of the criteria may be exclusionary, whereby the health information can exclude the patient information of all patients in the plurality of patients that satisfies the selected criteria or can include the patient information of all patients in the plurality of patients that do not satisfy the selected criteria. The process 3400 can then include all patient data associated with identified patients in the health information. Each identified patient can be included in the cohort of patients. In this way, the process 3400 can allow the user to analyze multiple aspects of the identified patients.

At 3416, the process 3400 can determine, for the cohort of patients, at least one data completeness measure for at least one of the features included in the set of features based on the health information, and at 3420, the process 3400 can cause the at least one data completeness feature to be displayed. In some embodiments, the data completeness measure may be a treatment indicator. In some embodiments, the process 3400 can cause the at least one data completeness feature to be displayed at the user interface. In some embodiments, the process 3400 can generate a Venn diagram or other image representative of how many patients are associated with patient information including populated values associated with modality data including clinical data, DNA data, RNA data, and/or imaging data. In this way, the user can visualize what the most common forms of modality data are for the cohort of patients, which may inform the user on how to best compare patients since some modalities may be more commonly populated than others (e.g., most patients are associated with imaging data but not clinical data, most patients associated with DNA data are also associated with RNA data, etc.).

In some embodiments, the process 3400 can generate a Venn diagram or other image representative of how many patients are associated with patient information including populated values associated with umbrella data including multiple categorical data categories each including multiple features. For example, as described above, the process can generate a Venn diagram or other image for modality data (i.e., umbrella data) including clinical data, DNA data, RNA data, and/or imaging data (i.e., categorical data categories). Each of the clinical data, DNA data, RNA data, and imaging data can include a plurality of features. For example, imaging data can include MRI data, x-ray data, ultrasound data, and/or other imaging data. In some embodiments, the umbrella data can be genetic sequencing data, and the categorical data categories can include DNA sequencing data and RNA sequencing data. In some embodiments, each of the DNA sequencing data and the RNA sequencing data can include one or more DNA panels, a presence of one or more gene variants, and/or other relevant testing data.

In some embodiments, datasets may contain a plurality of uncategorized features which must first be categorized according to one or more categorical data categories. In an exemplary embodiment, categories may include one or more of: Treatment, Outcome, Demographics, Assessments, Cancer Diagnosis, Next-Generation Sequencing, and/or Curated Molecular. Patient datasets may include hundreds of thousands to millions of underlying features that belong to one or more categories.

In one example the Treatment category may include one or more sub-categories, selected from: Associated Outcomes, Drug Class, Drug Class Group, Individual Medication, Line of Therapy, Procedure, Radiotherapy, Radiotherapy Measurement, Radiotherapy Quantity, Radiotherapy Site, Regimen, Surgical Margins, Time on Medication, or other types of treatments which may be grouped together.

In one example the Outcomes category may include one or more sub-categories, selected from: Adverse Events, Deceased, Disease Response, or other types of outcomes which may be grouped together. Subcategories, for example disease response, may be populated from physician notes or imputed from the medical record such as complete response, partial responses, absence of response, stringent response, progressive disease, stable disease, no evidence of neoplasm, no neoplasm, recurrent tumor, minimal therapeutic response. primary refractory, relapse, or other responses. Adverse events may similarly be populated to include occurrences of dyspnea, hypokalemia, white blood cell disorders, nausea, abdominal pain, vomiting, fatigue, fever, diarrhea, pain, or other adverse events.

In one example the Demographics category may include one or more sub-categories, selected from: Age at Diagnosis, Ethnicity, Gender, Race, or other types of demographics which may be grouped together.

In one example the Assessments category may include one or more sub-categories, selected from: Comorbidities, ECOG Score, Gleason Score, Gravidity, Karnofsky Score, Lab Quantity Unit Type, Lab Result Quantity, Lab Test, Lab Test Result, Menopausal Status at Diagnosis, Most Recent Menopausal Status, Most Recent Smoking Status, Primary Gleason Score, Secondary Gleason Score, Smoking Status at Diagnosis, or other types of assessments which may be grouped together.

In one example the Cancer Diagnosis category may include one or more sub-categories, selected from: CRPC, Derived Diagnosis, FIGO Stage, Grade, Histology, M Stage, Metastatic Site, N Stage, Primary Site, Stage, T Stage, or other types of cancer diagnosis which may be grouped together.

In one example the Next-Generation Sequencing category may include one or more sub-categories, selected from: Assay, Germline Pathogenicity, Germline Variant Description, Germline Variant Genes, MMR Stain, MSI, PD-L1 Immune Cell Staining, PD-L1 Panel, PD-L1 Tumor Cell Staining, Report Type, Somatic Pathogenicity, Somatic Variant Description, Somatic Variant Genes, Somatic Variant Type, TMB, Tissue Site, or other types of next-generation sequencing which may be grouped together.

In one example the Curated Molecular category may include one or more sub-categories, selected from: Biomarker, Curated NGS Allele Origin, Curated NGS Assay Method, Curated NGS Gene, Curated NGS Result, Curated NGS Test Provider, Curated NGS Variant Description, Curated NGS Variant Type, ER/PR/HER2 Status, or other types of curated molecular which may be grouped together.

A data completeness metric may be calculated for a sub-category by identifying each patient record that contains one or more data elements within the sub-category and a data completeness metric may be calculated for a category by aggregating the data completeness metric for each sub-category. In some examples, it may be the mean, average, or median of the sub-categories. In other examples it may include the minimum or maximum completeness of the sub-categories. Data completeness metrics of category may also be based upon a designation combination of sub-categories that have been identified as most important. Importance may be identified based on the preferences of the user or institution, or may be determined based on the respective subcategories which influence the performance of a trained model, analytics, or other objectives to the user.

For each of the categories and/or sub-categories listed above, the patient data entries may be manually curated to identify the most suitable patient data for each. Entries may be selected from a medical ontology such as Medical Dictionary for Regulatory Activities Terminology (MedDRA) (MEDDRA), SNOMED CT (SNOMEDCT), RxNORM (RXNORM), CPT—Current Procedural Terminology (CPT), Read Codes, Clinical Terms Version 3 (CTV3) (RCD), International Classification of Diseases, Version 9-Clinical Modification (ICD9CM), International Classification of Diseases, Version 10 (ICD10), National Cancer Institute Thesaurus (NCIT), Cancer Ontologies, or other related ontologies. In one embodiment, an ontology of ontologies may be referenced, such as the US National Library of Medicine (NLM) publishes a Unified Medical Language System (UMLS) including a Metathesaurus having drug vocabularies including CPT®, ICD-10-CM, LOINC®, MeSH®, RxNorm, and SNOMED CT®. Each of these drug vocabularies highlights and enumerates specific collections of relevant drugs. Other institutions such as insurance companies may also publish clinical drug lists providing all drugs covered by their insurance plans. By aggregating the drug listings from each of these providers, companies, and institutions, an enumerated list of clinical drugs that is universal in nature may be generated. Similarly, ontologies for other categories may also be generated.

For example, the feature space for an uncategorized dataset may include a plurality of features relating to the diagnosis and treatment history of a patient which may be categorized under clinical data. The process of identifying and categorizing features into clinical data may include electronic health records that have been integrated and curated into a structured format. The structured data may be organized manually, where a team of abstraction specialists work under the guidance of medical professionals in different fields to correctly identify the categorizations of each data element abstracted. For a laboratory or health institution handling data curation, respective data elements may be known apriori and entered according to the process that generated the respective elements. For example, a diagnostic testing laboratory knows that their generated results are clinical data for each respective patient and may have more refined qualifiers based on the type of testing performed. A larger clinic may tag all of their data as clinical data. A genetic sequencing laboratory may tag their structured data according to the type of assay that is performed on a respective patient, whether to identify DNA variants or RNA transcripts as molecular data, data elements related to images of an H&E or IHC stained slide as pathology data or imaged data. An imaging institution may tag their respective data elements related to x-rays, MRIs, or other radiological scans as radiological data or imaged data. Leveraging the purpose of respective procedures that generate data enables creating categorization of data that is generated from each institution quickly and efficiently.

The structured data may also be organized in a more automated manner, where data elements are sent to different artificial intelligence engines and/or machine learning algorithms. Supervised or unsupervised, data elements may be organized with respect to where they fall in the medical space. Those known elements may seed the discovery and categorization of new data elements based on relationships and associations in the underlying dataset, including, for example, the source documentation or the frequency of their occurrences in proximity to each other in documents, reports, or other documentation from medical files. Other associations may be discovered by the machine learning algorithms powering the categorization that are not as easily translated to common understanding. In one embodiment, related data elements may be grouped together via a structured element attached to the data, to identify which category the respective element falls under. In another embodiment, related data elements may be grouped together under a table dedicated for each respective category or a plurality of tables may be converted to a matrix, where a respective row or column represents a category and the elements within the corresponding rows or columns are tagged for data elements within that category.

TABLE 5

Example Grouping of Categories, Elements, and Sub-Elements

| Category | Element | Sub-Element |
|---|---|---|
| Cancer Diagnosis | Primary Diagnosis | Derived Diagnosis |
|  |  | Primary Site |
|  |  | Histology |
|  | Metastatic Site |  |
|  | Stage |  |
|  | CRPC |  |
| Tempus NGS | Somatic Variants | Gene |
|  |  | Pathogenicity |
|  |  | Variant Type |
|  |  | Variant Description |
|  | PD-L1 | Panel and Interpretation |
|  |  | Tumor Cell Staining |
|  |  | Immune Cell Staining |
|  | Immunotherapy | MSI |
|  |  | TMB |

TABLE 6

Exemplary Matrix of Data Completeness, by Patient and Category

| Patient | Derived Diagnosis | Primary Site | Histology | Metastatic Site | Comorbidities |
|---|---|---|---|---|---|
| AAA | 1 | 1 | 0 | 0 | 0 |
| XXX | 1 | 1 | 1 | 1 | 1 |
| YYY | 0 | 0 | 0 | 1 | 1 |

TABLE 7

Exemplary Subcategory Data Element Listing Comorbidities

| Smoking Status At Diagnosis | Most Recent Smoking Status | Menopausal Status At Diagnosis | Most Recent Menopausal Status |
|---|---|---|---|

Figure 35:
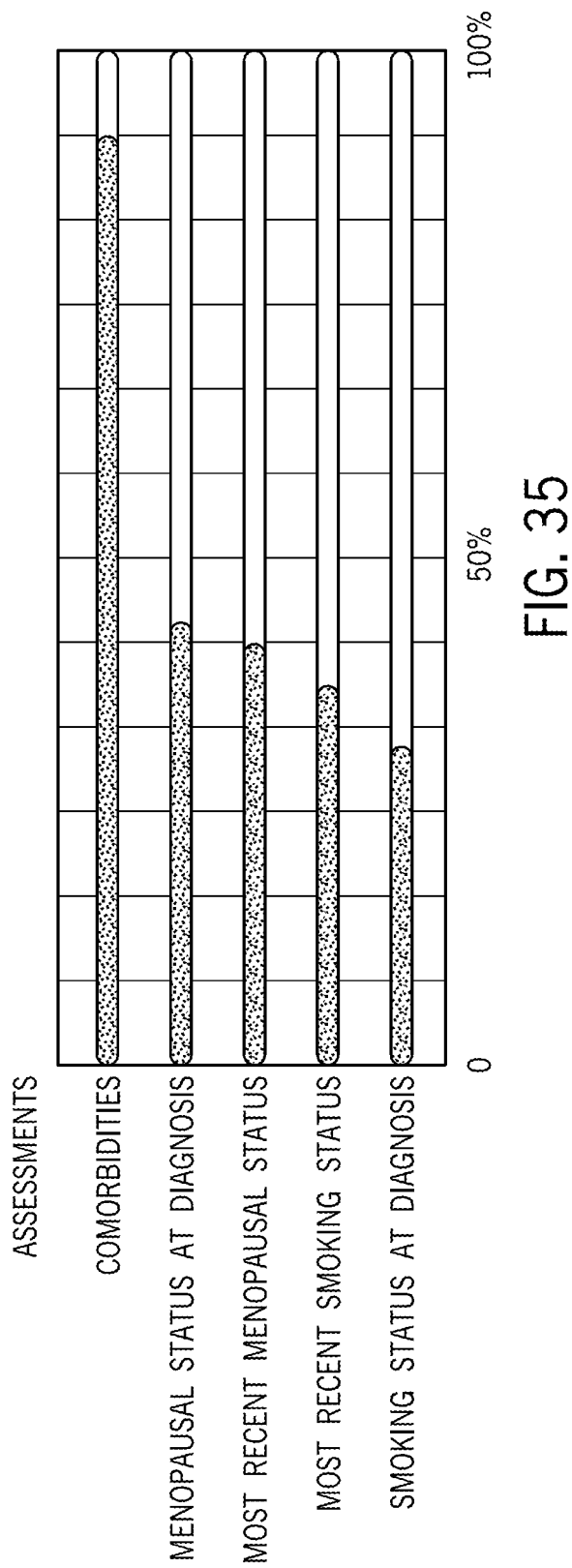
FIG. 35 illustrates an example of a display of a data completeness metric according to certain embodiments.

A data completeness metric may be based upon one or more categories, subcategories or individual data elements. In one embodiment, a user can select a data element, subcategory, or category for which to see the data completeness. The count of the selected data completeness elements can be retrieved from a precomputed value stored in a database or calculated dynamically. For example, if the user selects data completeness for data element "Deceased," the cohort of patients may be retrieved, the number of patients within the cohort stored as a denominator and the number of patients having a "deceased" entry populated in the underlying dataset may be stored as a numerator. In another example, only the numerator divided by the denominator may be stored. In another example, only the numerator is displayed, representing the total number of patients with the "deceased" entry. In one example, the value may be displayed as an image such as a bar or a pie chart where a portion of the bar or pie chart is represented differently than the rest of the bar or pie chart, the portion indicative of the value. In this manner, if the value 15% is to be displayed, only 15% of a bar or pie chart will be distinct to visually indicate that at least 15% of the patients in the data are complete with respect to the metric. The value may then be presented to the user according to any of the embodiments disclosed herein. One such display is shown in FIG. 35 with respect to an Assessments category, although it will be appreciated that the display may relate to any one or more of the categories or subcategories discussed above, or any other categories or subcategories.

In some embodiments, a somatic variant table can be used to analyze a patient. A somatic variant table can be a combination of reported variants and/or molecular data, which can provide a second source of reported variants. Using molecular/genomic results at the variant level of specificity across patients from both variants and a more raw source of underlying data for patients not associated with a report can provide a normalized somatic variant table to the user. In this manner, instead of the normalized table including every variant from the second source of reported variants, a threshold such as the top N variants or the most important variants that break patients into survival or popularity may be displayed. The top N may be top 5, top 100, top 1000, or other threshold as desired.

In some embodiments, a medications table can be used to analyze a patient. In some embodiments, the medications table can include one row per medication. In some embodiments, the medications table can include metadata associated with the patient. In some embodiments, the medications table can be aggregated upon itself and can have the data appended to the medications table. In some embodiments, each medication included in the medications table can be associated with other medications by an identifier, such as a care plan identifier that associates medications provided for in a single care plan, line of therapy, or regimen.

In some embodiments, the medications table can include, for each patient record, a complete regimen on each record such as a first line of therapy, second line of therapy, or plurality of regimens that were previously or are currently being administered to the patients of the cohort. Additionally, the medications table can include clinical outcomes, time on medication, and/or other regimen-related information. In some embodiments, an interface can allow a user to select a number of concepts that mirror how a medical professional would speak about medications. For example, the interface can allow a user to select concepts based on the input phrase "I'd like to know all patients given pembro in {any regimen/in a specific regimen} for 30-60 days and experienced associated progression on the drug." The resulting aggregated table would include medication pembrolizumab alone and in combination with other therapies or regimen which had both been administered between 30 and 60 days and had recorded outcomes from the regimen. The appended entries may then include the regimen, the time, and the associated outcomes.

In some embodiments, a data completeness metric may be based on information provided in a roll-up table. In one example, a somatic variant table may include the aggregation of a combination of reported variants and a molecular master file, which is a second source of that information. That data may be blended as part of the overall data model, by incorporating molecular/genomic results at the variant level across patients from both variants provided on reports and a more raw source of underlying data for patients for sequenced in another laboratory setting. Those two sources are aggregated together, normalized, then provided to the user as a single data source having a single data completeness metric.

The following table represents the structure of this aggregated view, and few illustrative rows Unification here may comprise renaming "copy number gain" in the dataset with "amplification" (or vice versa) and renaming "copy number loss" with "deletion" (or vice versa).

Data completeness may aggregate across medication data for each patient. Underlying tables in medications are one row per medication with associated metadata fields characterizing the medications listed. Aggregation may be performed by creating a table that is an aggregate upon itself and has additional data appended to it. Each medication when curated is associated with other medications by a care plan identifier (e.g. "care_plan_id") which may be associated with a regimen, or plurality of medications provided together such as a line of therapy. For each record, appending the entire regimen to the record and subsequent outcomes to the medication table provides additional completeness metrics. Other additional data that may be appended include time on medication. Filtering in the system allows the user to select a plurality of concepts that mirror how a

TABLE 8

Data Completeness Aggregation

| analysis_id | somatic_gene | somatic_sample_type | somatic_variant_significance_canonical_name | collection_time_from_index | bio_analysis_time_from_index | gene_variant_description | source |
|---|---|---|---|---|---|---|---|
| XYZ | ARHGAP39 | Short Variant | Uncertain significance | 3 | 65 | ARHGAP39 p.S666R | Reported Variants |
| XYZ | TRAF3 | Short Variant | Pathogenic | 3 | 65 | TRAF3 p.Q320* | Reported Variants |
| XYZ | CCDC6-ANK3 | Rearrangement | Not determined | 3 | 65 | CCDC6-ANK3 Rearrangement | MMF |

In Table 8, one of the enhancements provided in the aggregation is the normalization of variant annotation across sources. In some sources, protein-coding variants are described using a single character representing an amino acid (for example, p.E81K), and in others a three-letter amino acid structure is used (for example, p.Glu81Lys). Logic within this aggregation provides normalization to the single character method to ensure that each amino acid structure included is complete across all sources and eliminates spurious redundancy. For example, by replacing 'Ala' with 'A', 'Asx' with 'B', 'Cys' with 'C', 'Asp' with 'D', 'Glu' with 'E', 'Phe' with 'F', 'Gly' with 'G', 'His' with 'H', 'Ile' with 'I', 'Lys' with 'K', 'Leu' with 'L', 'Met' with 'M', 'Asn' with 'N', 'Pro' with 'P', 'Gln' with 'Q', 'Arg' with 'R', 'Ser' with 'S', 'Thr' with 'T', 'Val' with 'V', 'Trp' with 'W', 'Tyr' with 'Y', and 'Glx' with 'Z'.

Similarly, categorization/normalization may be performed for other columns in Table 5 as well, such as to ensure that different scales, whether written or numerical, are unified in representation so that data completeness accurately characterizes the patient data.

In another example, biological events, such as fusions and copy number variations may be renamed to a unified naming convention. For example, for fusions occurring between two chromosomes or a rearrangement configuration, the two chromosomes may be ordered in a structured format to ensure only one categorization exists per fusion that represents the same event. One example of such ordering is an ordering done to appropriately categorize the difference between 5'/3' imbalance fusion genes. In another example copy number variants may result in a copy number gain or a copy number loss. Another data source may reference the same events as amplifications or deletions, respectively.

physician would speak about medications. For example, "I'd like to know all patients given pembro in {any regimen/in a specific regimen} on therapy for 30-60 days and experienced associated progression on the drug." By aggregating medications, regimens, time on therapies, and outcomes to a single table, filtering becomes greatly simplified. Rather than polling several queries and attempting quality controls on each query to ensure they are related to the data in the other queries, the aggregated data completeness table is accessible and parsable via a single filter.

In another embodiment, gene alterations may be unified and aggregated. For example, across variant types such as single nucleotide variations or multiple nucleotide variations, insertion or deletions, and fusions and CNVs as mentioned above, unification or normalization may be implemented because patient health records may extend across data which is sourced from multiple entities, healthcare institutions, laboratories, or other locations. Additionally, even within a laboratory, different departments may generate data differently. For example, a laboratory reporting next-generation sequencing results may have a first collection of variants which are curated and used for reporting, a second collection of less filtered and non-pathology reviewed variants from the sequencing results, and a third collection of variants curated from clinical data. Unification and normalization may be implemented by pulling this data together and aggregating into a single file. In one example, such as the first and second collections of variants, the first collection of variants may be used to limit the second collection of variants to a smaller subset of more important/relevant genes.

In another embodiment, RNA/Transcripts may be unified and aggregated. For example, different source label RNA transcripts with different naming conventions. In one example, data sources of different ages may need to be unified under the current HUGO Gene Nomenclature Committee (HGNC) guidelines for naming not only protein-coding but also RNA genes and pseudogenes.

The system may be configured to maintain concurrence between different modalities. For example, if DNA sequencing and RNA sequencing have both been performed on a subject, then the sequencing results may be confirmed as coming from the same biopsied specimen before being included in the data completeness metric. In one example, if DNA sequencing and RNA sequencing have both been performed on a subject, but the sequencing results are not confirmed as coming from the same biopsied specimen, the sequencing results are excluded from the data completeness metric.

In some embodiments, data in a roll-up table may result from a coalescence of external data which may be added or imputed to the current data set. For example, death data maintained by a third party may be imputed into a data completeness table. In some embodiments, data in a roll-up table may result from a coalescence, or blending of data (where available) from multiple tables into a single column. An example of this involves the merging or coalescence of mortality data (describing the timing of death for a given patient) from our primary methods (curation, or via EHR integrations) and other third-party sources of mortality data. These events may be stored in separate tables, but to facilitate easier filtering and a more intuitive experience, primary data may be used first, and if that is not available, fill the column of the new table with any available data from the third party source.

In some embodiments, similar data may be organized with various levels of precision into a single view to again abstract some of the complexity away from the user experience. One example of this relates to treatment of two related concepts—the primary anatomic site of disease and the histology of the disease. When we curate these concepts via an abstraction flow, when the relationship between the site and histology are explicit in the source documents, they will be related in the data by a concept called a condition_id. In cases where this data comes directly from EHR integrations (and is therefore not explicitly linkable via a condition_id), they will not share this relationship. This presents the option of choosing to honor the link when it exists (to take advantage of the improved precision of those linked concepts), but not requiring it where it does not.

Other data roll-up tables may coalesce including information on the diagnosis for each patient including anatomic location (curated and not curated), primary site location, histological data extracted from that primary site location such as a stained slide image from a biopsy taken from the site location. A subsequent aggregated table may include a row having, for each patient, the diagnosis, anatomic location, primary site, and histology data and/or imaging. Other coalescence of data may include one or more of regimens, time on treatment, drug class/group rollups, line of therapy, and associated outcomes.

In some examples, EHR data may exist in a vacuum, where histology data, if it exists, is not explicitly linked to an anatomic site. This data may be imputed, for example, certain terminology may be linked to certain histology based on the data as known. In this view, where the cases are linked together, honor those linkages and ignore unlinked data to avoid false positives or negatives based on the unknown state. For example, the roll-up table may combine histology and primary site to permit an anatomic site of "blood cancer" to be linked with "AML" histology because a histology of AML is linked by imputation with blood cancer. Similarly, a record for anatomical location of "breast" may be linked by imputation with "invasive ductal carcinoma" due to their known relation. In LENS, due to data completeness and roll-up tables, a search for blood cancers may get a data search "hit" even if AML is the data in the system because the aggregation tables link the terminology together under a single metric.

Figure 36:
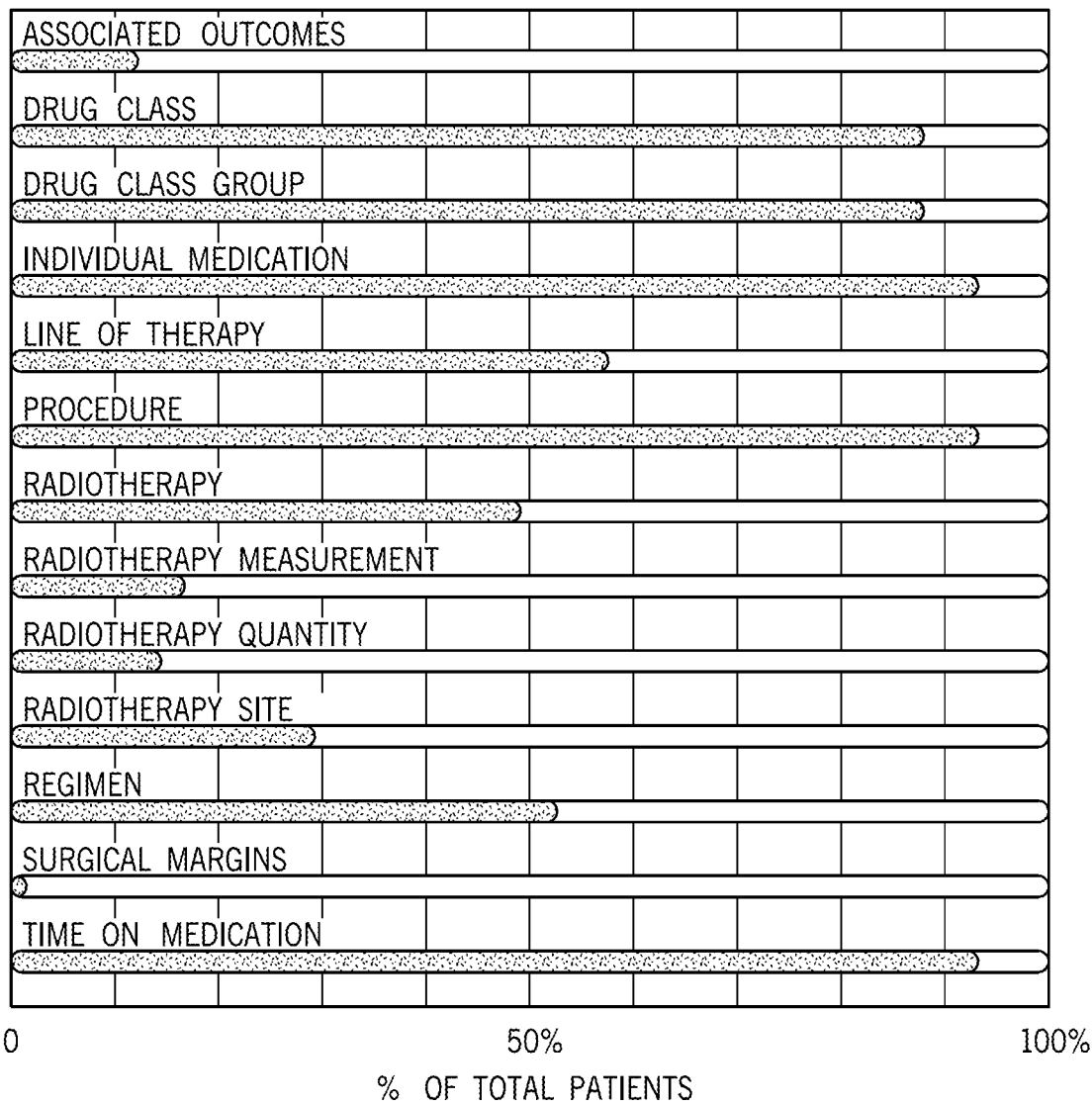
FIG. 36 illustrates an example of a display of a data completeness metric according to certain embodiments.

Roll-up tables may include support for pairwise comparisons which are not related in order to support the enormous quantities of information within health records. In one example, a pairwise comparison may include a query for patients having both "blood cancer" and "invasive ductal carcinoma." The resulting data completeness metric would include data aggregation tables for each independent roll-up table, aggregated together. For example, a Treatment data completeness may include associated outcomes from both blood cancer and invasive ductal carcinoma. Whereas an unlinked data set may not distinguish between associated outcomes from any specific term, roll-up tables linking data enables a robust system to identify data completeness for patients having associated outcomes related to specifically to the terms searched and then combining them so that the resulting image displays the data completeness for both at the same time, as seen, for example, in FIG. 36.

Figure 37:
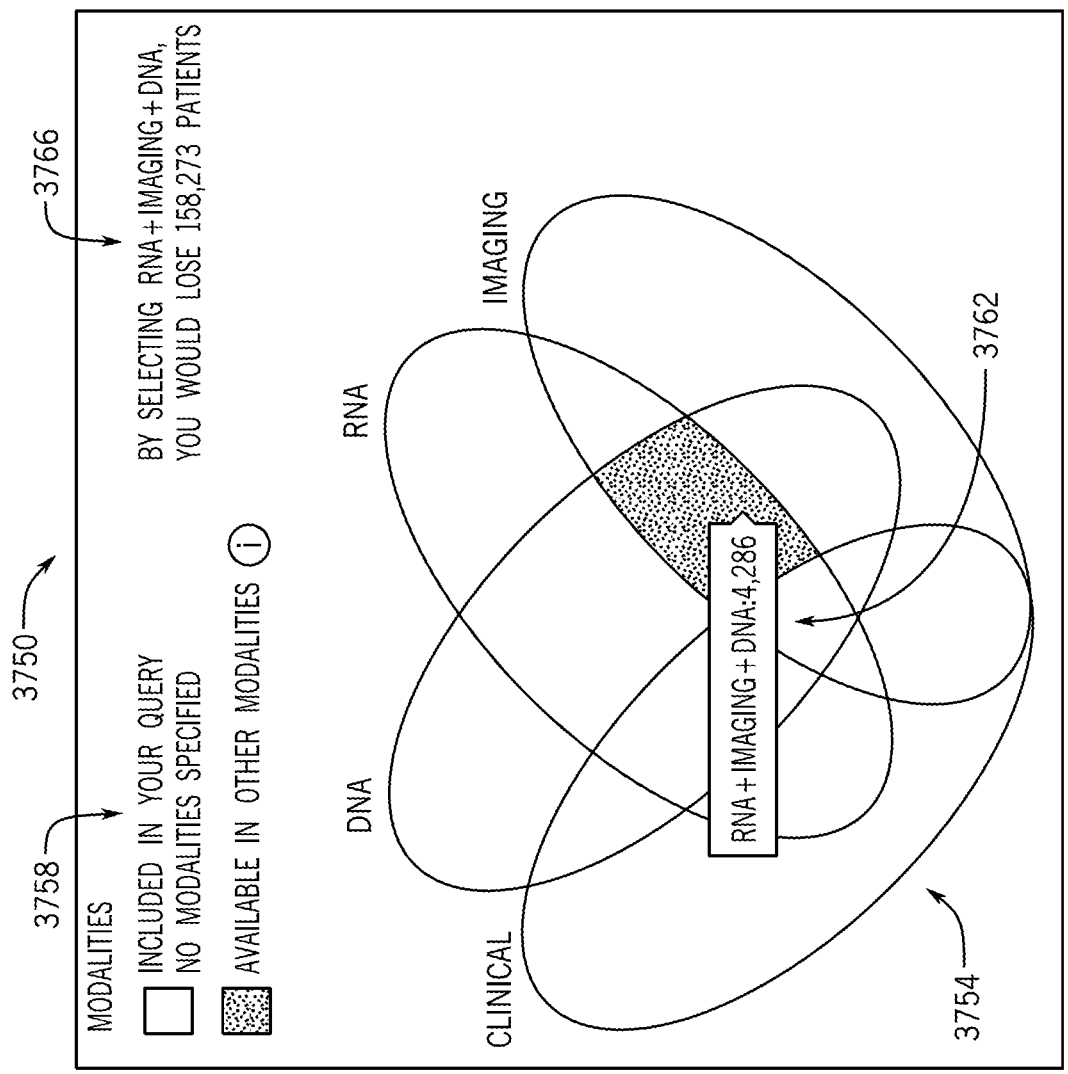
FIG. 37 illustrates an example of a user interface of the Interactive Analysis Portal for displaying an interactive graph for generating a cohort.

In another example, data completeness may be visualized and/or selected based on one or more modalities from which the underlying data encompasses. For example, differing modalities may come from different types of data sources. A DNA modality may come from genetic sequencing of DNA, RNA modality may come from genetic sequencing of RNA, lab diagnostic modalities may come from wet lab testing results, imaging data may come from x-rays, MRIs, CAT scans, histopathology slides, and other imaged data. A plurality of overlapping Venn diagrams may indicate which data overlaps for patients in a search query. For example, a patient with both RNA and DNA data would have data from both modalities, so a Venn diagram would show all of RNA, DNA, and the overlap and RNA and DNA as active. In examples where patients are not uniformly represented, such as some patients have RNA data, some patients have DNA data, and some patients have both data, a user may interact with a modality interface to filter the resulting collection of patients to only those who have the selected modalities. As seen in FIG. 37, in the four modality example of clinical, DNA, RNA, and imaging modalities, a selection of the Venn diagram overlaps for all four modalities would filter out patients who did not have all four modalities present in the respective data so that the results provided to the user only include those who have all four. More complex interactions and selections may be performed by selecting more than one Venn oval or overlap between any two or more modalities such that a complex filter is generated for patients who satisfy all of the selected criteria. In the event of redundant queries, only the most restrictive query may be parsed. For example, if the user selects the field of overlap to be all four modalities, and additionally selects another field for any subset of two or three modalities, the resulting query may be parsed as only patients who have all four modalities represented. While selections are presented as inclusive, exclusions are represented by selecting Venn oval overlaps which do not have a modality present.

In another embodiment, the user may select between any one or more data completeness filters and any modality filter for a composite query of patients having the plurality of features desired and the plurality of modalities desired.

In some embodiments, the at least one data completeness measure can include at least one visual indicator. The at least one visual indicator may, when displayed, better communicate to a user how complete one or more specific features and/or specific umbrella data is (e.g., how many patients in the cohort of patients are associated with populated values for a specific feature vs how many patients are in the cohort of patients). In some embodiments, the at least one data completeness measure can be a graph, a chart, a bar (e.g., a percentage bar), a color and/or colored region (e.g., red text for less complete features and green text for more complete features), a symbol (e.g., an "X" for less complete features and a check mark for more complete features), and/or other visual indicators.

In some embodiments the process 3400 can generate a visual indicator based on one or more commonality metric representative of, for a specific feature included in the set of features, how many patients included in the cohort of patients are associated with patient information including populated values for the specific feature. The specific feature may or may not be included in the selected criteria. In some embodiments, the commonality metric can be a percentage. In this way, the user can visually identify what portion of the patients have data for one or more specific features. In some embodiments, the at least one data completeness measure can include a plurality of commonality metrics representative of, for the number of specific features included in the set of features, how many patients included in the cohort of patients are associated with patient information including populated values for the specific features. In this way, the user can identify which specific features have the most populated values. In some embodiments, the specific features with the most populated values (e.g., the top five most populated values) and/or the specific features with the least populated values (e.g., the top five least populated values) can be included in the at least one data completeness measure. Additionally, specific features may be arranged in such a way as to provide immediate visual feedback to a user of their respective commonality metrics, e.g., they may be arranged in decreasing or increasing order of completeness. The specific features may or may not be included in the selected criteria.

Additionally, or alternatively, commonality metrics for one or more specific features included in the selected criteria can be included in the at least one data completeness measure. In some embodiments, the selected criteria can include a plurality of specific features, and the at least one data completeness measure can include a plurality of commonality metrics representative of how many patients included in the plurality of patients are associated with patient information including populated values for the plurality of specific features. In this way, the user can identify which filters included in the selected criteria are most commonly populated for patients in the plurality of patients, which may aid the user in choosing one or more filters to generate the cohort. For example, the user can identify which filters are overly restricting and select the filters accordingly (e.g., if most of the patients included in the plurality of patients are not associated with RNA data, the user may opt to eschew selecting RNA data filters). In some embodiments, the at least one data completeness measure can include visual indicators generated based on the commonality metrics (e.g., bar graphs, bar graphs, pie charts, etc.). In one embodiment, a plurality of data completeness measures may be presented, e.g., by sorting the filters into a plurality of categories, such as the categories identified above (modality data, demographic data, assessment data, diagnosis data, next-generation sequencing (NGS) data, molecular data, treatment data, and/or outcome data).

At 3424, the process 3400 can determine, for the cohort of patients, at least one data summary measure, and at 3428, the process 3400 can cause the at least one data summary feature to be displayed. In some embodiments, the process 3400 can cause the at least one data summary feature to be displayed at the user interface.

In some embodiments, the process 3400 can generate at least one data summary feature for at least a portion of the selected criteria based on the patient information associated with each patient included in the cohort of patients. In some embodiments, the selected criteria can include a specific feature. The specific feature can be populated with a specific value included in a set of specific values. In these embodiments, the at least one data summary measure can include a chart or graph indicative of, for each specific value in the set of specific values, a number of patients included in the cohort of patients associated with populated values equal to the specific value. In this way, the user can visualize which specific values are more and/or less common for the specific feature.

In some embodiments, the selected criteria can include a first specific feature that can be populated with a specific value included in a first set of specific values, and the set of features can include a second specific feature that can be populated with a specific value included in a second set of specific values. In these embodiments, the at least one data summary measure can include a chart or graph indicative of, for each specific value in the first set of specific values, a number of patients included in the cohort of patients associated with populated values equal to the specific value and each of the specific values included in the second set of specific values. For example, the first specific feature can be a cancer stage that can be populated with stage 1, stage 2, stage 3, or stage 4, and the second specific feature can be cancer type that can be populated by lung, pancreas, colon, rectum, or hematopoietic system. In this example, the chart or graph can indicate how many patients that have a cancer type of lung, pancreas, colon, rectum, or hematopoietic system are at each cancer stage (i.e., stage 1, stage 2, stage 3, or stage 4).

As another example, the first specific feature can be a drug class group that can be populated with line of therapy (LOT) 1, LOT 2, LOT 3, or LOT 4, and the second specific feature can be treatment type that can be populated by chemotherapy, hormone, other antineoplastic, biologic, immunotherapy IO checkpoint inhibitor, targeted (e.g., small molecule), immunological, antibody-drug-conjugate, or IO bispecific t-cell engager. In this example, the chart or graph can indicate, for each populated value of the treatment type, how many patients have received LOT 1, LOT 2, LOT 3, or LOT 4 class drugs.

At 3432, the process 3400 can determine, for the cohort of patients, at least one data comparison measure, and at 3436, the process 3400 can cause the at least one data comparison measure to be displayed. In some embodiments, the process 3400 can cause the at least one data comparison measure to be displayed at the user interface.

In some embodiments, the process 3400 can determine at least one data comparison measure between a first health information source and a second health information source included in the one or more health information sources based on the health information. For example, the first health information source can be a database associated with a hospital, and the second health information source can be a database associated with a healthcare network. At least a portion of the cohort of patients can be associated with the first health information source, and at least a portion of the cohort of patients can be associated with the second health information source.

In some embodiments, the at least one data comparison measure can include at least one data completeness measure and/or data summary measure for each of the first health information source and the second health information source. In some embodiments, the at least one data comparison measure can include a first commonality metric representative of, for a specific feature included in the set of features, how many patients included in the cohort of patients and associated with the first health information source are associated with patient information including populated values for the specific feature. The at least one data comparison measure can also include a second commonality metric representative of, for the specific feature, how many patients included in the cohort of patients and associated with the second health information source are associated with patient information including populated values for the specific feature. In this way, the user can visually compare the data completeness for the first health information source against data completeness for the second health information source.

In some embodiments, the selected criteria can include a first specific feature that can be populated with a specific value included in a first set of specific values, and the set of features can include a second specific feature that can be populated with a specific value included in a second set of specific values. In some embodiments, the at least one data comparison measure can include a chart or graph indicative of, for each specific value in a first set of specific values, a number of patients included in the cohort of patients and associated with the first health information source that are associated with populated values equal to the specific value and each of the specific values included in a second set of specific values. The chart or graph can be further indicative of, for each specific value in the first set of specific values, a number of patients included in the cohort of patients and associated with the second health information source that are associated with populated values equal to the specific value and each of the specific values included in the second set of specific values. In this way, the user can compare patients between the first health information source and the second information source based on the first specific feature and the second specific feature. In some embodiments, the process 3400 can determine at least one data comparison measure between more than two health information sources (e.g., three health information sources, four health information sources, etc.).

At 3440, the process 3400 can cause the cohort of patients to be output. In some embodiments, the process 3400 can cause the cohort to be saved in a protected database. In some embodiments, the process 3400 can cause the cohort to be shared with a secondary user. In some embodiments, the process 3400 can verify that the secondary user has appropriate credentials to view the cohort of patients and/or that the user has appropriate credentials to share the cohort of patients before causing the cohort of patients to be shared with the secondary user.

Embodiments for the application of the process 3400 may include data completeness metrics one or more initiatives such as establishing a research project between one or more collaborators and stakeholders; identifying and defining requirements for a cohort of patient, such as identifying which characteristics a model may be trained on due to the completeness of the patients in the cohort; and identifying and defining data scopes whether to individual files or subgroupings of files. In some embodiments, an exemplary research project may include stepping from one to the other of the aforementioned initiatives.

FIG. 38 illustrates an example of a user interface 3800 of the Interactive Analysis Portal 22 for generating a new cohort according to certain embodiments. The user interface 3800 can include a define a cohort button 3804 and/or a list of previously generated cohorts 3808.

Figure 39:
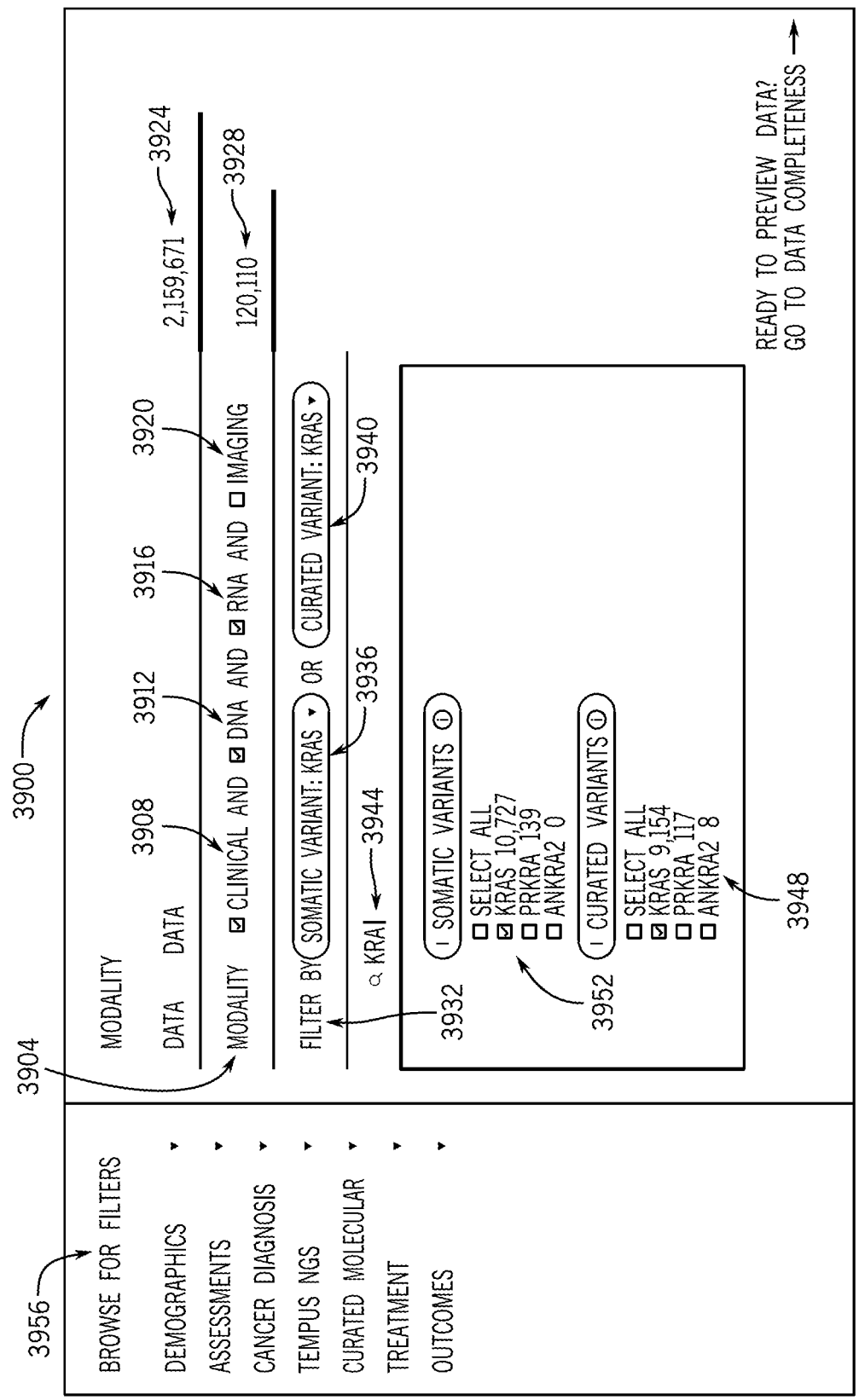
FIG. 39 illustrates an example of a user interface of the Interactive Analysis Portal for generating the new cohort using one or more filters according to certain embodiments.

FIG. 39 illustrates an example of a user interface 3900 of the Interactive Analysis Portal 22 for generating the new cohort using one or more filters according to certain embodiments. In some embodiments, the user interface 3900 can be displayed in response to a user selecting the define a cohort button 3804. In some embodiments, the user interface 3900 can be displayed at 3404 in the process 3400 in FIG. 34. In some embodiments, the user interface 3900 can include a modality section 3904 that can allow the user to select a number of modality data filters. The modality data filters can include a clinical data filter 3908, a DNA data filter 3912, an RNA data filter 3916, and/or an imaging data filter 3920. In some embodiments, the user interface 3900 can include a total patients indicator 3924 indicating how many patients are available (e.g., how many patients are included in a plurality of patients). In some embodiments, the user interface 3900 can include a remaining patients indicator 3928 indicating how many patients are currently included in a cohort of patients based on any selected filters.

In some embodiments, the user interface 3900 can include a filter selection portion 3932. The filter selection portion 3932 can allow the user to generate one or more filters for a feature and/or populated values for a feature. In some embodiments, the filter selection portion 3932 can include a number of dropdown elements 3936, 3940 that allow the user to select one or more filters for a feature and/or populated values for a feature. In some embodiments, the filter selection portion 3932 can include a search bar 3944 that can allow the user to search for filters. In some embodiments, the filter selection portion 3932 can include search results 3948, 3952 for input into the search bar. As shown, the user interface 3900 can identify filters containing the string "KRA," (e.g., filters related to KRAS), and display the relevant filters (e.g., a somatic variants filters having a selectable "KRAS" populated value and/or a curated variants filters having a selectable "KRAS" populated value). In some embodiments, the user interface 3600 can include a hierarchical filter selection portion 3956 that allows users to browse a hierarchy (e.g., a tree) of available filters.

Figure 40:
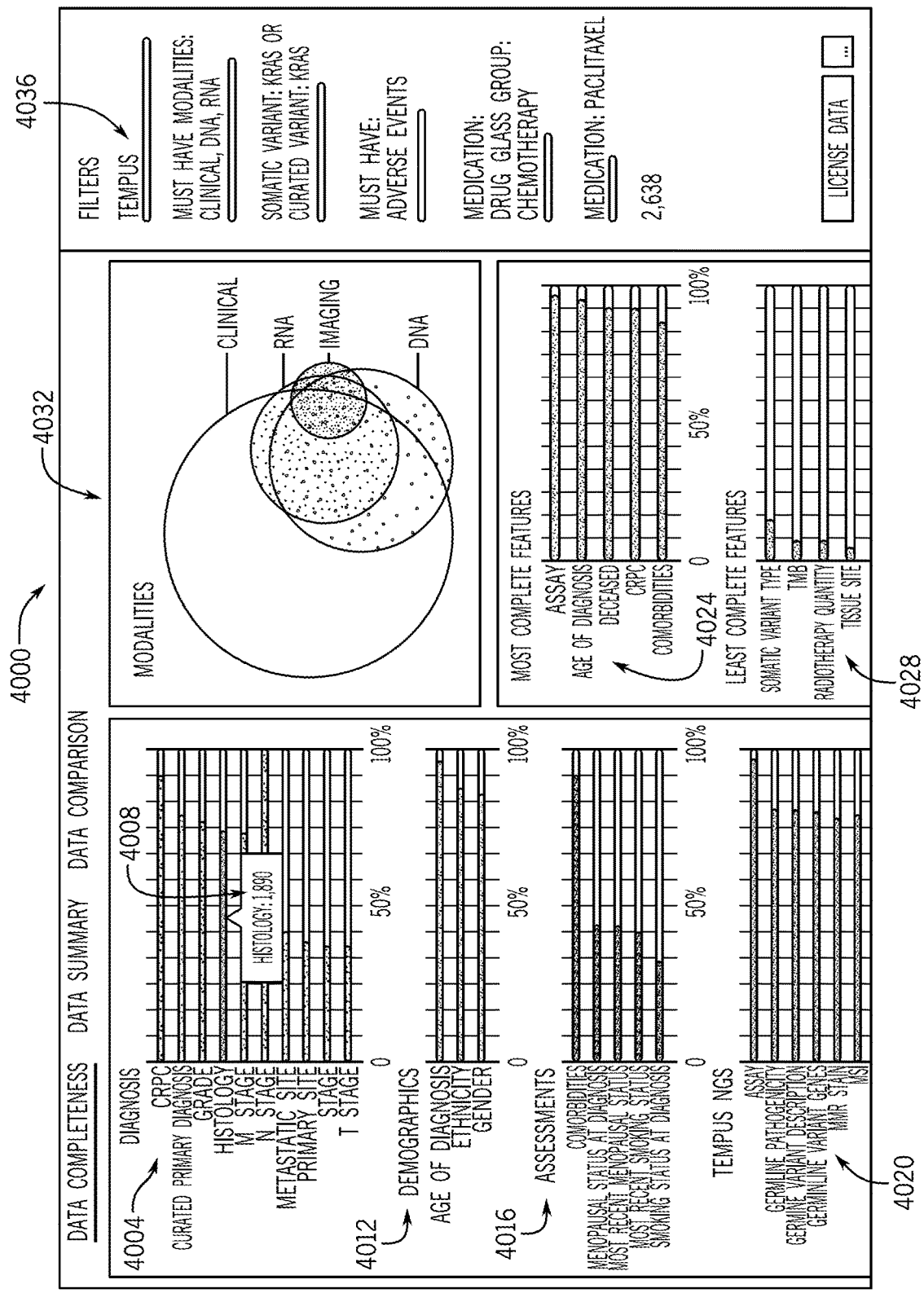
FIG. 40 illustrates an example of a user interface of the Interactive Analysis Portal for displaying one or more data completeness measures according to certain embodiments.

FIG. 40 illustrates an example of a user interface 4000 of the Interactive Analysis Portal 22 for displaying one or more data completeness measures according to certain embodiments. In some embodiments, the user interface 4000 can include a diagnosis data completeness graph 4004 displaying data completeness (e.g., as a percentage) in the cohort of patients for a number of diagnosis features. In some embodiments, the user interface 4000 can include a raw number indicator 4008 that displays the exact number of patients in the cohort of patients that include populated values for a given feature (e.g., histology). In some embodiments, the raw number indicator 4008 can be selectively displayed in response to input from the user (e.g., hovering a cursor over the feature, clicking on the feature, touching the feature, etc.).

In some embodiments, the user interface 4000 can include a demographics data completeness graph 4012 displaying data completeness (e.g., as a percentage) in the cohort of patients for a number of demographics features. In some embodiments, the user interface 4000 can include an assessments data completeness graph 4016 displaying data completeness (e.g., as a percentage) in the cohort of patients for a number of assessments features. In some embodiments, the user interface 4000 can include an NGS data completeness graph 4020 displaying data completeness (e.g., as a percentage) in the cohort of patients for a number of NGS features.

In some embodiments, the user interface 4000 can include a most complete features graph 4024 displaying data completeness (e.g., as a percentage) in the cohort of patients for a number of the most complete data features (e.g., five most complete features). The most complete data features can be included in different types of data features (e.g., demographic data, assessment data, diagnosis data, next-generation sequencing (NGS) data, molecular data, treatment data, and/or outcome data).

In some embodiments, the user interface 4000 can include a least complete features graph 4028 displaying data completeness (e.g., as a percentage) in the cohort of patients for a number of the least complete data features (e.g., five least complete features). The least complete data features can be included in different types of data features (e.g., demographic data, assessment data, diagnosis data, next-generation sequencing (NGS) data, molecular data, treatment data, and/or outcome data).

In some embodiments, the user interface 4000 can include a Venn diagram 4032 representative of how many patients included in the cohort of patients are associated with patient information including populated values associated with the modality data. The Venn Diagram 4032 can show how many patients are associated with patient information including populated values associated with modality data including clinical data, DNA data, RNA data, and/or imaging data. In some embodiments, the user interface 4000 can include a selected filters completeness portion 4036 that includes visual indicators (e.g., graphical bars) that show the relative commonality of the selected filters to the original plurality of patients.

FIG. 37, discussed above, illustrates an example of a user interface 3750 of the Interactive Analysis Portal for displaying an interactive graph for generating a cohort. In some embodiments, the user interface 3750 can include an interactive Venn diagram 3754 and/or a modalities key 3758. The modalities key 3758 can indicate what modalities are available and/or are included in a current query in the Venn diagram 3754. The Venn diagram 3754 can allow a user to select one or more modalities to filter patients in the plurality of patients. For example, the user can select a portion 3762 of the Venn diagram 3754 corresponding to RNA data, imaging data, and DNA data. A process can then automatically filter patients and generate a cohort including patients that have populated values for RNA data, imaging data, and DNA data. In some embodiments, the user interface 3750 can include a cohort population indicator 3766, which can indicate how many patients in the plurality of patients would not be included in the cohort based on the current selected portion(s) of the Venn diagram 3754.

Figure 41:
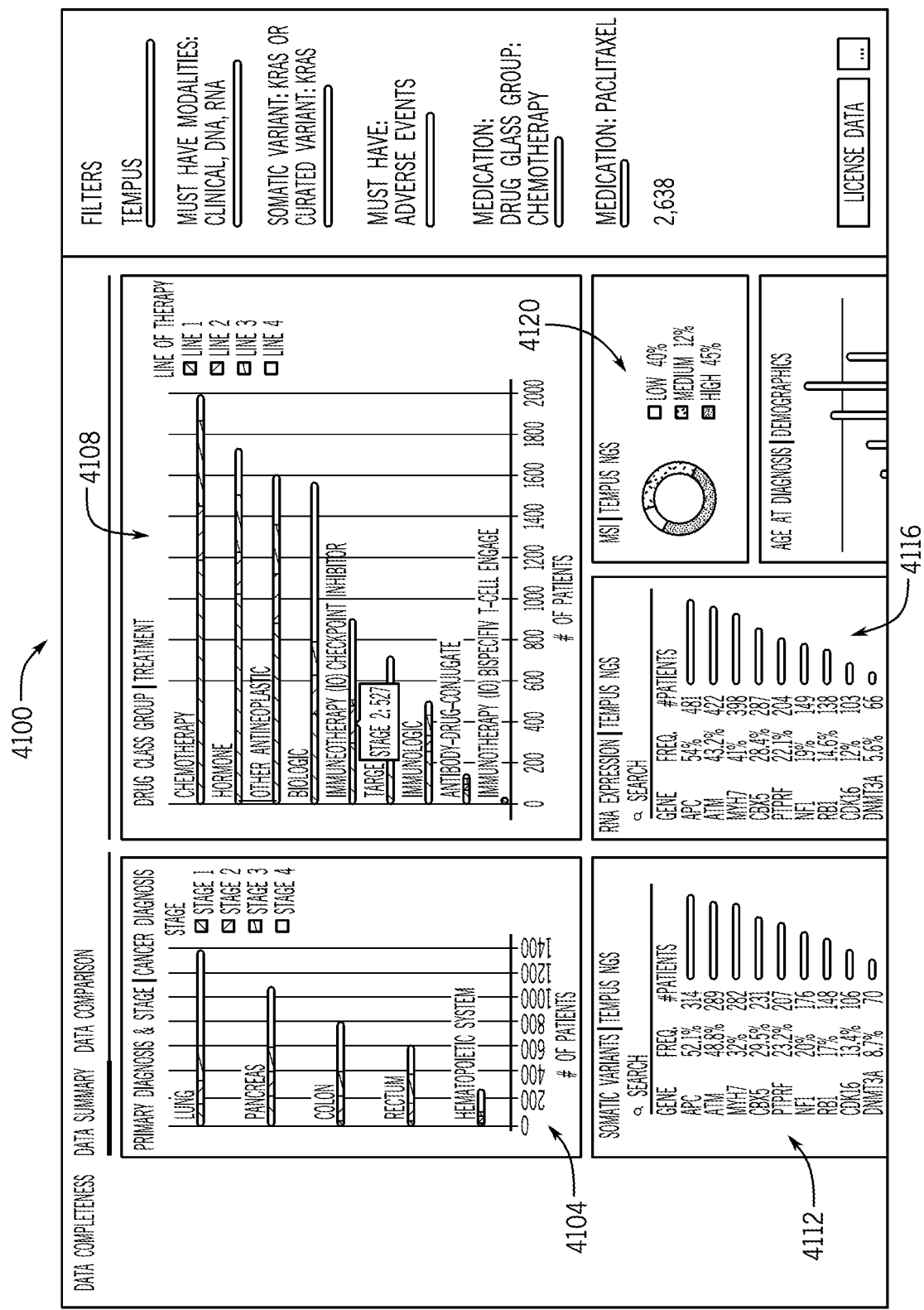
FIG. 41 illustrates an example of a user interface of the Interactive Analysis Portal for displaying one or more data summary measures according to certain embodiments.

FIG. 41 illustrates an example of a user interface 4100 of the Interactive Analysis Portal 22 for displaying one or more data summary measures according to certain embodiments. In some embodiments, the user interface 4100 can include a dual feature comparison chart or graph 4104. The dual feature comparison chart or graph 4104 can show, for each specific value in a first set of specific values, a number of patients included in the cohort of patients that are associated with populated values equal to the specific value and each specific value included in a second set of specific values. For example, the first specific feature can be a cancer stage that can be populated with stage 1, stage 2, stage 3, or stage 4, and the second specific feature can be cancer type that can be populated by lung, pancreas, colon, rectum, or hematopoietic system. In this example, the dual feature comparison chart or graph 4104 can indicate how many patients that have a cancer type of lung, pancreas, colon, rectum, or hematopoietic system are at each cancer stage (i.e., stage 1, stage 2, stage 3, or stage 4).

In some embodiments, the user interface 4100 can include a second dual feature comparison chart or graph 4108. The second dual feature comparison chart or graph 4108 can show, for each specific value in a first set of specific values, a number of patients included in the cohort of patients that are associated with populated values equal to the specific value and each specific value included in a second set of specific values. For example, the first specific feature can be a drug class group that can be populated with LOT 1, LOT 2, LOT 3, or LOT 4, and the second specific feature can be treatment type that can be populated by chemotherapy, hormone, other antineoplastic, biologic, immunotherapy 10 checkpoint inhibitor, targeted (e.g., small molecule), immunological, antibody-drug-conjugate, or 10 bispecific t-cell engager The second dual feature comparison chart or graph 4108 can indicate, for each populated value of the treatment type, how many patients have received LOT 1, LOT 2, LOT 3, or LOT 4 class drugs.

In some embodiments, the user interface 4100 can include a populated values comparison graph or chart 4112. The populated values comparison graph or chart 4112 can show a ranked ordering of the most common to least common populated values for a collection of related features. As shown, the populated values comparison graph or chart 4112 can include a set of somatic variants most commonly associated with patients in the cohort of patients (e.g., APC, ATM, MYH7, etc.).

In some embodiments, the user interface 4100 can include a second populated values comparison graph or chart 4116. The second populated values comparison graph or chart 4116 can show a ranked ordering of the most common to least common populated values for a collection of related features. As shown, the second populated values comparison graph or chart 4116 can include a set of RNA gene expressions most commonly associated with patients in the cohort of patients (e.g., APC, ATM, MYH7, etc.).

In some embodiments, the user interface 4100 can include a prominence pie chart 4120. The prominence pie chart 4120 can indicate the most common populated values (e.g., low, medium, and high) for a given feature (e.g., MSI) for patients in the cohort of patients.

Figure 42:
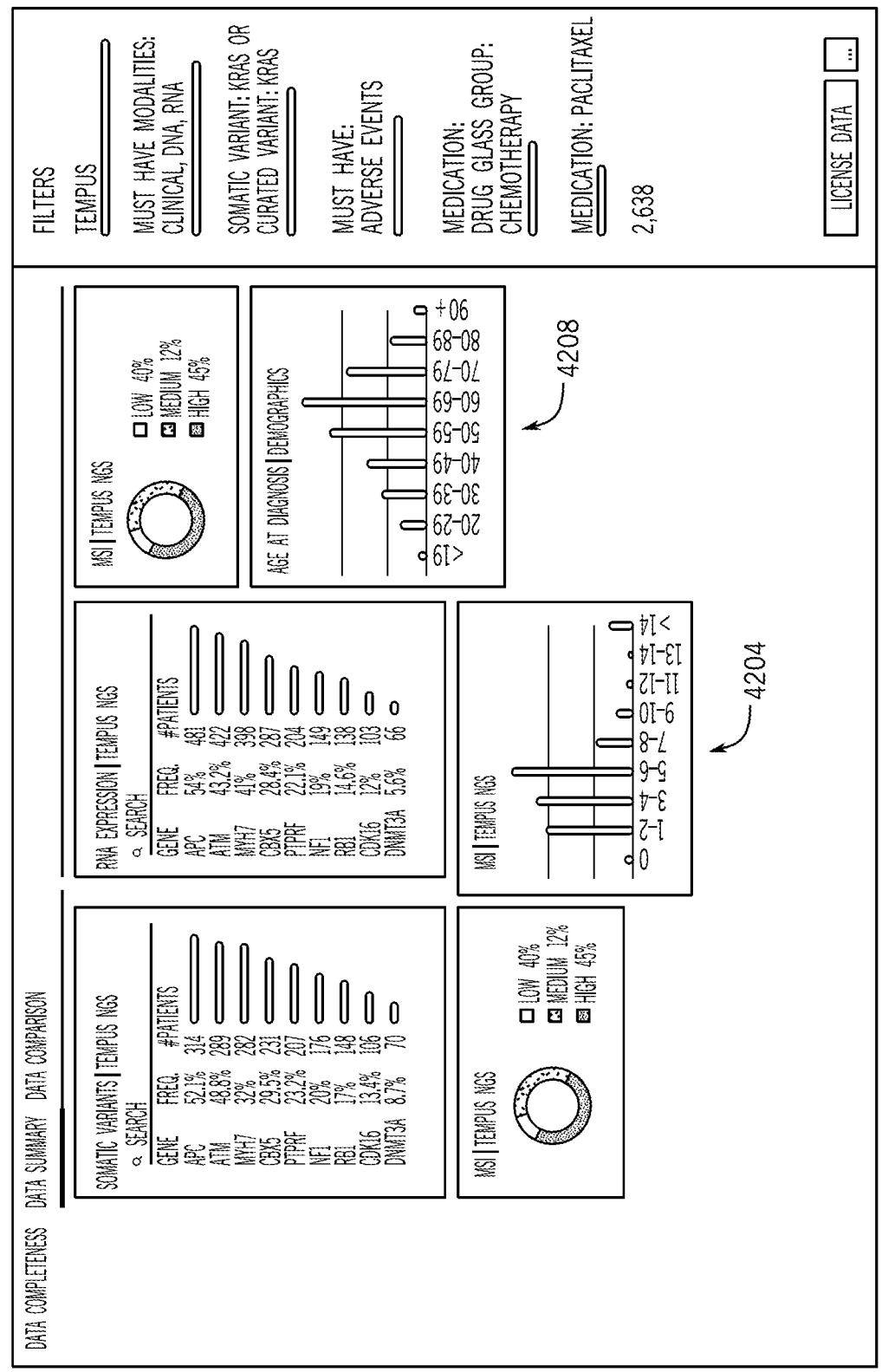
FIG. 42 illustrates another example of a user interface of the Interactive Analysis Portal for displaying one or more data summary measures according to certain embodiments.

FIG. 42 illustrates another example of a user interface 4200 of the Interactive Analysis Portal 22 for displaying one or more data summary measures according to certain embodiments. In some embodiments, the user interface 4200 can include a populated values comparison graph or chart 4204. In some embodiments, the populated values comparison graph or chart 4204 can include a number of bins each corresponding to a range of values for a specific feature. As shown, the populated values comparison graph or chart 4204 can be a TMB bar chart including a bar for each bin included in a number of bins for TMB values. In some embodiments, the user interface 4200 can include a second populated values comparison graph or chart 4208. In some embodiments, the second populated values comparison graph or chart 4208 can include a number of bins each corresponding to a range of values for a specific feature. As shown, the second populated values comparison graph or chart 4208 can be an age at diagnosis bar chart including a bar for each bin included in a number of bins for age values.

Figure 43:
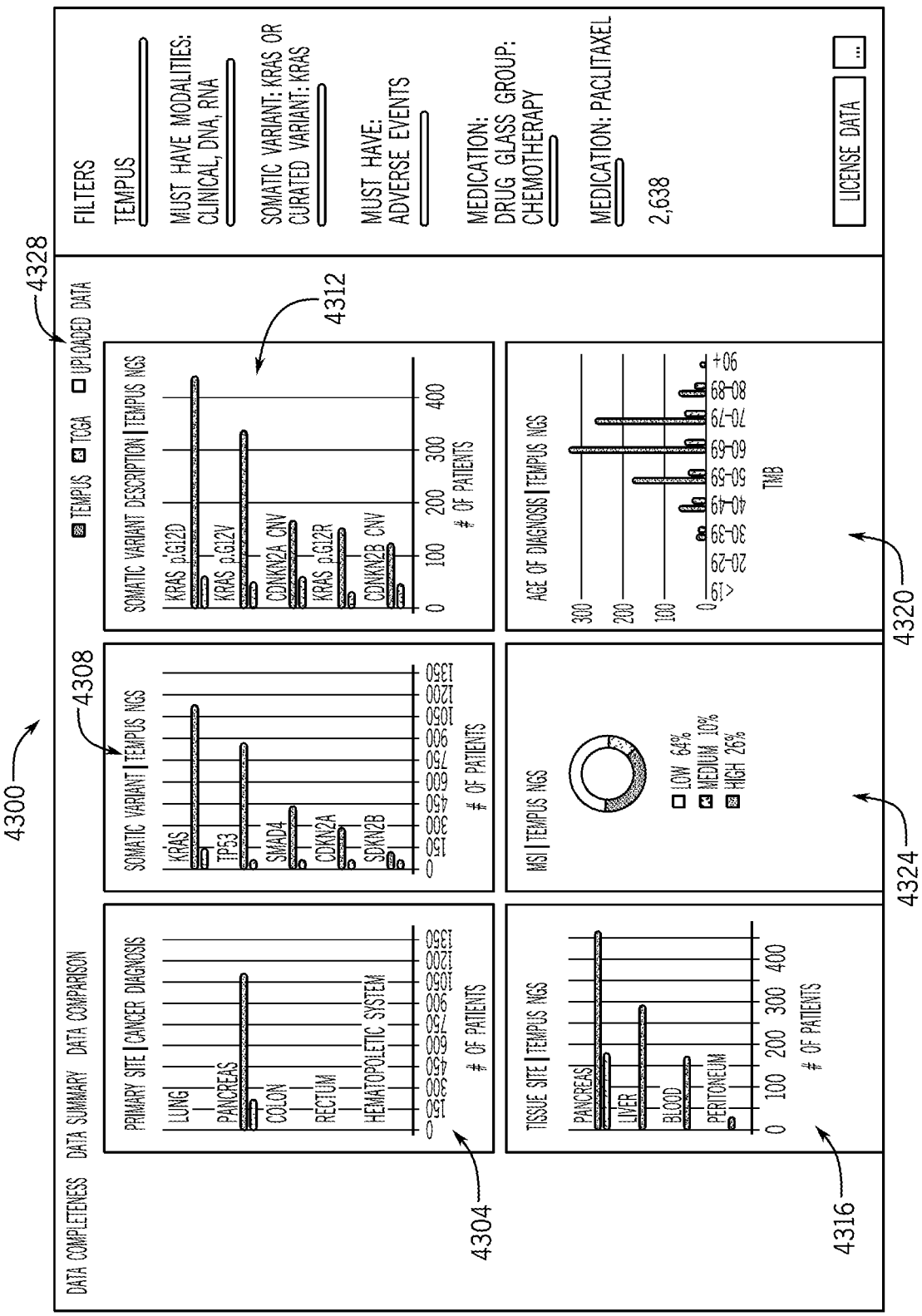
FIG. 43 illustrates an example of a user interface of the Interactive Analysis Portal for displaying one or more data comparison measures according to certain embodiments.

FIG. 43 illustrates an example of a user interface 4300 of the Interactive Analysis Portal 22 for displaying one or more data comparison measures according to certain embodiments. The user interface 4300 can include a number of graphs and/or charts for comparing patients associated with a first health institution and a second institution. In some embodiments, the user interface 4300 can include a first graph 4304, a second graph 4308, a third graph 4312, a fourth graph 4316, and a fifth graph 4320 comparing patient breakdowns for primary site cancer diagnosis, somatic variant type, somatic variant description, tissue site, and age at diagnosis between the first health institution and the second institution, respectively. Each of the first graph 4304, the second graph 4308, the third graph 4312, the fourth graph 4316, and the fifth graph 4320 can be clustered bar charts. In some embodiments, the user interface 4300 can include a prominence pie chart 4324. The prominence pie chart 4324 can indicate the most common populated values (e.g., low, medium, and high) for a given feature (e.g., MSI) for patients in the first health institution and/or the second health institution. In some embodiments, the prominence pie chart 4324 may only display data associated with the first health institution if the second health institution does not include any relevant patient data (e.g., no MSI testing data). The user interface 4300 further may include an institution selector 4328 to permit the user to designate one or more institutions from which to analyze data in order to perform the data comparison measures depicted therein.

Figure 44:
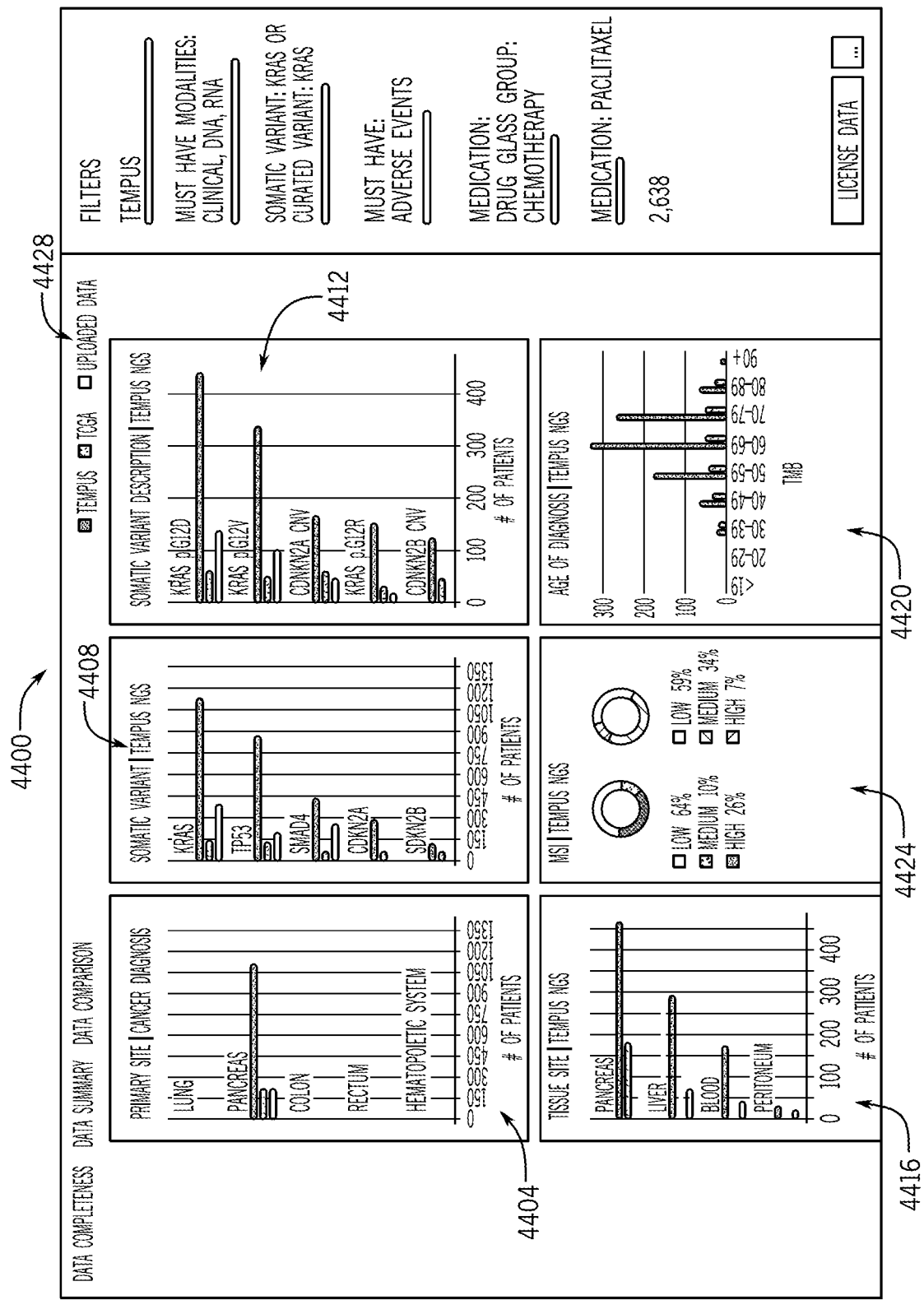
FIG. 44 illustrates another example of a user interface of the Interactive Analysis Portal for displaying one or more data comparison measures according to certain embodiments.

FIG. 44 illustrates another example of a user interface 4400 of the Interactive Analysis Portal 22 for displaying one or more data comparison measures according to certain embodiments. The user interface 4400 can include a number of graphs and/or charts for comparing patients associated with a first health institution, a second institution, and a third institution. In some embodiments, the user interface 4400 can include a first graph 4404, a second graph 4408, a third graph 4412, a fourth graph 4416, and a fifth graph 4420 comparing patient breakdowns for primary site cancer diagnosis, somatic variant type, somatic variant description, tissue site, and age at diagnosis between the first health institution, the second institution, and the third institution, respectively. Each of the first graph 4404, the second graph 4408, the third graph 4412, the fourth graph 4416, and the fifth graph 4420 can be clustered bar charts. In some embodiments, the user interface 4400 can include a prominence pie chart 4424. The prominence pie chart 4424 can indicate the most common populated values (e.g., low, medium, and high) for a given feature (e.g., MSI) for patients in the first health institution, the second health institution, and/or the third health institution. In some embodiments, the prominence pie chart 4424 may only display data associated with the first health institution and the third health institution if the second health institution does not include any relevant patient data (e.g., no MSI testing data). In these embodiments, the prominence pie chart 4424 can include two sub-charts. The user interface 4400 further may include an institution selector 4428 to permit the user to designate one or more institutions from which to analyze data in order to perform the data comparison measures depicted therein.

Patient Similarities

In various embodiments, the system may permit a user to evaluate a cohort of patients by identifying and presenting one or more similarities shared by patients within the cohort relative to a reference patient, where those similarities may include features such as similar biomarkers, similar disease states, similar drugs taken or treatments provided, etc. Such a process may be helpful to a physician in order to evaluate treatment plans of patients similarly situated with respect to a reference patient. For example, after identifying similarly situated patients, the system may include a user interface presenting treatment regimen information about one or more of those patients including when the user started his or her regimen, where they are on that treatment plan, as well as information regarding the efficacy of the treatment plan.

Alternatively, the system may permit a user to identify one or more criteria upon which a cohort of patients is to be evaluated in order to determine how the cohort itself compares to a selected patient. For example, the user may want to know how many patients, like the reference patient, have stage 3 lung cancer or have a KRAS mutation and then, from there, evaluate how the treatment regimens of those patients compare to the reference patient, e.g., what number or percentage of that cohort of patients are taking sotorasib. The system then may permit the user to tailor the shared features of the cohort and/or individual patients within the cohort to evaluate more information concerning those patients.

In particular, the system may include a user interface through which a user can select a cohort of patients included in a patient database and then select a health record relating to a first patient. From there, the system may establish selected criteria based on the health record. The selected criteria may be at least one populated value of a first feature, and in one embodiment the first feature is a genetic mutation of the first patient. The system may request that the user affirm the selected criteria and, upon receiving such affirmation, identify a cohort of patient records included in a patient database based on the selected criteria, where each patient record included in the cohort satisfies the selected criteria. Based on the cohort of patient records and the selected criteria, the system then may generate and display at the user interface at least one comparative patient indicator, which may take the form of a graphical indicator indicative of a popularity of a populated value of a second feature such as a treatment, a therapy, a study, or procedure amongst patient records in the cohort. For example, the indicator may be a bar or other graph in which the number or percentage of patients possessing the second feature is displayed relative to a total number of patients in the cohort of patients possessing the first feature.

The populated value may relate to or comprise a disease state, which may be a cancer including at least one of a melanoma, a lung cancer, a breast cancer, a bladder cancer, or any other cancer as would be appreciated by one of ordinary skill in the art. The system may be used to evaluate multiple types of therapies, including but not limited to drug regimens comprising the administration of at least one drug, treatments such as radiation or chemotherapy, procedures, hormone treatments, stem cell transplants, monoclonal or therapeutic antibody therapies, etc. Drug therapies may include, e.g., biologic drugs, immunotherapy checkpoint inhibitor drugs, targeted drugs, immunological drugs, antibody-drug-conjugate drugs, an immunotherapy bispecific t-cell engager drug, or any combination thereof. The therapy also may be a therapy regimen that may include a plurality of regimens and/or a plurality of lines of therapy. The procedure may be a surgical procedure such as a biopsy or a cancer removal surgery.

The at least one patient similarity indicator may include a graphical or quantitative indicator of the size of the relevant cohort, such as a number of how many patients are included in the cohort. Additionally or alternatively, the at least one patient similarity indicator may include at least one qualitative indicator such as a graph or chart reflecting a relevance within the cohort of a populated value of the second feature.

The health information associated with patients included in the patient database may be used to determine at least one data completeness measure based on health information associated with patients included in the patient database. Then, a subset of the features that have the highest data completeness may be determined and displayed at the user interface in at least one interactive region, where that region is designed to receive a selection of one or more of the features made up of the selected criteria.

Patient similarities may be evaluated across cohorts with respect to a number of disease states. Disease states including oncology, cardiography, endocrinology, mental health, laboratory diagnostics, and even general medicine, amongst others. In the field of oncology, it may be desirable to identify patients having a similar tumor to the identified patient by identifying a cohort of patient records having the same primary site of tumor, genetic alterations, fusions, molecular biomarkers, MSI status, staging, TNM, metastasis, or other oncological biomarkers of interest. In the field of cardiology, such as for a cardiovascular disease such as aortic stenosis or atrial fibrillation, it may be desirable to identify patients having similar electrocardiogram or echocardiogram to the identified patient by identifying a cohort of patient records having the same molecular biomarkers, genetic alterations, fusions, symptoms, clinical details, or other cardiographic biomarkers of interest. In the field of endocrinology, such as diabetes, or other endocrinological diseases, it may be desirable to identify patients having similar clinical history, genetic alterations, fusions, molecular biomarkers, symptoms, or other endocrinological biomarkers of interest. In the field of mental health, such as depression, alzheimers, or other mental health diseases or disorders, it may be desirable to identify patients having similar clinical history, genetic alterations, fusions, molecular biomarkers, symptoms, or other mental health biomarkers of interest. In the field of laboratory diagnostics, such as metabolic panels performed on blood draws or other diagnostics, it may be desirable to identify patients having similar clinical history, geographic proximity, genetic alterations, fustions, molecular biomarkers, or other diagnostic biomarkers of interest. While biomarkers for each respective disease state are suggested herein in an illustrative manner, they should not be construed as limiting the applicable biomarkers to only the embodiments as may be determined by a medical health professional in the respective field as the biomarkers may be fully configured according to the professional's desired characteristics. In one example predetermined selection criteria may include identification of the biomarkers of interest. Selection criteria may be hand selected by the professional or may be identified through analytics, such as by identifying which biomarkers result in the largest variance within patient response to treatments, patient health, or diagnostic outcomes. Analytics may include identification of professionals' selections over time whereas the default selection criteria may include, by example, the most common final selection criteria physicians of a specific institution may use before being successful with the results and clicking through the interface. In some examples, this may be identified via the affirmation of the selection criteria the user performs.

When applying patient similarity analytics to a patient's health record, such as through a laboratory report user interface, a number of predefined/predetermined selection criteria may be extracted or referenced from one or more genomic test results. Genomic test results may exist in a number of different formats. In one example, those formats may include a specific assay that was performed, such as a whole genome sequencing, a limited genome sequencing tailored to the particular disease state, a tissue sequencing, tumor sequencing, tumor-normal sequencing, a liquid biopsy sequencing, a cell-free DNA sequencing, DNA sequencing, RNA/transcriptome sequencing, next-generation sequencing panels, or other assays for identifying genomic alterations, fusions, or molecular biomarkers within a patient's genome. Panels and assays tailored to a particular disease state may include limited targeting for a specific number of important genes within the field of the disease state. For particular disease states, some assays or panels may be preferential in identifying genetic alterations, fusions, or genetic biomarkers than other assays or panels. Additionally, sometimes a selected genetic test result of the plurality of available genetic test reports has a later addendum or amendment issued. It may be desirable to search through the remaining test results, even after identifying the test results which will be used to ensure that any addendums or amendments to the selected test result are also considered at the same time as the identified or selected test result. When selecting between a plurality of assays for each disease state, it may be advantageous to consider the genes of the assay, the biopsy on which the assay is performed, and the date of each assay and how they relate to each other assay in time. In the example of oncological assays, for example, there may exist a solid tissue DNA assay and a liquid biopsy assay such as a cell-free DNA assay. The process for identifying which assay to use may include first identifying if a successful genetic test report exists for the patient at all, if one does, then the routine may continue. If more than one genetic test result exists, the results may be selected according to a rule set. The result may first identify all of the solid tumor results and select the newest in time result as a potential genetic test result for reference for the identified patient. If the potential result was generated more than a threshold of time ago, such as 6 months, 12 months or other time period, then the genetic test result list may be checked for a newer in time liquid biopsy test result, and if one is found then use the newest liquid biopsy result in the list. If only one type of assay result exists, then the newest may be selected. Once a report is finally selected, a cursory check may be performed to identify addenda or amendments to the report which may need to be considered at the same time. If an addendum exists, the two reports may be combined and considered together and if an amendment exists, the amendment may be considered instead of the original report.

Population of selection criteria may include extracting the genetic alterations, fusions, or other molecular biomarkers from the selected test report. In some embodiments, all criteria are populated and used in the cohort of patient record selection. In other embodiments, the selection criteria may be populated based on which criteria exists within the test record. For example, in the field of oncology, a fusion may be considered more divisive than a genomic alteration, therefore if the genetic test result indicates a presence of a fusion, only the fusion may be included as selection criteria for a genomic alteration. When no fusion is identified, then any identified genetic alterations may be included instead. When both exist, and no preferential rule set exists, then both may be used to populate the selection criteria.

Given a known set of hyperparameters for each disease state, such as those listed above, it may be advantageous to consider the impacts of a selected feature set for each disease state. For example, a feature set for DNA related features (DNA variant calls) may include a calculation of the maximum effect a gene may have from sequencing results for the gene and source set forth in Table 9. A max effect calculation may include identifying an integer in a range from 0 to 7, wherein a 0 represents no effect and a 7 represents the highest effect a gene may impact a patient's disease state diagnosis. While the values 0-7 are used for illustrative purposes, other values may be used according to a desired resolution for measuring the effect. The values may be classified from a variant science pipeline based upon a characterization of the variant effect as pathogenic, benign, or unknown. In one example, a variant having a pathogenic classification may be assigned a value of 7 where a variant having a benign classification may be assigned a value of 0. Values of differing degrees may be awarded when mitigating or aggravating factors are present. For example, a variant which has substantial documentation within the medical community for relating to the disease state may be assigned a higher value than a variant which has nominal documentation within the medical community. In one example, genetic variants are assigned a max effect value and a model may be trained on a variant by variant basis. A variant by variant model may be trained on variant max effects and a supervisory signal identifying patient metastasis. In another example, genetic variants are assigned a max effect value, but a model may be trained on a gene by gene basis. Converting variant max effect into gene max effect may include a number of approaches such as taking the highest max effect or applying customized weights to each max effect based upon the number of reads associated with the variant from sequencing of the patient's tumor. In one example, where the highest max effect is assigned, variants for each gene are compared to identify the highest max effect relating to the gene, and the highest max effect is assigned to the gene. Where the max effects are provided a customized weighting schema, each variant may be assigned a weight to scale the max effect and those max effects are combined into a gene max effect. For example, a gene with four identified variants may scale each max effect by 0.25 and sum the combined, scaled max effects into a gene max effect, effectively averaging the max effects. In another aspect, a gene with four variants having raw reads of 25, 50, 100, 250, and 75 may scale each max effect by 25/450, 100/450, 250/450, and 75/450 respectively. A gene with no called variants (variants identified in the patient's genome) for a particular gene is assigned a max effect of 0.

TABLE 9

| |
|---|
| ABCB1 |
| ACTA2 |
| ACTC1 |
| ALK |
| AMER1 |
| APC |
| APOB |
| AR |
| ARHGAP35 |
| ARID1A |
| ARID1B |
| ARID2 |
| ASXL1 |
| ATM |
| ATP7B |
| ATR |

TABLE 9-continued

| |
|---|
| ATRX |
| AXIN2 |
| BACH1 |
| BCL11B |
| BCLAF1 |
| BCOR |
| BCORL1 |
| BCR |
| BMPR1A |
| BRAF |
| BRCA1 |
| BRCA2 |
| BRD4 |
| BRIP1 |
| CACNA1S |
| CARD11 |
| CASR |
| CD274 |
| CDH1 |
| CDK12 |
| CDKN2A |
| CEBPA |
| CFTR |
| CHD2 |
| CHD4 |
| CHEK2 |
| CIC |
| COL3A1 |
| CREBBP |
| CTNNB1 |
| CUX1 |
| DICER1 |
| DOT1L |
| DPYD |
| DSC2 |
| DSG2 |
| DSP |
| DYNC2H1 |
| EGFR |
| EP300 |
| EPCAM |
| EPHA2 |
| EPHA7 |
| EPHB1 |
| ERBB2 |
| ERBB3 |
| ERBB4 |
| ESR1 |
| ETV6 |
| FANCA |
| FANCD2 |
| FANCI |
| FANCL |
| FANCM |
| FAT1 |
| FBN1 |
| FBW7 |
| FGFR3 |
| FH |
| FLCN |
| FLG |
| FLT1 |
| FLT4 |
| GATA2 |
| GATA3 |
| GATA4 |
| GATA6 |
| GLA |
| GNAS |
| GRIN2A |
| GRM3 |
| HDAC4 |
| HGF |
| IDH1 |
| IKZF1 |
| IRS2 |
| JAK3 |
| KCNH2 |
| KCNQ1 |
| KDM5A |

TABLE 9-continued

| | |
|---|---|
| KDM5C | RNF43 |
| KDM6A | ROS1 |
| KDR | RPTOR |
| KEAP1 | RUNX1 |
| KEL | RUNX1T1 |
| KIF1B | RYR1 |
| KMT2A | RYR2 |
| KMT2B | SCN5A |
| KMT2C | SDHAF2 |
| KMT2D | SDHB |
| KRAS | SDHC |
| LDLR | SDHD |
| LMNA | SETBP1 |
| LRP1B | SETD2 |
| MAP3K1 | SH2B3 |
| MED12 | SLIT2 |
| MEN1 | SLX4 |
| MET | SMAD3 |
| MKI67 | SMAD4 |
| MLH1 | SMARCA4 |
| MSH2 | SOX9 |
| MSH3 | SPEN |
| MSH6 | STAG2 |
| MTOR | STK11 |
| MUTYH | TAF1 |
| MYBPC3 | TBX3 |
| MYCN | TCF7L2 |
| MYH11 | TERT |
| MYH7 | TET2 |
| MYL2 | TGFBR1 |
| MYL3 | TGFBR2 |
| NBN | TMEM43 |
| NCOR1 | TNNI3 |
| NCOR2 | TNNT2 |
| NF1 | TP53 |
| NF2 | TPM1 |
| NOTCH1 | TSC1 |
| NOTCH2 | TSC2 |
| NOTCH3 | VHL |
| NRG1 | WT1 |
| NSD1 | XRCC3 |
| NTRK1 | ZFHX3 |
| NTRK3 | |
| NUP98 | |
| OTC | |
| PALB2 | |
| PALLD | |
| PBRM1 | |
| PCSK9 | |
| PDGFRA | |
| PDGFRB | |
| PGR | |
| PIK3C2B | |
| PIK3CA | |
| PIK3CG | |
| PIK3R1 | |
| PIK3R2 | |
| PKP2 | |
| PLCG2 | |
| PML | |
| PMS2 | |
| POLD1 | |
| POLE | |
| PREX2 | |
| PRKAG2 | |
| PTCH1 | |
| PTEN | |
| PTPN13 | |
| PTPRD | |
| RAD51B | |
| RAD51C | |
| RAD51D | |
| RAD52 | |
| RAD54L | |
| RANBP2 | |
| RB1 | |
| RBM10 | |
| RECQL4 | |
| RET | |
| RICTOR | |

For endocrinological diseases, additional consideration may be given to genes CASR, RET, HNF1A, GCK, MEN1, MEN2, CYP21A2, CDC73, SDHB, PPGL, FMR1, or other genes of interest.

For cardiovascular diseases, additional consideration may be given to genes COL3A1, FBN1, TGFBR1, TGFBR2, SMAD3, ACTA2, MYH11, MYBPC3, MYH7, TNNT2, TNNI3, TPM1, MYL3, ACTC1, PRKAG2, GLA, MYL2, LMNA, RYR2, PKP2, DSP, DSC2, TMEM43, DSG2, KCNQ1, KCNH2, SCNSA, LDLR, APOB, PCSK9 or other genes of interest.

For mental health diseases, additional consideration may be given to genes SLC6A4, 5HT2C, 5HT2A, SULT4A1, DRD1, DRD2, DRD4, DAT1, SLC6A3, DBH, CACNA1C, ANK3, ANK3, MTHFR, GABA, OPRMI, OPRK1, CYP2D6, CYP2C19, CYP3A4, CYP1A2, CYP2C9, CYP2B6, ABCB1, UGT1A4, SULT4A1, SLC6A4, 5HT2C, 5HT2A, DRD1, DRD2, DRD4, DAT1, DBH, CACNA1C, ANK3, COMT, MTHFR, GABA, OPRK1, OPRM1, CYP450, CYP2D6, CYP2C19, CYP3A4, CYP1A2, CYP2C9, CYP2B6, P2B6, UBT1A4, ABCB1, MC4R, ADRA2A, BDNF, GRIK1, or other genes of interest.

These and other aspects may be seen and explained in greater detail with respect to the following figures.

Figure 45:
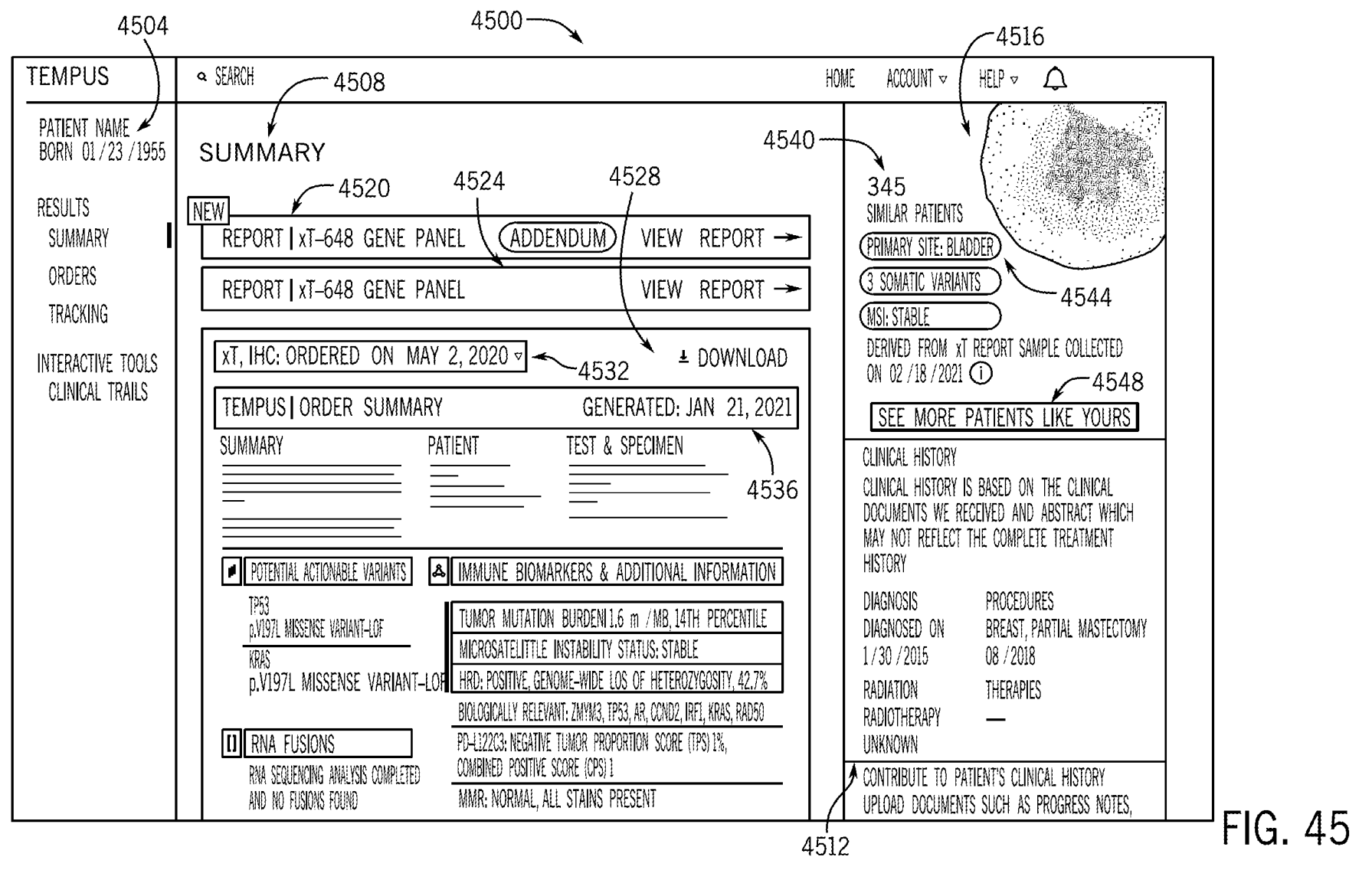

FIG. 45 illustrates an example of a user interface 4500 of the Interactive Analysis Portal 22 for generating a cohort having patients that are similar to a target patient. In some embodiments, the user interface 4500 can include a patient name section 4504, a patient sequencing information section 4508, a patient clinical history information section 4512, and a similar patients information section 4516. The patient name section 4504, patient sequencing information section 4508, and the patient clinical history information section 4512 can be associated with the target patient. In some embodiments, the patient name section 4504 can include a name and/or other patient information such as a birthdate, a gender, and/or other personal information.

In some embodiments, the patient sequencing information section 4508 can include a new report indicator 4520, a pending reports indicator 4524, and/or a report viewer section 4528. In some embodiments, the new report indicator 4520 can include information about a most recent report available for the target patient, a report type, and/or a link (e.g., a hyperlink) to the most recent report. In some embodiments, the pending reports indicator 4524 can include an indicator of how many reports are pending for the target patient and/or a link (e.g., a hyperlink) to one or more pending reports. In some embodiments, the report viewer section 4528 can include a report selector 4532 (e.g., a dropdown menu) and/or a report window 4536 displaying at least a portion of a selected report. The selected report can be a predetermined report (e.g., the most recent report) and/or a report selected using the report selector 4532.

In some embodiments, the patient clinical history information section 4512 can include one or more indicators of clinical history for the patients. In some embodiments, the patient clinical history information section 4512 can include a diagnosis indicator, a procedures indicator, a radiation indicator, and/or a therapies indicator.

In some embodiments, the similar patients information section 4516 can include a cohort population indicator 4540 (e.g., an indicator of how many similar patients are available). In some embodiments, the cohort can be generated based on one or more populated values 4544 included in one or more reports associated with the target patient (e.g., the most recent report associated with the target patient). In some embodiments, a process can determine one or more of the populated values 4544 based on a predetermined set of features used to generate cohorts. For example, the predetermined set of features can include one or more features that can be used to filter a plurality of patients and generate the cohort. The process can determine the populated values 4544 based on the predetermined set of features and the report(s) associated with the patient by identifying populated values associated with the one or more features in the report(s). In some embodiments, the predetermined set of features can be generated by one or more physicians. In some embodiments, the similar patients information section 4516 can include a similar patients selection button 4548.

FIG. 46 illustrates another example of a user interface 4600 of the Interactive Analysis Portal 22 for generating a cohort having patients that are similar to a target patient. In some embodiments, the user interface 4600 can include a similar patients summary section 4604. In some embodiments, the similar patients summary section 4604 can be displayed upon selection of the similar patients selection button 4548 in FIG. 45 (e.g., selection by a user). In some embodiments, the similar patients summary section 4604 can include information about how the cohort was selected. For example, the similar patients summary section 4604 can include information about a report used to determine the populated values 4544 in FIG. 45. In some embodiments, the user interface 4600 can include a link 4608 (e.g., a hyperlink) to an external cohort analysis application, such as the cohort analysis application described above and depicted in FIGS. 2-24.

FIG. 47 illustrates yet another example of a user interface 4700 of the Interactive Analysis Portal 22 for generating a cohort having patients that are similar to a target patient. In some embodiments, the user interface 4700 can include an external cohort analysis application warning 4704. In some embodiments, the external cohort analysis application warning 4704 can be displayed upon selection of the link 4608 in FIG. 46 (e.g., selection by a user). In some embodiments, the external cohort analysis application warning 4704 can provide information about the external cohort analysis application and/or a warning that the user will be proceeding to an external application. For example, the similar patients summary section 4704 can include information about a report used to determine the populated values 4544 in FIG. 45. In some embodiments, the user interface 4700 can include a link 4708 (e.g., a hyperlink) to an external cohort analysis application, such as the cohort analysis application described above and depicted in FIGS. 2-24.

FIG. 48 illustrates still yet another example of a user interface 4800 of the Interactive Analysis Portal 22 for generating a cohort having patients that are similar to a target patient. In some embodiments, the user interface 4800 can include a similar patients information section 4804.

In some embodiments, the similar patients information section 4804 can include a cohort population indicator 4808 (e.g., an indicator of how many similar patients are available). In some embodiments, the cohort can be generated based on one or more populated values 4812 included in one or more reports associated with the target patient (e.g., the most recent report associated with the target patient). In some embodiments, a process can determine one or more of the populated values 4812 based on a predetermined set of features used to generate cohorts. For example, the predetermined set of features can include one or more features that can be used to filter a plurality of patients and generate the cohort. The process can determine the populated values 4812 based on the predetermined or user-selected set of features and the report(s) associated with the patient by identifying populated values associated with the one or more features in the report(s). In some embodiments, the predetermined set of features can be generated by one or more physicians. In some embodiments, the similar patients information section 4804 can include a similar patients selection button 4816 to provide more information about the patients identified by the cohort population indicator 4808.

As shown, the populated values 4812 can include a single populated value for a given feature (e.g., a populated value of "Bladder" for the feature of "Primary site"). Using a single populated value can increase the number of similar patients available as compared to using multiple populated values (e.g., as shown in FIG. 45). In some embodiments, a process can prepopulate the populated values 4812 with multiple populated values, and a user can remove one or more of the populated values 4812 in order to broaden the number of similar patients and/or the size of the cohort.

In addition, although not labeled, it should be understood that the user interface of FIG. 48 also may include features similar to the other features discussed above with respect to the user interface of FIG. 45.

FIG. 49 illustrates a further example of a user interface 4900 of the Interactive Analysis Portal 22 for generating a cohort having patients that are similar to a target patient. In some embodiments, the user interface 4900 can include an external cohort analysis application warning 4604. In some embodiments, the external cohort analysis application warning 4904 can be displayed upon selection of the similar patients selection button 4816 in FIG. 48 (e.g., selection by a user). In some embodiments, the external cohort analysis application warning 4904 can provide information about the external cohort analysis application and/or a warning that the user will be proceeding to an external application. For example, the similar patients summary section 4904 can include information about a report used to determine the populated values 4812 in FIG. 48. In some embodiments, the user interface 4900 can include a link 4908 (e.g., a hyperlink) to an external cohort analysis application, such as the cohort analysis application described above and depicted in FIGS. 2-24.

Figure 50:
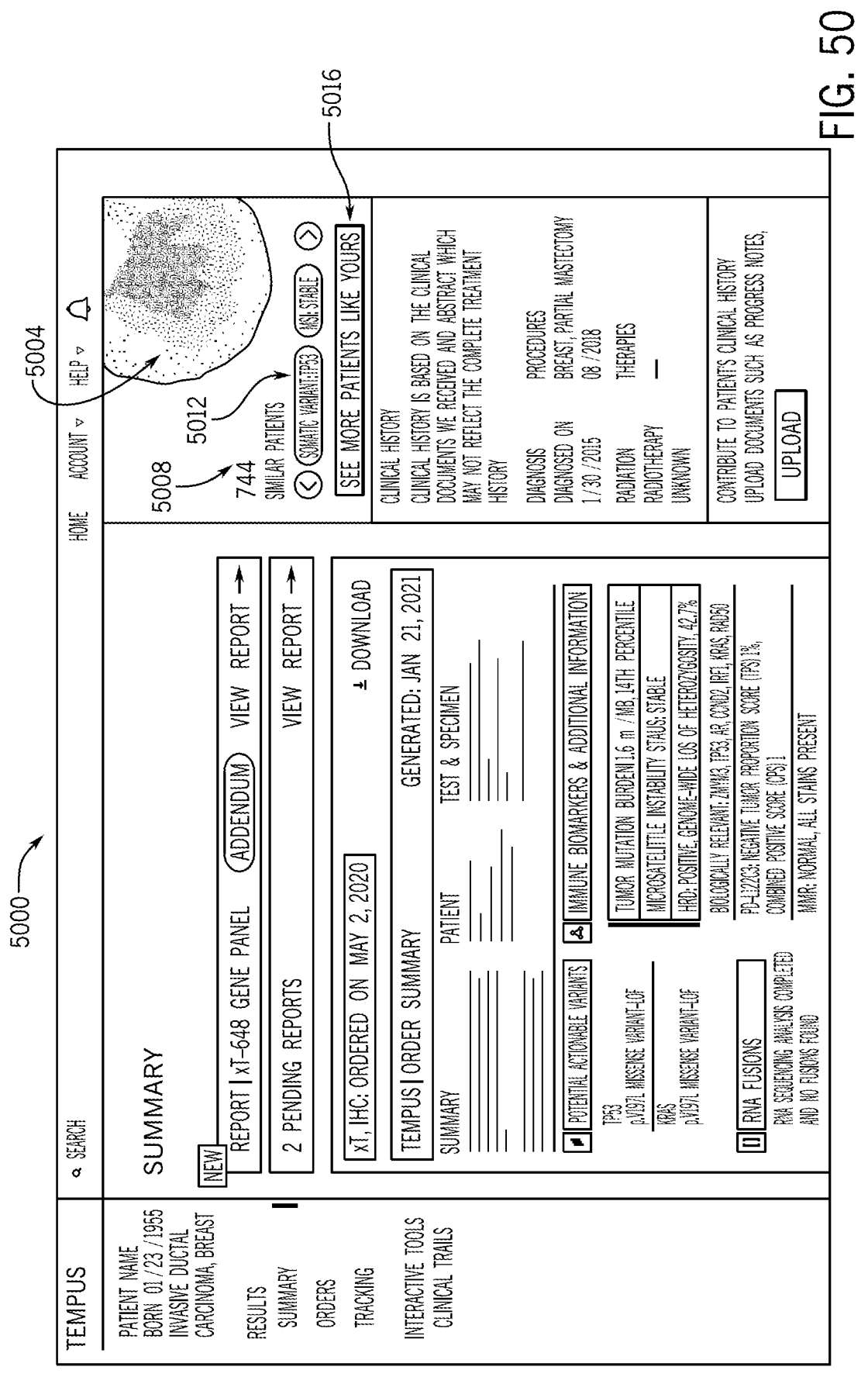

FIG. 50 illustrates another further example of a user interface 5000 of the Interactive Analysis Portal 22 for generating a cohort having patients that are similar to a target patient. In some embodiments, the user interface 5000 can include a similar patient information section 5004.

In some embodiments, the similar patients information section 5004 can include a cohort population indicator 5008 (e.g., an indicator of how many similar patients are available). In some embodiments, the cohort can be generated based on one or more populated values 5012 included in one or more reports associated with the target patient (e.g., the most recent report associated with the target patient). In some embodiments, a process can determine one or more of the populated values 5012 based on a predetermined set of features used to generate cohorts. For example, the predetermined set of features can include one or more features that can be used to filter a plurality of patients and generate the cohort. The process can determine the populated values 5012 based on the predetermined set of features and the report(s) associated with the patient by identifying populated values associated with the one or more features in the report(s). In some embodiments, the predetermined set of features can be generated by one or more physicians. In some embodiments, the similar patients information section 5004 can include a similar patients selection button 5016.

As shown, the populated values 5012 can include a plurality of populated values for a given feature (e.g., a populated value of "TP53" for the feature of "Somatic variant" and a populated value of "Stable" for the feature of "MSI status"). Using a subset of populated values can increase the number of similar patients available as compared to using a fuller set of populated values (e.g., as shown in FIG. 45). Conversely, although the interface of FIG. 50 relies on a larger number of populated values as compared to the interface of FIG. 48, and the number of similar patients available in the former case is smaller than the number of patients available in the latter case, there may not be a correlation between the number of populated values and the number of patients available in this instance, where the interface using the smaller number of populated values is not a subset of the larger number of values. For example, in this case, there is no overlap between the values in FIG. 48 ("Primary site: bladder") and in FIG. 50 ("Somatic variant: TP53" and "MSI: Stable"). In some embodiments, a process can prepopulate the populated values 5012 with multiple populated values, and a user can remove one or more of the populated values 5012 in order to broaden the number of similar patients and/or the size of the cohort.

In addition, although not labeled, it should be understood that the user interface of FIG. 50 also may include features similar to the other features discussed above with respect to the user interface of FIG. 45.

FIG. 51 illustrates yet another example of a user interface 5100 of the Interactive Analysis Portal 22 for generating a cohort having patients that are similar to a target patient. In some embodiments, the user interface 5100 can include an external cohort analysis application warning 5104. In some embodiments, the external cohort analysis application warning 5104 can be displayed upon selection of the similar patients selection button 5016 in FIG. 50 (e.g., selection by a user). In some embodiments, the external cohort analysis application warning 5104 can provide information about the external cohort analysis application and/or a warning that the user will be proceeding to an external application. For example, the similar patients summary section 5104 can include information about a report used to determine the populated values 5012 in FIG. 50. In some embodiments, the user interface 5100 can include a link 5108 (e.g., a hyperlink) to an external cohort analysis application, such as the cohort analysis application described above and depicted in FIGS. 2-24.

Figure 52:
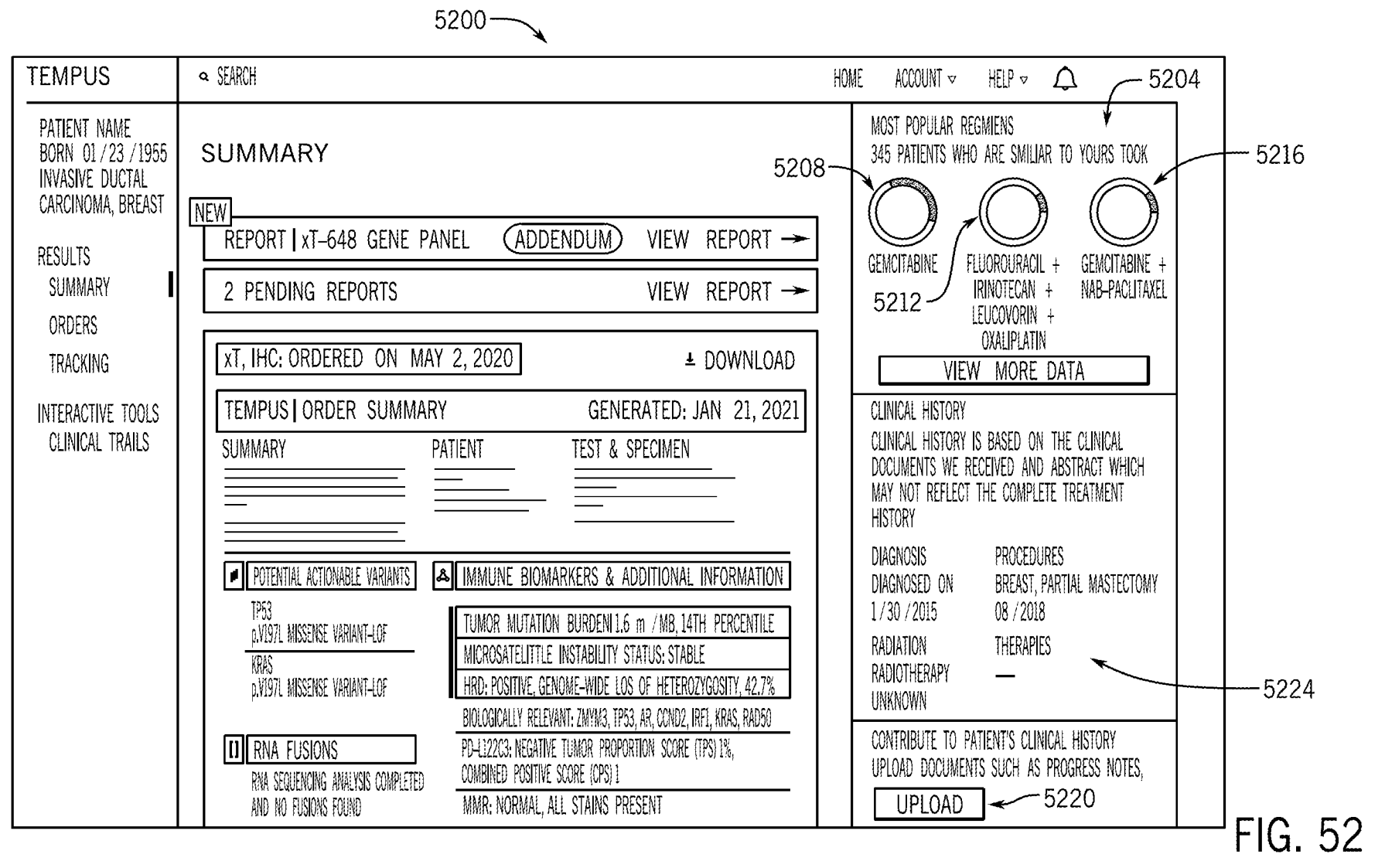

FIG. 52 illustrates a still further example of a user interface 5200 of the Interactive Analysis Portal 22 for generating a cohort having patients that are similar to a target patient. In some embodiments, the user interface 5200 can include a popular regimens information section 5204.

In some embodiments, the popular regimens information section 5204 can include one or more popularity indicators such as graphs, charts, and/or other graphical indicators that indicate a relative popularity of a regimen (e.g., a drug treatment, a therapeutic treatment, etc.) that patients in the cohort have received. For example, the popular regimens information section 5204 can include a first popularity indicator 5208, a second popularity indicator 5212, and/or a third popularity indicator 5216. In some embodiments, the first popularity indicator 5208 can be associated with a most popular regimen that patients in the cohort have received, the second popularity indicator 5212 can be associated with a second most popular regimen that patients in the cohort have received, and the third popularity indicator 5216 can be associated with a third most popular regimen that patients in the cohort have received.

In some embodiments, each popularity indicator (e.g., the first popularity indicator 5208) can indicate the popularity (e.g., as a numerical or visually generally discernible percentage) of a populated value of a feature. For example, the first popularity indicator 5208 can indicate the popularity of gemcitabine for a treatment feature, where the indicator comprises a bar or other type of graph with the percentage of patients sharing that feature represented with a first visual indicator such as a first color, as compared to an entirety of patients represented in a second visual indicator such as a second color. In this way, although the interface may not expressly state the numerical percentage of patients sharing that feature, the user may be able to discern the general or approximate percentage of patients with that feature by comparing the first and second visual indicators.

In some embodiments, the interface 5200 can include an upload clinical history element 5220 and/or a clinical history section 5224. In some embodiments, the upload clinical history element 5220 can be a button that can be selected (e.g., by a user) in order to upload one or more additional clinical documents for the target patient. In some embodiments, a process can receive the one or more additional clinical documents, generate clinical information based on the one or more additional clinical documents, and update the clinical history section 5224 based on the clinical information.

In addition, although not labeled, it should be understood that the user interface of FIG. 52 also may include features similar to the other features discussed above with respect to the user interface of FIG. 45.

Figure 53:
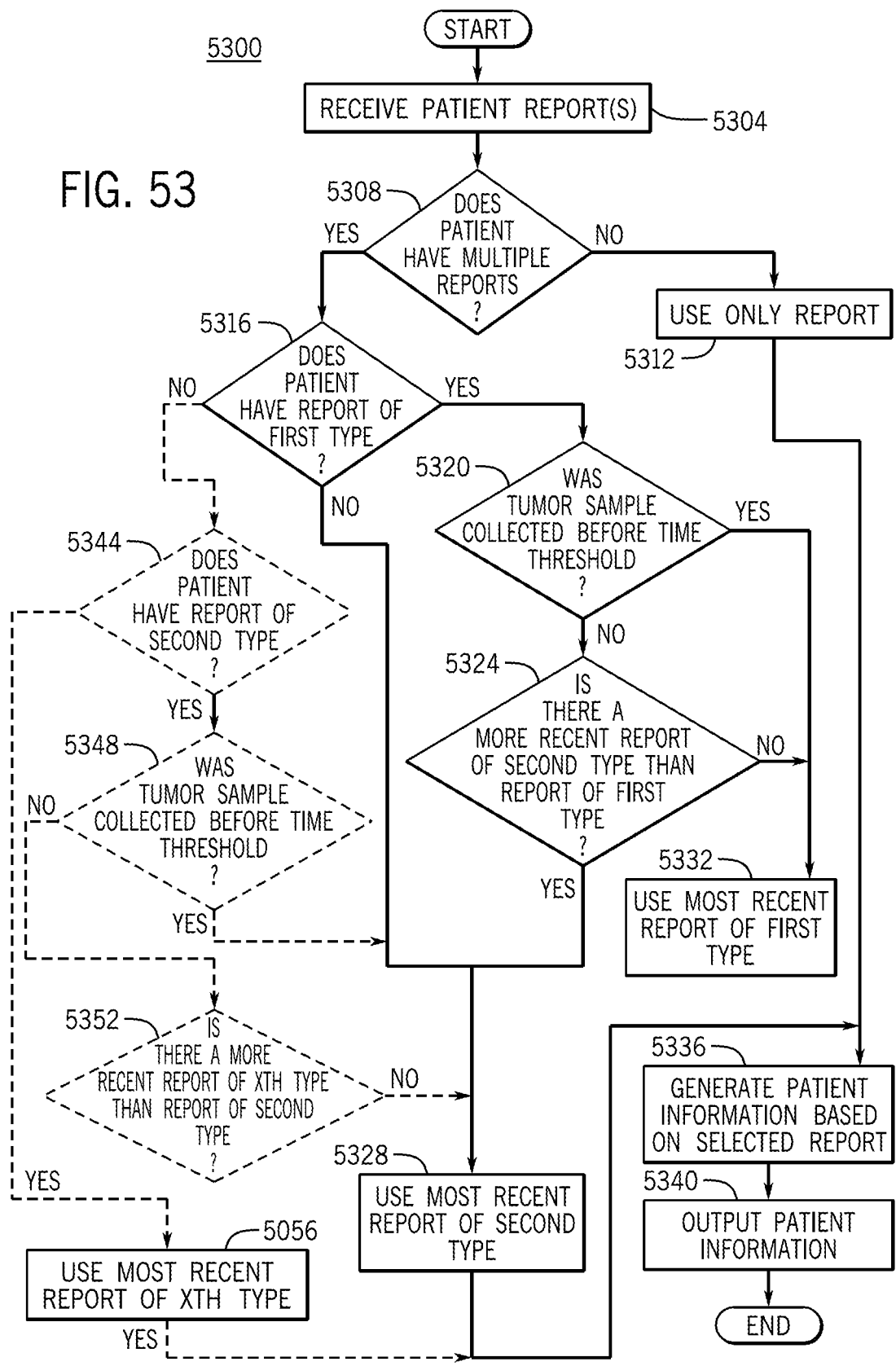
FIG. 53 illustrates an exemplary process for populating patient similarities information based on a report according to some embodiments.

FIG. 53 illustrates an exemplary process 5300 for populating patient similarities information based on a report according to some embodiments. The process 5300 can be implemented as computer readable instructions on one or more memories or other non-transitory computer readable media, and executed by one or more processors in communication with the one or more memories or other media.

At 5304, the process 5300 can receive one or more patient reports associated with a patient. In some embodiments, each patient report can be of a first type (e.g., a liquid biopsy) and/or a second type (e.g., a solid biopsy). In some embodiments, the process 5300 can receive another type of report (i.e., an Xth type of report). It is noted that 5344-5356 are optional steps and may only be included if there are more than two types of reports being considered.

At 5308, the process can determine whether or not there are multiple reports associated with the patient. If there are not multiple reports, the process 5300 can proceed to 5312. If there are multiple reports, the process 5300 can proceed to 5316.

At 5312, the process 5300 can select the report received at 5304 as the selected report.

At 5316, the process 5300 can determine if there is a report of the first type for the patient. The first type may be a preferred type of report. For example, liquid biopsy reports may be more preferable than solid biopsy reports. As another example, solid biopsy reports may be more preferable than liquid biopsy reports. If there is a report of the first type for the patient, the process 5300 can proceed to 5320. If there is not a report of the first type for the patient, the process 5300 can proceed to 5328.

At 5320, the process 5300 can determine if a tumor sample associated with the report of the first type was collected before a predetermined time threshold. For example, the process 5300 can determine if a tumor sample associated with the report of the first type was collected in the last six months. If there are one or more reports of the first type that are associated with a tumor sample collected before the predetermined time threshold, the process 5300 can proceed to 5332. If there are no reports of the first type that are associated with a tumor sample collected before the predetermined time threshold, the process 5300 can proceed to 5324.

At 5324, the process 5300 can determine whether there is a report of the second type that is more recent than any report(s) of the first type. Specifically, the process 5300 can determine if there are any reports of the second type that are associated with tumor samples harvested more recently than any of the tumor sample(s) associated with the report(s) of the first type. If there is a more recent report of the second type, the process 5300 can proceed to 5328. If there is not a more recent report of the second type, the process 5300 can proceed to 5332.

At 5328, the process 5300 can select the most recent report of the second type received at 5304 as the selected report. Specifically, the process 5300 can select the report of the second type associated with the tumor sample harvested most recently as the selected report.

At 5332, the process 5300 can select the most recent report of the first type received at 5304 as the selected report. Specifically, the process 5300 can select the report of the first type associated with the tumor sample harvested most recently as the selected report.

At 5336, the process 5300 can generate patient information based on the selected report, In some embodiments, the process 5300 can generate diagnosis information, somatic variants information, and/or MSI information based on the patient information. In some embodiments, the diagnosis information can include primary diagnosis information, such as a primary site. In some embodiments, the somatic variants information can include PA+BioRel somatic variants information. In some embodiments, the MSI information can include immunotherapy MSI information.

At 5340, the process 5300 can output the patient information. In some embodiments, the process 5300 can populate one or more user interfaces (e.g., interfaces 4500-5200) with the patient information.

At optional 5344, the process 5300 can determine if there is a report of the second type for the patient. The second type may be more preferable than an Xth type of report. If there is a report of the second type for the patient, the process 5300 can proceed to 5348. If there is not a report of the second type for the patient, the process 5300 can proceed to 5356.

At 5348, the process 5300 can determine if a tumor sample associated with the report of the second type was collected before a predetermined time threshold. For example, the process 5300 can determine if a tumor sample associated with the report of the second type was collected in the last six months. If there are one or more reports of the second type that are associated with a tumor sample collected before the predetermined time threshold, the process 5300 can proceed to 5328. If there are no reports of the second type that are associated with a tumor sample collected before the predetermined time threshold, the process 5300 can proceed to 5352.

At 5352, the process 5300 can determine whether there is a report of the Xth type that is more recent than any report(s) of the second type. Specifically, the process 5300 can determine if there are any reports of the Xth type that are associated with tumor samples harvested more recently than any of the tumor sample(s) associated with the report(s) of the second type. If there is a more recent report of the Xth type, the process 5300 can proceed to 5356. If there is not a more recent report of the second type, the process 5300 can proceed to 5328.

Figure 54:
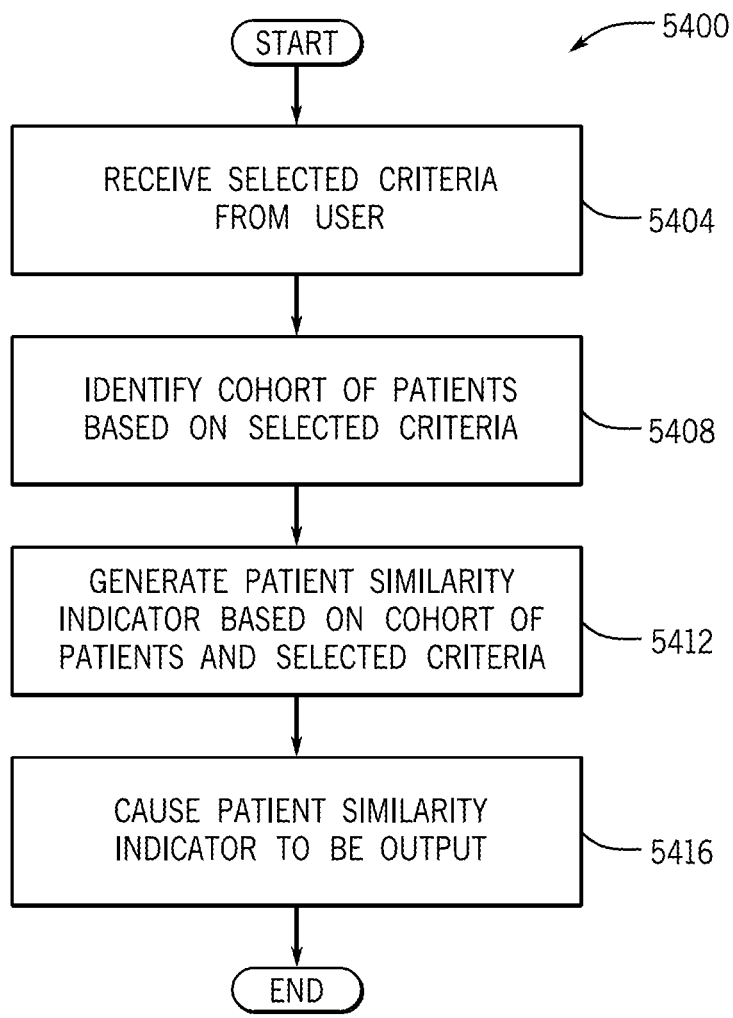
FIG. 54 illustrates an exemplary process for applying data which has been curated, deidentified, and aggregated to generate at least one patient similarity according to some embodiments.

FIG. 54 illustrates an exemplary process 5400 for applying data which has been curated, deidentified, and aggregated to generate at least one patient similarity according to some embodiments. The process 5400 can be implemented as computer readable instructions on one or more memories or other non-transitory computer readable media, and executed by one or more processors in communication with the one or more memories or other media.

At 5404, the process 5400 can receive selected criteria from a user. In some embodiments, the selected criteria can include at least one populated value of a feature. The feature can be included in a plurality of features. In some embodiments, the at least one populated value can include a cancer. In some embodiments, the cancer can include at least one of a melanoma, a lung cancer, a breast cancer, or a bladder cancer. In some embodiments, the selected criteria can be associated with a target patient. In some embodiments, the process 5400 can display, at the user interface, at least a portion of a report associated with the target patient. In some embodiments, the report can be a next-generation sequencing report. In some embodiments, the report can be a liquid biopsy test. In some embodiments, the report can be a solid biopsy test. In some embodiments, the report can be a next-generation sequencing report. In some embodiments, the report can include at least one of clinically actionable variants, fusion data, or biomarker information. In some embodiments, the fusion data can include RNA fusion data. In some embodiments, the process 5400 can display, at the user interface, a report selection element. In some embodiments, the process 5400 can display, at the user interface, at least one selectable criteria option. In some embodiments, the process 5400 can determine at least one data completeness measure for at least one features included in a set of features based on health information associated with patients included in the patient database, determine a subset of the set of features that have the highest data completeness, and displaying, at the user interface, the subset of features. In some embodiments, the process 5400 can receive a selection of at least one feature included in the subset of features, and the selected criteria can include the at least one feature included in the subset of features.

At 5408, the process 5400 can identify a cohort of patients included in a patient database based on the selected criteria. In some embodiments, each patient included in the cohort can satisfy the selected criteria. In some embodiments, the patient database may require higher authentication credentials to access than the user interface.

At 5412, the process 5400 can generate at least one patient similarity indicator based on the cohort of patients and the selected criteria. In some embodiments, the at least one visual indicator being a graphical indicator can be indicative of a popularity of a populated value of a second feature included in the plurality of features. In some embodiments, the second feature can include at least one of a treatment, a therapy, a study, or procedure amongst patients in the cohort. In some embodiments, the treatment can be a radiation treatment. In some embodiments, the radiation treatment can be a chemotherapy treatment. In some embodiments, the treatment can be a drug regimen including at least one drug. In some embodiments, the at least one drug can include at least one of a biologic drug, an immunotherapy checkpoint inhibitor drug, a targeted drug, an immunological drug, an antibody-drug-conjugate drug, and/or an immunotherapy bispecific t-cell engager drug. In some embodiments, the at least one drug can include a drug that is approved by the United States Food and Drug Administration. In some embodiments, the at least one drug can include a drug that is not approved by the United States Food and Drug Administration. In some embodiments, the at least one populated value can include a disease, and the at least one drug can include a drug that is not approved by the United States Food and Drug Administration to treat the disease. In some embodiments, the at least one populated value can include a disease, and the at least one drug can include a drug that is approved by the United States Food and Drug Administration to treat the disease. In some embodiments, the procedure can be a surgical procedure. In some embodiments, the surgical procedure can be a cancer removal surgery. In some embodiments, the at least one patient similarity indicator can include a number of how many patients are included in the cohort. In some embodiments, the at least one patient similarity indicator can include at least one of a graph or a chart indicative of the popularity of the populated value of the second feature. In some embodiments, the at least one of a graph or a chart can include a text representation of the second feature.

At 5416, the process 5400 can display, at the user interface, the at least one patient similarity indicator. In some embodiments, the process 5400 can display, at the user interface, a link to the patient database.

Figure 55:
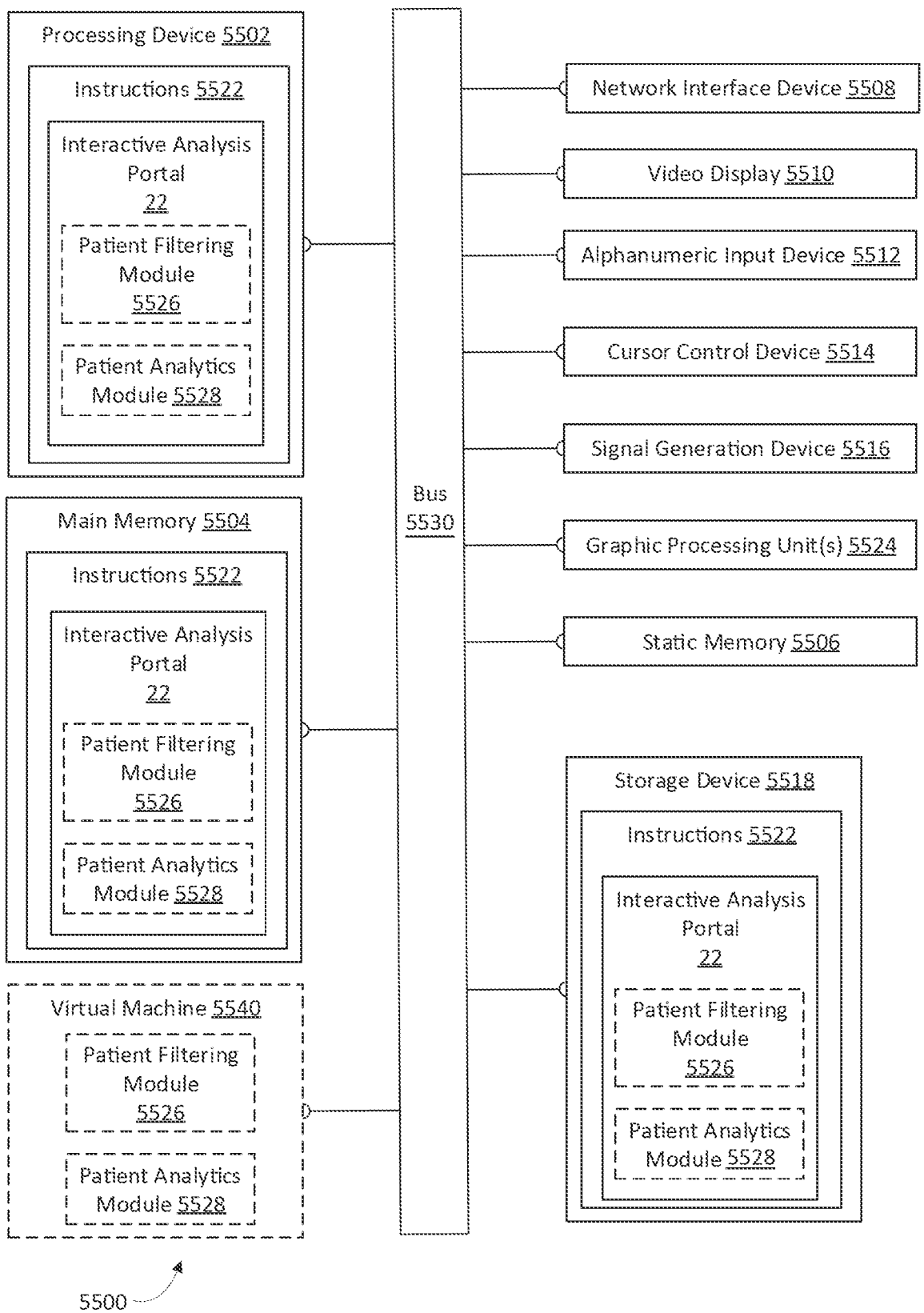
FIG. 55 is an illustration of a block diagram of an implementation of a computer system in which some implementations of the disclosure may operate.

FIG. 55 is an illustration of an example machine of a computer system 5500 within which a set of instructions, for causing the machine to perform any one or more of the methodologies discussed herein, may be executed. In alternative implementations, the machine may be connected (such as networked) to other machines in a LAN, an intranet, an extranet, and/or the Internet.

The machine may operate in the capacity of a server or a client machine in a client-server network environment, as a peer machine in a peer-to-peer (or distributed) network environment, or as a server or a client machine in a cloud computing infrastructure or environment. The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 5500 includes a processing device 5502, a main memory 5504 (such as read-only memory (ROM), flash memory, dynamic random access memory (DRAM) such as synchronous DRAM (SDRAM) or DRAM, etc.), a static memory 5506 (such as flash memory, static random access memory (SRAM), etc.), and a data storage device 5518, which communicate with each other via a bus 5530.

Processing device 5502 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 5502 may also be one or more special-purpose processing devices such as an application specific integrated circuit (ASIC), a field programmable gate array (FPGA), a digital signal processor (DSP), network processor, or the like. The processing device 5502 is configured to execute instructions 5522 for performing the operations and steps discussed herein.

The computer system 5500 may further include a network interface device 5508 for connecting to the LAN, intranet, internee, and/or the extranet. The computer system 5500 also may include a video display unit 5510 (such as a liquid crystal display (LCD) or a cathode ray tube (CRT)), an alphanumeric input device 5512 (such as a keyboard), a cursor control device 5514 (such as a mouse), a signal generation device 5516 (such as a speaker), and a graphic processing unit 5524 (such as a graphics card).

The data storage device 5518 may be a machine-readable storage medium (also known as a computer-readable medium) on which is stored one or more sets of instructions or software 5522 embodying any one or more of the methodologies or functions described herein. The instructions 5522 may also reside, completely or at least partially, within the main memory 5504 and/or within the processing device 5502 during execution thereof by the computer system 5500, the main memory 5504 and the processing device 5502 also constituting machine-readable storage media.

In one implementation, the instructions 5522 include instructions for an interactive analysis portal (such as interactive analysis portal 22 of FIG. 1) and/or a software library containing methods that function as an interactive analysis portal. The instructions 5522 may further include instructions for a patient filtering module 5526 (such as the interactive cohort selection filtering interface 24 of FIG. 1) and a patient analytics module 5528 (such as the cohort funnel and population analysis interface 26, the patient timeline analysis user interface 28, the patient survival analysis user interface 30, and/or the patient event likelihood analysis user interface 32 of FIG. 1). While the data storage device 5518/machine-readable storage medium is shown in an example implementation to be a single medium, the term "machine-readable storage medium" should be taken to include a single medium or multiple media (such as a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media. The term "machine-readable storage medium" shall accordingly exclude transitory storage mediums such as signals unless otherwise specified by identifying the machine readable storage medium as a transitory storage medium or transitory machine-readable storage medium.

In another implementation, a virtual machine 5540 may include a module for executing instructions for a patient filtering module 5526 (such as the interactive cohort selection filtering interface 24 of FIG. 1) and a patient analytics module 5528 (such as the cohort funnel and population analysis interface 26, the patient timeline analysis user interface 28, the patient survival analysis user interface 30, and/or the patient event likelihood analysis user interface 32 of FIG. 1). In computing, a virtual machine (VM) is an emulation of a computer system. Virtual machines are based on computer architectures and provide functionality of a physical computer. Their implementations may involve specialized hardware, software, or a combination of hardware and software.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "providing" or "calculating" or "determining" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMS), EPROMs, EEPROMs, magnetic or optical cards, or any type of media suitable for storing electronic instructions, each coupled to a computer system bus.

The algorithms and displays presented herein are not inherently related to any particular computer or other apparatus. Various general purpose systems may be used with programs in accordance with the teachings herein, or it may prove convenient to construct a more specialized apparatus to perform the method. The structure for a variety of these systems will appear as set forth in the description below. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (such as a computer). For example, a machine-readable (such as computer-readable) medium includes a machine (such as a computer) readable storage medium such as a read only memory ("ROM"), random access memory ("RAM"), magnetic disk storage media, optical storage media, flash memory devices, etc.

In the foregoing specification, implementations of the disclosure have been described with reference to specific example implementations thereof. It will be evident that various modifications may be made thereto without departing from the broader spirit and scope of implementations of the disclosure as set forth in the following claims. The specification and drawings are, accordingly, to be regarded in an illustrative sense rather than a restrictive sense.

It will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

What is claimed is:

1. A method of permitting a user to select a cohort of health information, the method comprising:
   causing filter criteria to be displayed at a user interface, the filter criteria comprising at least one of modality data, demographic data, assessment data, diagnosis data, next-generation sequencing (NGS) data, molecular data, treatment data, or outcome data;
   receiving, at the user interface, selected criteria from a user, the selected criteria comprising at least a portion of the filter criteria;
   identifying health information associated with a cohort of subjects that meets the selected criteria from at least one health information source, the health information comprising, for each subject, subject information associated with the subject and comprising populated values for a number of features distinct from the selected criteria and comprising a subset of a predetermined set of features;

aggregating the health information corresponding to the subset of features to a single database table in a computer system;

determining, using the single database table, a plurality of data completeness measures for a cohort of subjects, the plurality of data completeness measures corresponding to a plurality of the subset of features, wherein each data completeness measure measures a number of subjects having entries stored in fields in the database table that are associated with a corresponding feature, and wherein the user does not have access to at least some of the health information stored in the database table and corresponding to the data completeness measures;

generating a plurality of visualizations at the user interface, each of the plurality of visualizations displaying a corresponding one of the plurality of data completeness measures, wherein at least one visualization of the plurality of visualizations is configured to be selectable by the user, wherein, in response to a user selection of one or more of the at least one visualizations, the cohort of subjects is filtered to include only a subset of subjects corresponding to the data completeness measure determined from the single database table and corresponding to the at least one visualization; and provisioning, to the user, subject data from the subset of subjects.

2. The method of claim 1, wherein the selected criteria comprises modality data comprising at least two of clinical data, DNA data, RNA data, or imaging data, and the determining at least one data completeness measure further comprises:

generating a Venn Diagram representative of how many subjects are associated with subject information including populated values associated with the modality data.

3. The method of claim 1 further comprising:

determining at least one data comparison measure between a first health information source and a second health information source included in the at least one health information source based on the health information; and causing the at least one data comparison measure to be displayed at the user interface.

4. The method of claim 3, wherein the first health information source and the second health information source are healthcare databases.

5. The method of claim 1 further comprising:

providing, at the user interface, an option to save a cohort generated based on the selected criteria and the health information.

6. The method of claim 1 further comprising:

providing, at the user interface, an option to share at least one of a query comprising the selected criteria or a cohort generated based on the selected criteria with a second user.

7. The method of claim 6 further comprising:

determining that the user is authorized to share the at least one of the query or a cohort with the second user.

8. The method of claim 1, wherein the set of features comprises at least one of a diagnosis feature, a demographic feature, an assessment feature, or an NGS feature.

9. The method of claim 1, wherein the set of features comprises at least two of a diagnosis feature, a demographic feature, an assessment feature, or an NGS feature.

10. The method of claim 1, wherein the modality data comprises at least one of clinical data, DNA data, RNA data, or imaging data.

11. The method of claim 1, wherein the molecular data is curated from at least one of an electronic health record or a genetic sequencing report.

12. The method of claim 1, wherein the cohort of subjects comprises a subset of a plurality of subjects comprising at least one million subjects.

13. The method of claim 1, wherein the method is implemented as instructions on at least one non-transitory computer readable media.

14. The method of claim 1, wherein the set of features comprises at least one of diagnoses, responses to treatment regimens, genetic profiles, clinical characteristics, phenotypic characteristics, molecular data, imaging data, tumor infiltration, programmed death-ligand 1 (PD-L1) status, human leukocyte antigen (HLA) status, symptoms, therapies, outcomes, subject name, date of birth, gender, ethnicity, date of death, address, smoking status, diagnosis dates for cancer, illness, disease, diabetes, depression, other physical or mental maladies, personal medical history, family medical history, date of initial diagnosis, date of metastatic diagnosis, cancer staging, tumor characterization, tissue of origin, line of therapy, therapy groups, clinical trials, medication prescribed, medication taken, surgery, radiotherapy, imaging, adverse effects, associated outcomes, performance scores, lab tests, pathology results, prognostic indicators, date of genetic testing, testing provider used, testing method used, genetic sequencing method, gene panel, gene results, genes, variants, or expression levels.

15. The method of claim 1 further comprising:

determining at least one data summary measure for at least a portion of the selected criteria based on the subject information associated with each subject included in the cohort of subjects; and causing the at least one data summary measure to be displayed at the user interface.

16. The method of claim 15, wherein the selected criteria comprises a specific feature that can be populated with a specific value included in a set of specific values, and the at least one data summary measure comprises a chart or graph indicative of, for each specific value in the set of specific values, a number of subjects included in the cohort of subjects associated with populated values equal to the specific value.

17. The method of claim 15, wherein the selected criteria comprises a first specific feature that can be populated with a specific value included in a first set of specific values, the set of features comprises a second specific feature that can be populated with a specific value included in a second set of specific values, and the at least one data summary measure comprises a chart or graph indicative of, for each specific value in the first set of specific values, a number of subjects included in the cohort of subjects associated with populated values equal to the specific value and each of the specific values included in the second set of specific values.

18. A cohort selection system comprising at least one processor and at least one memory comprising instructions to:

cause filter criteria to be displayed at a user interface, the filter criteria comprising at least one of modality data, demographic data, assessment data, diagnosis data, next-generation sequencing (NGS) data, molecular data, treatment data, or outcome data;

receive, at the user interface, selected criteria from a user, the selected criteria comprising at least a portion of the filter criteria;

identify health information associated with a cohort of subjects that meets the selected criteria from at least one health information source, the health information comprising, for each subject, subject information associated with the subject and comprising populated values for a number of features distinct from the selected criteria and comprising a subset of a predetermined set of features;

aggregate the health information corresponding to the subset of features to a single database table in a computer system;

determine, using the single database table, a plurality of data completeness measures for a cohort of subjects, the plurality of data completeness measures corresponding to a plurality of the subset of features, wherein each data completeness measure measures a number of subjects having entries stored in fields in the database table that are associated with a corresponding feature, and wherein the user does not have access to at least some of the health information stored in the database table and corresponding to the data completeness measures;

generate a plurality of visualizations at the user interface, each of the plurality of visualizations displaying a corresponding one of the plurality of data completeness measures, wherein at least one visualization of the plurality of visualizations is configured to be selectable by the user, wherein, in response to a user selection of one or more of the at least one visualizations, the cohort of subjects is filtered to include only a subset of subjects corresponding to the data completeness measure determined from the single database table and corresponding to the at least one visualization; and provision, to the user, subject data from the subset of subjects.

19. A method of permitting a user to select a cohort of health information, the method comprising:

causing filter criteria to be displayed at a user interface, the filter criteria comprising at least one of modality data, demographic data, assessment data, diagnosis data, next-generation sequencing (NGS) data, molecular data, treatment data, or outcome data;

receiving, at the user interface, selected criteria from a user, the selected criteria comprising at least a portion of the filter criteria;

identifying health information associated with a cohort of subjects that meets the selected criteria from at least one health information source, the health information comprising, for each subject, subject information associated with the subject and comprising populated values for a number of features distinct from the selected criteria and comprising a subset of a predetermined set of features;

determining, by a processor, for each subject within a first cohort of subjects of the cohort of subjects associated with a first health information source included in the at least one health information source and a second cohort of subjects of the cohort of subjects associated with a second health information source included in the at least one health information source, which fields in the one or more databases are populated with values;

aggregating the health information corresponding to the subset of features for a first cohort of subjects of the cohort of subjects from a first health information source included in the at least one health information source and for a second cohort of subjects of the cohort of subjects from a second health information source included in the at least one health information source to a single database table in a computer system;

determining, using the single database table, a plurality of data completeness measures between the first cohort of subjects and the second cohort of subjects, the plurality of data completeness measures corresponding to a plurality of the subset of features, wherein each data completeness measure measures a number of subjects having entries stored in fields in the database table that are associated with a corresponding feature, and wherein the user does not have access to at least some of the health information stored in the database table and corresponding to the data completeness measures;

generating a plurality of visualizations at the user interface, each of the plurality of visualizations displaying a corresponding one of the plurality of data completeness measures, wherein at least one visualization of the plurality of visualizations is configured to be selectable by the user, wherein, in response to a user selection of one or more of the at least one visualizations, the subject data cohort is filtered to include only a subset of subjects corresponding to the data completeness measure determined from the single database table and corresponding to the at least one visualization; and provisioning, to the user, subject data from the subset of subjects.

* * * * *